(12) United States Patent
Rice et al.

(10) Patent No.: US 7,576,074 B2
(45) Date of Patent: Aug. 18, 2009

(54) RECEPTOR-TYPE KINASE MODULATORS AND METHODS OF USE

(76) Inventors: Kenneth D. Rice, 802 Autumn La., Mill Valley, CA (US) 94941; Neel K. Anand, 977 El Camino Real, Unit #303, Burlingame, CA (US) 94010; Joerg Bussenius, 1042 Helm La., Foster City, CA (US) 94404; Abigail R. Kennedy, 15175 Swenson St., San Leandro, CA (US) 94579; Angie I. Kim, 928 Shoal Dr., San Mateo, CA (US) 94404; Csaba J. Peto, 965 Shorepoint Ct., #305, Alameda, CA (US) 94501; Tsze H. Tsang, 8367 Kent Dr., El Cerrito, CA (US) 94530

( * ) Notice: Subject to any disclaimer, the term of this patent is extended or adjusted under 35 U.S.C. 154(b) by 475 days.

(21) Appl. No.: 10/522,004

(22) PCT Filed: Jul. 14, 2003

(86) PCT No.: PCT/US03/21923

§ 371 (c)(1),
(2), (4) Date: Apr. 11, 2005

(87) PCT Pub. No.: WO2004/006846

PCT Pub. Date: Jan. 22, 2004

(65) Prior Publication Data

US 2006/0069077 A1  Mar. 30, 2006

(51) Int. Cl.
| | |
|---|---|
| A01N 43/00 | (2006.01) |
| A61K 31/33 | (2006.01) |
| A01N 43/54 | (2006.01) |
| A61K 31/517 | (2006.01) |
| C07D 401/00 | (2006.01) |
| C07D 403/00 | (2006.01) |
| C07D 413/00 | (2006.01) |
| C07D 417/00 | (2006.01) |
| C07D 419/00 | (2006.01) |
| C07D 239/72 | (2006.01) |

(52) U.S. Cl. .................. 514/183; 514/266.2; 514/266.3; 514/266.4; 544/284; 544/287; 544/293

(58) Field of Classification Search .................. None
See application file for complete search history.

(56) References Cited

U.S. PATENT DOCUMENTS

| 5,747,498 | A | 5/1998 | Schnur et al. |
| 5,962,458 | A | 10/1999 | Lohmann et al. |
| 6,184,225 | B1 | 2/2001 | Thomas et al. |
| 2002/0049197 | A1 | 4/2002 | Himmelsbach et al. |

FOREIGN PATENT DOCUMENTS

| WO | WO97/22596 | * | 6/1997 |
| WO | WO 98/13354 | | 4/1998 |
| WO | WO 00/20402 | | 4/2000 |
| WO | WO 01/21594 A1 | | 3/2001 |
| WO | WO 01/21595 | | 3/2001 |
| WO | WO 01/21596 A1 | | 3/2001 |
| WO | WO 01/32651 A1 | | 5/2001 |
| WO | WO 01/74360 A1 | | 10/2001 |
| WO | WO 01/77085 A1 | | 10/2001 |
| WO | WO 02/18372 A2 | | 3/2002 |
| WO | WO 03/000188 | | 1/2003 |
| WO | WO03082831 | | 10/2003 |

OTHER PUBLICATIONS

Bridges, et. al., Journal of Medicinal Chemistry (1996), 39(1), 267-76.*
Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
Bonasera et al Potential 18F-labeled biomarkers for epidermal growth factor receptor tyrosine kinase. Nuclear Medicine and Biology (2001), 28(4), 359-374.
Christensen JG et al. Proc Amer Assoc Cancer Res [94th annual Meeting Amer Assoc Cancer Res- AACR (Jul. 11-14, Washington DC) 2003] 2003, 44: Abstract 4963.
MAulik G. et al Proc Amer Assoc Cancer Res [94th annual Meeting Amer Assoc Cancer Res- AACR (Jul. 11-14, Washington, DC) 2003] 2003, 44: Abstract 6200.
Sattler et al. Proc Amer Assoc Cancer Res [94th annual Meeting Amer Assoc Cancer Res- AACR (Jul. 11-14, Washington, DC) 2003] 2003, 44: Abstract 1005.
Hennequin, L.F. et al., "Design and Structure-Activity Relationship of a New Class of Potent VEGF Receptor Tyrosine Kinase Inhibitors", Journal of Medicinal Chemistry, American Chemical Society, vol. 42, 1999, pp. 5369-5389.
Supplementary European Search Report, European Application No. EP03764599.

* cited by examiner

Primary Examiner—James O Wilson
Assistant Examiner—Jeffrey H Murray
(74) Attorney, Agent, or Firm—Janice V. Rice; McDonnell Boehnen Hulbert & Berghoff LLP

(57) ABSTRACT

The present invention provides compounds for modulating receptor kinase activity, particularly ephrin and EGFR, and methods of treating diseases mediated by receptor kinase activity utilizing the compounds and pharmaceutical compositions thereof. Diseases mediated by receptor kinase activity include, but are not limited to, diseases characterized in part by abnormal levels of cell proliferation (i.e. tumor growth), programmed cell death (apoptosis), cell migration and invasion and angiogenesis associated with tumor growth. Compounds of the invention include "spectrum selective" kinase modulators, compounds that inhibit, regulate and/or modulate signal transduction across subfamilies of receptor-type tyrosine kinases, including ephrin and EGFR.

47 Claims, No Drawings

RECEPTOR-TYPE KINASE MODULATORS AND METHODS OF USE

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to quinazolines which inhibit, regulate and/or modulate kinase receptor signal transduction pathways related to the changes in cellular activities as mentioned above, compositions which contain these compounds, and methods of using them to treat kinase-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity are staggering; cell differentiation and proliferation; i.e., virtually all aspects of cell life in one-way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular domain, while non-receptor type tyrosine kinases are wholly intracellular.

Receptor-type tyrosine kinases are comprised of a large number of transmembrane receptors with diverse biological activity. In fact, about twenty different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta-receptors, CSFIR, c-kit and FLK-II. Additionally there is the FLK family, which is comprised of the kinase insert domain receptor (KDR), fetal liver kinase-1 (FLK-1), fetal liver kinase-4 (FK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6): 334-339, 1994, which is hereby incorporated by reference for all purposes.

The non-receptor type of tyrosine kinases is also comprised of numerous subfamilies, including Src, Frk, Btk, Csk, Abl, Zap70, Fes/Fps, Fak, Jak, Ack, and LIMK. Each of these subfamilies is further sub-divided into varying receptors. For example, the Src subfamily is one of the largest and includes Src, Yes, Fyn, Lyn, Lck, Blk, Hck, Fgr, and Yrk. The Src subfamily of enzymes has been linked to oncogenesis. For a more detailed discussion of the non-receptor type of tyrosine kinases, see Bolen, Oncogene, 8:2025-2031 (1993), which is hereby incorporated by reference for all purposes.

Since protein kinases and their ligands play critical roles in various cellular activities, deregulation of protein kinase enzymatic activity can lead to altered cellular properties, such as uncontrolled cell growth associated with cancer. In addition to oncological indications, altered kinase signaling is implicated in numerous other pathological diseases. These include, but are not limited to: immunological disorders, cardiovascular diseases, inflammatory diseases, and degenerative diseases. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stroma cancers (GIST). Gleevec is a c-Kit and Abl kinase inhibitor.

Modulation (particularly inhibition) of cell proliferation and angiogenesis, two key cellular processes needed for tumor growth and survival (Matter A. Drug Disc Technol 2001 6, 1005-1024), is an attractive goal for development of small-molecule drugs. Anti-angiogenic therapy represents a potentially important approach for the treatment of solid tumors and other diseases associated with dysregulated vascularization, including ischemic coronary artery disease, diabetic retinopathy, psoriasis and rheumatoid arthritis. As well, cell antiproliferative agents are desirable to slow or stop the growth of tumors.

Inhibition of EGF, VEGF and ephrin signal transduction will prevent cell proliferation and angiogenesis, two key cellular processes needed for tumor growth and survival (Matter A. Drug Disc Technol 2001 6, 1005-1024). VEGF receptors are previously described targets for small molecule inhibition.

The Eph receptors comprise the largest family of receptor tyrosine kinases and are divided into two groups, EphA and EphB, based on their sequence homology. The ligands for the Eph receptors are ephrin, which are membrane anchored. Ephrin A ligands bind preferentially to EphA receptors whilst ephrin B ligands bind to EphB receptors. Binding of ephrin to Eph receptors causes receptor autophosphorylation and typically requires a cell-cell interaction since both receptor and ligand are membrane bound.

Overexpression of Eph receptors has been linked to increased cell proliferation in a variety of tumors (Zhou R 1998 Pharmacol Ther. 77, 151-181; Kiyokawa E, Takai S, Tanaka M et al 1994 Cancer Res 54, 3645-3650; Takai N Miyazaki T, Fujisawa K, Nasu K and Miyakawa. 2001 Oncology reports 8, 567-573). The family of Eph receptor tyrosine kinases and their ephrin ligands play important roles in a variety of processes during embryonic development and also in pathological angiogenesis and potentially metastasis. Therefore modulation of Eph receptor kinase activity should provide means to treat or prevent disease states associated with abnormal cell proliferation such as those described above.

The epidermal growth factor receptor (EGFR, HER1, erbB1) is part of a family of plasmam membrane receptor tyrosine kinases that control cellular growth, proliferation and apoptosis. The ligand for EGFR is the epidermal growth factor and dysregulation of the EGFR signal transduction pathway has been implicated in tumorigenesis and cancer progression thus making it a clinically relevant target for novel anticancer treatments Drevs J et al 2003 Curr Drug Targets 4, 113-121; Ciardiello F and Tortora G. 2001 Clin. Cancer Res. 7, 2958-2970; Thomas M. 2002 Semin One. Nurs. 18, 20-27).

EGPR is overexpressed in different human cancers especially non-small cell lung cancer and glioblastomas. In these cancers, EGFR overexpression is commonly associated with advanced disease and poor prognosis (Baselga J et al 1999 Semin. Oncol. 26, 78-83).

Accordingly, the identification of small-molecule compounds that specifically inhibit, regulate and/or modulate the signal transduction of tyrosine kinases, particularly ephrin and EGFR receptor kinases, is desirable as a means to treat or prevent disease states associated with abnormal cell proliferation and is an object of this invention.

SUMMARY OF THE INVENTION

In one aspect, the present invention provides compounds for modulating kinase activity, particularly ephrin receptor kinase (from herein denoted "ephrin") activity and/or EGFR activity; methods of treating diseases mediated by such activity utilizing the compounds and pharmaceutical compositions thereof. Diseases mediated by ephrin include, but are not limited to, diseases characterized in part by abnormal cell migration and invasion and angiogenesis associated with tumor growth. Diseases mediated by EGF driven signal transduction include, but are not limited to, diseases characterized by abnormal levels of cell proliferation (i.e. tumor growth) and programmed cell death (apoptosis). Diseases mediated by both ephrin and EGF include diseases characterized by both abnormal cell proliferation and angiogenesis which are associated with tumor growth.

Inhibitors that are selective for a particular kinase, for example ephrin and EGFR, are included in this invention. However, another aspect of the invention are compounds that inhibit, regulate and/or modulate the signal transduction receptor tyrosine kinase families, family members, or otherwise related sets of kinases. Such related kinase families may include receptor-type tyrosine kinases of the HER, FLK and insulin subfamilies, which demonstrate similarity in both structure and broad biochemical function. Thus quinazolines of the invention include "spectrum selective" kinase modulators. "Spectrum selective" kinase modulators are defined as quinazolines of the invention that inhibit, regulate and/or modulate signal transduction across various subfamilies of receptor-type tyrosine kinases including those of ephrin and EGFR receptor tyrosine kinase subfamilies.

In another aspect, the invention provides methods of screening for modulators of receptor tyrosine kinase activity, for example activity of ephrin and EGFR. The methods comprise combining a composition of the invention, a receptor tyrosine kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more tyrosine receptor kinase activity modulators as described herein. Such kits can also include, for example, other compounds and/or compositions (for example, diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below with reference to the associated drawings.

DETAILED DESCRIPTION OF THE INVENTION

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as artheroscrosis, myocardioinfarction, ischemia, stroke and restenosis; other inflammatory and degenerative diseases such as interbowel diseases, osteoarthritus, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

The present invention comprises a compound for modulating tyrosine kinase activity of Formula I,

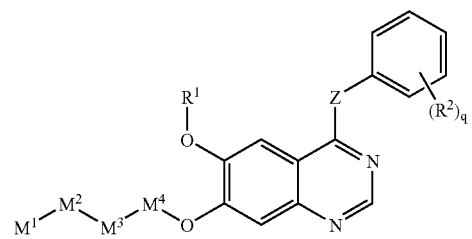

I or a pharmaceutically acceptable salt, hydrate, or prodrug thereof, wherein, $R^1$ is $C_1$-$C_3$ alkyl optionally substituted with between one and three $R^{50}$ substituents;

$R^2$ is selected from —H, halogen, trihalomethyl, —CN, —NH$_2$, —NO$_2$, —OR$^3$, —N(R$^3$)R$^4$, —S(O)$_{0-2}$R$^4$, —SO$_2$N(R$^3$)R$^4$, —CO$_2$R$^3$, —C(=O)N(R$^3$)R$^4$, —N(R$^3$)SO$_2$R$^4$, —N(R$^3$)C(=O)R$^3$, —N(R$^3$)CO$_2$R$^4$, —C(=O)R$^3$, optionally substituted lower alkyl, optionally substituted lower alkenyl, and optionally substituted lower alkynyl;

$R^3$ is —H or $R^4$;

$R^4$ is selected from optionally substituted lower alkyl, optionally substituted aryl, optionally substituted lower arylalkyl, optionally substituted heterocyclyl, and optionally substituted lower heterocyclylalkyl; or $R^3$ and $R^4$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

q is zero to five;

Z is selected from —OCH$_2$—, —O—, —S(O)$_{0-2}$—, —N(R$^5$)CH$_2$—, and —NR$^5$—;

R$^5$ is —H or optionally substituted lower alkyl;

M$^1$ is —H, C$_1$-C$_8$ alkyl-L$^2$-L$^1$- optionally substituted by R$^{50}$, G(CH$_2$)$_{0-3}$—, or R$^{53}$(R$^{54}$)N(CH$_2$)$_{0-3}$—; wherein G is a saturated five- to seven-membered heterocyclyl containing one or two annular heteroatoms and optionally substituted with between one and three R$^{50}$ substituents; L$^1$ is —C=O— or —SO$_2$—; L$^2$ is a direct bond, —O—, or —NH—; and R$^{53}$ and R$^{54}$ are independently C$_1$-C$_3$ alkyl optionally substituted with between one and three R$^{50}$ substituents;

M$^2$ is a saturated or mono- or poly-unsaturated C$_3$-C$_{14}$ mono- or fused-polycyclic hydrocarbyl optionally containing one, two, or three annular heteroatoms per ring and optionally substituted with between zero and four R$^{50}$ substituents; and M$^3$ is —NR$^9$—, —O—, or absent;

M$^4$ is —CH$_2$—, —CH$_2$CH$_2$—, —CH$_2$CH$_2$CH$_2$—, or absent;

R$^9$ is —H or optionally substituted lower alkyl;

R$^{50}$ is —H, halo, trihalomethyl, —OR$^3$, —N(R$^3$)R$^4$, —S(O)$_{0-2}$R$^4$, —SO$_2$N(R$^3$)R$^4$, —CO$_2$R$^3$, —C(=O)N(R$^3$)R$^4$, —C(=NR$^{25}$)N(R$^3$)R$^4$, —C(=NR$^{25}$)R$^4$, —N(R$^3$)SO$_2$R$^4$, —N(R$^3$)C(O)R$^3$, —NCO$_2$R$^3$, —C(=O)R$^3$, optionally substituted alkoxy, optionally substituted lower alkyl, optionally substituted aryl, optionally substituted lower arylalkyl, optionally substituted heterocyclyl, and optionally substituted lower heterocyclylalkyl; or two of R$^{50}$, when taken together on the same carbon are oxo; or two of R$^{50}$, when taken together with a common carbon to which they are attached, form a optionally substituted three- to seven-membered spirocyclyl, said optionally substituted three- to seven-membered spirocyclyl optionally containing at least one additional heteroatom selected from N, O, S, and P; and R$^{25}$ is selected from —H, —CN, —NO$_2$, —OR$^3$, —S(O)$_{0-2}$R$^4$, —CO$_2$R$^3$, optionally substituted lower alkyl, optionally substituted lower alkenyl, and optionally substituted lower alkynyl.

Embodiment [0025]: In one example, the compound is according to Formula I, wherein M$^4$ is —CH$_2$—.

Embodiment [0026]: In another example, the compound is according to Embodiment [0025], wherein Z is —NR$^5$—.

Embodiment [0027]: In another example, the compound is according to Embodiment [0026], wherein R$^1$ is CH$_3$—.

Embodiment [0028]: In another example, the compound is according to Embodiment [0027], wherein

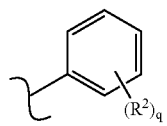

of I is selected from:

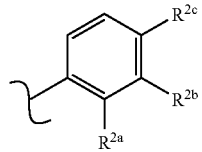 and 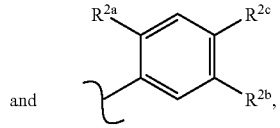

wherein R$^{2a}$ is selected from —H, F, Cl, and Br; and R$^{2b}$ and R$^{2c}$ are each independently selected from F, Cl, and Br.

Embodiment [0029]: In one example, the compound is according to Embodiment [0028], wherein M$^2$ is a monocyclic five- to seven-membered heterocyclyl or a five- to six-membered heteroaryl, each optionally substituted with between one and three of R$^{50}$.

Embodiment [0030]: In another example, the compound is according to Embodiment [0029], wherein M$^2$ is selected from the group consisting of morpholinyl, thiazolyl, oxadiazolyl, tetrahydropyranyl, and oxazepanyl, each optionally substituted with between one and three of R$^{50}$.

Embodiment [0031]: In another example, the compound is according to Embodiment [0030], wherein M$^1$ is selected from the group consisting of —H, dimethylaminomethyl, (4-methylpiperazin-1-yl)methyl, piperidinyl, 1-methylpiperidin-4-yl, morpholin-4-ylmethyl, and phenylmethyl.

Embodiment [0032]: In another example, the compound is according to Embodiment [0031], wherein

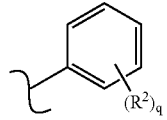

of I is

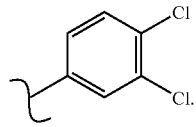

Embodiment [0033]: In another example, the compound is according to Embodiment [0028], wherein M$^1$ is either a three- to seven-membered saturated carbocyclyl or a heterocyclyl with one or two annular heteroatoms, wherein the either of the aforementioned are optionally substituted with at least one of C$_1$-C$_3$ alkyl, C$_1$-C$_3$ alkoxy, C$_1$-C$_3$ hydroxyalkyl, R$^{10}$(R$^{11}$)N—, and hydroxy, provided there are no geminal heteroatom substitutions; and wherein R$^{10}$ and R$^{11}$ are each independently C$_1$-C$_3$ alkyl.

Embodiment [0034]: In another example, the compound is according to Embodiment [0033], wherein

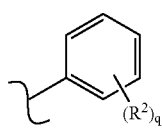

of I is

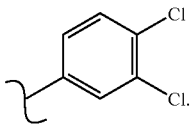

Embodiment [0035]: In another example, the compound is according to Embodiment [0024], wherein $M^1$-$M^2$-$M^3$-$M^4$- together are according to formula II;

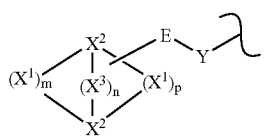

wherein $X^1$, $X^2$, and optionally $X^3$, represent the atoms of a saturated bridged ring system, said saturated bridged ring system containing up to three annular heteroatoms represented by any of $X^1$, $X^2$, and $X^3$; wherein,
each $X^1$ is independently selected from —C($R^6$)$R^7$—, —O—, —S(O)$_{0-2}$—, and —N$R^8$—;
each $X^2$ is independently a bridgehead methine optionally substituted with $R^6$, or a bridgehead nitrogen;
each $X^3$ is independently selected from —C($R^6$)$R^7$—, —O—, —S(O)$_{0-2}$—, and —N$R^8$—;
provided, for $X^1$, $X^2$, and $X^3$, there are no nitrogen-nitrogen annular bonds nor geminal di-nitrogen substitutions;
E is selected from —N$R^9$—, —O—, and absent;
Y is either:
a $C_{1-3}$ alkylene linker, between the oxygen at the 7-position of the quinazoline ring system of I and either E, or when E is absent, any ring atom of the saturated bridged ring system except $X^2$, when $X^2$ is a bridgehead nitrogen; provided there are at least two carbon atoms between the oxygen at the 7-position of the quinazoline ring system of I and either E, or when E is absent, any heteroatom represented by $X^1$, $X^2$ or $X^3$; or
Y is absent, when Y is absent, E is also absent; said saturated bridged ring system is directly attached to the oxygen at the 7-position of the quinazoline ring system of I via a carbon atom of said saturated bridged ring system;
m and p are each independently between one and four;
n is between zero and two, when n is zero, then there is a direct single bond between the two bridgehead $X^2$'s;
$R^6$ and $R^7$ are each independently selected from —H, halogen, trihalomethyl, —CN, —NH$_2$, —NO$_2$, —O$R^3$, —N($R^3$)$R^4$, —S(O)$_{0-2}$$R^4$, —SO$_2$N($R^3$)$R^4$, —CO$_2$$R^3$, —C(O)N($R^3$)$R^4$, —N($R^3$)SO$_2$$R^4$, —N($R^3$)C(O)$R^3$; —NCO$_2$$R^3$, —C(O)$R^3$, optionally substituted lower alkyl, optionally substituted aryl, optionally substituted lower arylalkyl, optionally substituted heterocyclyl, optionally substituted lower heterocyclylalkyl; or
$R^6$ and $R^7$, when taken together are oxo; or
$R^6$ and $R^7$, when taken together with a common carbon to which they are attached, form a optionally substituted three- to seven-membered spirocyclyl, said optionally substituted three- to seven-membered spirocyclyl optionally containing at least one additional heteroatom selected from N, O, S, and P; and
$R^8$ is selected from $R^3$, —SO$_2$N($R^3$)$R^4$, —CO$_2$$R^3$, —C(O)N ($R^3$)$R^4$, —SO$_2$$R^4$, and —C(O)$R^3$.
with the proviso that when Y is a $C_{1-3}$ alkylene linker; E is absent, Z is —NH— or —N(CH$_3$)—; $R^1$ is a $C_{1-3}$ alkyl; $R^2$ is —H or halogen; n=0; and, the atoms, $X^1$, of one bridge of the saturated bridged ring system, when combined with both bridgehead atoms, $X^2$, of the saturated bridged ring system, represent:
either a pyrrolidine ring or a piperidine ring, and any atom, $X^1$ or $X^2$, of either of said pyrrolidine ring or said piperidine ring is attached to Y, then the other bridge of said saturated bridged ring system cannot be any one of —OC(O)CH$_2$—, —CH$_2$OC(O)—, —OC(O)CH$_2$CH$_2$—, —CH$_2$OC(O)CH$_2$—, —CH$_2$CH$_2$OC(O)—, —OC(O)CH$_2$NH—, —OC(O)CH$_2$N(C$_{1-4}$alkyl)-, and —OC(O)CH$_2$O—; or
either a piperazine ring or a 4-(C$_{1-4}$ alkyl)-piperazine ring, and any atom, $X^1$ or $X^2$, of either of said piperazine ring or said 4-(C$_{1-4}$ alkyl)-piperazine ring is attached to Y, then the other bridge of said saturated bridged ring system, only when attached via the 2- and the 3-position of either of said piperazine ring or said 4-(C$_{1-4}$ alkyl)-piperazine ring, cannot be one of —CH$_2$OC(O)CH$_2$—, —CH$_2$CH$_2$OC(O)—, and either of the two aforementioned bridges optionally substituted by one or two C$_{1-2}$alkyl groups; or
a piperazine ring, and any atom, $X^1$ or $X^2$, of said piperazine ring is attached to Y, then the other bridge of said saturated bridged ring system, only when attached via the 3- and the 4-position of said piperazine ring, cannot be one of —C(O)OCH$_2$CH$_2$—, —CH$_2$OC(O)CH$_2$—, and either of the two aforementioned bridges optionally substituted by one or two C$_{1-2}$ alkyl groups, and only when either of the two aforementioned bridges are attached to the 3-position of said piperazine ring via their left-hand end as depicted above; or
a 2-oxomorpholine ring, said 2-oxomorpholine ring attached to Y via its 4-position, then the other bridge of said saturated bridged ring system, only when attached via the 5- and the 6-position of said 2-oxomorpholine ring, cannot be one of —(CH$_2$)$_g$—, —CH$_2$WCH$_2$—, —CH$_2$WCH$_2$CH$_2$—, and —CH$_2$CH$_2$WCH$_2$—, wherein W is —O—, —S(O)$_{0-2}$—, —NH—, or —N(C$_{1-4}$ alkyl)- wherein g is 2, 3, or 4.

Embodiment [0036]: In one example, the compound is according to Embodiment [0035], wherein Z is —N$R^5$—.

Embodiment [0037]: In another example, the compound is according to Embodiment [0036], wherein $R^2$ is selected from —H, halogen, trihalomethyl, —CN, —NO$_2$, —O$R^3$, and optionally substituted lower alkyl.

Embodiment [0038]: In another example, the compound is according to Embodiment [0037], wherein $R^1$ is an unsubstituted C$_{1-3}$ alkyl.

Embodiment [0039]: In another example, the compound is according to Embodiment [0038], wherein the saturated bridged ring system has a geometry selected from the group consisting of [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2], and [2.2.1].

Embodiment [0040]: In another example, the compound is according to Embodiment [0039], wherein Y is selected from —CH$_2$CH$_2$—, —CH$_2$—, and absent.

Embodiment [0041]: In another example, the compound is according to Embodiment [0040], wherein q is one, two, or three.

Embodiment [0042]: In another example, the compound is according to Embodiment [0041], wherein $R^5$ is —H.

Embodiment [0043]: In another example, the compound is according to Embodiment [0042], wherein $R^1$ is methyl.

Embodiment [0044]: In another example, the compound is according to Embodiment [0043], wherein the saturated bridged ring system has a geometry selected from the group consisting of [4.4.0], [4.3.0], [4.2.0], [4.1.0], [3.3.0], [3.2.0], and [3.1.0].

Embodiment [0045]: In another example, the compound is according to Embodiment [0044], wherein said saturated bridged ring system contains one or two annular nitrogens, said one or two annular nitrogens are selected from —$NR^8$—, when $X^1$, and a bridgehead nitrogen, when $X^2$.

Embodiment [0046]: In another example, the compound is according to Embodiment [0045], wherein E is absent.

Embodiment [0047]: In another example, the compound is according to Embodiment [0046], wherein said saturated bridged ring system is according to formula III;

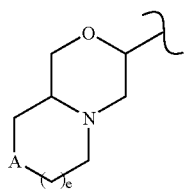

III wherein A is selected from —O—, —$S(O)_{0-2}$—, —$NR^8$—, and absent; and e is 0 or 1.

Embodiment [0048]: In another example, the compounds is according to Embodiment [0047], wherein Y is —$CH_2$—.

Embodiment [0049]: In another example, the compound is according to Embodiment [0048], wherein A is selected from —$NR^8$—, wherein $R^8$ is selected from —H, optionally substituted lower alkyl, —$CO_2R^3$, —$C(O)N(R^3)R^4$, —$SO_2R^4$, and —$C(O)R^3$; —O—; and absent.

Embodiment [0050]: In another example, the compound is according to Embodiment [0049], wherein

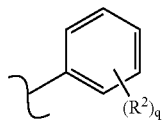

of I is selected from:

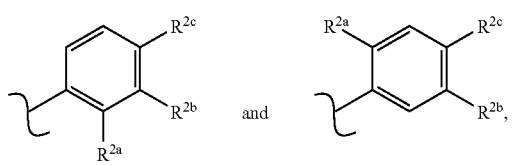

wherein $R^{2a}$, $R^{2b}$, and $R^{2c}$ are each independently selected from F, Cl, and Br.

Embodiment [0051]: In another example, the compound is according to Embodiment [0050], wherein $R^{2a}$ is F $R^{2b}$ is Cl, and $R^{2c}$ is either Cl or Br.

Embodiment [0052]: In another example, the compound is according to Formula:

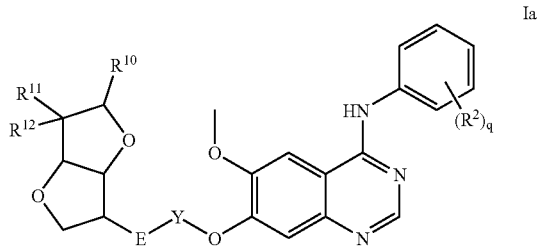

Ia or a pharmaceutically acceptable salt or hydrate thereof, wherein q is 1, 2, or 3;

$R^2$ is selected from —H, halogen, trihalomethyl, —CN, —$NO_2$, —$OR^3$, and optionally substituted lower alkyl;

E is selected from —$NR^9$—, —O—, and absent;

Y is selected from —$CH_2CH_2$—, —$CH_2$—, and absent;

$R^{10}$ is selected from —H, optionally substituted alkyl, and —$OR^{13}$; and $R^{11}$ and $R^{12}$ are each independently selected from —H, —$CF_3$, —F, —$N(R^3)R^4$, —$N(C=O)R^3$, —$N(R^3)SO_2R^3$, —$S(O)_{0-2}R^{13}$, and $OR^{13}$; or $R^{10}$ is selected from —H, and —$OR^{13}$; and $R^{11}$ and $R^{12}$, when taken together, are oxo, exo-alkenyl, or when taken together with the carbon to which they are attached, form a three- to seven-membered spirocyclyl;

$R^{13}$ is selected from —H, —$C(=O)R^4$, optionally substituted lower alkynyl, optionally substituted lower arylalkynyl, optionally substituted lower heterocyclylalkynyl, optionally substituted lower alkenyl, optionally substituted lower arylalkynyl, optionally substituted lower heterocyclylalkynyl, optionally substituted lower alkyl, optionally substituted lower arylalkyl, optionally substituted aryl, optionally substituted lower heterocyclylalkyl, and optionally substituted heterocyclyl; or two $R^{13}$'s, when taken together, form 1) a corresponding spirocyclic ketal from $R^{11}$, $R^{12}$ and the carbon to which they are attached, when $R^{11}$ and $R^{12}$ are both —$OR^{13}$, or 2) a corresponding cyclic ketal from $R^{10}$ and one of $R^{11}$ and $R^{12}$, and the corresponding carbons to which they are attached, when $R^{10}$ is —$OR^{13}$, and at least one of $R^{11}$ and $R^{12}$ is also —$OR^{13}$.

Embodiment [0053]: In another example, the compounds is according to Embodiment [0052], wherein Y is either —$CH_2$— or absent.

Embodiment [0054]: In another example, the compounds is according to Embodiment [0053], wherein one of $R^{11}$ and $R^{12}$ is —$OR^{13}$, wherein $R^{13}$ is selected from —H, —$C(O)R^4$, and optionally substituted lower alkyl; and $R^{10}$ and the other of $R^{11}$ and $R^{12}$ are both —H.

Embodiment [0055]: In another example, the compounds is according to Embodiment [0053], wherein one of $R^{11}$ and $R^{12}$ is —F; and $R^{10}$ and the other of $R^{11}$ and $R^{12}$ are both —H.

Embodiment [0056]: In another example, the compounds is according to Embodiment [0053], wherein $R^{13}$ is an alkyl group containing at least one fluorine substitution thereon.

Embodiment [0057]: In another example, the compound is according to Embodiment [0053], wherein q is two or three.

Embodiment [0058]: In another example, the compound is according to Embodiment [0057], wherein each $R^2$ is independently selected from —F, —Cl, —Br, —CF$_3$, —CH$_3$, and —OR$^{25}$; wherein R$^{25}$ is either methyl or aryl, each optionally substituted with one to three halogens.

Embodiment [0059]: In another example, the compound is according to pafagfaphEmbodiment [0045], wherein said saturated bridged ring system is according to either formula V or formula VI;

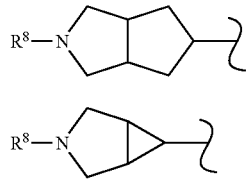

wherein $R^8$ is selected from —H, optionally substituted lower alkyl, —CO$_2$R$^3$, —C(O)N(R$^3$)R$^4$, —SO$_2$R$^4$, and —C(O)R$^3$.

Embodiment [0060]: In another example, the compound is according to Embodiment [0059], wherein Y is either —CH$_2$— or absent.

Embodiment [0061]: In another example, the compound is according to Embodiment [0060], wherein

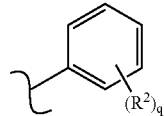

of I is selected from:

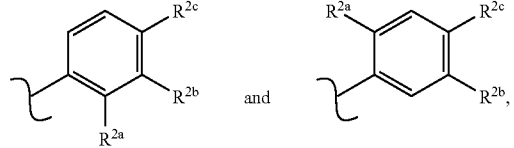

wherein $R^{2a}$, $R^{2b}$, and $R^{2c}$ are each independently selected from F, Cl, and Br.

Embodiment [0062]: In another example, the compound is according to Embodiment [0061], wherein $R^{2a}$ is F, $R^{2b}$ is Cl, and $R^{2c}$ is either Cl or Br.

Embodiment [0063]: In another example, the compound is according to Embodiment [0062], wherein $R^8$ is methyl or ethyl.

Embodiment [0064]: In another example, the compound is according to Embodiment [0046], wherein said saturated bridged ring system is according to formula VII;

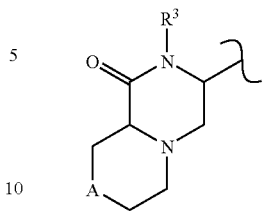

wherein A is selected from —O—, —S(O)$_{0-2}$—, —NR$^8$—, —CR$^6$R$^7$—, and absent.

Embodiment [0065]: In another example, the compound is according to Embodiment [0064], wherein R$^3$ is selected from —H and optionally substituted alkyl.

Embodiment [0066]: In another example, the compound is according to Embodiment [0065], wherein A is either —C(R$^6$)R$^7$— or absent.

Embodiment [0067]: In another example, the compound is according to Embodiment [0066], wherein A is either —CH$_2$— or absent.

Embodiment [0068]: In another example, the compounds is according to Embodiment [0067], wherein Y is —CH$_2$—.

Embodiment [0069]: In another example, the compound is according to Embodiment [0068], wherein q is 3.

Embodiment [0070]: In another example, the compound is according to Embodiment [0069], wherein

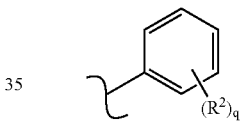

of I is selected from:

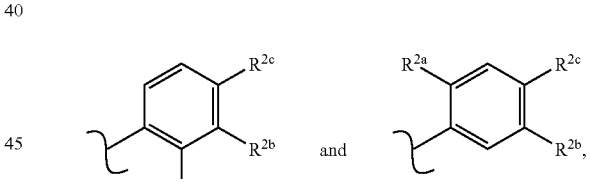

wherein $R^{2a}$, $R^{2b}$, and $R^{2c}$ are each independently selected from F, Cl, and Br.

Embodiment [0071]: In another example, the compound is according to Embodiment [0070], wherein $R^{2a}$ is F, $R^{2b}$ is Cl, and $R^{2c}$ is either Cl or Br.

Embodiment [0072]: In another example, the compound is according to Embodiment [0043], wherein the saturated bridged ring system has a geometry selected from the group consisting of [3.3.1], [3.2.1], and [2.2.1].

Embodiment [0073]: In another example, the compound is according to Embodiment [0072], wherein said saturated bridged ring system contains one or two annular nitrogens, said one or two annular nitrogens are selected from —NR$^8$—, when X$^1$, and a bridgehead nitrogen, when X$^2$.

Embodiment [0074]: In another example, the compound is according to Embodiment [0073], wherein said saturated bridged ring system is according to formula VIII or formula IX;

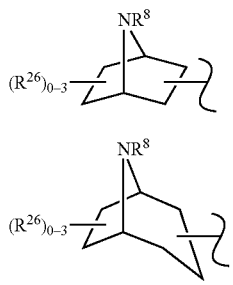

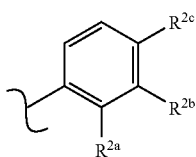

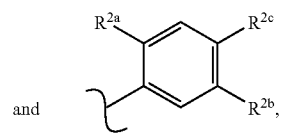

wherein $R^8$ is selected from —H, optionally substituted lower alkyl, —CO$_2$R$^3$, —C(O)N(R$^3$)R$^4$, —SO$_2$R$^4$, and —C(O)R$^3$; and $R^{26}$ is $C_{1-3}$ alkyl.

Embodiment [0075]: In another example, the compound is according to Embodiment [0074], wherein Y is —CH$_2$CH$_2$—; and E is either absent or —N(R$^9$)—.

Embodiment [0076]: In another example, the compound is according to Embodiment [0075], wherein q is 3.

Embodiment [0077]: In another example, the compound is according to Embodiment [0076], wherein of I is selected from:

wherein $R^{2a}$, $R^{2b}$, and $R^{2c}$ are each independently selected from F, Cl, and Br.

Embodiment [0078]: In another example, the compound is according to Embodiment [0077], wherein $R^{2a}$ is F, $R^{2b}$ is Cl, and $R^{2c}$ is either Cl or Br.

Embodiment [0079]: In another example, the compound is according to Embodiment [0078], wherein $R^8$ is methyl or ethyl.

Embodiment [0080]: In another example, the compound is according to Formula I or Ia, selected from Table 1:

TABLE 1

| Entry | Name | Structure |
|---|---|---|
| 1 | N-(3,4-dichloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine; | 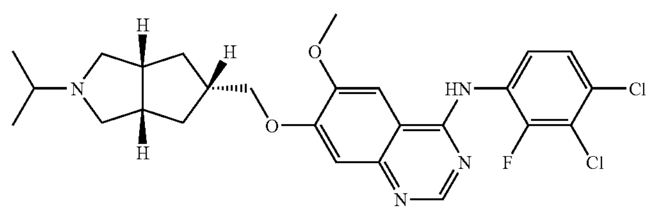 |
| | N-(3,4-dichloro-2-fluorophenyl)-7-({[(3aR,6aS)-2-(1-methylethyl)octahydrocyclopenta[c]pyrrol-5-yl]methyl}oxy)-6-(methyloxy)quinazolin-4-amine | |
| 2 | N-(4-bromo-3-chloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine; | 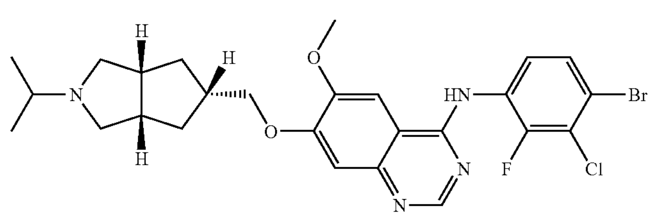 |

TABLE 1-continued

| Entry | Name | Structure |
|---|---|---|
| | N-(4-bromo-3-chloro-2-fluorophenyl)-7-({[(3aR,6aS)-2-(1-methylethyl)octahydrocyclopenta[c]pyrrol-5-yl]methyl}oxy)-6-(methyloxy)quinazolin-4-amine | |
| 3 | 7-({[(3aR,5r,6aS)-2-yllmethyl}oxy)-N-(4-bromo-3-chloro-2-acetyloctahydrocyclopenta[c]pyrrol-5-fluorophenyl)-6-(methyloxy)quinazolin-4-amine; | 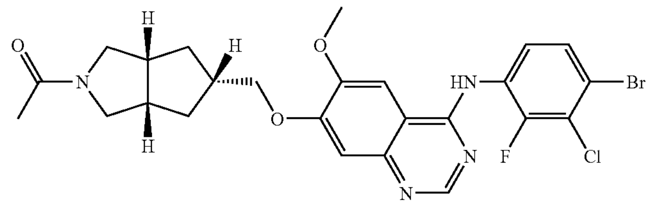 |
| | 7-({[(3aR,6aS)-2-yllmethyl}oxy)-N-(4-bromo-3-chloro-2-acetyloctahydrocyclopenta[c]pyrrol-5-fluorophenyl)-6-(methyloxy)quinazolin-4-amine | |
| 4 | N-(4-bromo-3-chloro-2-fluorophenyl)-6-(methyloxy)-7-([(3aR,5r,6aS)-octahydrocyclopenta[c]pyrrol-5-ylmethyl]oxy}quinazolin-4-amine; | 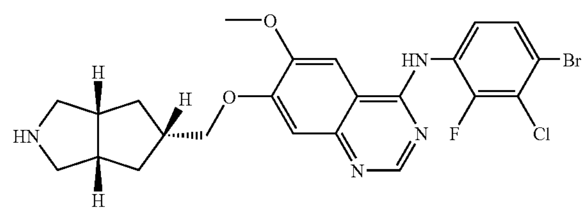 |
| | N-(4-bromo-3-chloro-2-fluorophenyl)-6-(methyloxy)-7-([(3aR,6aS)-octahydrocyclopenta[c]pyrrol-5-ylmethyl]oxy}quinazolin-4-amine | |
| 6 | N-(4-bromo-3-chloro-2-fluorophenyl)-6-(methyloxy-7-({[(3aR,5r,6aS)-2-(methylsulfonyl)octahydrocyclopenta[c]pyrrol-5-yl]methyl}oxy)quinazolin-4-amine; | 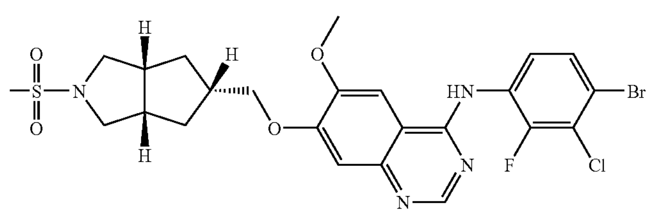 |
| | N-(4-bromo-3-chloro-2-fluorophenyl)-6-(methyloxy-7-({[(3aR,6aS)-2-(methylsulfonyl)octahydrocyclopenta[c]pyrrol-5-yl]methyl}oxy)quinazolin-4-amine | |

TABLE 1-continued

| Entry | Name | Structure |
|-------|------|-----------|
| 7 | N-(3,4-dichloro-2-fluorophenyl)-7-({[(3aR,5r,6aS)-2-ethyloctahydrocyclopenta[c]pyrrol-5-yl]methyl}oxy)-6-(methyloxy)quinazolin-4-amine; | 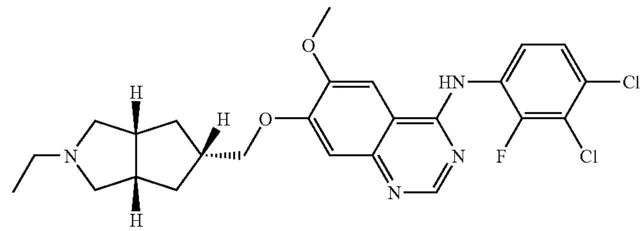 |
| | N-(3,4-dichloro-2-fluorophenyl)-7-({[(3aR,6aS)-2-ethyloctahydrocyclopenta[c]pyrrol-5-yl]methyl}oxy)-6-(methyloxy)quinazolin-4-amine | |
| 8 | N-(3,4-dichloro-2-fluorophenyl)-6-(methyloxy)-7-({[(3aR,5r,6aS)-2-(2-methylpropyl)octahydracyclopenta[c]pyrrol-5-yl]methyl}oxy)quinazolin-4-amine; | 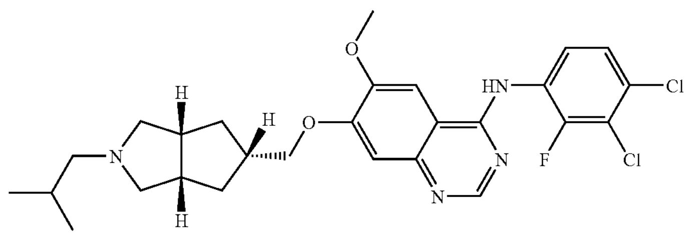 |
| | N-(3,4-dichloro-2-fluorophenyl)-6-(methyloxy)-7-({[(3aR,6aS)-2-(2-methylpropyl)octahydracyclopenta[c]pyrrol-5-yl]methyl}oxy)quinazolin-4-amine | |
| 9 | N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine; | 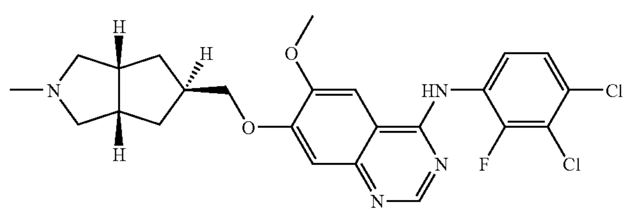 |
| | N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine | |
| 10 | N-(4-bromo-3-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine; | 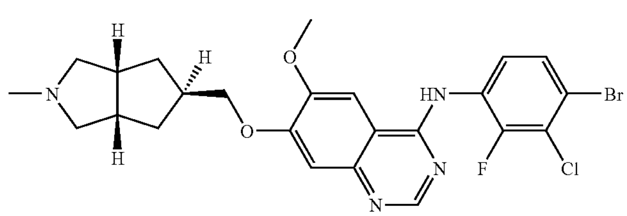 |

TABLE 1-continued

| Entry | Name | Structure |
|---|---|---|
|  | N-(4-bromo-3-chloro-2-fluorophenyl)-7-({[(3aR,6aS)-2-methylootahydrocyclopenta[c]pyrrol-5-yl]methyl}oxy)-6-(methyloxy)quinazolin-4-amine |  |
| 11 | N-(3-chloro-2,4-difluorophenyl)-7-({[(3aR,5s,6aS)-2-methyloctahydrocyclopenta[c]pyrrol-5-yl]methyl}oxy)-6-(methyloxy)quinazolin-4-amine; | 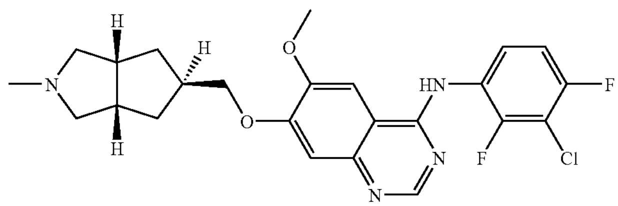 |
|  | N-(3-chloro-2,4-difluorophenyl)-7-({[(3aR,6aS)-2-methyloctahydrocyclopenta[c]pyrrol-5-yl]methyl}oxy)-6-(methyloxy)quinazolin-4-amine |  |
| 12 | N-(4,5-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine; | 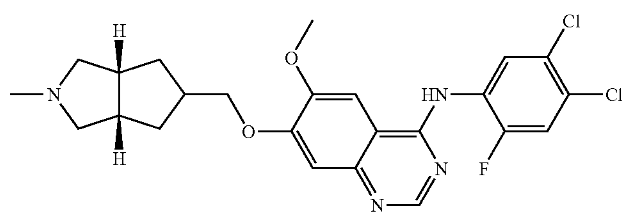 |
|  | N-(4,5-dichloro-2-fluorophenyl)-7-({[(3aR,6aS)-2-methyloctahydrocyclopenta[c]pyrrol-5-yl]methyl}oxy)-6-(methyloxy)quinazolin-4-amine |  |
| 13 | N-(4-bromo-5-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine; | 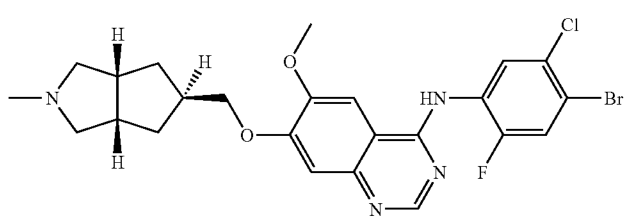 |
|  | N-(4-bromo-5-chloro-2-fluorophenyl)-7-({[(3aR,6aS)-2-methyloctahydrocyclopenta[c]pyrrol-5-yl]methyl}oxy)-6-(methyloxy)quinazolin-4-amine |  |

TABLE 1-continued

| Entry | Name | Structure |
|---|---|---|
| 14 | N-(4-bromo-2,3-dichlorophenyl)-7-({[(3aR,5s,6aS)-2-methyloctahydrocyclopenta[c]pyrrol-5-yl]methyl}oxy)-6-(methyloxy)quinazolin-4-amine; | 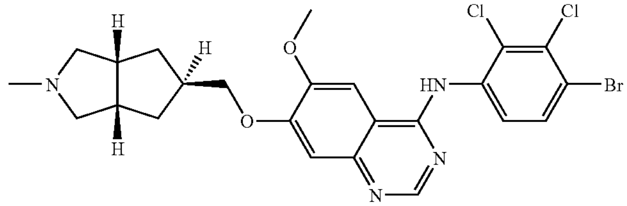 |
| | N-(4-bromo-2,3-dichlorophenyl)-7-({[(3aR,6aS)-2-methyloctahydrocyclopenta[c]pyrrol-5-yl]methyl}oxy)-6-(methyloxy)quinazolin-4-amine | |
| 15 | N-(3,4-dichlorophenyl)-7-({[(3aR,5s,6aS)-2-methyloctahydrocyclopenta[c]pyrrol-5-yl]methyl}oxy)-6-(methyloxy)quinazolin-4-amine; | 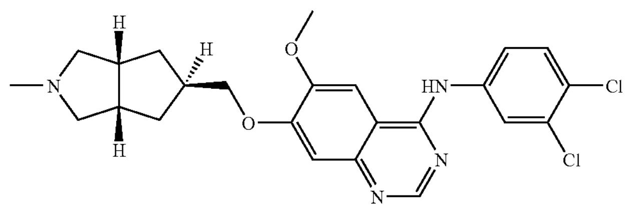 |
| | N-(3,4-dichlorophenyl)-7-({[(3aR,6aS)-2-methyloctahydrocyclopenta[c]pyrrol-5-yl]methyl}oxy)-6-(methyloxy)quinazolin-4-amine | |
| 16 | N-(4-bromo-3-chloro-2-fluorophenyl)-7-({[(3aR,5r,6aS)-2-yl]methyl}oxy)-6-(methyloxy)quinazolin-4-ethyloctahydrocyclopenta[c]pyrrol-5-amine; | 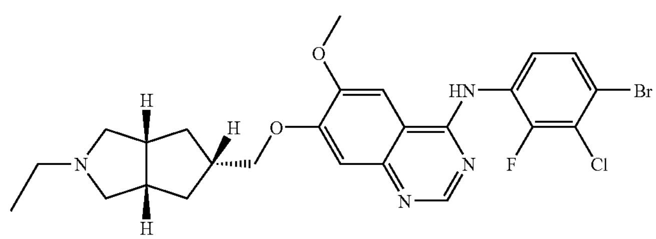 |
| | N-(4-bromo-3-chloro-2-fluorophenyl)-7-({[(3aR,6aS)-2-yl]methyl}oxy)-6-(methyloxy)quinazolin-4-ethyloctahydrocyclopenta[c]pyrrol-5-amine | |
| 17 | N-(4-bromo-3-chloro-2-fluorophenyl)-6-(methyloxy)-7-({[(3aR,5r,6aS)-2-(2-methylpropyl)octahydrocyclopenta[c]pyrrol-5-yl]methyl}oxy)quinazolin-4-amine; | 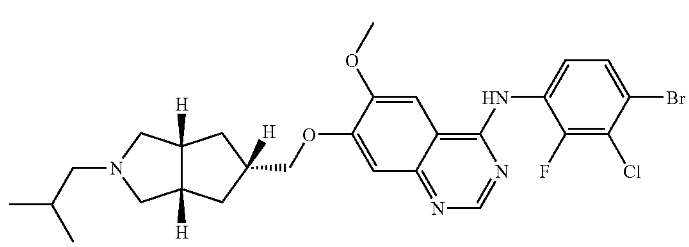 |

TABLE 1-continued

| Entry | Name | Structure |
|---|---|---|
| | N-(4-bromo-3-chloro-2-fluorophenyl)-6-(methyloxy)-7-({[(3aR,6aS)-2-(2-methylpropyl)octahydrocyclopenta[c]pyrrol-5-yl]methyl}oxy)quinazolin-4-amine | |
| 22 | N-(3,4-dichloro-2-fluorophenyl)-7-{[(3S,9aS)-hexahydro-1H-[1,4]oxazino(3,4-c)[1,4]oxazin-3-ylmethyl]oxy}-6-(methyloxy)quinazolin-4-amine | 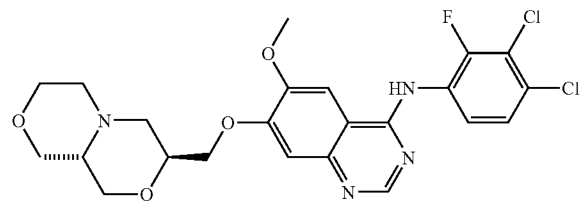 |
| 23 | N-(4-bromo-3-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine | 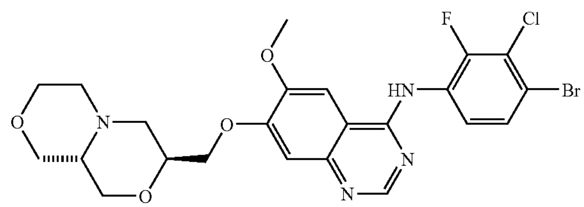 |
| 24 | N-(3-chloro-2,4-difluorophenyl)-7-{[(3S,9aS)-hexahydro-1H-[1,4]oxazino[3,4-c][1,4]oxazin-3-ylmethyl]oxy}-6-(methyloxy)quinazolin-4-amine | 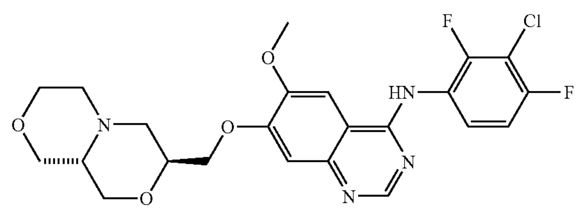 |
| 26 | N-(4,5-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine | 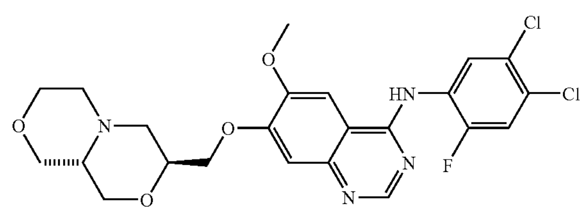 |
| 27 | N-(4-bromo-2,3-dichlorophenyl)-7-{[(3S,9aS)-hexahydro-1H-[1,4]oxazino[3,4-c][1,4]oxazin-3-ylmethyl]oxy}-6-(methyloxy)quinazolin-4-amine | 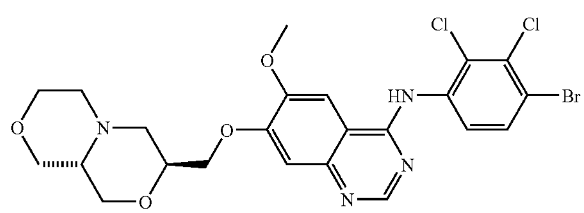 |
| 28 | N-(4-bromo-5-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine | 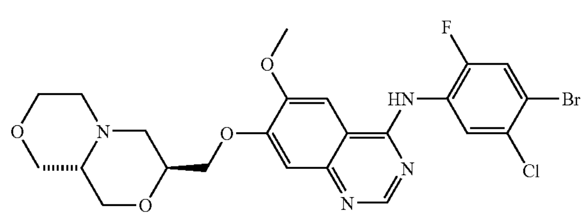 |

TABLE 1-continued

| Entry | Name | Structure |
|---|---|---|
| 31 | N-(3,4-dichlorophenyl)-7-{[(3R,8aR)-hexahydro-1H-pyrrolo[2,1-c][1,4]oxazin-3-ylmethyl]oxy}-6-(methyloxy)quinazolin-4-amine | 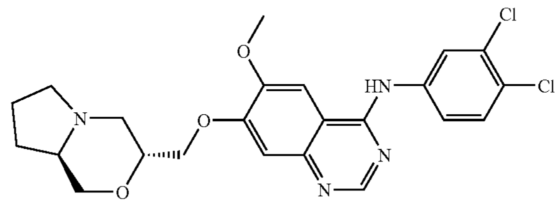 |
| 32 | N-(4-bromo-5-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine | 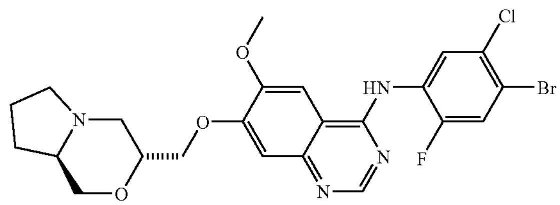 |
| 33 | N-(3,4-dichlorophenyl)-7-{[(3S,8aR)-hexahydro-1H-pyrrolo[2,1-c][1,4]oxazin-3-ylmethyt]oxy}-6-(methyloxy)quinazolin-4-amine | 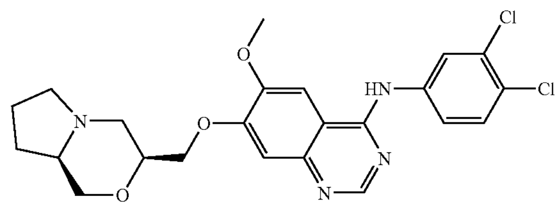 |
| 34 | N-(3,4-dichlorophenyl)-7-{[(3S,8aS)-ylmethyl]oxy}-6-(methyloxy)quinazolin-4-hexahydro-1H-pyrrolo[2,1-c][1,4]oxazin-3-amine | 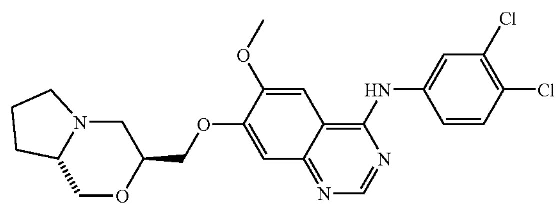 |
| 35 | N-(3,4-dichlorophenyl)-7-{[(3R,8aS)-hexahydro-1H-pyrrolo[2,1-c][1,4]oxazin-3-ylmethyl]oxy}-6-(methyloxy)quinazolin-4-amine | 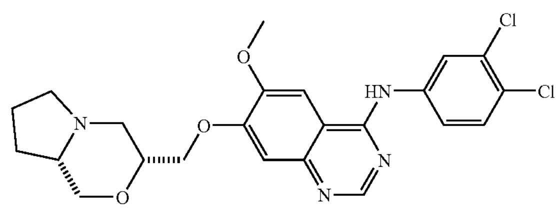 |
| 36 | N-(3,4-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine | 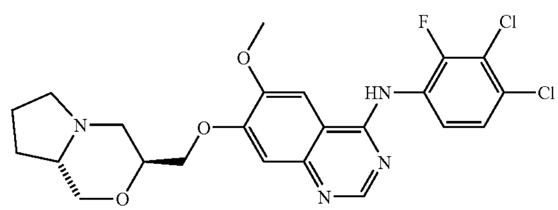 |
| 37 | N-(4-bromo-3-chloro-2-fluorophenyl)-7-{[(3S,8aS)-hexahydro-1H-pyrrolo[2,1-c][1,4]oxazin-3-methy]oxy}-6-(methyloxy)quinazolin-4-amine | 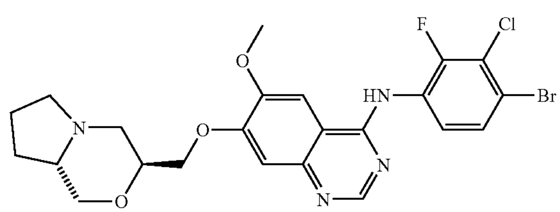 |

TABLE 1-continued

| Entry | Name | Structure |
|---|---|---|
| 38 | N-(3-chloro-2,4-difluorophenyl)-7-{[(3S,8aS)-hexahydro-1H-pyrrolo[2,1-c][1,4]oxazin-3-ylmethyl]oxy}-6-(methyloxy)quinazolin-4-amine | 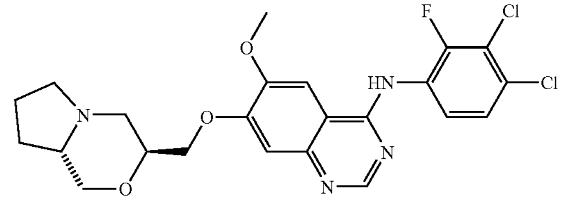 |
| 39 | N-(4-bromo-2,3-dichlorophenyl)-7-{[(3S,8aS)-hexahydro-1H-pyrrolo[2,1-c][1,4]oxazin-3-ylmethyl]oxy}-6-(methyloxy)quinazolin-4-amine | 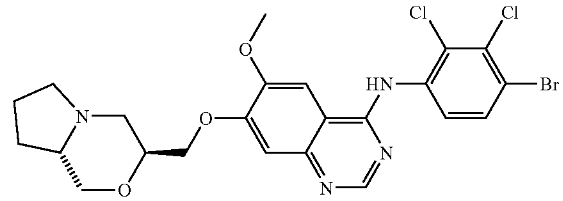 |
| 40 | N-(4,5-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine | 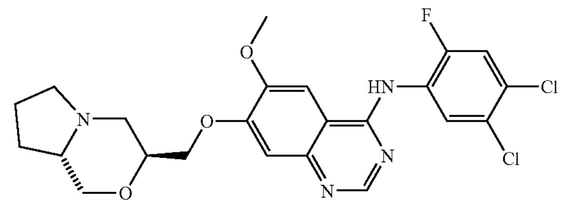 |
| 41 | 1,4:3,6-dianhydro-5-({[4-[(4-bromo-5-chloro-2-fluorophenyl)amino]-6-(methyloxy)quinazolin-7-yl]oxy}methyl)-5-deoxy-2-O-methyl-D-xylo-hexitol | 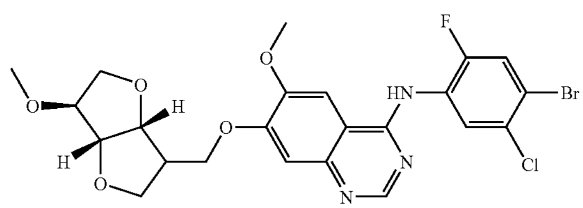 |
| 42 | 1,4:3,6-dianhydro-5-deoxy-5-({[4-[(3,4-dichlorophenyl)amino]-6-(methyloxy)quinazolin-7-yl]oxy}methyl)-2-O-methyl-D-glucitol | 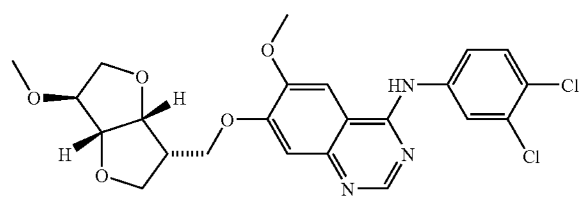 |
| 43 | 1,4:3,6-dianhydro-5-deoxy-5-({[4-[(3,4-dichloro-2-fluorophenyl)amino]-6-(methyloxy)quinazolin-7-yl]oxy}methyl)-2-O-methyl-D-xylo-hexitol | 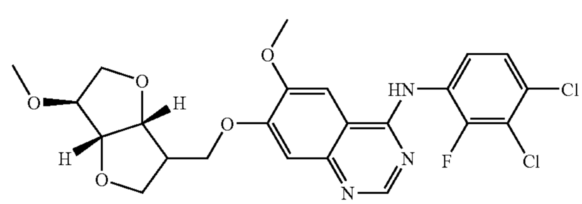 |
| 44 | 1,4:3,6-dianhydro-5-({[4-[(4-bromo-3-chloro-2-fluorophenyl)amino]-6-(methyloxy)quinazolin-7-yl]oxy}methyl)-5-deoxy-2-O-methyl-D-xylo-hexitol | 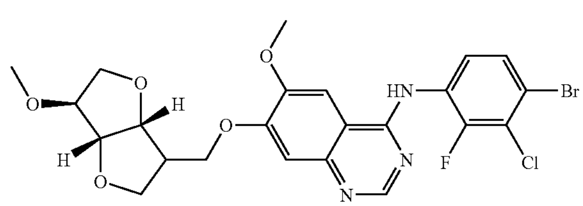 |

TABLE 1-continued

| Entry | Name | Structure |
|---|---|---|
| 45 | 1,4:3,6-dianhydro-5-({[4-[(3-chloro-2,4-dichlorophenyl)amino]-6-(methyloxy)quinazolin-7-yl]oxy}methyl)-5-deoxy-2-O-methyl-D-xylo-hexitol | 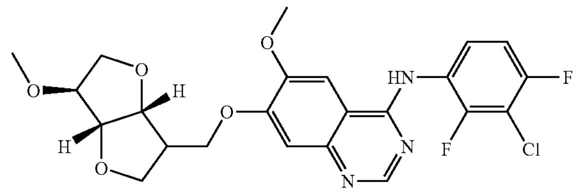 |
| 46 | 1,4:3,6-dianhydro-5-({[4-[(4-bromo-2,3-dichlorophenyl)amino]-6-(methyloxy)quinazolin-7-yl]oxy}methyl)-5-deoxy-2-O-methyl-D-glucitol | 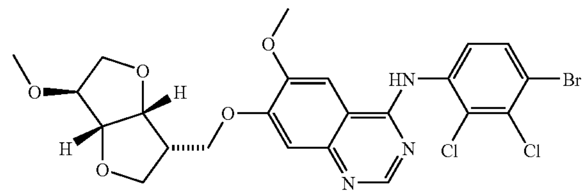 |
| 47 | 1,4:3,6-dianhydro-2-deoxy-2-({4-[(3,4-dichlorophenyl)amino]-6-(methyloxy)quinazolin-7-yl]oxy}methyl)-5-O-methyl-D-threo-hexitol | 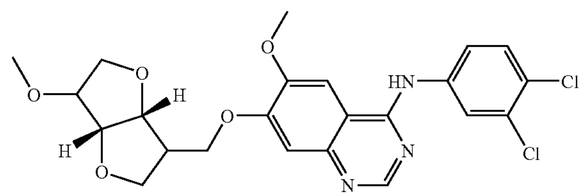 |
| 48 | 1,4:3,6-dianhydro-5-deoxy-5-({[4-[(4,5-dichloro-2-fluorophenyl)amino]-6-(methyloxy)quinazolin-7-yl]oxy}methyl)-2-O-methyl-D-glucitol | 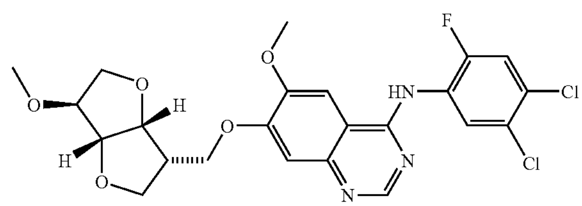 |
| 49 | (3S,9aS)-3-({[4-[(3,4-dichloro-2-fluorophenyl)amino]-6-(methyloxy)quinazolin-7-yl]oxy}methyl)hexahydro-2H-pyrido[1,2-a]pyrazin-1(6H)-one | 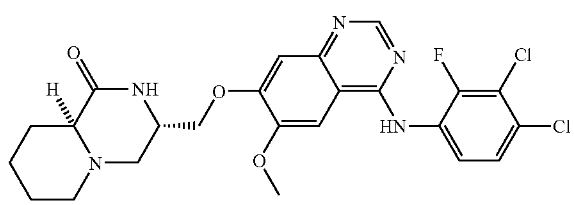 |
| 50 | (3S,9aR)-3-({[4-[(3,4-diohloro-2-fluorophenyl)amino]-6-(methyloxy)quinazolin-7-yl]oxy}methyl)hexahydro-2H-pyrido[1,2-a]pyrazin-1(6H)-one | 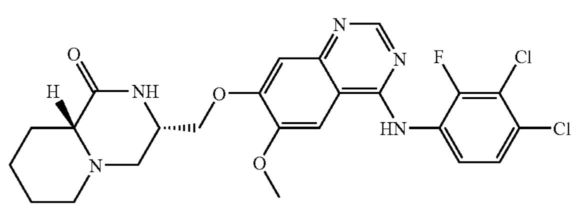 |
| 51 | (3S,8aS)-3-({[4-[(3,4-dichloro-2-fluorophenyl)amino]-6-(methyloxy)quinazolin-7-yl]oxylmethyl)hexahydropyrrolo[1,2-a]pyrazin-1(2H)-one | 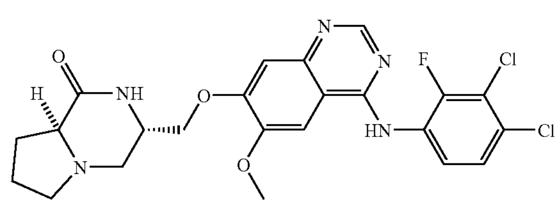 |

TABLE 1-continued

| Entry | Name |
|---|---|
| 52 | (3S,8aR)-3-({[4-[(3,4-dichloro-2-fluorophenyl)amino]-6-(methyloxy)quinazolin-7-yl]oxy}methyl)hexahydropyrrolo[1,2-a]pyrazin-1(2H)-one |
| 53 | (3S,8aS)-3-({[4-[(4-bromo-3-chloro-2-fluorophenyl)amino]-6-(methyloxy)quinazolin-7-yl]oxy}methyl)hexahydropyrrolo[1,2-a]pyrazin-1(2H)-one |
| 54 | (3S,8aS)-3-({[4-[(3,4-dichloro-2-fluorophenyl)amino]-6-(methyloxy)quinazolin-7-yl]oxy}methyl)-2-methylhexahydropyrrolo[1,2-a]pyrazin-1(2H)-one |
| 55 | N-(3,4-dichlorophenyl)-7-({2-[(8-methyl-8-azabicyclo[3.2.1]oct-3-yl)amino]ethyl}oxy)-6-(methyloxy)quinazolin-4-amine |
| 56 | N-(3,4-dichlorophenyl)-6-(methyloxy)-7-{[(8aR)-tetrahydro-1H-[1,3]thiazolo[4,3-c][1,4]oxazin-6-ylmethyl]oxy}quinazolin-4-amine |
| 57 | N-(3,4-dichlorophenyl)-7-{[2-(8-methyl-8-azabicyclo[3.2.1]oct-3-yl)ethyl]oxy}-6-(methyloxy)quinazolin-4-amine |
| 58 | N-(3,4-dichlorophenyl)-7-{[(8-methyl-8-azabicyclo[3.2.1]oct-3-yl)methyl]oxy}-6-(methyloxy)quinazolin-4-amine |

TABLE 1-continued

| Entry | Name | Structure |
|---|---|---|
| 59 | N-(3,4-dichlorophenyl)-7-{[(3aR,6aS)-2-methyloctahydrocyclopenta[c]pyrrol-5-yl]oxyl-6-(methyloxy)quinazolin-4-amine | 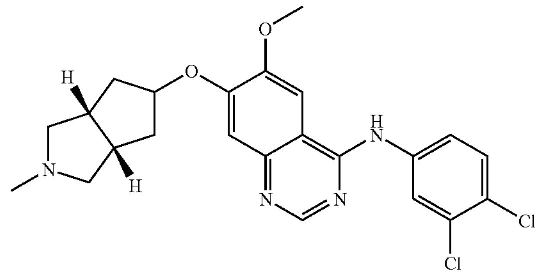 |
| 60 | N-(3,4-dichlorophenyl)-7-[(8-methyl-8-azabicyclo[3.2.1]oct-3-A)oxy]-6-(methyloxy)quinazolin-4-amine | 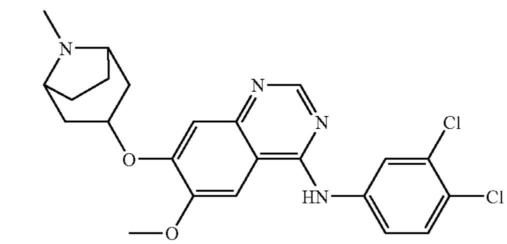 |
| 61 | 1,4:3,6-dianhydro-2-O-[4-[(4-bromo-5-chloro-2-fluorophenyl)amino]-6-(methyloxy)quinazolin-7-yl]-5-O-methyl-L-iditol | 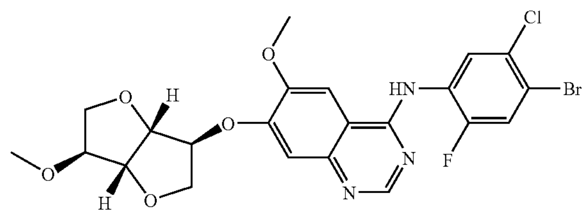 |
| 62 | 1,4:3,6-dianhydro-2-O-[4-[(3,4-dichloro-2-fluorophenyl)amino]-6-(methyloxy)quinazolin-7-yl]-5-O-methyl-L-iditol | 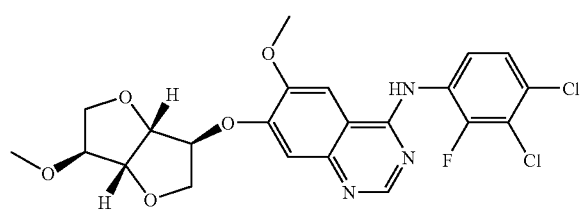 |
| 63 | 1,4:3,6-dianhydro-2-O-[4-[(4-bromo-3-chloro-2-fluorophenyl)amino]-6-(methyloxy)quinazolin-7-yl]-5-O-methyl-L-iditol | 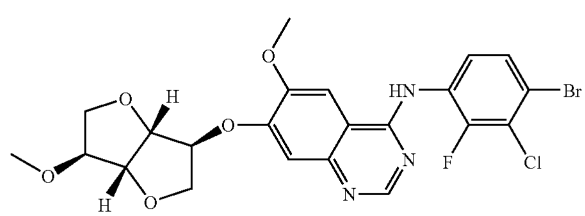 |
| 64 | 1,4:3,6-dianhydro-2-O-methyl-5-O-{6-(methyloxy)-4-[(2,3,4-trichlorophenyl)amino]quinazolin-7-yl}-L-iditol | 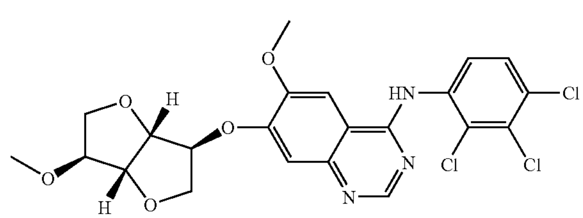 |

TABLE 1-continued

| Entry | Name | Structure |
|---|---|---|
| 65 | 1,4:3,6-dianhydro-5-O-[4-[(3,4-dichlorophenyl)amino]-6-(methyloxy)quinazoiin-7-yl]-2-O-methyl-D-xylo-hexitol | 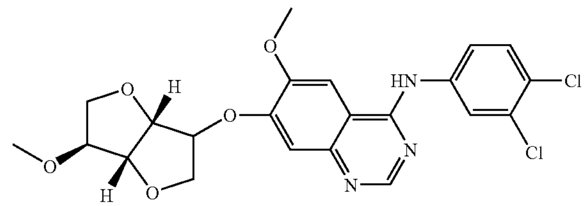 |
| 66 | 1,4:3,6-dianhydro-2-O-[4-[(4-bromo-2,3-dichlorophenyl)amino]-6-(methyloxy)quinazolin-7-y-5-O-methyl-L-iditol | 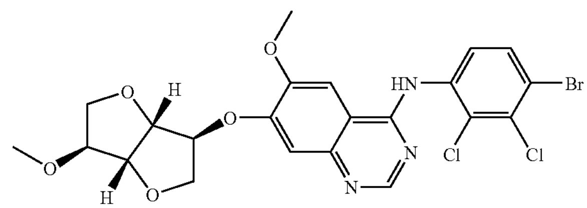 |
| 67 | dianhydro-5-O-[4-[(4-bromo-3-chlorophenyl)amino]-6-(methyloxy)-quinazolin-7-yl]-L-sorbose ethylene glycol acetal | 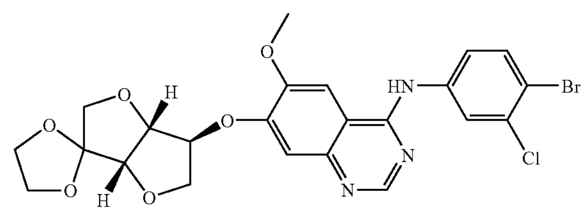 |
| 68 | 1,4:3,6-dianhydro-2-O-[4-[(3-chloro-2,4-(methyloxy)quinazolin-7-yl]-5-O-methyl-L-difluorophenyl)amino]-6-iditol | 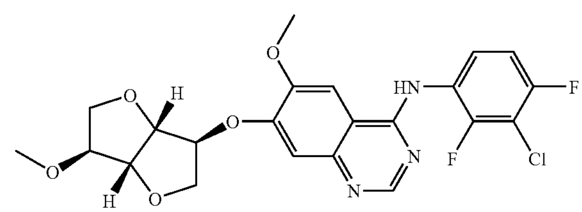 |
| 69 | 1H:3,6-dianhydro-2-O-[4-[(4,5-dichloro-2-fluorophenyl)amino]-6-(methyloxy)quinazolin-7-yl]-5-O-methyl-L-iditol | 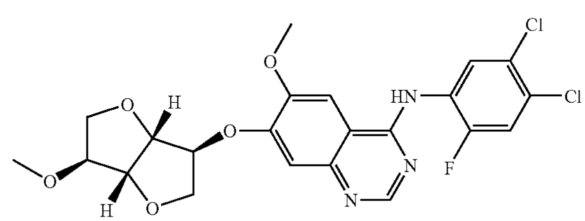 |
| 70 | 1,4:3,6-dianhydro-2-O-[4-[(4-bromo-3-chlorophenyl)amino]-6-(methyloxy)quinazolin-7-yl]-5-O-(difluoromethyl)-L-iditol | 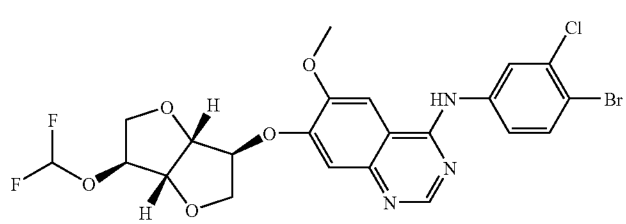 |
| 71 | 1,4:3,6-dianhydro-2-O-[4-[(3-chloro-2-fluorophenyl)amino)-6-(methyloxy)quinazolin-7-yl]-5-O-methyl-L-iditol | 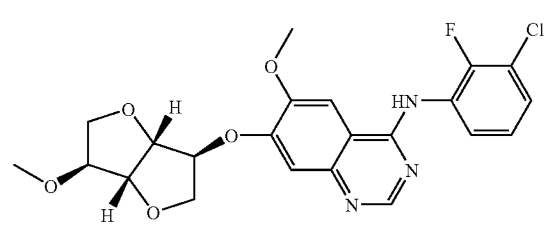 |

TABLE 1-continued

| Entry | Name | Structure |
|---|---|---|
| 72 | 1,4:3,6-dianhydro-2-O-[4-[(3,4-dichlorophenyl)amino]-6-(methyloxy)quinazolln-7-yl]-5-O-methyl-L-iditol | 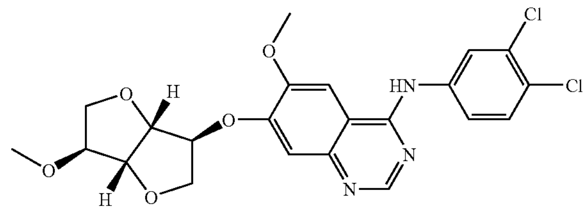 |
| 73 | 1,4:3,6-dianhydro-2-O-[4-[(4-bromo-3-chlorophenyl)amino]-6-(methyloxy)quinazolin-7-yl]-5-O-methyl-L-iditol | 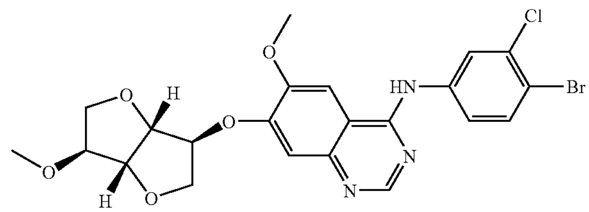 |
| 74 | 1,4:3,6-dianhydro-2-O-[4-[(4-bromo-3-chlorophenyl)amino]-6-(methyloxy)quinazolin-7-yl]-5-O-ethyl-L-iditol | 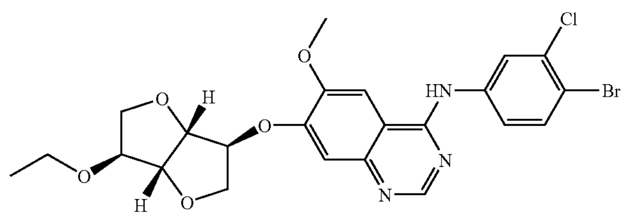 |
| 75 | 1,4:3,6-dianhydro-2-O-[4-[(3-bromo-2-methylphenyl)amino]-6-(methyloxy)quinazolin-7-yl]-5-O-methyl-L-iditol | 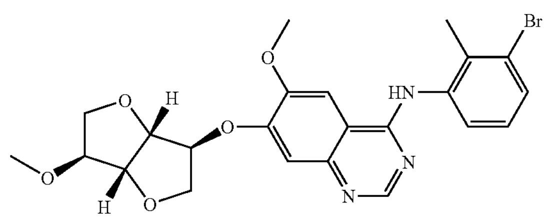 |
| 76 | 1,4:3,6-dianhydro-2-O-[4-[(3-chloro-2-methylphenyl)amino]-6-(methyloxy)quinazolin-7-yl]-5-O-methyl-L-iditol | 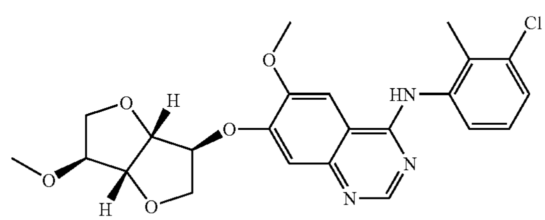 |
| 77 | 1,4:3,6-dianhydro-2-O-[4-[(4-bromo-3-chlorophenyl)amino]-6-(methyloxy)quinazolin-7-yl]-5-deoxy-D-xylo-hexitol | 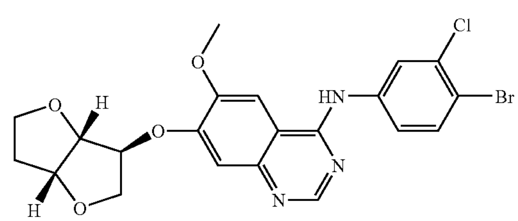 |
| 78 | 1,4:3,6-dianhydro-2-O-[4-[(4-bromo-3-chlorophenyl)aminol-6-(methyloxy)quinazolin-7-yl]-5-O-methyl-D-glucitol | 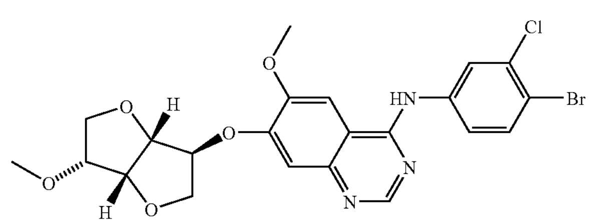 |

TABLE 1-continued

| Entry | Name |
|---|---|
| 79 | methyl 3,6-anhydro-5-O-[4-[(4-bromo-3-chlorophenyl)amino]-6-(methyloxy)quinazolin-7-yl]-2-O-methyl-alpha-L-idofuranoside |
| 80 | 3,6-anhydro-5-O-[4-[(4-bromo-3-chlorophenyl)amino]-6-(methyloxy)quinazolin-7-yl]-1,2-O-(1-methylethylidene)-beta-L-xylo-hexofuranose |
| 81 | 1,4:36-dianhydro-2-O-[4-[(4-bromo-3-chlorophenyl)amino]-6-(methyloxy)quinazolin-7-yl]-5-deoxy-5-methylidene-D-xylo-hexitol |
| 82 | methyl 3,6-anhydro-5-O-[4-[(4-bromo-3-chlorophenyl)amino]-6-(methyloxy)quinazolin-7-yl]-2-O-methyl-beta-L-idofuranoside |
| 83 | N-(3,4-dichloro-2-fluorophenyl)-6-(methyloxy)-7-[(octahydro-2H-quinolizin-3-ylmethyl)oxy]quinazolin-4-amine |
| 84 | 1,4:3,6-dianhydro-2-deoxy-2-fluoro-5-O-{6-(methyloxy)-4-[(2,3,4-trifluorophenyl)amino]quinazolin-7-yl}-D-iditol |
| 85 | 1,4;3,6-dianhydro-5-O-[4-[(2-chloro-4-fluorophenyl)amino]-6-(methyloxy)quinazolin-7-yl]-2-deoxy-2-fluoro-D-iditol |

TABLE 1-continued

| Entry | Name | Structure |
|---|---|---|
| 86 | 1,4:3,6-dianhydro-5-O-[4-[(2-bromo-4-fluorophenyl)amino]-6-(methyloxy)quinazolin-7-yl]-2-deoxy-2-fluoro-D-iditol | 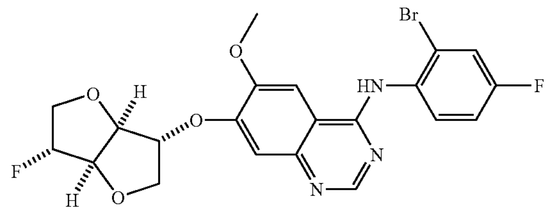 |
| 87 | 1,4:3,6-dianhydro-2-deoxy-5-O-[4-[(2,6-difluorophenyl)amino]-6-(methyloxy)quinazoUn-7-yl]-2-fluoro-D-iditol | 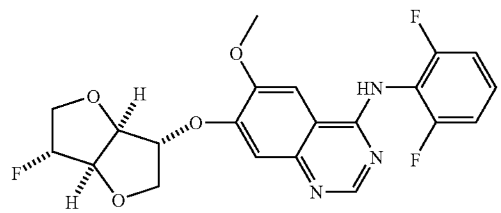 |
| 88 | 1,4:3,6-dianhydro-5-0-[4-[(3-chloro-2-fluorophenyl)amino]-6-(methyloxy)quiriazolin-7-yl]-2-deoxy-2-fluoro-D-iditoI | 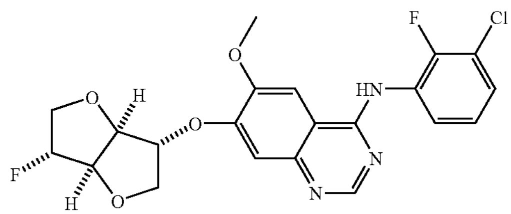 |
| 89 | 1,4:3,6-dianhydro-2-deoxy-2-fluoro-5-O-{4-{[4-fluoro-3-(trifluoromethyl)phenyl]amino}-6-(methyloxy)quinazolin-7-yl]-D-iditol | 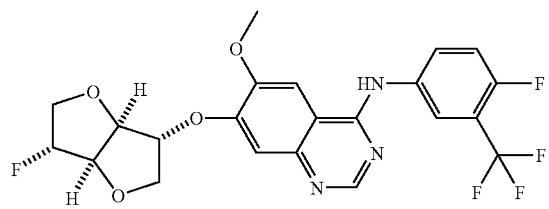 |
| 90 | 1,4:3,6-dianhydro-2-deoxy-5-O-[4-[(2,4-difluorophenyl)amino]-6-(methyloxy)quinazolin-7-yl]-2-fluoro-D-iditol | 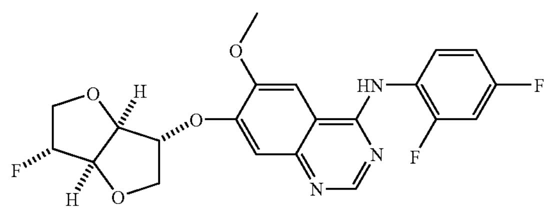 |
| 91 | 1,4:3,6-dianhydro-2-deoxy-5-O-[4-[(2,5-difluorophenyl)amino]-6-(methyloxy)quinazolin-7-yl]-2-fluoro-D-iditol | 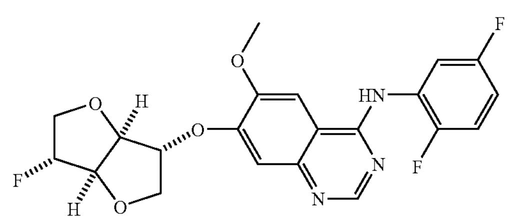 |
| 92 | 1,4:3,6-dianhydro-2-deoxy-5-O-[4-[(2,3-difluorophenyl)amino]-6-(methyloxy)quinazolin-7-yl]-2-fluoro-D-iditol | 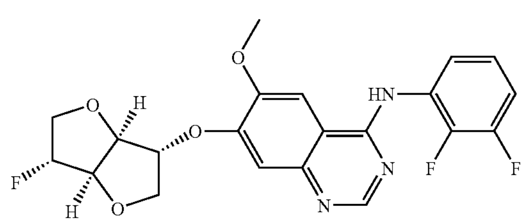 |

TABLE 1-continued

| Entry | Name | Structure |
|---|---|---|
| 93 | 1,4:3,6-dianhydro-5-O-[4-[(5-chloro-2-fluorophenyl)amino]-6-(methyloxy)quinazolin-7-yl]-2-deoxy-2-fluoro-D-iditol | 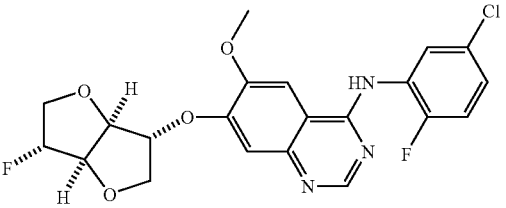 |
| 94 | 1,4:3,6-dianhydro-2-deoxy-5-O-[4-[(3,5-difluorophenyl)amino]-6-(methyloxy)quinazolin-7-yl]-2-fluoro-D-iditol | 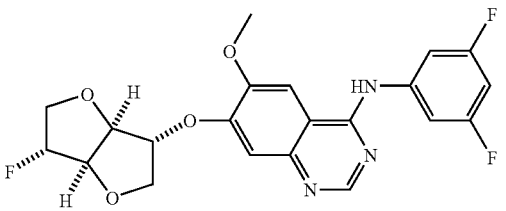 |
| 95 | 1,4:3,6-dianhydro-5-O-[4-[(3-chloro-4-fluorophenyl)amino]-6-(methyloxy)quinazolin-7-yl]-2-deoxy-2-fluoro-D-iditol | 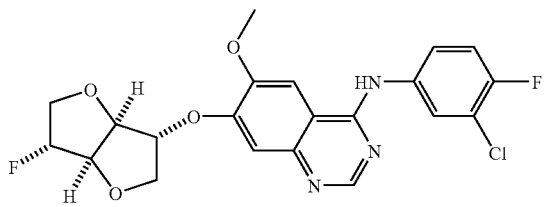 |
| 96 | 1,4:3,6-dianhydro-5-O-[4-[(4-bromo-2-chlorophenyl)amino]-6-(methyloxy)quinazolin-7-yl]-2-deoxy-2-fluoro-D-iditol | 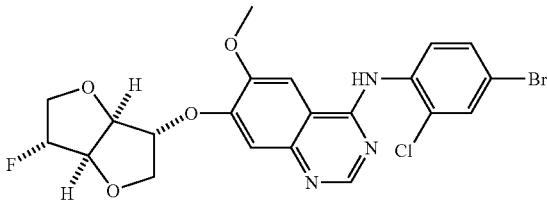 |
| 97 | 1,4:3,6-dianhydro-2-deoxy-5-O-[4-[(3,4-dichloro-2-fluorophenyl)amino]-6-(methyloxy)quinazolin-7-yl]-2-fluoro-D-iditol | 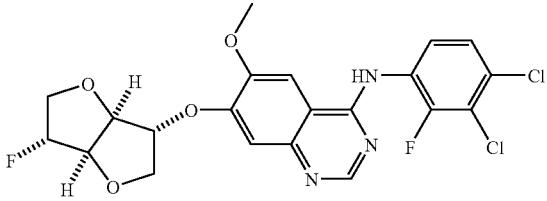 |
| 98 | 1,4:3,6-dianhydro-5-O-[4-[(4-bromo-5-chloro-2-fluorophenyl)amino]-6-(methyloxy)quinazolin-7-yl]-2-deoxy-2-fluoro-D-iditol | 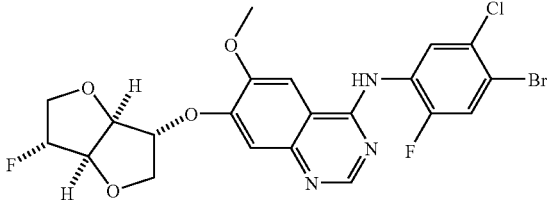 |
| 99 | 1,4:3,6-dianhydro-2-deoxy-2-fluoro-5-O-{6-(methyloxy)-4-[(2,4,5-trifluorophenyl)amino]quinazolin-7-yl}-D-iditol | 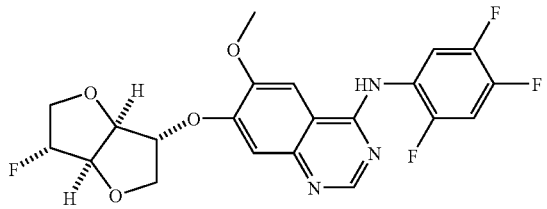 |

TABLE 1-continued

| Entry | Name | Structure |
|---|---|---|
| 100 | 1,4:3,6-dianhydro-2-deoxy-2-fluoro-5-O-{6-(methyloxy)-4-[(2,4,6-trifluorophenyl)amino]quinazolin-7-yl}-D-iditol | 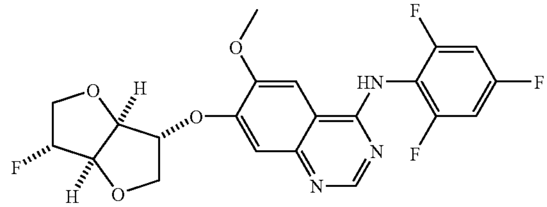 |
| 101 | 1,4:3,6-dianhydro-5-O-[4-({4-[(4-chlorophenyl)oxy]-3,5-difluorophenyl}amino)-6-(methyloxy)quinazolin-7-yl]-2-deoxy-2-fluoro-D-iditol | 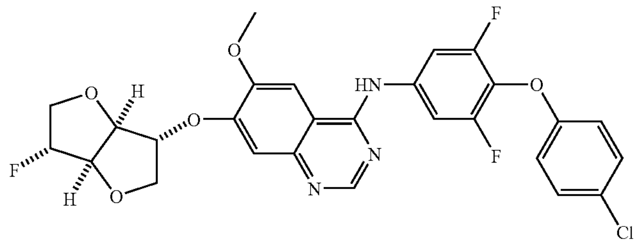 |
| 102 | 1,4:3,6-dianhydro-5-O-[4-[(4-bromo-3-chloro-2-fluorophenyl)amino]-6-(methyloxy)quinazolin-7-yl]-2-deoxy-2-fluoro-D-iditol | 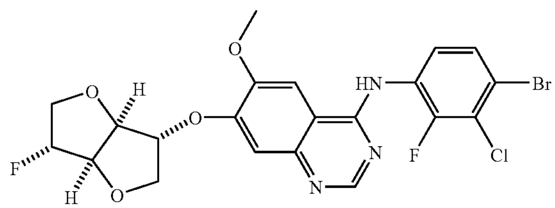 |
| 103 | 1,4:3,6-dianhydro-5-O-[4-[(4-bromo-2,3-dichlorophenyl)amino]-6-(methyloxy)quinazolin-7-yl]-2-deoxy-2-fluoro-D-iditol | 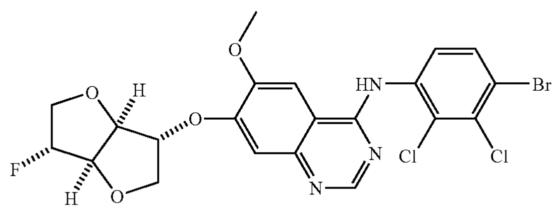 |
| 104 | 1,4:3,6-dianhydro-5-O-[4-[(4-bromo-3-chloro-5-fluorophenyl)amino]-6-(methyloxy)quinazolin-7-yl]-2-deoxy-2-fluoro-D-iditol | 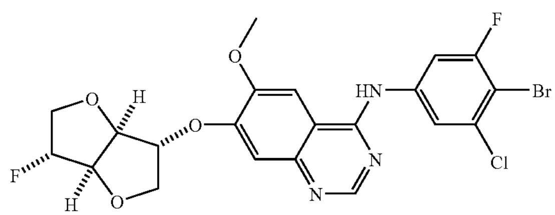 |
| 105 | 1,4:3,6-dianhydro-2-deoxy-5-O-[4-[(4,5-dichloro-2-fluorophenyl)amino]-6-(methyloxy)quinazolin-7-yl]-2-fluoro-D-iditol | 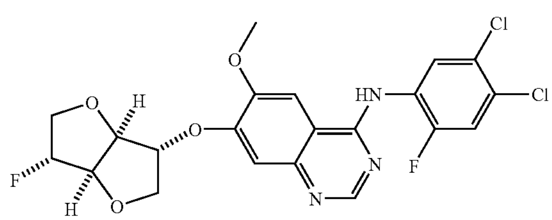 |
| 106 | 1,4:3,6-dianhydro-2-deoxy-2-fluoro-5-O-{6-(methyloxy)-4-[(2,3,4-trichlorophenyl)amino]quinazolin-7-yl}-D-iditol | 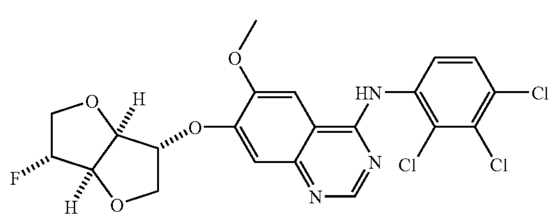 |

TABLE 1-continued

| Entry | Name | Structure |
|---|---|---|
| 107 | 1,4:3,6-dianhydro-2-deoxy-2-fluoro-5-O-{6-(methyloxy)-4-[(2,3,4-trichlorophenyl)amino]quinazolin-7-yl)-D-iditol | 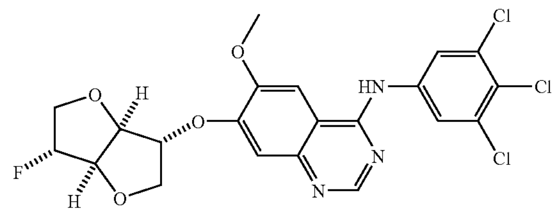 |
| 108 | 1,4:3,6-dianhydro-5-O-[4-[(4-bromo-2-fluorophenyl)amino]-6-(methyloxy)quiriazolin-7-yl]-2-deoxy-2-fluoro-D-iditol | 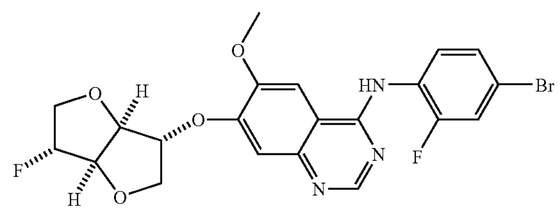 |
| 109 | 1,4:3,6-dianhydro-5-O-[4-[(4-chloro-2-fluorophenyl)amino]-6-(methyloxy)quinazolin-7-yl]-2-deoxy-2-fluoro-D-iditol | 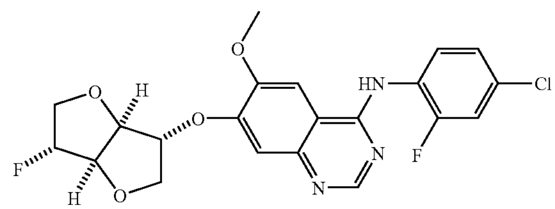 |
| 110 | 1,4:316-dianhydro-5-O-[4-[(3-chloro-2-methylphenyl)amino]-6-(methyloxy)quinazolin-7-yl]-2-deoxy-2-fluoro-D-iditol | 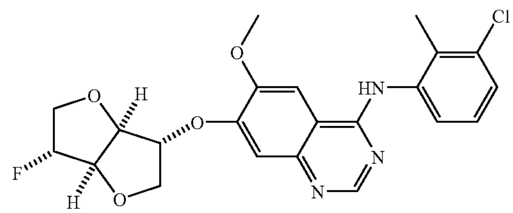 |
| 111 | 1,4:3,6-dianhydro-2-deoxy-5-O-t4-[(3,4-difluorophenyl)amino]-6-(methyloxy)quinazolin-7-yl]-2-fluoro-D-iditol | 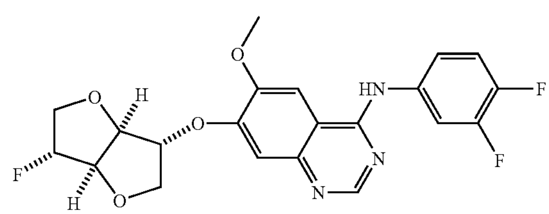 |
| 112 | 1,4:3,6-dianhydro-5-O-[4-[(2-chlorophenyl)amino]-6-(methyloxy)quinazolin-7-yl]-2-deoxy-2-fluoro-D-iditol | 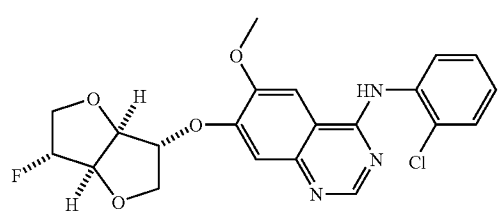 |
| 113 | 1,4:3,6-dianhydro-2-deoxy-2-fluoro-5-O-[4-[(2-fluorophenyl)amino]-6-(methyloxy)quinazolin-7-yl]-D-iditol | 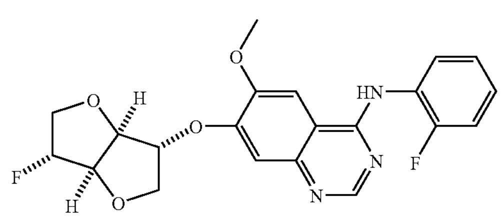 |

TABLE 1-continued

| Entry | Name | Structure |
|---|---|---|
| 114 | 1,4:3,6-dianhydro-5-O-(4-[(3-chlorophenyl)amino-6-(methyloxy)quinazolin-7-yl]-2-deoxy-2-fluoro-D-iditol | 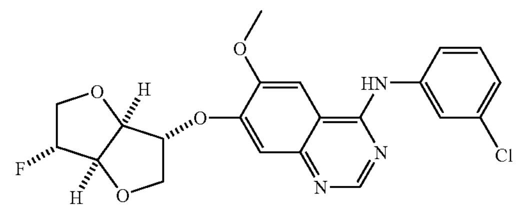 |
| 115 | 1,4:3,6-dianhydro-2-deoxy-2-fluoro-5-O-[4-[(4-fluorophenyl)amino]-6-(methyloxy)quinazolin-7-yl]-D-iditol | 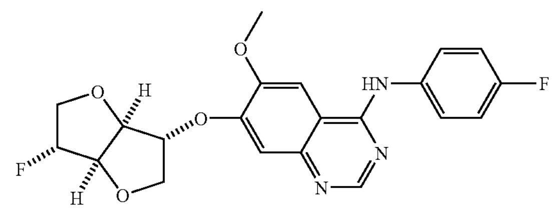 |
| 116 | 1,4:3,6-dnhydro-5-O-[4-[(4-chlorophenyl)amino-6-(methyloxy)quinazolin-7-yl]-2-deoxy-2-fluoro-D-iditol | 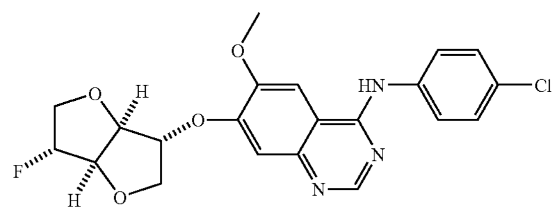 |
| 117 | 1,4:3,6-dianhydro-2-deoxy-5-O-[4-[(2,4-dichlorophenyl)amino]-6-(methyloxy)quinazolin-7-yl]-2-fluoro-D-iditol | 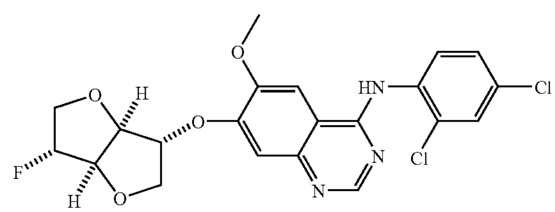 |
| 118 | 1,4:3,6-dianhydro-2-deoxy-5-O-[4-[(2,5-dichlorophenyl)amino]-6-(methyloxy)quinazolin-7-yl]-2-fluoro-D-iditol | 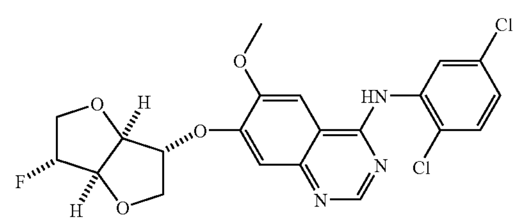 |
| 119 | 1,4:3,6-dianhydro-2-deoxy-5-O-[4-[(3,4-dichlorophenyl)amino]-6-(methyloxy)quinazolin-7-yl]-2-fluoro-D-iditol | 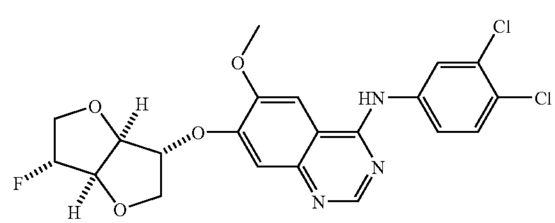 |
| 120 | 1,4:3,6-dianhydro-5-O-[4-[(2-bromo-4,6-difluorophenyl)amino]-6-(methyloxy)quinazolin-7-yl]-2-deoxy-2-fluoro-D-iditol | 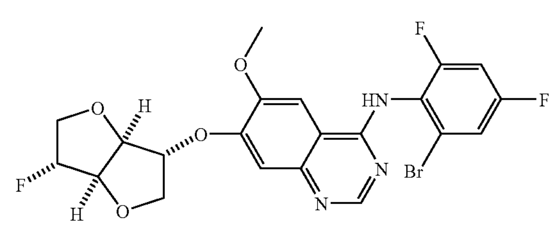 |

TABLE 1-continued

| Entry | Name | Structure |
|---|---|---|
| 121 | 1,4:3,6-dianhydro-5-O-[4-{[4-chloro-3-(trifluoromethyl)phenyl]amino}-6-(methyloxy)quinazolin-7-yl]-2-deoxy-2-fluoro-D-iditol | 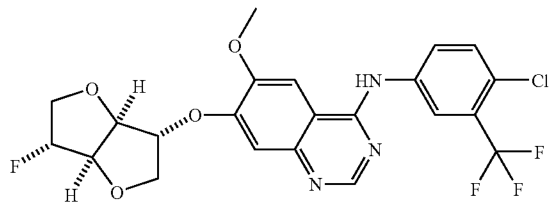 |
| 122 | 1,4:3,6-dianhydro-5-O-[4-{[2-chloro-5-(trifluoromethyl)phenyl]amino}-6-(methyloxy)quinazolin-7-yl]-2-deoxy-2-fluoro-D-iditol | 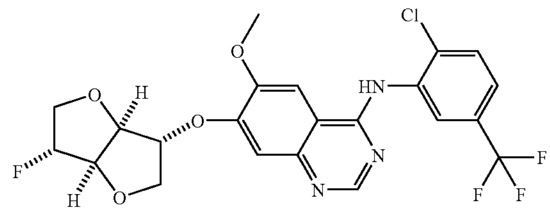 |
| 123 | 1,4:3,6-dianhydro-2-deoxy-2-fluoro-5-O-[4-{[2-fluoro-3-(trifluoromethyl)phenyl]amino}-6-(methyloxy)quinazolin-7-yl]-D-iditol | 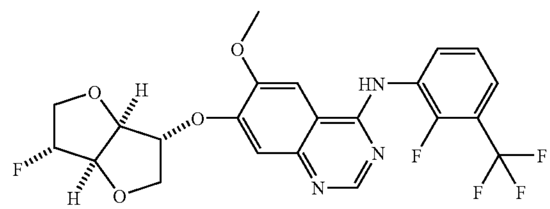 |
| 124 | 1,4:3,6-dianhydro-5-O-[4-{[2-bromo-5-(trifluoromethyl)phenyl]amino}-6-(methyloxy)quinazolin-7-yl]-2-deoxy-2-fluoro-D-iditol | 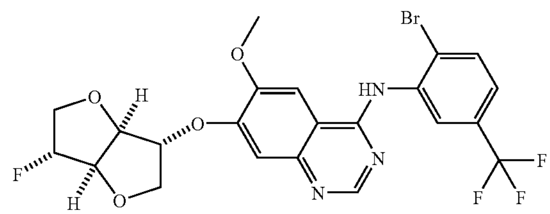 |
| 125 | 1,4:3,6-dianhydro-5-O-[4-{[2-bromo-4-(trifluoromethyl)phenyl]amino}-6-(methyloxy)quiriazolin-7-yl]-2-deoxy-2-fluoro-D-iditol | 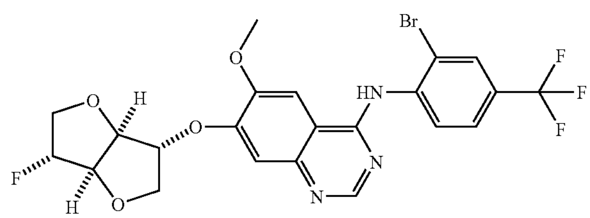 |
| 126 | 1,4:3,6-dianhydro-2-deoxy-2-fluoro-5-O-[4-{[4-fluoro-2-(trifluoromethyl)phenyl]amino}-6-(methyloxy)quinazolin-7-yl]-D-iditol | 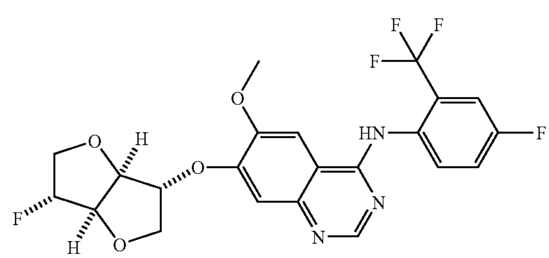 |
| 127 | 1,4:3,6-dianhydro-5-O-[4-{[3-bromo-5-(trifluoromethyl)phenyl]amino}-6-(methyloxy)quinazolin-7-yl]-2-deoxy-2-fluoro-D-iditol | 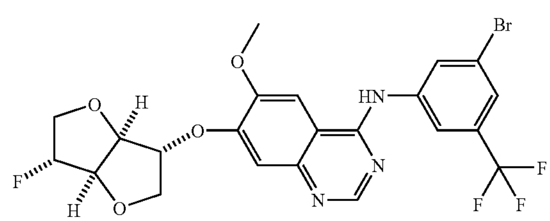 |

TABLE 1-continued

| Entry | Name | Structure |
|---|---|---|
| 128 | 1,4:3,6-dianhydro-5-O-[4-[(2-bromophenyl)amino]-6-(methyloxy)quinazolin-7-yl]-2-deoxy-2-fluoro-D-iditol | 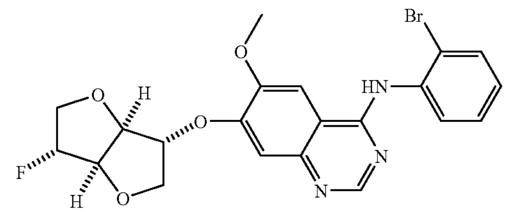 |
| 129 | 1,4:3,6-dianhydro-5-O-[4-[(3-bromophenyl)amino]-6-(methyloxy)quinazolin-7-yl]-2-deoxy-2-fluoro-D-iditol | 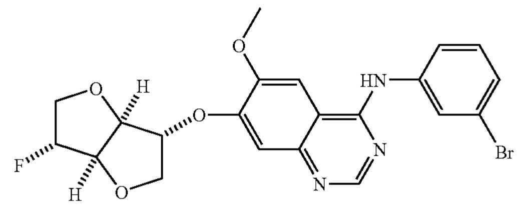 |
| 130 | 1,4:3,6-dianhydro-5-O-[4-[(4-bromophenyl)amino]-6-(methyloxy)quinazolin-7-yl]-2-deoxy-2-fluoro-D-iditol | 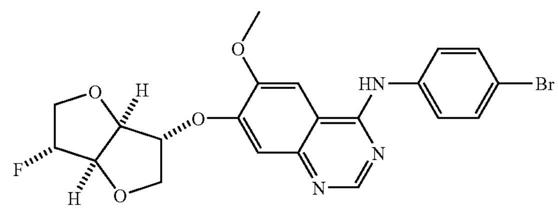 |
| 131 | 1,4:3,6-dianhydro-5-O-[4-{[(3-bromo-4-methylphenyl)amino]-6-(methyloxy)quinazolin-7-yl]-2-deoxy-2-fluoro-D-iditol | 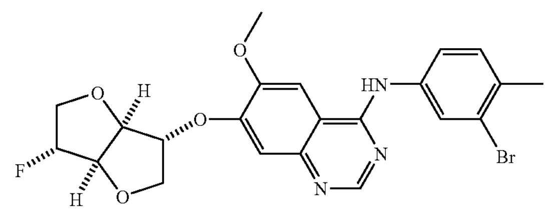 |
| 132 | 1,4:3,6-dianhydro-5-O-[4-[(5-chloro-2-methylphenyl)amino]-6-(methyloxy)quinazolin-7-yl]-2-deoxy-2-fluoro-D-iditol | 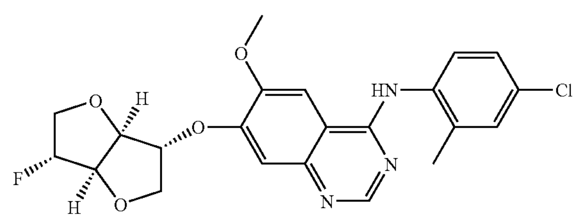 |
| 133 | 1,4:3,6-dianhydro-2-deoxy-5-O-[4-[(3,5-dimethylphenyl)amino]-6-(methyloxy)quinazolin-7-yt]-2-fluoro-D-iditol | 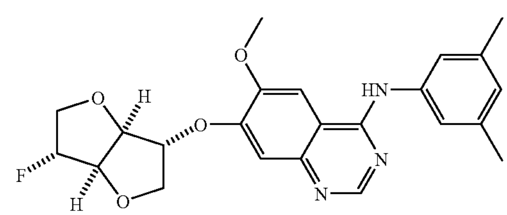 |
| 134 | 1,4:3,6-dianhydro-5-O-[4-{[2,5-bis(methyloxy)phenyl]amino}-6-(methyloxy)quinazolin-7-yl]-2-deoxy-2-fluoro-D-iditol | 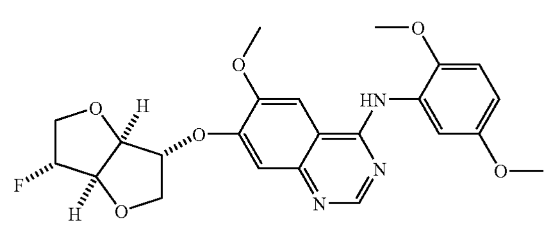 |

TABLE 1-continued

| Entry | Name | Structure |
|---|---|---|
| 135 | 1,4:3,6-dianhydro-5-O-[4-{[5-chloro-2,4-bis(methyloxy)phenyl]amino}-6-(methyloxy)quinazolin-7-yl]-2-deoxy-2-fluoro-D-iditol | 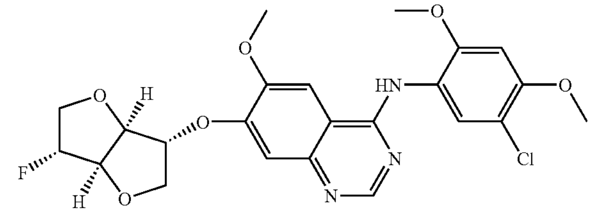 |
| 136 | 1,4:3,6-dianhydro-5-O-[4-{[4-chloro-2,5-bis(methyloxy)phenyl]amino}-6-(methyloxy)quinazolin-7-yl]-2-deoxy-2-fluoro-D-iditol | 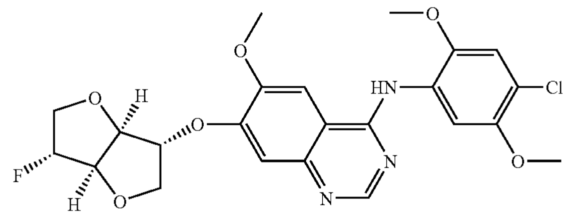 |
| 137 | 1,4:3,6-dianhydro-5-O-[4-[(3-chloro-2,4-difluorophenyl)amino]-6-(methyloxy)quinazolin-7-yl]-2-deoxy-2-fluoro D-iditol | 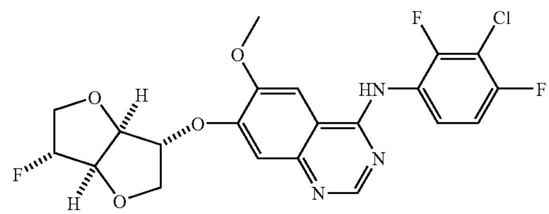 |
| 138 | N-(3,4-dichtorophenyl)-7-[({5-[(dimethylamino)methyl]-1,2,4-oxadiazol-3-yl}methyl)oxy]-6-(methyloxy)quinazolin-4-amine | 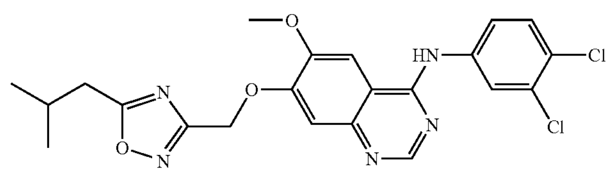 |
| 139 | N-(3,4-dichlorophenyl)-7-[({3-[(dimethylamino)methyl]-1,2,4-oxadiazol-5-yl}methyl)oxy]-6-(methyloxy)qulnazolin-4-amine | 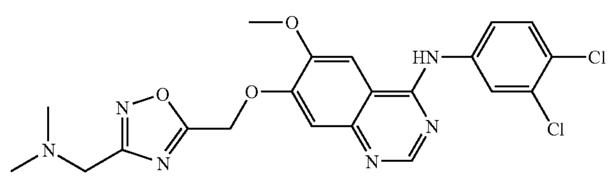 |
| 140 | N-(3,4-dichlorophenyl)-6-(methyloxy)-7-[({3-[(4-methylpiperazin-1-yl)methyl]-1,2,4-oxadiazol-5-yl}methyl)oxy]quinazolin-4-amine | 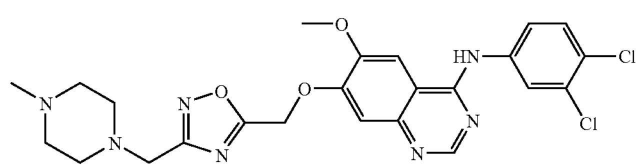 |
| 141 | N-(3,4-dichlorophenyl)-6-(methyloxy)-7-{[(5-piperidin-4-yl-1,2,4-oxadiazol-3-yl)methyl]oxy}quinazolin-4-amine | 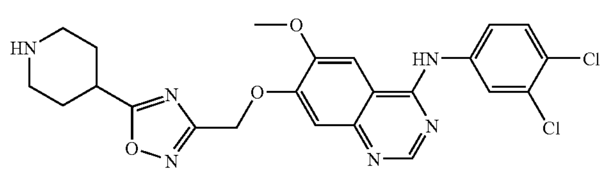 |
| 142 | N-(3,4-dichlorophenyl)-6-(methyloxy)-7-({[5-(1-methylpiperidin-4-yl)-1,2,4-oxadiazol-3-yl]methyl}oxy)quinazolin-4-amine | 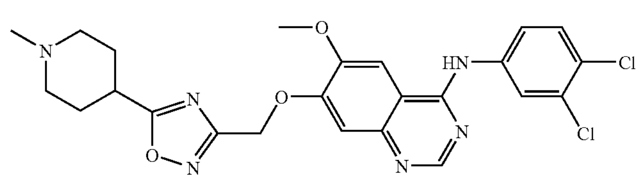 |

TABLE 1-continued

| Entry | Name | Structure |
|---|---|---|
| 143 | N-(3,4-dichlorophenyl)-6-(methyloxy)-7-({[3-(morpholin-4-ylmethyl)-1,2,4-oxadiazol-5-yl]methyl}oxy)quinazolin-4-amine | 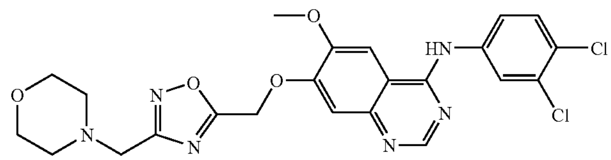 |
| 144 | N-(3,4-dichtorophenyl)-6-(methyloxy)-7-[(morpholin-2-ylmethyl)oxy]quinazolin-4-amine | 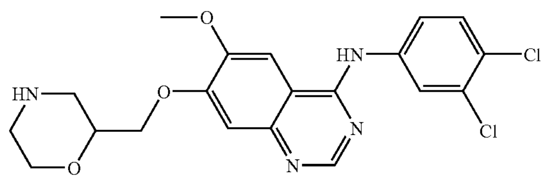 |
| 145 | N-(3,4-dichlorophenyl)-6-(methyloxy)-7-{[(5-piperidin-2-yl-1,2,4-oxadiazol-3-yl)methyl]oxy]quinazoliri-4-amine | 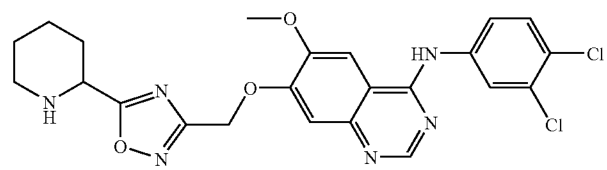 |
| 146 | N-(3,4-dichlorophenyl)-7-[({2-[(dimethylamino)methyl]-1,3-thiazol-4-yl}methyl)oxy]-6-(methyloxy)quinazolin-4-amine | 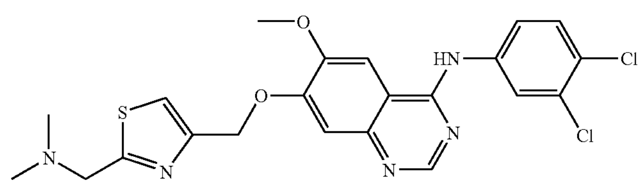 |
| 147 | N-(3,4-dichlorophenyl)-6-(methyloxy)-7-({[4-(phenylmethyl)morpholin-2-yl]methyl}oxy)quinazolin-4-amine | 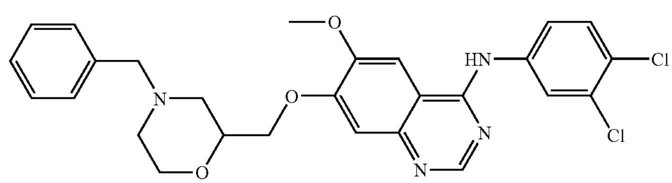 |
| 148 | 1,1-dimethylethyl 2-({[4-[(3,4-dichlorophenyl)amino]-6-(methyloxy)quinazolin-7-yl]oxy}methyl)morpholine-4-carboxylate | 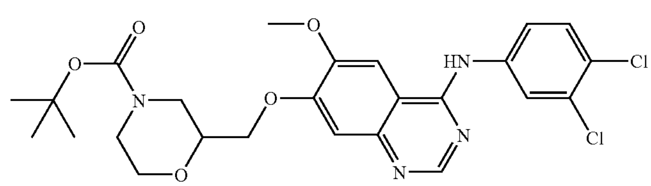 |
| 149 | N-(3,4-dichlorophenyl)-6-(methyloxy)-7-({[2-(morpholin-4-ylmethyl)-1,3-thiazol-4-yl]methyl)oxy)quinazolin-4-amine | 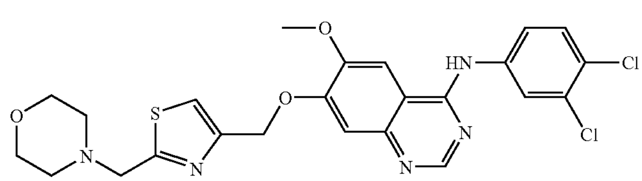 |
| 150 | N-(3,4-dichlorophenyl)-6-(methyloxy)-7[({2-[(4-methylpiperazin-1-yl)methyl]-1,3-thiazol-4-yl}methyl)oxy]quinazolin-4-amine | 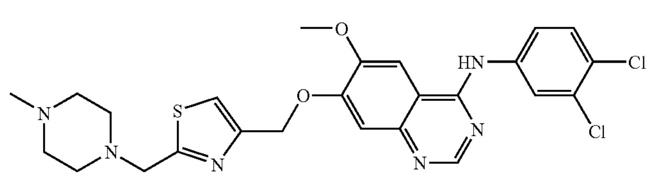 |

TABLE 1-continued

| Entry | Name | Structure |
|---|---|---|
| 151 | N-(3,4-dichlorophenyl)-7-[({2-methylmorpholin-2-yl)methyl]oxy}-6-(methyloxy)quinazolin-4-amine | 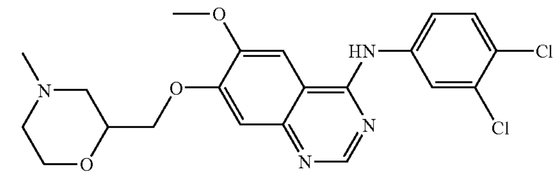 |
| 152 | N-(3,4-dichlorophenyl)-6-(methyloxy-7-[(1,4-oxazepan-2-ylmethyl)oxy]quinazolin-4-amine | 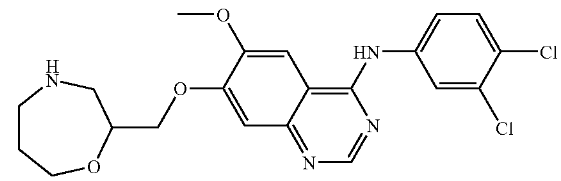 |
| 153 | N-(3,4-dichlorophenyl)-6-(methyloxy)-7-{[(5-piperidin-3-yl-1,2,4-oxadiazol-3-yl)methyl]oxy}quinazolin-4-amine | 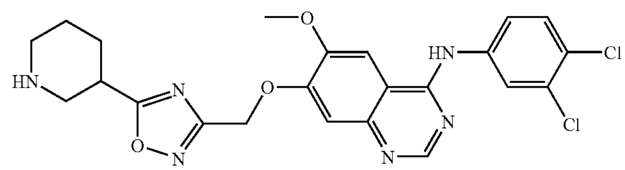 |
| 154 | N-(3,4-dichlorophenyl)-6-(methyloxy)-7-({[5-(1-methylpiperidin-2-yl)-1,2,4-oxadiazol-3-yl]methyl}oxy)quinazolin-4-amine | 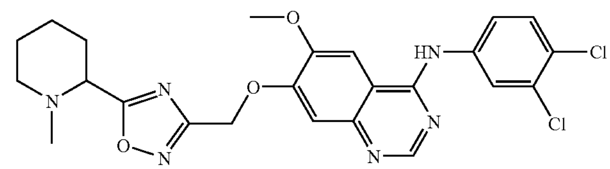 |
| 155 | N-(3,4-dichlorophenyl)-7-{[(4-methyl-1,4-oxazepan-2-yl)methyl]oxyl-6-(methyloxy)quinazolin-4-amine | 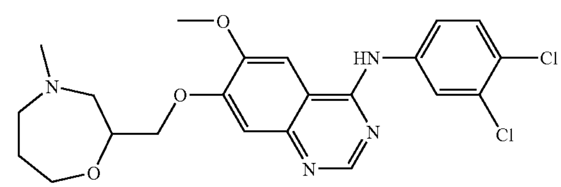 |
| 156 | N-(3,4-dichlorophenyl)-6-(methyloxy)-7-({[5-(1-methylpiperidin-3-yl)-1,2,4-oxadiazol-3-yl]methyl}oxy)quinazolin-4-amine | 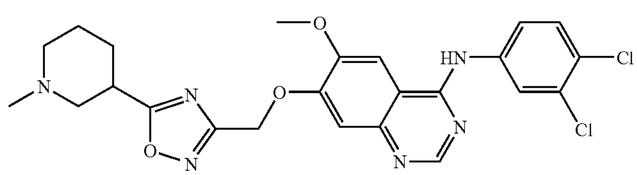 |
| 157 | N-(3,4-dichlorophenyl)-7-({15-(1,1-dimethylethyl)-1,2,4-oxadiazol-3-yl]methyl}oxy)-6-(methyloxy)quinazolin-4-amine | 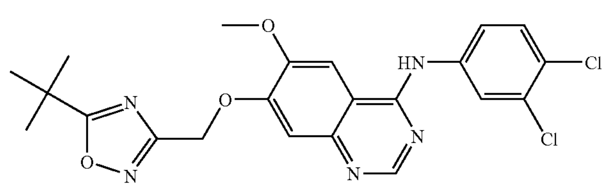 |
| 158 | N-(3,4-dichlorophenyl)-6-(methyloxy)-7-{[(2-phenyl-1,3-thiazol-4-yl)methyl]oxy}quinazolin-4-amine | 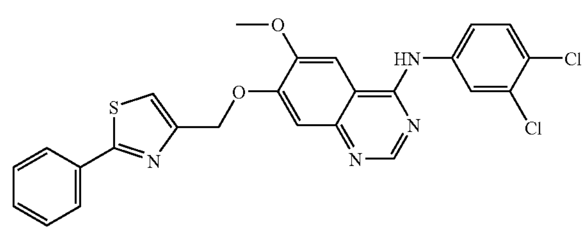 |

TABLE 1-continued

| Entry | Name | Structure |
|---|---|---|
| 159 | 7-[(2,1,3-benzothiadiazol-4-ylmethyl)oxyl-N-(3,4-dichlorophenyl)-6-(methyloxy)quinazolin-4-amine | 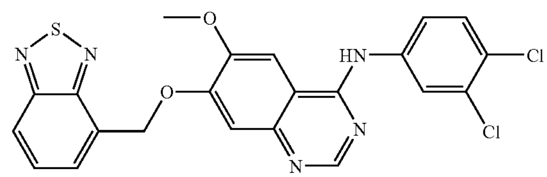 |
| 160 | N-(3,4-dichlorophenyl)-7-{[(5-methylisoxazol-3-yl)methyl]oxy}-6-(methyloxy)quinazolin-4-amine | 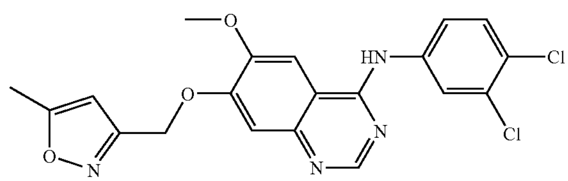 |
| 161 | N-(3,4-dichlorophenyl)-6-(methyloxy)-7-{[(5-methyl-4-phenylisoxazol-3-yl)methyl]oxy}quinazolin-4-amine | 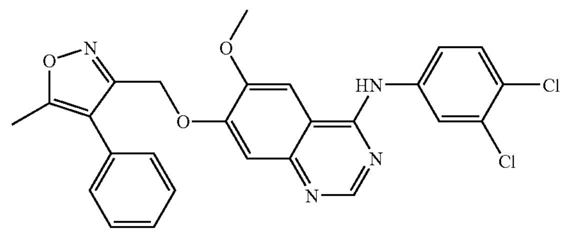 |
| 162 | 7-[(1,3-benzothiazol-2-ylmethyl)oxy]-N-(3,4-dichlorophenyl)-6-(methyloxy)quinazolin-4-amine | 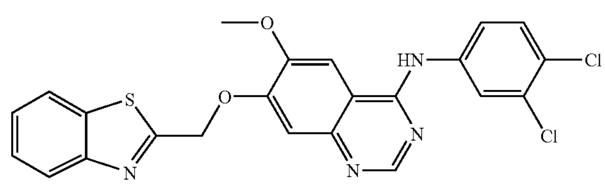 |
| 163 | 7-[(2,1,3-benzoxadiazol-5-ylmethyl)oxy]-N-(3,4-dichlorophenyl)-6-(methyloxy)quinazolin-4-amine | 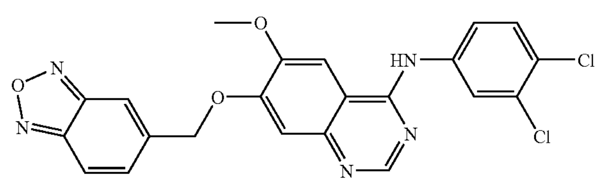 |
| 164 | N-(3,4-dichlorophenyl)-6-(methyloxy)-7-({[2-(2-thienyl)-1,3-thiazol-4-yl]methyl}oxy)quinazolin-4-amine | 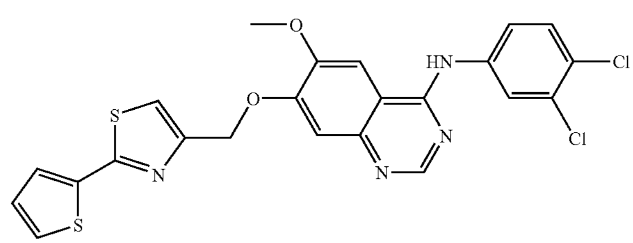 |
| 165 | N-(3,4-dichlorophenyl)-6-(methyloxy)-7-{[(1-phenyl-1H-pyrazol-4-yl)methyl]oxy}quinazolin-4-amine | 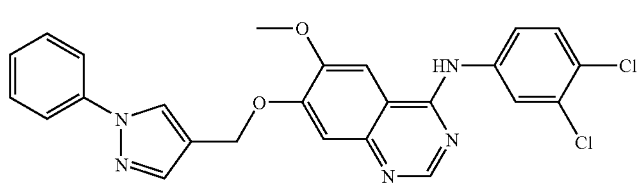 |

TABLE 1-continued

| Entry | Name | Structure |
|---|---|---|
| 166 | N-(3,4-dichlorophenyl)-6-(methyloxy)-7-[({5-[3-(trifluoromethyl)phenyl]-1,2,4-oxadiazol-3-yl}methyl)oxy]quinazolin-4-amine | 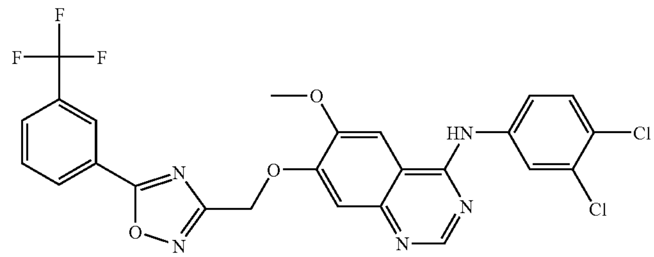 |
| 167 | N-(3,4-dichlorophenyl)-6-(methyloxy)-7-[({5-[4-(trifluoromethyl)phenyl]-1,2,4-oxadiazol-3-yl}methyl)oxy]quinazolin-4-amine | 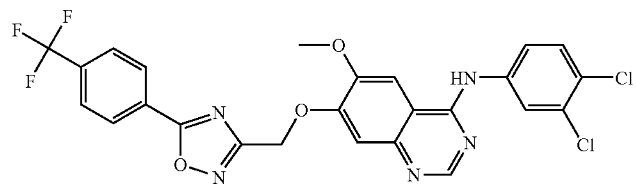 |
| 168 | 7-({[3-(4-chlorophenyl)-1,2,4-oxadiazol-5-yl]methyl}oxy)-N-(3,4-dichlorophenyl)-6-(methyloxy)quinazolin-4-amine | 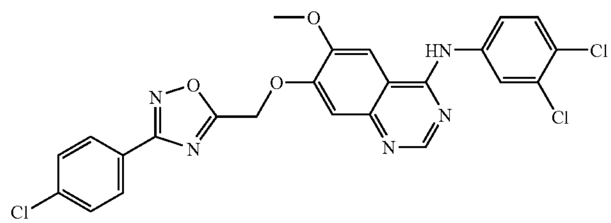 |
| 169 | 7-({[6-bromo-2-(methyloxy)naphthalen-1-yl]methyl}oxy)-N-(3,4-dichlorophenyl)-6-(methyloxy)quinazolin-4-amine | 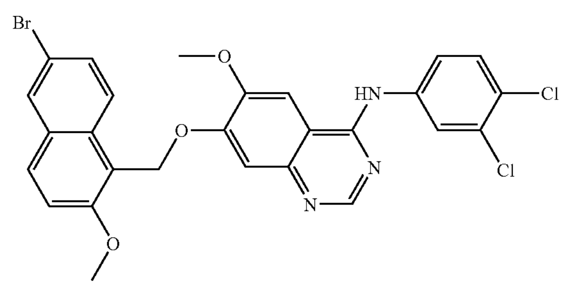 |
| 170 | N-(3,4-dichlorophenyl)-6-(methyloxy)-7-[(1,3-thiazol-4-ylmethyl)oxy]quinazolin-4-amine | 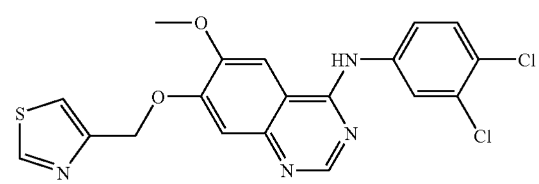 |
| 171 | 7-{[(6-chloropyridin-3-yl)methyl]oxy}-N-(3,4-dichlorophenyl)-6-(methyloxy)quinazolin-4-amine | 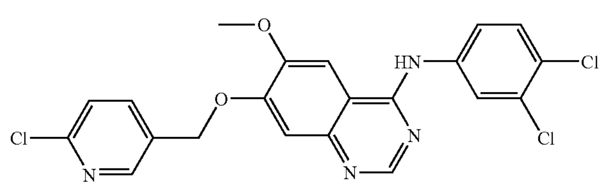 |
| 172 | N-(3,4-dichlorophenyl)-6-(methyloxy)-7-[(pyridin-4-ylmethyl)oxy]quinazolin-4-amine | 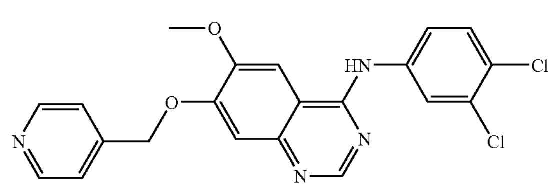 |

TABLE 1-continued

| Entry | Name | Structure |
|---|---|---|
| 173 | N-(3,4-dichlorophenyl)-6-(methyloxy)-7-{[(2-methyl-1,3-thiazol-4-yl)methyl]oxy)quinazolin-4-amine | 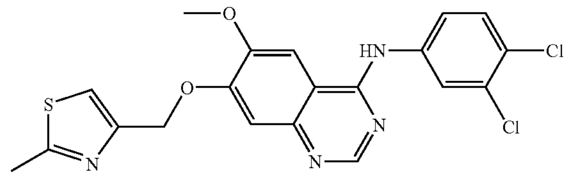 |
| 174 | 7-{[(6-chloro-4H-1,3-benzodioxin-8-yl)methyl]oxy}-N-(3,4-dichlorophenyl)-6-(methyloxy)quinazolin-4-amine | 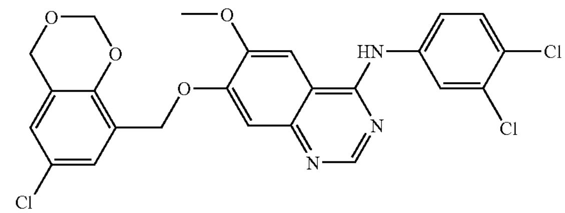 |
| 175 | 7-{[(5-chloro-1-methyl-3-phenyl-1H-pyrazol-4-yl)methyl]oxy}-N-(3,4-dichlorophenyl)-6-(methyloxy)quinazolin-4-amine | 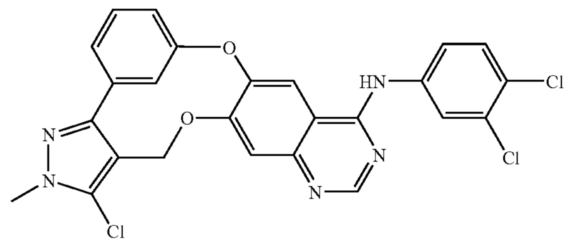 |
| 176 | N-(3,4-dichlorophenyl)-6-(methyloxy)-7-({[1-methyl-3-(trifluoromethyl)-1H-thieno(2,3-c]pyrazol-5-yl]methyl}oxy)quinazolin-4-amine | 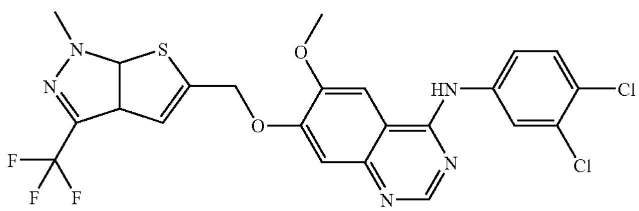 |
| 177 | N-(3,4-dichlorophenyl)-6-(methyloxy)-7-{[(3-phenylisoxazol-5-yl)methyoxy}quinazolin-4-amine | 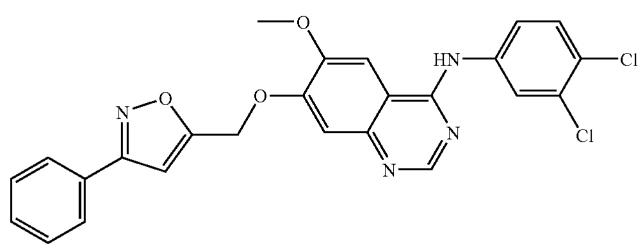 |
| 178 | N-(3,4-dichlorophenyl)-6-(methyloxy)-7-{[(2,4,6-trimethylphenyl)methyl]oxy}quinazolin-4-amine | 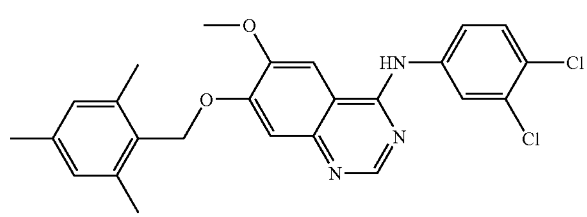 |
| 179 | N-(3,4-dichlorophenyl)-6-(methyloxy)-7-[(pyridin-3-ylmethyl)oxy]quinazolin-4-amine | 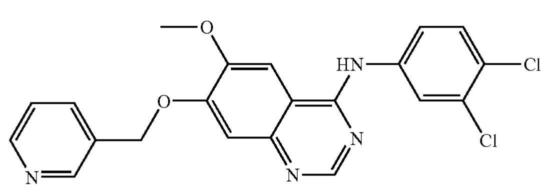 |

TABLE 1-continued

| Entry | Name | Structure |
|---|---|---|
| 180 | N-(3,4-dichlorophenyl)-6-(methyloxy)-7-[({3-[4-(methyloxy)phenyl]isoxazol-5-yl}methyl)oxy]quinazolin-4-amine | 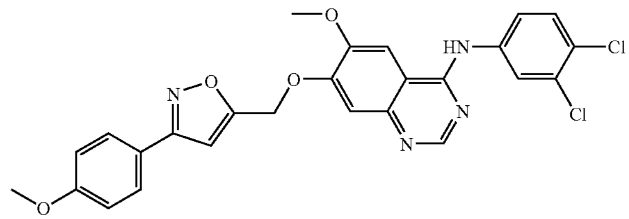 |
| 181 | N-(3,4-dichlorophenyl)-7-({[5-[(2,4-dichlorophenyl)oxy]-1-methyl-3-(trifluoromethyl)-1H-pyrazol-4-yl]methyl}oxy)-6-(methyloxy)quinazolin-4-amine | 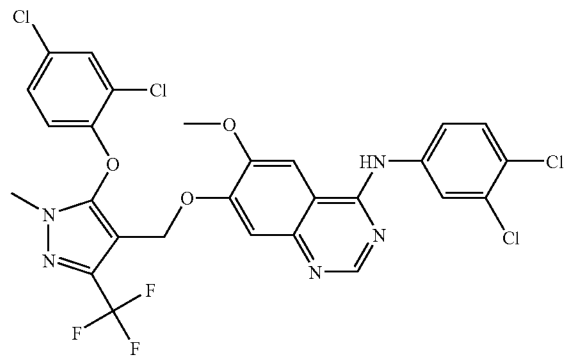 |
| 182 | 7-[(cyclopropylmethyl)oxy]-N-(3,4-dichlorophenyl)-6-(methyloxy)quinazolin-4-amine | 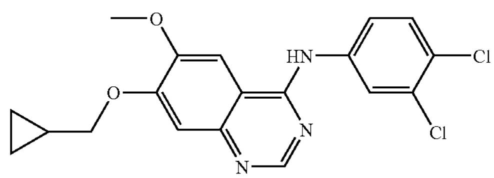 |
| 183 | N-(3,4-dichlorophenyl)-6-(methyloxy)-7-[(tetrahydrofuran-2-ylmethyl)oxy]quinazolin-4-amine | 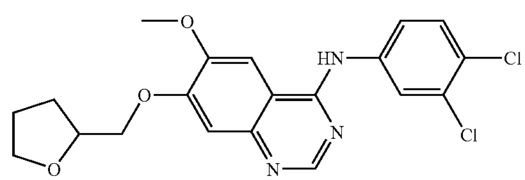 |
| 184 | 7-(cyclopentyloxy)-N-(3,4-dichlorophenyl)-6-(methyloxy)quinazolin-4-amine | 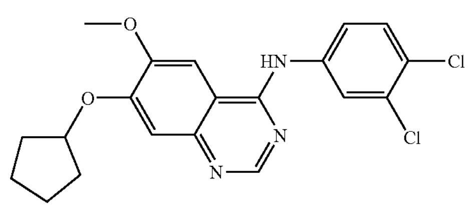 |
| 185 | 7-[(2-cyclohexylethyl)oxy]-N-(3,4-dichlorophenyl)-6-(methyloxy)quinazolin-4-amine | 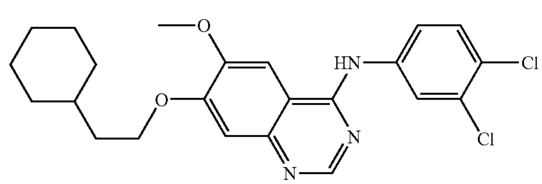 |
| 186 | 7-[(cyclohexylmethyl)oxy]-N-(3,4-dichlorophenyl)-6-(methyloxy)quinazolin-4-amine | 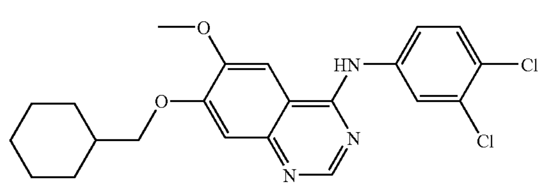 |

TABLE 1-continued

| Entry | Name | Structure |
|---|---|---|
| 187 | 7-[(cyclobutylmethyl)oxy]-N-(3,4-dichlorophenyl)-6-(methyloxy)quinazolin-4-amine | 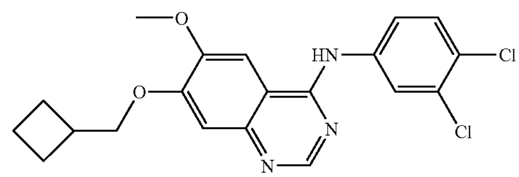 |
| 188 | N-(3,4-dichlorophenyl)-7-{[2-(1,3-dioxolan-2-yl)ethyl]oxy}-6-(methyloxy)quinazolin-4-amine | 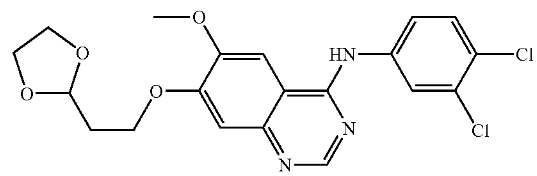 |
| 189 | N-(3,4-dichlorophenyl)-7-{[2-(1,3-dioxan-2-yl)ethyl]oxy-6-(methyloxy)quinazolin-4-amine | 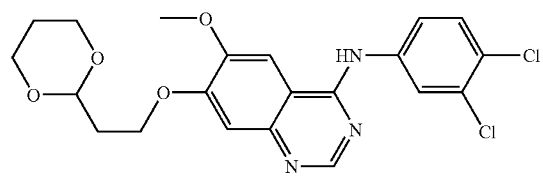 |
| 190 | N-(3,4-dichlorophenyl)-6-(methyloxy)-7-[(2-marpholin-4-ylethyl)oxy]quinazolin-4-amine | 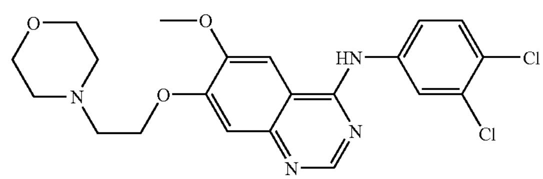 |
| 191 | N(3,4-dichlorophenyl)-6-(methyloxy)7-[(2-pyrrolldin-1-ylethyl)oxy]quinazolin-4-amine | 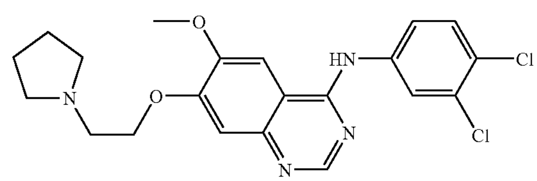 |
| 192 | N-(3,4-dichlorophenyl)-6-(methyloxy)-7-[(2-piperidin-1-ylethyl)oxy]quinazolin-4-amine | 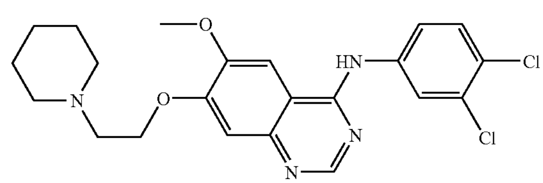 |
| 193 | 2-(2-{[4-[(3,4-dichlorophenyl)amino]-6-(methyloxy)quinazolin-7-yl]oxy}ethyl)-1H-isoiridole-1,3(2H)-dione | 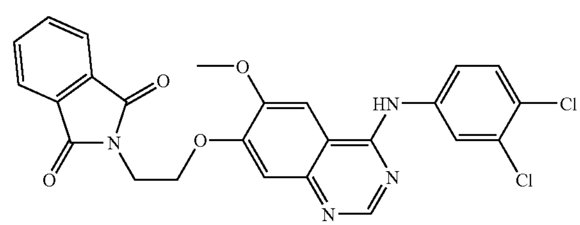 |
| 194 | methyl 6-O-[4-[(3,4-dichlorophenyl)amino]-6-(methyloxy)quinazolin-7-yl]-alpha-D-glucopyranoside | 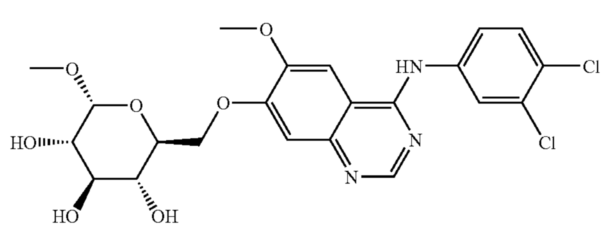 |

TABLE 1-continued

| Entry | Name | Structure |
|---|---|---|
| 195 | N-(3,4-dichlorophenyl)-6-(methyloxy)-7-[(2-morpholin-4-yl-2-oxoethyl)oxy]quinazolin-4-amine | 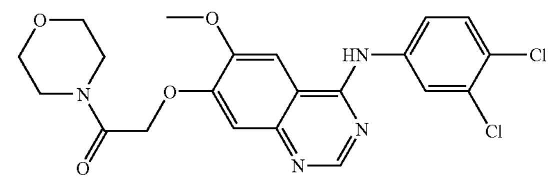 |
| 196 | 1,1-dimethylethyl 2-[3-({[4-[(3,4-dichlorophenyl)amino]-6-(methyloxy)quinazolin-7-yl]oxy}methyl)-1,2,4-oxadiazol-5-yl]piperidine-1-carboxylate | 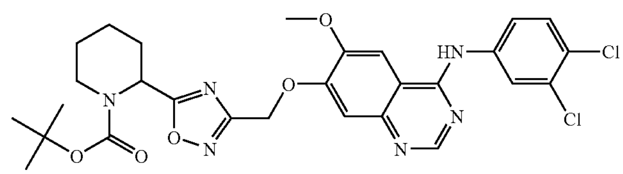 |
| 197 | 1,1-dimethylethyl 4-{3-({[4-[(3,4-dichlorophenyl)amino]-6-(methyloxy)quinazolin-7-yl]oxylmethyl)-1,2,4-oxadiazol-5-yl]piperidine-1-carboxylate | 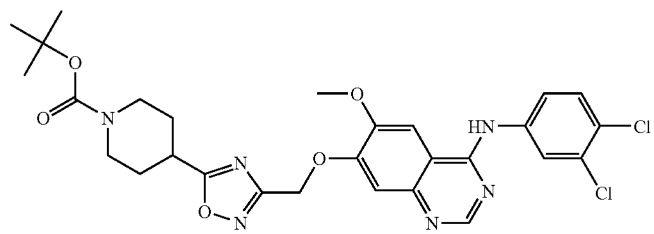 |
| 198 | N-(3,4-dichlorophenyl)-6-(methyloxy)-7-({[4-(4-pyrrolidin-1-ylphenyl)-1,3-thiazol-2-yl]methyl}oxy)quinazolin-4-amine | 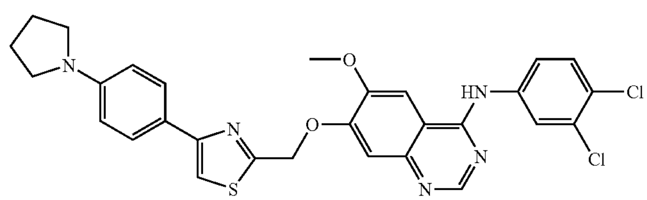 |
| 199 | N-(3,4-dichlorophenyl)-7-[({4-[4-(diethylamino)phenyl]-1,3-thiazol-2-yl}methyl)oxy]-6-(methyloxy)quinazolin-4-amine | 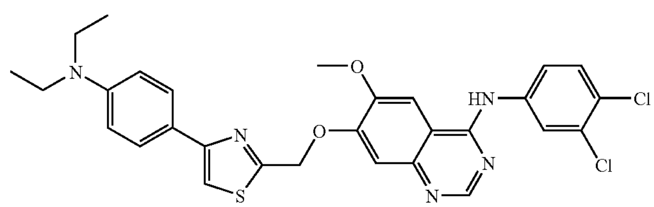 |
| 200 | 5-[2-({[4-[(3,4-dichlorophenyl)amino]-6-(methyloxy)quinazolin-7-yl]oxylmethyl)-1,3-thiazol-4-y-2-hydroxybenzamide | 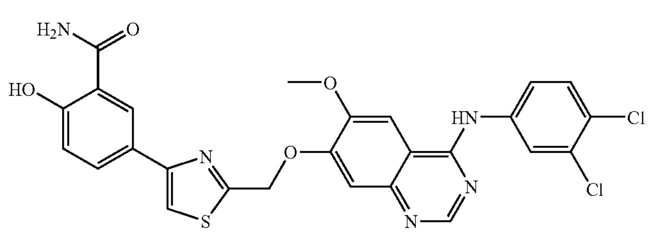 |
| 201 | N-(3,4-dichlorophenyl)-6-(methyloxy)-7-{[(4-pyridin-3-yl-1,3-thiazol-2-yl)methyl]oxy}quinazolin-4-amine | 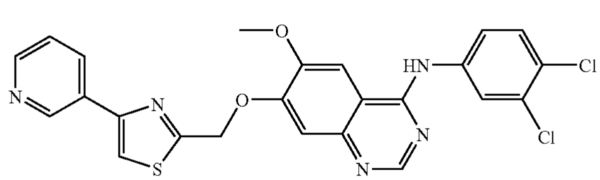 |

TABLE 1-continued

| Entry | Name | Structure |
|---|---|---|
| 202 | N-(3,4-dichlorophenyl)-6-(methyloxy)-7-{[(4-pyridin-2-yl-1,3-thiazol-2-yl)methyl]oxy}quinazolin-4-amine | 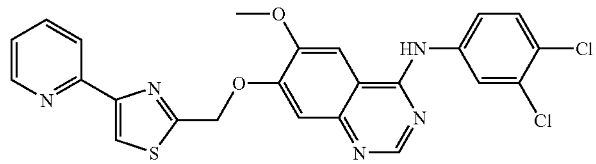 |
| 203 | N-(3,4-dichlorophenyl)6-(methyloxy)-7-{[(4-pyridin-4-yl-1,3-thiazol-2-yl)methyl]oxy}quinazolin-4-amine | 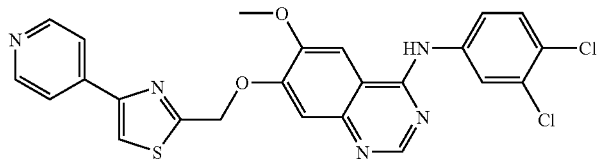 |
| 204 | N-(3,4-dichlorophenyl)-6-(methyloxy)-7-{[(2-morpholin-4-yl-1,3-thiazol-4-yl)methyl]oxy}quinazolin-4-amine | 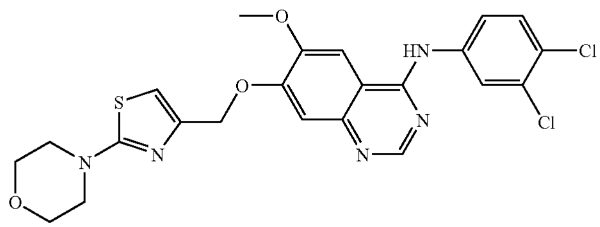 |
| 205 | N-(3,4-dichlorophenyl)-6-(methyloxy)-7-{[(3-morpholin-4-yl-1,2,4-oxadiazol-5-yl)methyl]oxy}quinazolin-4-amine | 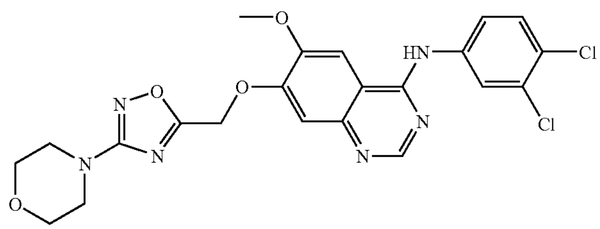 |
| 206 | N-(314-dichlorophenyl)-7-({[3-(dimethylamino)-1,2,4-oxadiazol-5-yl]methyl}oxy)-6-(methyloxy)quinazolin-4-amine | 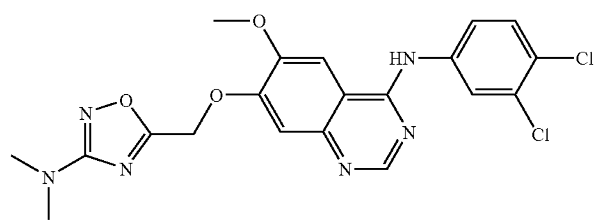 |
| 207 | N-(3,4-dichlorophenyl)-6-(methyloxy)-7-[({4-[(4-methylpiperazin-1-yl)methyl]-1,3-thiazol-2-yl}methyl)oxy]quinazolin-4-amine | 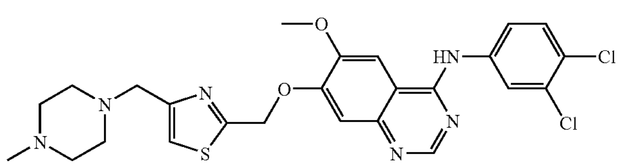 |
| 208 | N-(3,4-dichlorophenyl)-6-(methyloxy)-7-(4,5,6,7-tetrahydro[1,3]thiazolo[5,4-c]pyridin-2-ylmethyl)oxy]quinazolin-4-amine | 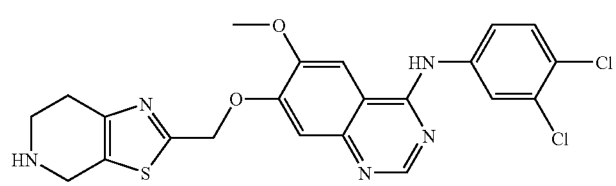 |
| 209 | N-(3,4-dichlorophenyl)-6-(methyloxy)-7-({[4-(morpholin-4-ylmethyl)-1,3-thiazol-2-yl]methyl}oxy)quinazolin-4-amine | 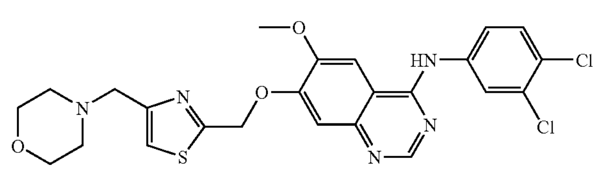 |

TABLE 1-continued

| Entry | Name | Structure |
|---|---|---|
| 210 | N-(3,4-dichlorophenyl)-7-[({4-[(4-methyl-1,4-diazepan-1-yl)methyl]-1,3-thiazol-2-yl}methyl)oxy]-6-(methyloxy)quinazolin-4-amine | 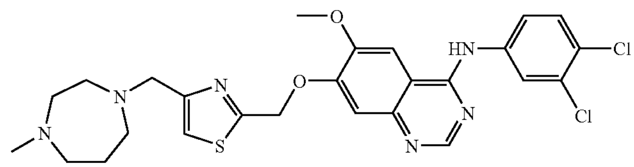 |
| 211 | N-(3,4-dichlorophenyl)-6-(methyloxy)-7-{[(5-{[(phenylmethyl)oxy]methyl}-1,2,4-oxadiazol-3-yl)methyl]oxy}quinazolin-4-amine | 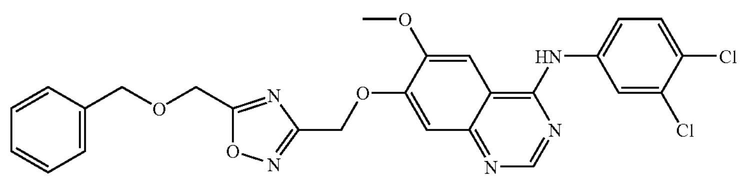 |
| 212 | N-(3,4-dichlorophenyl)-7-{[(4-ethylmorpholin-2-yl)methyoxy}-6-(methyloxy)quinazolin-4-amine | 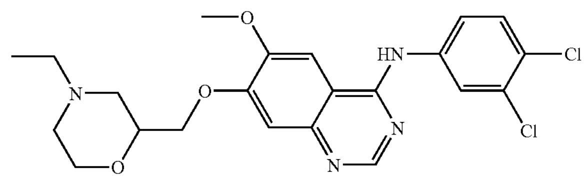 |
| 213 | N-(3,4-dichlorophenyl)-6-(methyloxy)-7-{[(2-piperidin-4-yl-1,3-thiazol-4-yl)methyl]oxy}quinazolin-4-amine | 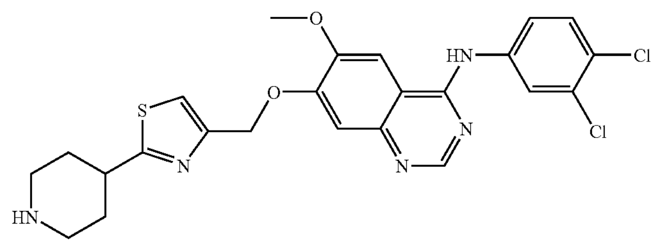 |
| 214 | N-(3,4-dichlorophenyl)-6-(methyloxy)-7-({[2-(1-methylpiperidin-4-yl)-1,3-thiazol-4-yl]methyl}oxy)quinazolin-4-amine | 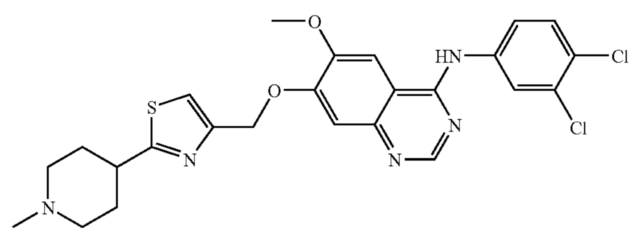 |
| 215 | 1,1 dimethylethyl 4-[5-(({4-[(3,4-dichlorophenyl)amino]-6-(methyloxy)quinazolin-7-yl]oxy}methyl)-1,2,4-oxadiazol-3-yl]piperazine-1-carboxylate | 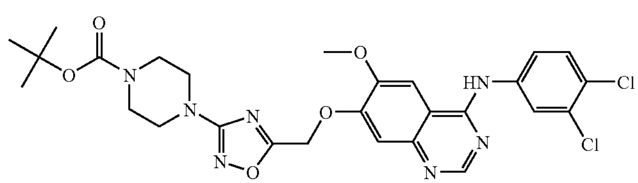 |

TABLE 1

| 217 | N-(3,4-dichlorophenyl)-6-(methyloxy)-7-{[(3-piperazin-1-yl-1,2,4-oxadiazol-5-yl)methyl]oxy}quinazolin-4-amine | |

TABLE 1-continued

| 218 | N-(3,4-dichloropheriyl)-6-(methyloxy)-7-({[3-(4-methylpiperazin-1-yl)-1,2,4-oxadiazol-5-yl]methyl}oxy)quinazolin-4-amine |
| --- | --- |
| 219 | N-(3,4-dichlorophenyl)-7-({[5-(1-ethylpiperidin-2-yl)-1,2,4-oxadiazol-3-yl]methyl}oxy)-6-(methyloxy)quinazolin-4-amine |
| 220 | N-(3,4-dichlorophenyl)-7-({[3-(4-ethylpiperazin-1-yl)-1,2,4-oxadiazol-5-yl]methyl}oxy)-6-(methyloxy)quinazolin-4-amine |
| 221 | N-(3,4-dichlorophenyl)-6-(methyloxy)-7-[({5-[4-(methyloxy)phenyl]-1,2,4-oxadiazol-3-yl}methyl)oxy]quinazolin-4-amine |
| 222 | N-(3,4-dichlorophenyl)-6-(methyloxy)-7-[({2-[4-(trifluoromethyl)phenyl]-1,3-thiazol-4-yl}methyl)oxy]quinazolin-4-amine |
| 223 | 7-({[2-(4-chlorophenyl)-1,3-thiazol-4-yl]methyl{loxy)-N-(3,4-dichlorophenyl)-6-(methoxy)quinazolin-4-amine |
| 224 | N-(3,4-dichlorophenyl)-7-({[5-(3,5-dimethytisoxazol-4-yl)-1,2,4-oxadiazol-3-yl]methyl}oxy)-6-(methyloxy)quinazolin-4-amine |

TABLE 1-continued

| | | |
|---|---|---|
| 225 | 7-{[(5-chloro-1-benzothien-3-yl)methyl]oxy}-N-(3,4-dichlorophenyl)-6-(methyloxy)quinazolin-4-amine | |
| 226 | N-(3,4-dichlorophenyl)-7-[({3-[4-(1,1-dimethylethyl)phenyl]-1,2,4-oxadiazol-5-yl}methyl)oxy]-6-(methyloxy)quinazolin-4-amine | |
| 227 | N-(3,4-dichlorophenyl)-6-(methyloxy)-7-[({5-[2-(methyloxy-phenyl]-1,2,4-oxadiazol-3-yl}methyl)oxylquinazolin-4-amine | |
| 228 | N-(3,4-dichlorophenyl)-6-(methyloxy)-7-({[5-(4-methylphenyl)-1,3,4-oxadiazol-2-yl]methyl}oxy)quinazolin-4-amine | |
| 229 | N-(3,4-dichlorophenyl)-6-(methyloxy)-7-({[1-(phenylmethyl)-1H-imidazol-2-yl]methyl}oxy)quinazolin-4-amine | |
| 230 | N-(3,4-dichlorophenyl)-7-({[3-(2,6-dichlorophenyl)-5-methylisoxazol-4-yl]methyl)oxy)-6-(methyloxy)quinazolin-4-amine | |

TABLE 1-continued

| 231 | N-(3,4-dichlorophenyl)-7-{[(6-fluoro-4H-1,3-benzodioxin-8-yl)methyl]oxy]-6-(methyloxy)quinazolin-4-amine |
| 232 | 7-{[(3,5-dibromophenyl)methyl]oxy}-N-(3,4-dichlorophenyl)-6-(methyloxy)quinazolin-4-amine |
| 233 | N-(3,4-dichlorophenyl)-7-{[(2,6-difluorophenyl)methyl]oxy}-6-(methyloxy)quinazolin-4-amine |
| 234 | N-(3,4-dichlorophenyl)-6-(methyloxy)-7-[({3-[(pyridin-2-ylsulfonyl)methyl]-1,2,4-oxadiazol-5-yl}methyl)oxy]quinazolin-4-amine |
| 235 | N-(3,4-dichlorophenyl)-6-(methyloxy)-7-{[(5-phenyl-1,2,4-oxadiazol-3-yl)methyl]oxy}quinazolin-4-amine |
| 236 | 7-({-4-chloro-2-(trifluoromethyl)quinolin-6-yl]methyl}oxy)-N-(3,4-dichlorophenyl)-6-(methyloxy)quinazolin-4-amine |
| 237 | N-(3,4-dichlorophenyl)-6-(methyloxy)-7-{[2-(1-methylpyrrolidin-2-yl)ethyl]oxy}quinazolin-4-amine |
| 238 | N-(3,4-dichlorophenyl)-7-({[5-(1-ethylpiperidin-4-yl)-1,2,4-oxadiazol-3-yl]methyl}oxy)-6-(methyloxy)quinazolin-4-amine |

TABLE 1-continued

| | | |
|---|---|---|
| 239 | N-(3,4-dichlorophenyl)-7-({[5-(1-ethylpiperidin-3-yl)-1,2,4-oxadiazol-3-y-methyl}oxy)-6-(methyloxy)quinazolin-4-amine | |
| 240 | N-(3,4-dichlorophenyl)-7-({[2-(dimethylamino)-1,3-thiazol-4-yl]methyl}oxy)-6-(methyloxy)quinazolin-4-amine | |
| 241 | N-(3,4-dichlorophenyl)-7-([[(4-ethyl-1,4-oxazepan-2-yl)methyl]oxy}-6-(methyloxy)quinazolin-4-amine | |
| 242 | N-(3,4-dichlorophenyl)-7-({[2-(1-ethylpiperidin-4-yl)-1,3-thiazol-4-yl]methyl}oxy)-6-(methyloxy)quinazolin-4-amine | |
| 243 | N-(3,4-dichlorophenyl)-6-(methyloxy)-7-[({3-[(2S)-pyrrolidin-2-yl]-1,2,4-oxadiazol-5-yl}methyl)oxy]quinazolin-4-amine | |
| 244 | N-(3,4-dichlorophenyl)-6-(methyloxy)-7-[({2-[(2s)-pyrrolidin-2-yl]-1,3-thiazol-4-yl}methyl)oxy]quinazolin-4-amine | |
| 245 | [4-({[4-[(3,4-dichlorophenyl)amino]-6-(methyloxy)quinazolin-7-yl]oxy}methyl)-1,3-thiazol-2-yl]methyl benzoate | |
| 246 | [4-({[4-[(3,4-dichlorophenyl)amino]-6-(methyloxy)quinazolin-7-yl]oxy}methyl)-1,3-thiazol-2-yl]methanol | |

TABLE 1-continued

| | | |
|---|---|---|
| 247 | N-(3,4-dichlorophenyl)-6-(methyloxy)-7-{[(5-methyl-4,5,6,7-tetrahydro[1,3]thiazolo[5,4-c]pyridin-2-yl)methyl]oxy}quinazolin-4-amine | |
| 248 | N-(3,4-dichlorophenyl)-6-(methyloxy)-7-[({2-[(4s)-1,3-thiazolidin-4-yl]-1,3-thiazol-4-yl}methyl)oxy]quinazolin-4-amine | |
| 249 | N-(3,4-dichlorophenyl)-6-(methyloxy)-7-{[(2-piperidin-2-yl-1,3-thiazol-4-yl)methyl]oxy}quinazolin-4-amine | |
| 250 | N-(3,4-diohlorophenyl)-6-(methyloxy)-7-({[2-(1-methylpiperidin-2-yl)-1,3-(3-thiazol-4-y-methyl}oxy)quinazolin-4-amine | |
| 251 | N-(3,4-dichlorophenyl)-6-(methyloxy)-7-{[(2-piperidin-3-yl-1,3-thiazol-4-yl)methyl]oxy}quinazolin-4-amine | |
| 252 | N-(3,4-dichlorophenyl)-6-(methyloxy)-7-({[2-(1-methylpiperidin-3-yl)-1,3-thiazol-4-yl]methyl-oxy)quinazolin-4-amine | |
| 253 | N-(3,4-dichlorophenyl)-7-({[2-(1-ethylpiperidin-2-yl)-1,3-thiazol-4-yl]methyl}oxy)-6-(methyloxy)quinazolin-4-amine | |

TABLE 1-continued

| | | |
|---|---|---|
| 254 | N-(3,4-dichlorophenyl)-7-({[2-(1-ethylpiperidin-3-yl)-1,3-thiazol-4-yl]methyl}oxy)-6-(methyloxy)quinazolin-4-amine | |
| 255 | N-(3,4-dichlorophenyl)-7-[({3-[(2S)-1-ethylpyrrolidin-2-yl]-1,2,4-oxadiazol-5-yl}methyl)oxy]-6-(methyloxy)quinazolin-4-amine | |
| 256 | N-(3,4-dichlorophenyl)-7-[({2-[(2S)-1-ethylpyrrolidin-2-yl]-1,3-thiazol-4-yl-methyl)oxy]-6-(methyloxy)quinazolin-4-amine | |
| 257 | N-(3,4-dichlorophenyl)-7-{[(5-ethyl-4,5,6,7-tetrahydro[1,3]thiazolo[5,4-c]pyridin-2-yl)methyl]oxy}-6-(methyloxy)quinazolin-4-amine | |
| 258 | N-(3,4-dichlorophenyl)-6-(methyloxy)-7-{[(4-propyl-1,4-oxazepan-2-yl)methyl]oxy}quinazolin-4-amine | |
| 259 | 7-({[4-(cyclopropylmethyl)-1,4-oxazepan-2-yl]methyl}oxy)-N-(3,4-dichlorophenyl)-6-(methyloxy)quinazolin-4-amine | |
| 260 | N-(3,4-dichlorophenyl)-6-(methyloxy)-7-[({4-[2-(methyloxy)ethyl]-1,4-oxazepan-2-yl}methyl)oxy]quinazolin-4-amine | |
| 261 | N-(3,4-dichlorophenyl)-7-({[4-(1-methylethyl)-1,4-oxazepan-2-yl]methyl}oxy)-6-(methyloxy)quinazolin-4-amine | |

TABLE 1-continued

| | | |
|---|---|---|
| 262 | N-(3,4-dichlorophenyl)-6-(methyloxy)-7-{[(2-piperazin-1-yl-1,3-thiazol-4-yl)methyl]oxy}quinazolin-4-amine | |
| 263 | N-(3,4-dichlorophenyl)-6-(methyloxy)-7-{[(5-pyrrolidin-2-yl-1,2,4-oxadiazol-3-yl)methyl]oxy}quinazolin-4-amine | |
| 264 | N-(3,4-dichlorophenyl)-7-({[5-(1-ethylpyrrolidin-2-yl)-1,2,4-oxadiazol-3-yl]methyl}oxy)-6-(methyloxy)quinazolin-4-amine | |
| 265 | N-(3,4-dichlorophenyl)-6-(methyloxy)-7-[({3-[(2S)-1-methylpyrrolidin-2-yl]-1,2,4-oxadiazol-5-yl}methyl)oxy]quinazolin-4-amine | |
| 266 | N-(3,4-dichlorophenyl)-6-(methyloxy)-7-[({2-[(2S)-1-methylpyrrolidin-2-yl]-1,3-thiazol-4-yl}methyl)oxy]quinazolin-4-amine | |
| 267 | N-(3,4-dichlorophenyl)-7-({[2-(4-ethylpiperazin-1-yl)-1,3-thiazol-4-yl]methyl}oxy)-6-(methyloxy)quinazolin-4-amine | |
| 268 | N-(3,4-dichlorophenyl)-7-{[(1,4-dimethylpiperazin-2-yl)methyl]oxy}-6-(methyloxy)quinazolin-4-amine | |
| 269 | 7-{[(4-cyclopentylmorpholin-2-yl)methyl]oxy}-N-(3,4-dichlorophenyl)-6-(methyloxy)quinazolin-4-amine | |

TABLE 1-continued

| | | |
|---|---|---|
| 270 | N-(3,4-dichlorophenyl)-7-({[4-(1-methylethyl)morpholin-2-yl]methyl}oxy)-6-(methyloxy)quinazolin-4-amine | |
| 271 | N-(3,4-dichlorophenyl)-6-(methyloxy)-7-({[4-(3-phenylpropyl)morpholin-2-yl]methyl}oxy)quinazolin-4-amine | |
| 272 | N-(3,4-dichlorophenyl)-6-(methyloxy)-7-[({4-[2-(methyloxy)ethyl]morpholin-2-yl}methyl)oxy]quinazolin-4-amine | |
| 273 | ethyl 2-[2-({[4-[(3,4-dichlorophenyl)amino]-6-(methyloxy)quinazolin-7-yl]oxy}methyl)morpholin-4-yl]propanoate | |
| 274 | N-(3,4-dichlorophenyl)-7-{[(4-hex-5-en-1-ylmorpholin-2-yl)methyl]oxy}-6-(methyloxy)quinazolin-4-amine | |
| 275 | 2-({2-[2-({[4-[(3,4-dichlorophenyl-amino]-6-(methyloxy)quinazolin-7-yl]oxy}methyl)morpholin-4-yl]ethyl}oxy)ethanol | |
| 276 | methyl 3-[2-({[4-[(3,4-dichlorophenyl)amino]-6-(methyloxy)quinazolin-7-yl]oxy}methyl)morpholin-4-yl]propanoate | |
| 277 | 6-[2-({[4-[(3,4-dichlorophenyl)amino]-6-(methyloxy)quinazolin-7-yl]oxy}methyl)morpholin-4-yl]hexanenitrile | |

TABLE 1-continued

| | | |
|---|---|---|
| 278 | N-(3,4-dichlorophenyl)-6-(methyloxy)-7-({[4-(tetrahydro-2H-pyran-2-ylmethyl)morpholin-2-yl]methyl}oxy)quinazolin-4-amine | |
| 279 | 4-[2-({[4-[(3,4-dichlorophenyl)amino]-6-(methyloxy)quinazolin-7-yl]oxy}methyl)morpholin-4-yl]butanenitrile | |
| 280 | N-(3,4-dichlorophenyl)-7-[({4-[(4-fluorophenyl)methyl]morpholin-2-yl}methyl)oxy]-6-(methyloxy)quinazolin-4-amine | |
| 281 | methyl 5-[2-({[4-[(3,4-dichlorophenyl)amino]-6-(methyloxy)quinazolin-7-yl]oxy}methyl)morpholin-4-yl]pentanoate | |
| 282 | N-(3,4-dichlorophenyl)-6-(methyloxy)-7-{[(4-oct-7-en-1-ylmorpholin-2-yl)methyl]oxy}quinazolin-4-amine | |
| 283 | N-(3,4-dichlorophenyl)-6-(methyloxy)-7-{[(4-propylmorpholin-2-yl)methyl]oxy}quinazolin-4-amine | |
| 284 | 6-[2-({[4-[(3,4-dichlorophenyl)amino]-6-(methyloxy)quinazolin-7-yl]oxy}methyl)morpholin-4-yl]hexan-1-ol | |
| 285 | 7-({[(4-acetylmorpholin-2-yl)methyl]oxy}-N-(3,4-dichlorophenyl)-6-(methyloxy)quinazolin-4-amine | |

TABLE 1-continued

| | | |
|---|---|---|
| 286 | 7-({[4-(cycloproplmethyl)morpholin-2-yl]methyl}oxy)-N-(3,4-dichlorophenyl)-6-(methyloxy)quinazolin-4-amine | |
| 287 | N-(3,4-dichlorophenyl)-6-(methyloxy)-7-{[(4-prop-2-yn-1-ylmorpholin-2-yl)methyl]oxy}quinazolin-4-amine | |
| 288 | N-(3,4-dichlorophenyl)-6-(methyloxy)-7-{[(4-pyridin-4-ylmorpholin-2-yl)methyl]oxy}quinazolin-4-amine | |
| 289 | N-(3,4-dichlorophenyl)-6-(methyloxy)-7-({[4-(pyridin-2-ylmethyl)morpholin-2-yl]methyl}oxy)quinazolin-4-amine | |
| 290 | N-(3,4-dichlorophenyl)-6-(methyloxy)-7-{[(4-pent-2-yn-1-ylmorpholin-2-yl)methyl]oxy}quinazolin-4-amine | |
| 291 | N-(3,4-dichlorophenyl)-6-(methyloxy)-7-({[2-(4-methylpiperazin-1-yl)-1,3-thiazol-4-yl]methyl}oxy)quinazolin-4-amine | |
| 292 | N-(3,4-dichlorophenyl)-6-(methyloxy)-7-({[5-(1-methylpyrrolidin-2-yl)-1,2,4-oxadiazol-3-yl]methyl}oxy)quinazolin-4-amine | |
| 293 | N-(3-chloro-4-fluorophenyl)-7-{[(4-methylmorpholin-2-yl)methyl]oxy}-6-(methyloxy)quinazolin-4-amine | |

TABLE 1-continued

| | | |
|---|---|---|
| 294 | 7-{[(4-butyl-1,4-oxazepan-2-yl)methyl]oxy}-N-(3,4-dichlorophenyl)-6-(methyloxy)quinazolin-4-amine | |
| 295 | (3,4-dichlorophenyl)[7-(methyloxy)-6-({[4-(2-methylpropyl)-1,4-oxazepan-2-yl]methyl}oxy)quinazolin-4-amine | |
| 296 | 7-{[(acetyl-1-ethylpiperazin-2-yl)methyl]oxy}-N-(3,4-dichlorophenyl)-6-(methyloxy)quinazolin-4-amine | |
| 297 | (3,4-dichlorophenyl)(6-(methyloxy)-7-{[(4-pentyl-1,4-oxazepan-2-yl)methyl]oxy}quinazolin-4-amine | |
| 298 | (3,4-dichlorophenyl)[6-(methyloxy)-7-({[4-(tetrahydro-2H-pyran-2-ylmethyl)-1,4-oxazepan-2-yl]methyl}oxy)quinazolin-4-amine | |
| 299 | (3,4-dichlorophenyl)[6-(methyloxy)-7-({[4-(3-thienylmethyl)-1,4-oxazepan-2-yl]methyl}oxy)quinazolin-4-amine | |
| 300 | N-[4-chloro-2,5-bis(methyloxy)pheny]-7-{[(4-methylmorpholin-2-yl)methyl]oxy}-6-(methyloxy)quinazolin-4-amine | |

TABLE 1-continued

| | | |
|---|---|---|
| 301 | N-(3-bromo-2-methylphenyl)-7-{[(4-methylmorpholin-2-yl)methyl]oxy}-6-(methyloxy)quinazolin-4-amine | |
| 302 | 7-{[(4-methylmorpholin-2-yl)methyl]oxyl-6-(methyloxy)-N-(3,4,5-trichlorophenyl)quinazolin-4-amine | |
| 303 | N-(3-chloro-2-methylphenyl)-7-{[(4-methylmorpholin-2-yl)methyl]oxy}-6-(methyloxy)quinazolin-4-amine | |
| 304 | N-(3,4-dichlorophenyl)-7-{[(4-ethanimidoyl-1,4-oxazepan-2-yl)methyl]oxy}-6-(methyloxy)quinazolin-4-amine | |
| 305 | N-(4-bromo-2-fluorophenyl)-7-{[(4-methylmorpholin-2-yl)methyl]oxyl-6-(methyloxy)quinazolin-4-amine | |
| 306 | N-(5-chloro-2-fluorophenyl)-7-{[(4-methylmorpholin-2-yl)methyl]oxy}-6-(methyloxy)quinazolin-4-amine | |
| 307 | N-(4-chloro-2-fluorophenyl)-7-{[(4-methylmorpholin-2-yl)methyl]oxy}-6-(methyloxy)quinazolin-4-amine | |
| 308 | N-(2,4-dichlorophenyl)-7-{[(4-methylmorpholin-2-yl)methyl]oxy}-6-(methyloxy)quinazolin-4-amine | |

TABLE 1-continued

| | | |
|---|---|---|
| 309 | N-(2,4-dibromophenyl)-7-{[(4-methylmorpholin-2-yl)methyl]oxy}-6-(methyloxy)quinazolin-4-amine | 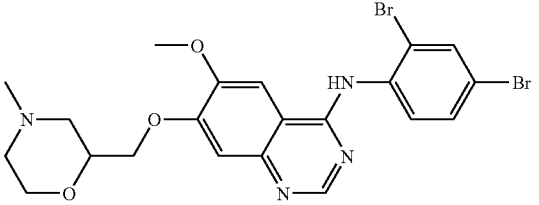 |
| 310 | 7-{[(4-methylmorpholin-2-yl)methyl]oxy}-6-(methyloxy)-N-(2,3,4-trichlorophenyl)quinazolin-4-amine | 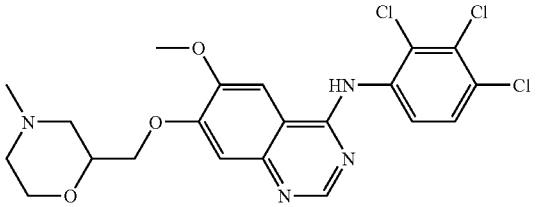 |
| 311 | N-(3,4-dichlorophenyl)-7-{[(1-ethyl-4-methylpiperazin-2-yl)methyl]oxy}-6-(methyloxy)quinazolin-4-amine | 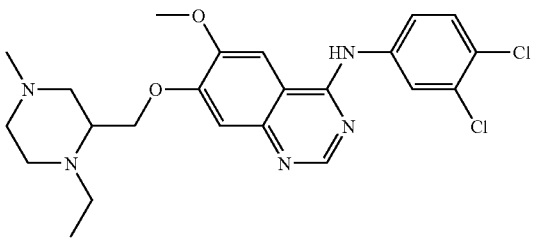 |
| 312 | N'-cyano-2-({-4-[(3,4-dichtorophenyl)aminol-6-(methyloxy)quinazolin-7-yl]oxy}methyl)morpholine-4-carboximidamide | 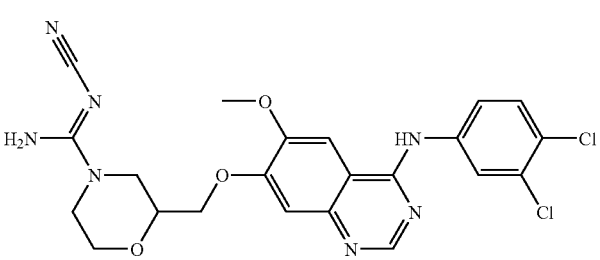 |
| 313 | N-(3,4-dichlorophenyl)-6-(methyloxy)-7-({[2-(pyrrolidin-1-ylmethyl)-1,3-thiazol-4-yl]methyl}oxy)quinazolin-4-amine | 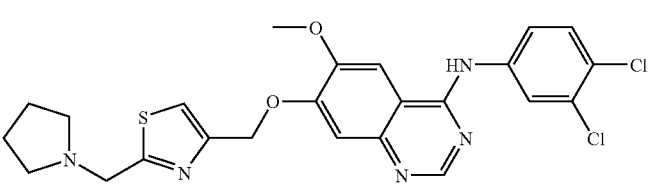 |
| 314 | N-(3,4-dichlorophenyl)-6-(methyloxy)-7-({[4-(tetrahydro-2H-pyran-4-yl)morpholin-2-yl]methyl}oxy)quinazolin-4-amine | 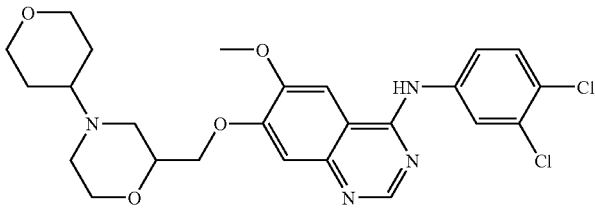 |
| 315 | N-(3,4-dichlorophenyl)-7-({[4-(2-ethylbutyl)morpholin-2-yl]methyl]oxy})-6-(methyloxy)quinazolin-4-amine | 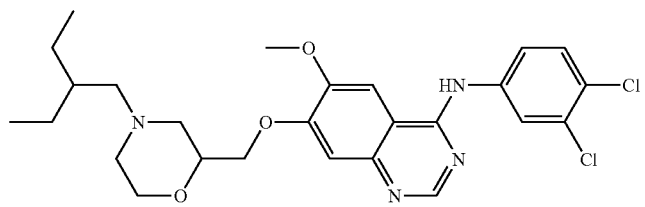 |

TABLE 1-continued

| | | |
|---|---|---|
| 316 | 7-({[4-(cyclohexylmethyl)morpholin-2-yl]methyl}oxy)-N-(3,4-dichlorophenyl)-6-(methyloxy)quinazolin-4-amine | |
| 317 | 2-[2-({[4-[(3,4-dichlorophenyl)amino]-6-(methyloxy)quinazolin-7-yl]oxy}methyl)morpholin-4-yl]ethanol | |
| 318 | 7-{[(4-but-2-yn-1-ylmorpholin-2-yl)methyl]oxy}-N-(3,4-dichlorophenyl)-6-(methyloxy)quinazolin-4-amine | |
| 319 | 7-{[(4-cyclobutylmorpholin-2-yl)methyl]oxy}-N-(3,4-dichlorophenyl)-6-(methyloxy)quinazolin-4-amine | |
| 320 | N-(3,4-dichlorophenyl)-7-[({4-[2-(1,3-dioxolan-2-yl)ethyl]morpholin-2-yl}methyl)oxy]-6-(methyloxy)quinazolin-4-amine | |
| 321 | 7-({[4-(2-cyclohexylethyl)morpholin-2-yl]methyl}oxy)-N-(3,4-dichlorophenyl)-6-(methyloxy)quinazolin-4-amine | |
| 322 | N-(3,4-dichlorophenyl)-7-[({4-[2-(1,3-dioxan-2-yl)ethyl]morpholin-2-yl}methyl)oxy]-6-(methyloxy)quinazolin-4-amine | |

TABLE 1-continued

| | | |
|---|---|---|
| 323 | N-(3,4-dichlarophenyl)-6-(methyloxy)-7-{[(4-pent-4-en-1-ylmorpholin-2-yl)methyl]oxy}quinazolin-4-amine | |
| 324 | N-(3,4-dichlorophenyl)-7-[({4-[(2R)-2-methylbutyl]morpholin-2-yl}methyl)oxy]-6-(methyloxy)quinazolin-4-amine | |
| 325 | N-(3,4-dichlorophenyl)-7-({[4-(4-fluorobutyl)morpholin-2-yl]methyl}oxy)-6-(methyloxy)quinazolin-4-amine | |
| 326 | 3-[2-({[4-[(3,4-dichlorophenyl)aminol-6-(methyloxy)quinazolin-7-yl]oxy}methyl)morpholin-4-y-butan-2-one | |
| 327 | 1-[2-({[4-[(3,4-dichlorophenyl)amino]-6-(methyloxy)quinazolin-7-yl]oxy}methyl)morpholin-4-yl]butan-2-one | |
| 328 | N-(3,4-dichlorophenyl)-6-(methyloxy)-7-{[(4-pentylmorpholin-2-yl)methyl]oxy}quinazolin-4-amine | |
| 329 | N-(3,4-dichlorophenyl)-7-{[(4-hexylmorpholin-2-yl)methyl]oxy}-6-(methyloxy)quinazolin-4-amine | |
| 330 | N-(3,4-dichlorophenyl)-7-{[(4-heptylmorpholin-2-yl)methyl]oxy)-6-(methyloxy)quinazolin-4-amine - | |

TABLE 1-continued

| | | |
|---|---|---|
| 331 | N-(3,4-dichlorophenyl)-6-(methyloxy)-7-{[(4-octylmorpholin-2-yl)methyl]oxy}quinazolin-4-amine | |
| 332 | N-(3,4-dichlorophenyl)-6-(methyloxy)-7-({[4-(2-phenylethyl)morpholin-2-yl]methyl}oxy)quinazolin-4-amine | |
| 333 | 7-{[(4-butylmorpholin-2-yl)methyl]oxy}-N-(3,4-dichlorophenyl)-6-(methyloxy)quinazolin-4-amine | |
| 334 | N-(3,4-dichlorophenyl)-6-(methyloxy)-7-{[(4-prop-2-en-1-ylmorpholin-2-yl)methyl]oxy}quinazolin-4-amine | |
| 335 | 2-[2-({[44(3,4-dichlorophenyl)amino]-6-(methyloxy)quinazolin-7-yl]oxy}methyl)morpholin-4-yl]-1-phenylethanone | |
| 336 | N-(3,4-dichlorophenyl)-7-({[4-(2-fluoroethyl)morpholin-2-yl]methyl}oxy)-6-(methyloxy)quinazolin-4-amine | |
| 337 | N-(3,4-dichlorophenyl)-7-({[4-(3-methylbut-2-en-1-yl)morpholin-2-yl]methyl}oxy)-6-(methyloxy)quinazolin-4-amine | |
| 338 | 7-[({4-[(2E)-3-bromoprop-2-en-1-yl]morpholin-2-yl}methyl)oxy]-N-(3,4-dichlorophenyl)-6-(methyloxy)quinazolin-4-amine | |

TABLE 1-continued

| | | |
|---|---|---|
| 339 | 2-[2-({[4-[(3,4-dichlorophenyl)amino]-6-(methyloxy)quinazolin-7-yl]oxy}methyl)morpholin-4-yl]acetamide | |
| 340 | N-(3,4-dichlorophenyl)-6-(methyloxy-7-[({4-(3-tetrahydro-2H-pyran-2-yloxy)propyl]-1,4-oxazepan-2-yl}methyl)oxy]quinazolin-4-amine | |
| 341 | N-(3,4-dichlorophenyl)-7-({[4-(3-methylbutyl)-1,4-oxazepan-2-yl]methyl}oxy)-6-(methyloxy)quinazolin-4-amine | |
| 342 | 7-({[4-(cyclohexylmethyl)-1,4-oxazepan-2-yl]methyl}oxy)-4-[(3,4-dichlorophenyl)methyl]-6-(methyloxy)quinazoline | |
| 343 | 7-({[4-(2-cyclohexylethyl)-1,4-oxazepan-2-yl]methy}oxy)-4-[(3,4-dichlorophenyl)methyl]-6-(methyloxy)quinazoline | |
| 345 | N-(3,4-dichlorophenyl)-7-({[4-(2-ethylbutyl)-1,4-oxazepan-2-yl]methyl}oxy)-6-(methyloxy)quinazolin-4-amine | |
| 346 | N-(3,4-dichlorophenyl)-6-(methyloxy)-7-({[4-(methylsulfonyl)-1,4-oxazepan-2-yl]methyl}oxy)quinazolin-4-amine | |

TABLE 1-continued

| | | |
|---|---|---|
| 347 | N-(3,4-dichlorophenyl)-6-(methyloxy)-7-({[4-(1-methylpiperidin-4-yl)morpholin-2-yl]methyl}oxy)quinazolin-4-amine | 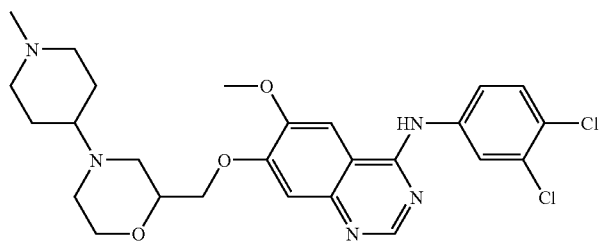 |
| 348 | N-(3-chloro-2-fluorophenyl)-7-{[(4-methylmorpholin-2-yl)methyl]oxy}-6-(methyloxy)quinazolin-4-amine | 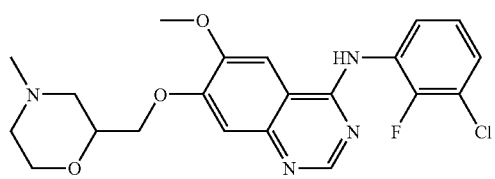 |
| 349 | N'-cyano-2-({[4-[(3,4-dichlorophenyl)amino]-6-(methyloxy)quinazolin-7-yl]oxy]methyl)-1,4-oxazepane-4-carboximidamide | 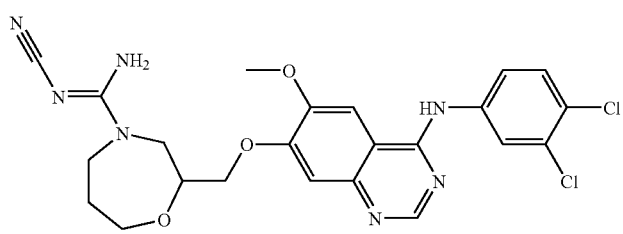 |
| 350 | N-(3-bromo-4-methylphenyl)-7-{[(4-methylmorpholin-2-yl)methyl]oxy}-6-(methyloxy)quinazolin-4-amine | 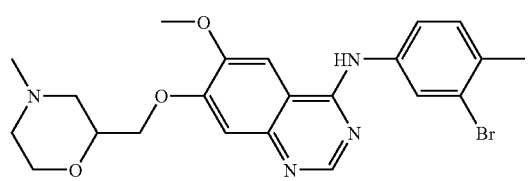 |
| 351 | N-(3,4-dichlorophenyl)-7-{[(1,4-diethylpiperazin-2-yl)methyl]oxy}-6-(methyloxy)quinazolin-4-amine | 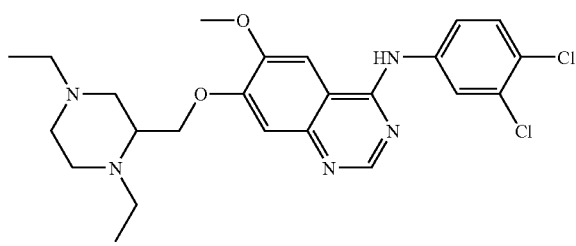 |
| 352 | 4-({[4-[(4-bromo-2-fluorophenyl)amino]-6-(methyloxy)quinazolin-7-yl]oxy}methyl)-N'-cyanopiperidine-1-carboximidamide | 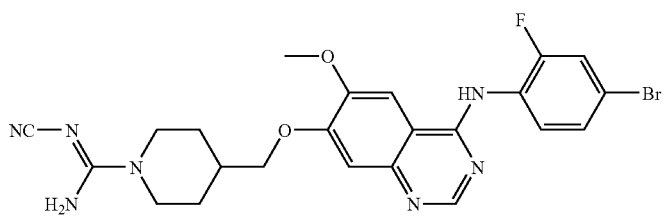 |
| 353 | N-(3,4-dichlorophenyl)-6-(methyloxy)-7-({[4-(methylsulfonyl)morpholin-2-yl]methyl}oxy)quinazolin-4-amine | 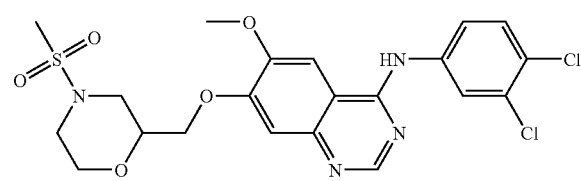 |

TABLE 1-continued

| | | |
|---|---|---|
| 354 | N-(3,4-dichlorophenyl)-6-(methyloxy)-7-[({4-[(phenylmethyl)sulfonyl]morpholin-2-yl}methyl)oxy]quinazolin-4-amine | 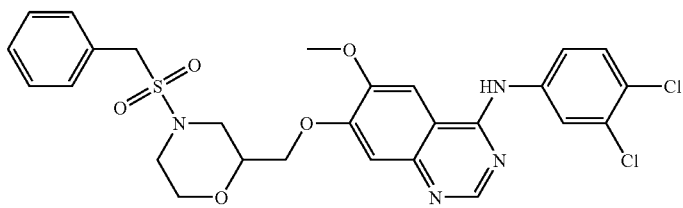 |
| 355 | N-(3,4-dichlorophenyl)-7-[({4-[(4-fluorophenyl)sulfonyl]morpholin-2-yl}methyl)oxy]-6-(methyloxy)quinazolin-4-amine | 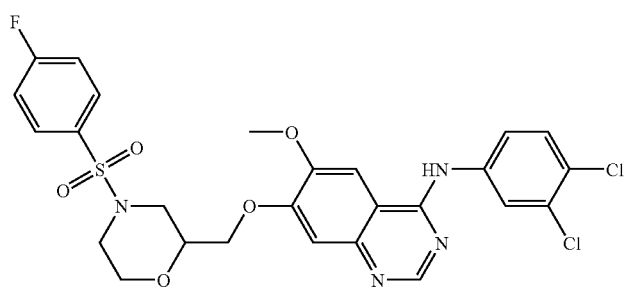 |
| 356 | N-(3,4-dichlorophenyl)-7-({[4-(ethylsulfonyl)morpholin-2-yl]methyl}oxy)-6-(methyloxy)quinazolin-4-amine | 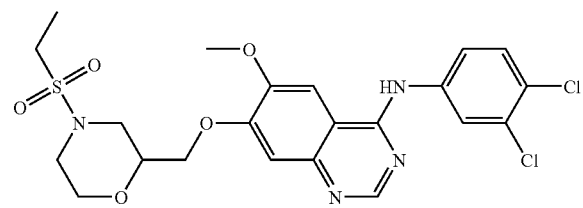 |
| 357 | N-(3,4-dichlorophenyl)-6-(methyloxy)-7-({[4-(phenylsulfonyl)morpholin-2-yl]methyl}oxy)quinazolin-4-amine | 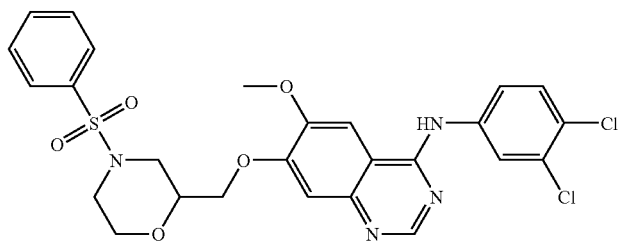 |
| 358 | 7-[({4-[(3-chloropropyl)sulfonyl]morpholin-2-yl}methyl)oxy]-N-(3,4-dichlorophenyl)-6-(methyloxy)quinazolin-4-amine | 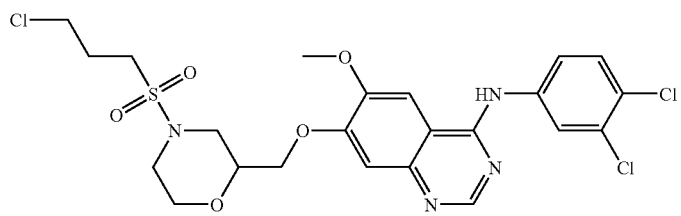 |
| 359 | 7-({[4-(butylsulfonyl)morpholin-2-yl]methyl}oxy)-N-(3,4-dichlorophenyl)-6-(methyloxy)quinazolin-4-amine | 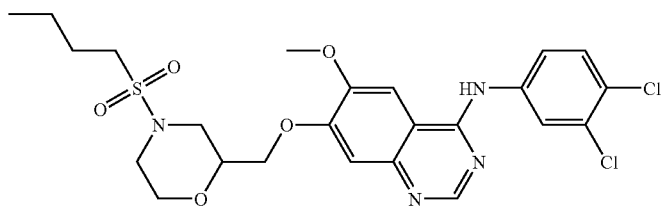 |

TABLE 1-continued

| | | |
|---|---|---|
| 360 | N-(3,4-dichlorophenyl)-6-(methyloxy)-7-[({4-[(4-methylphenyl)sulfonyl]morpholin-2-yl}methyl)oxy]quinazolin-4-amine | |
| 361 | N-(3,4-dichlorophenyl)-7-[({4-[(3,5-dimethylisoxazol-4-yl)carbonyl]morpholin-2-yl}methyl)oxy]-6-(methyloxy)quinazolin-4-amine | |
| 362 | N-(3,4-dichlorophenyl)-6-(methyloxy)-7-{[(4-{[3-(methyloxy)phenyl]acetyl}morpholin-2-yl)methyl]oxy}quinazolin-4-amine | |
| 363 | N-(3,4-dichlorophenyl)-6-(methyloxy)-7-({[4-(2-methylpentanoyl)morpholin-2-yl]methyl}oxy)quinazolin-4-amine | |
| 364 | 7-[({4-[(4-butylphenyl)carbonyl]morpholin-2-yl}methyl)oxy]-N-(3,4-dichlorophenyl)-6-(methyloxy)quinazolin-4-amine | |
| 365 | 7-[({4-[(4-chlorophenyl)acetyl]morpholin-2-yl}methyl)oxy]-N-(3,4-dichlorophenyl)-6-(methyloxy)quinazolin-4-amine | |
| 366 | N-(3,4-dichlorophenyl)-6-(methyloxy)-7-({[4-(2-propylpentanoyl)morpholin-2-yl]methyl-oxy)quinazolin-4-amine | |

TABLE 1-continued

| | | |
|---|---|---|
| 367 | N-(3,4-dichlorophenyl)-6-(methyloxy)-7-({[4-(4-methylpentanoyl)morpholin-2-yl]methyl}oxy)quinazolin-4-amine | 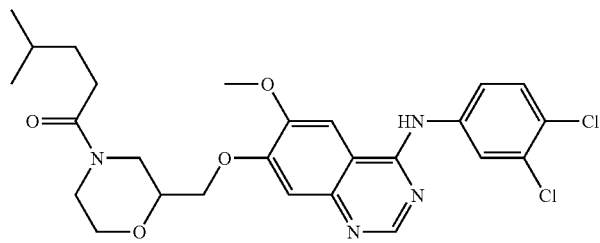 |
| 368 | N-(3,4-dichlorophenyl)-7-[({4-[(2,5-difluorophenyl)carbonyl]morpholin-2-yl}methyl)oxy]-6-(methyloxy)quinazolin-4-amine | 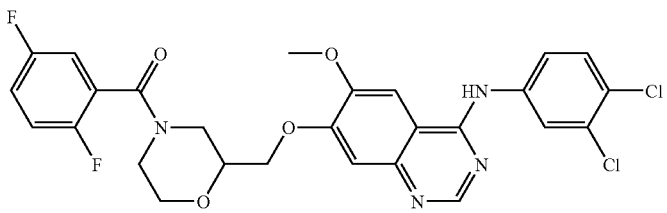 |
| 369 | 7-({[4-(cyclopentylcarbonyl)morpholin-2-yl]methyl-oxy)-N-(3,4-dichlorophenyl)-6-(methyloxy)quinazolin-4-amine | 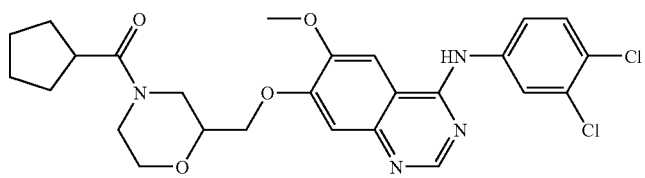 |
| 370 | N-(3,4-dichlorophenyl)-6-(methyloxy)-7-({[4-(2-phenyLbutanoyl)morpholin-2-yl]methyl}oxy)quinazolin-4-amine | 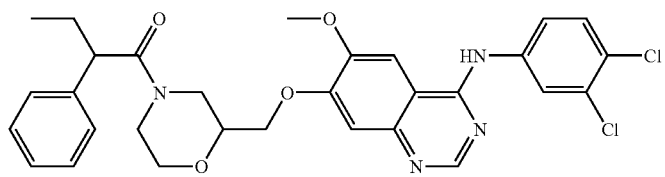 |
| 371 | N-(3,4-dichlorophenyl)-6-(methyloxy)-7-[({4-[(2,3,6-trifluorophenyl)carbonyl]morpholin-2-yl}methyl)oxy]quinazolin-4-amine | 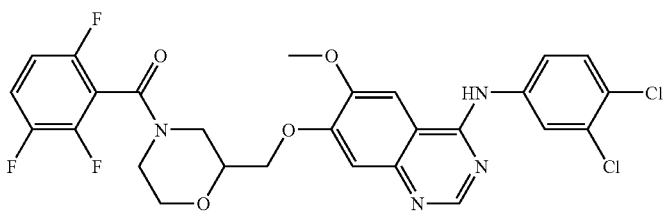 |
| 372 | N-(3,4-dichlorophenyl)-7-({[4-(furan-3-ylcarbonyl)morpholin-2-yl]methyl}oxy)-6-(methyloxy)quinazolin-4-amine | 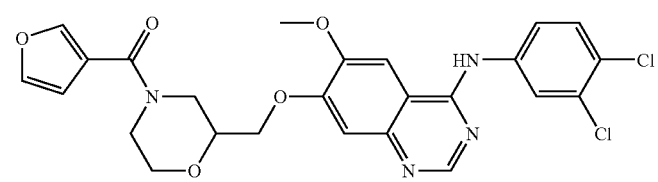 |
| 373 | N-(3,4-dichlorophenyl)-6-(methyloxy)-7-{[(4-propanoylmorpholin-2-yl)methyl]oxy}quinazolin-4-amine | 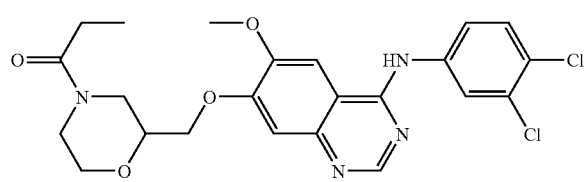 |
| 374 | N-(3,4-dichlorophenyl)-7-{[(4-hexanoylmorpholin-2-yl)methyl]oxy}-6-(methyloxy)quinazolin-4-amine | 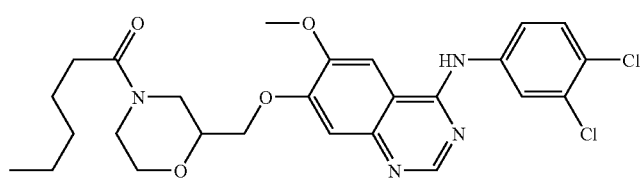 |

TABLE 1-continued

| 375 | N-(3,4-dichlorophenyl)-7-({[4-(2-ethylhexanoyl)morpholin-2-yl]methyl}oxy)-6-(methyloxy)quinazolin-4-amine | 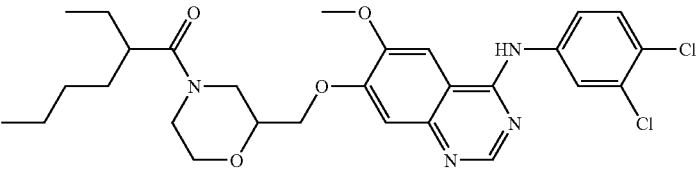 |
| --- | --- | --- |
| 376 | N-(3,4-dichlorophenyl)-6-(methyloxy)-7-({[4-(3-phenylpropanoyl)morpholin-2-yl]methyl}oxy)quinazolin-4-amine | 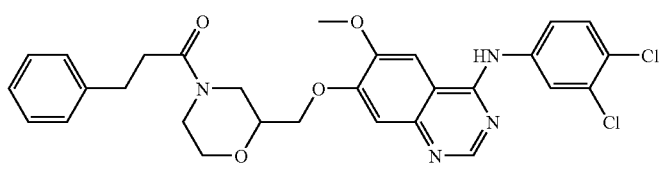 |
| 377 | N-(3,4-dichlorophenyl)-7-({[4-(2,2-dimethylpropanoyl)morpholin-2-yl]methyl)oxy)-6-(methyloxy)quinazolin-4-amine | 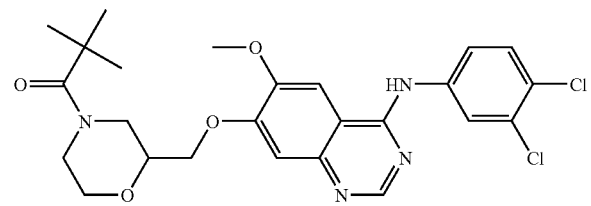 |
| 378 | N-(3,4-dichlorophenyl)-6-(methyloxy)-7-({[4-(naphthalen-1-ylcarbonyl)morpholin-2-yl]methyl)oxy)quinazolin-4-amine | 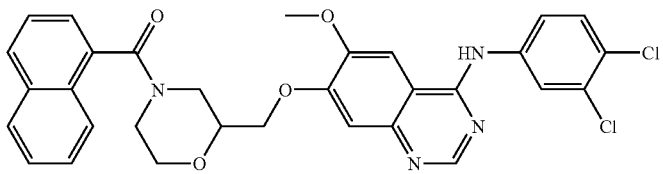 |
| 379 | 7-[({4-[(2-chloropyridin-3-yl)carbonyl]morpholin-2-yl}methyl)oxy]-N-(3,4-dichlorophenyl)-6-(methyloxy)quinazolin-4-amine | 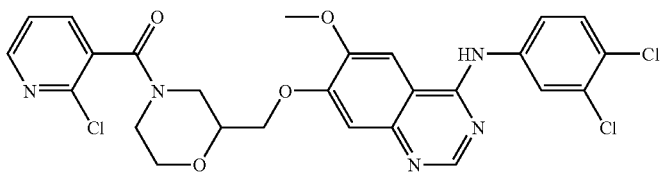 |
| 380 | 7-[({4-[(6-chloropyridin-3-yl)carbonyl]morpholin-2-yl}methyl)oxy]-N-(3,4-dichlorophenyl)-6-(methyloxy)quinazolin-4-amine | 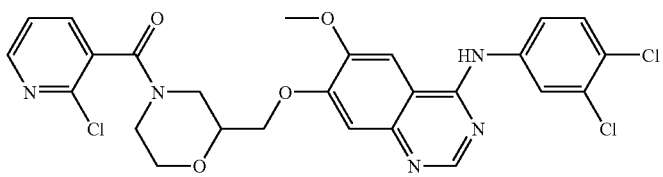 |
| 381 | 7-({[4-(1,3-benzodioxol-5-ylcarbonyl)morpholin-2-yl]methyl]oxy)-N-(3,4-dichlorophenyl)-6-(methyloxy)quinazolin-4-amine | 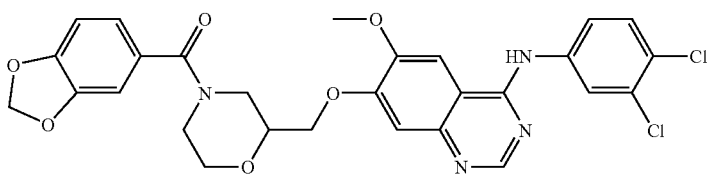 |
| 382 | N-(3,4-dichlorophenyl)-6-[(1-methylethyl)oxy]-7-[(morpholin-2-ylmethyl)oxy]quinazolin-4-amine | 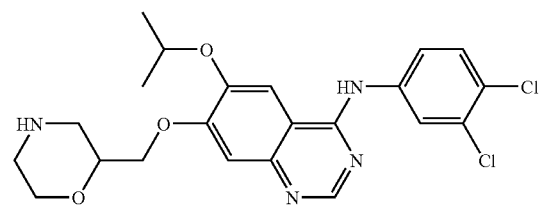 |

TABLE 1-continued

| | | |
|---|---|---|
| 383 | N-(3,4-dichlorophenyl)-6-{[2-(methyloxy)ethyl]oxy}-7-[(morpholin-2-ylmethyl)oxy]quinazolin-4-amine | |
| 384 | N-(3,4-dichlorophenyl)-6-(ethyloxy)-7-[(morpholin-2-ylmethyl)oxy]quinazolin-4-amine | |
| 385 | N-(3,4-dichlorophenyl)-6-(ethyloxy)-7-{[(4-methylmorpholin-2-yl)methyl]oxy}quinazolin-4-amine | |
| 386 | N-(4-bromo-2-methylphenyl)-7-{[(4-methylmorpholin-2-yl)methyl]oxy}-6-(methyloxy)quinazolin-4-amine | |
| 387 | N-(4-chloro-3-methylphenyl)-7-{[(4-methylmorpholin-2-yl)methyl]oxy}-6-(methyloxy)quinazolin-4-amine | |
| 388 | N'-cyano-2-({[4-[(3,4-diohlorophenyl)amino]-6-(methyloxy)quinazolin-7-yl]oxy}methyl)-N-methylmorpholine-4-carboximidamide | |
| 389 | N-(4-bromo-3-chlorophenyl)-7-{[(4-methylmorpholin-2-yl)methyl]oxy}-6-(methyloxy)quinazolin-4-amine | |
| 390 | N-(3,4-dichlorophenyl)-6-[(1-methylethyl)oxy]-7-{[(4-methylmorpholin-2-yl)methyl]oxy}quinazolin-4-amine | |

TABLE 1-continued

| | | |
|---|---|---|
| 391 | N-(3,4-dichlorophenyl)-7-{[(4-methylmorpholin-2-yl)methyl]oxy}-6-{[2-(methyloxy)ethyl]oxy}quinazolin-4-amine | |
| 392 | N-(4-bromo-2-chlorophenyl)-7-{[(4-methylmorpholin-2-yl)methyl]oxy}-6-(methyloxy)quinazolin-4-amine | |
| 393 | 7-{[(4-acetyl-1,4-oxazepan-2-yl)methyl]oxy}-N-(3,4-dichlorophenyl)-6-(methyloxy)quinazolin-4-amine | |
| 394 | 4-((3,4-dichlorophenyl)aminol-7-{[(4-methylmorphoiin-2-yl)methyl]oxy}quinazolin-6-ol | |
| 395 | N-(3-bromo-4-chlorophenyl)-7-{[(4-methylmorpholin-2-yl)methyl]oxy}-6-(methyloxy)quinazolin-4-amine | |
| 396 | 3-[2-({[4-[(3,4-dichlorophenyl)amino]-6-(methyloxy)quinazolin-7-yl]oxy}methyl)morpholin-4-yl]-3-oxopropanoic acid | |
| 397 | methyl 4-[2-(({[4-[(3,4-dichlorophenyl)amino]-6-(methyloxy)quinazolin-7-yl]oxy}methyl)morpholin-4-yl]-4-oxobutanoate | |
| 398 | N-(3,4-dichlorophenyl)-7-{[(4-methylmorpholin-3-yl)methyl]oxy}-6-(methyloxy)quinazolin-4-amine | |

TABLE 1-continued

| | | |
|---|---|---|
| 399 | N-(3-bromo-2-chlorophenyl)-7-{[(4-methylmorpholin-2-yl)methyl]oxy}-6-(methyloxy)quinazolin-4-amine | |
| 400 | N'-cyano-2-({[4-[(3,4-dichlorophenyl)amino]-6-(methyloxy)quinazolin-7-yl]oxy}methyl)-N-[2-(methyloxy)ethyl]morpholine-4-carboximidamide | |
| 401 | N'-cyano-2-({[4-[(3,4-dichlorophenyl)amino]-6-(methyloxy)quinazolin-7-yl]oxy]methyl)-N-ethylmorpholine-4-carboximidamide | |
| 402 | [(1E)-[2-({[4-[(3,4-dichlorophenyl)amino]-6-(methyloxy)quinazolin-7-yl]oxy}methyl)morphoiin-4-yl](piperidin-1-yl)methylidene]cyanamide | |
| 403 | [(1E)-[2-({[4-1(3,4-dichlorophenyl)amino]-6-(methyloxy)quinazolin-7-yl-oxy}methyl)morpholin-4-yl](pyrrolidin-1-yl)methylidene]cyanamide | |
| 404 | [(1E)-[2-({[4-[(3,4-dichlorophenyl)amino]-6-(methyloxy)quinazolin-7-yl]oxy}methyl)morpholin-4-yl](4-methylpiperazin-1-yl)methylidene]cyanamide | |

TABLE 1-continued

| | | |
|---|---|---|
| 405 | N-(3,4-dichlorophenyl)-7-{[(6-ethyl-4,6-dimethylmorpholin-2-yl)methyl]oxy}-6-(methyloxy)quinazolin-4-amine | |
| 406 | N-(4-bromo-3-methylphenyl)-7-{[(4-methylmorpholin-2-yl)methyl]oxy}-6-(methyloxy)quinazolin-4-amine | |
| 407 | N-(3,4-dichlorophenyl)-7-{[(6,6-dimethylmorpholin-2-yl)methyl]oxy}-6-(methyloxy)quinazolin-4-amine | |
| 408 | N-(3,4-dichlorophenyl)-6-(methyloxy)-7-{[(4,6,6-trimethylmorpholin-2-yl)methyl]oxy}quinazolin-4-amine | |
| 409 | N-(3,4-dichlorophenyl)-7-{[2-(5,5-dimethylmorpholin-2-yl)ethyl]oxy}-6-(methyloxy)quinazolin-4-amine | |
| 410 | N-(3,4-dichlorophenyl)-6-(methyloxy)-7-{[2-(4,5,5-trimethylmorpholin-2-yl)ethyl]oxy}quinazolin-4-amine | |
| 411 | 1,1-dimethylethyl 2-(2-{[4-[(3,4-dichlorophenyl)amino]-6-(methyloxy)quinazolin-7-yl]oxy}ethyl)-5,5-dimethylmorpholine-4-carboxylate | |

TABLE 1-continued

| | | |
|---|---|---|
| 412 | N-(3,4-dichlorophenyl)-6-(methyloxy)-7-{[(4,5,5-trimethylmorpholin-2-yl)methyl]oxy}quinazolin-4-amine | |
| 413 | N-(4-bromo-2,3-dichloropheriyl)-7-{[(4-methylmorpholin-2-yl)methyl]oxy]-6-(methyloxy)quinazolin-4-amine | |
| 414 | N-(4,5-dichloro-2-fluorophenyl)-7-{[(4-methylmorpholin-2-yl)methyl]oxy}-6-(methyloxy)quinazolin-4-amine | |
| 415 | N-(3,4-dichlorophenyl)-6-(methyloxy)-7-{[2-(4,6,6-trimethylmorpholin-2-yl)ethyl]oxy}quinazolin-4-amine | |
| 416 | N-(4-bromo-2,3-difluorophenyl)-7-{[(4-methylmorpholin-2-yl)methyl]oxy}-6-(methyloxy)quinazolin-4-amine | |
| 417 | N-(4-bromo-2,5-difluorophenyl)-7-{[(4-methylmorpholin-2-yl)methyl]oxy)-6-(methyloxy)quinazolin-4-amine | |
| 418 | N-(4-bromo-3,5-difluorophenyl)-7-{[(4-methylmorpholin-2-yl)methyl]oxy}-6-(methyloxy)quinazolin-4-amine | |

TABLE 1-continued

| | | |
|---|---|---|
| 419 | N-(3,4-dichloro-2-methylphenyl)-7-{[(4-methylmorpholin-2-yl)methyl]oxy}-6-(methyloxy)quinazolin-4-amine | |
| 420 | N-(3,4-dichlorophenyl)-7-({[(2R,5s,6S)-5,6-dimethylmorpholin-2-yl]methyl}oxy)-6-(methyloxy)quinazolin-4-amine | |
| 421 | N-(3,4-dichlorophenyl)-6-(methyloxy)-7-({[(2R,5s,6S)-4,5,6-trimethylmorpholin-2-yl]methyl}oxy)quinazolin-4-amine | |
| 422 | N-(3,4-dichlorophenyl)-6-(methyloxy)-7-({[(2s,5s,6S)-4,5,6-trimethylmorpholin-2-yl]methyl}oxy)quinazolin-4-amine | |
| 423 | N-(4-bromo-3-chloro-2-methylphenyl)-7-{[(4-methylmorpholin-2-yl)methyl]oxy}-6-(methyloxy)quinazolin-4-amine | |
| 424 | N-(4-bromo-5-chloro-2-fluorophenyl)-7-{[(4-methylmorpholin-2-yl)methyl]oxy}-6-(methyloxy)quinazolin-4-amine | |
| 425 | N-(4-bromo-3-chloro-2-fluorophenyl)-7-{[(4-methylmorpholin-2-yl)methyl]oxy}-6-(methyloxy)quinazolin-4-amine | |
| 426 | N-(3,4-dichloro-2-fluorophenyl)-7-{[(4-methylmorpholin-2-yl)methyl]oxy}-6-(methyloxy)quinazolin-4-amine | |

TABLE 1-continued

| | | |
|---|---|---|
| 427 | N-(3-chloro-2,4-difluorophenyl)-7-{[(4-methylmorpholin-2-yl)methyl]oxy}-6-(methyloxy)quinazolin-4-amine | |
| 428 | N-(2,3-dichloro-4-methylphenyl)-7-{[(4-methylmorpholin-2-yl)methyl]oxy}-6-(methyloxy)quinazolin-4-amine | |
| 429 | 6-({[4-(3,4-dichlorophenyl)amino]-6-(methyloxy)quinazolin-7-yl]oxy}methyl)-3,3,4-trimethylmorpholin-2-one | |
| 430 | N-(4-bromo-2,3-dichlorophenyl)-6-(methyloxy)-7-{[(4,5,5-trimethylmorpholin-2-yl)methyl]oxy}quinazolin-4-amine | |
| 431 | N-(4-bromo-5-chloro-2-fluorophenyl)-6-(methyloxy)-7-{[(4,5,5-trimethylmorpholin-2-yl)methyl]oxy}quinazolin-4-amine | |
| 432 | N-(4,5-dichloro-2-fluorophenyl)-6-(methyloxy)-7-{[(4,5,5-trimethylmorpholin-2-yl)methyl]oxy}quinazolin-4-amine | |
| 433 | N-(3,4-dichloro-2-fluorophenyl)-6-(methyloxy)-7-{[(4,5,5-trimethylmorpholin-2-yl)methyl]oxy}quinazolin-4-amine | |

TABLE 1-continued

| | | |
|---|---|---|
| 434 | N-(4-bromo-3-chloro-2-fluorophenyl)-6-(methyloxy)-7-{[(4,5,5-trimethylmorpholin-2-yl)methyl]oxy}quinazolin-4-amine | |
| 435 | N-(3-chloro-2,4-difluorophenyl)-6-(methyloxy)-7-{[(4,5,5-trimethylfluorpholin-2-yl)methyl]oxy}quinazolin-4-amine | |
| 436 | (6S)-6-({[4-[(4-bromo-3-chloro-2-fluorophenyl)amino]-6-(methyloxy)quinazolin-7-yl]oxy}methyl)-4-methylpiperazin-2-one | |
| 437 | (6S)-6-({[4-[(3,4-dichloro-2-fluorophenyl)amino]-6-(methyloxy)quinazolin-7-yl]oxylmethyl)-4-methylpiperazin-2-one | |
| 438 | (6S)-6-({[4-[(4-bromo-3-chloro-2-fluorophenyl)amino)-6-(methyloxy)quinazolin-7-yl]oxy}methyl)-1,4-dimethylpiperazin-2-one | |
| 439 | (6S)-6-({[4-[(3,4-c]chloro-2-fluorophenyl)amino]-6-(methyloxy)quinazolin-7-yl]oxy}methyl)-1,4-dimethylpiperazin-2-one | |
| 440 | N-(4-bromo-3-chlorophenyl)-7-{[(3a'S,4R,6'S,6a'R)-2,2-dimethyltetrahydrospiro[1,3-dioxolane-4,3'-furo[3,2-b]furan]-6'-yl]oxyl-6-(methyloxy)quinazolin-4-amine | |

TABLE 1-continued

| | | |
|---|---|---|
| 441 | 1,4:3,6-anhydro-2-O-[4{(4-bromo-3-(methyloxy)quinazolin-7-yl]-5-O-methyl-5-C-[(methyloxy)methyl]-L-glucitol | |
| 442 | 1,4:3,6-dianhydro-2-O-[4-[(4-bromo-3-chlorophenyl)amino]-6-(methyloxy)quinazolin-7-yl]-5-O-(methylsulfonyl)-L-glucitol | |
| 443 | 1,4:3,6-dianhydro-2-O-14-[(4-bromo-3-chlorophenyl)amino]-6-(methyloxy)quinazolin-7-yl]-L-glucitol | |
| 444 | 1,4:3,6-dianhydro-2-O-[4-{(4-bromo-3-chlorophenyl)amino]-6-(methyloxy)quinazolin-7-yl]-5-S-methyl-5-thio-D-iditol | |
| 445 | 1,4:3,6-dianhydro-2-O-[4-{(4-bromo-3-chlorophenyl)amino]-6-(methyloxy)quinazolin-7-yl]-2-deoxy-2-morpholin-4-yl-D-iditol | |
| 446 | 1,4:3,6-dianhydro-5-O-[4-[(4-bromo-3-chlorophenyl)amino]-6-(methyloxy)quinazolin-7-yl]-2-deoxy-2-(4-methylpiperazin-1-yl)-D-iditol | |
| 447 | 1,4:3,6-dianhydro-5-0-[4-[(4-bromo-3-chlorophenyl)amino]-6-(methyloxy)quinazolin-7-yl]-2-deoxy-2-pyrrolidin-1-yl-D-iditol | |

TABLE 1-continued

| | | |
|---|---|---|
| 448 | 2-O-acetyl-1,4:3,6-dianhydro-5-O-[4-[(4-bromo-3-chlorophenyl)amino]-6-(methyloxy)quinazolin-7-yl]-D-iditol | |
| 449 | 1,4:3,6-dianhydro-2-O-[4-[(4-bromo-3-chlorophenyl)amino]-6-(methyloxy)quinazolin-7-yl]-D-iditol | |
| 450 | 1,4:3,6-dianhydro-5-O-[4-[(4-bromo-3-chlorophenyl)amino]-6-(methyloxy)quinazolin-7-yl]-2-deoxy-2-(methylsulfonyl)-D-iditol | |
| 451 | 2-amino-1,4:3,6-dianhydro-5-O-[4-[(4-bromo-3-chlorophenyl)amino]-6-(methyloxy)quinazolin-7-yl]-2-deoxy-D-iditol | |
| 452 | 1,4:3,6-dianhydro-5-O-[4-[(4-bromo-3-chloropheriyl)amino]-6-(methyloxy)quinazolin-7-yl]-2-deoxy-2-(dimethylamino)-D-iditol | |
| 453 | 1,4:3,6-dianhydro-5-O-[4-[(4-bromo-3-chlorophenyl)amino]-6-(methyloxy)quinazolin-7-yl]-2-deoxy-2-(diethylamino)-D-iditol | |
| 454 | 1,4:3,6-dianhydro-5-O-[4-[(4-bromo-3-chlorophenyl)amino]-6-(methyloxy)quinazolin-7-yl]-2-deoxy-2-piperidin-1-yl-D-iditol | |

TABLE 1-continued

| | | |
|---|---|---|
| 455 | 2-(acetylamino)-1,4:3,6-dianhydro-5-O-[4-[(4-bromo-3-chlorophenyl)amino]-6-(methyloxy)quinazolin-7-yl]-2-deoxy-D-iditoi | |
| 456 | 1,4:3,6-dianhydro-2-O-[4-[(4-bromo-3-chlorophenyl)aminol-6-(methyloxy)quinazolin-7-yl]-5-O-methyl-5-C-(trifluoromethyl)-L-giucitol | |
| 457 | 1,4:3,6-dianhydro-5-O-[4-[(4-bromo-3-chlorophenyl)amino]-6-(methyloxy)quinazolin-7-yl]-2-deoxy-2-[(methylsulfonyl)amino]-D-iditol | |
| 458 | N-(4-bromo-3-chlorophenyl)-6-(methyloxy)-7-[(1-methylpyrrolidin-3-yl)oxy]quinazolin-4-amine | |
| 459 | N-(4-bromo-3-chlorophenyl)-6-(methyloxy)-7-[(3R)-tetrahydrofuran-3-yloxy]quinazolin-4-amine | |
| 460 | N-(4-bromo-3-chlorophenyl)-6-(methyloxy)-7-{[(3S,4R)-4-(methyloxy)tetrahydrofuran-3-yl]oxy}quinazolin-4-amine | |
| 461 | 1,4:3,6-dianhydro-2-deoxy-2-fluoro-5-O-(6-(methyloxy)-4-{[4-(4-methylpiperazin-1-yl)phenyl]amino-quinazolin-7-yl)-D-iditol | |

TABLE 1-continued

| | | |
|---|---|---|
| 462 | 1,4:3,6-dianhydro-2-deoxy-2-fluoro-5-O-[4-{[3-fluoro-4-(4-methylpiperazin-1-yl)phenyl]amino}-6-(methyloxy)quinazolin-7-yl]-D-iditol | |
| 463 | 1,4:3,6-dianhydro-2-deoxy-5-O-[4-{[2,3-dichloro-4-(4-methylpiperazin-1-yl)phenyl]amino}-6-(methyloxy)quinazolin-7-yl]-2-fluoro-D-iditol | |
| 464 | 1,4:3,6-dianhydro-2-deoxy-5-O-[4-{[3,4-dichloro-2-(4-methylpiperazin-1-yl)phenyl]amino}-6-(methyloxy)quinazolin-7-yl]-2-fluoro-D-iditol | |
| 465 | 1,4:3,6-dianhydro-2-O-[4-[(4-bromo-3-chlorophenyl)amino]-6-(methyloxy)quinazolin-7-yl]-5-C-(trifluoromethyl)-D-glucitol | |
| 466 | (3,4-dichlorophenyl)[6-(methyloxy)-7-({[4-(tetrahydrofuran-2-ylmethyl)-1,4-oxazepan-2-yl]methyl}oxy)quinazolin-4-amine | |

Embodiment 81: Another aspect of the invention is a pharmaceutical composition comprising a compound according to any one of embodiments [0024]-[0080] and a pharmaceutically acceptable carrier.

Embodiment 82: Another aspect of the invention is a metabolite of the compound, and optionally together with a pharmaceutically acceptable carrier, according to any one of embodiments [0024]-[0081].

Embodiment 83: Another aspect of the invention is a method of modulating the in vivo activity of a kinase, the method comprising administering to a subject an effective amount of the compound, and optionally together with a pharmaceutically acceptable carrier, according to any of embodiments [0024]-[0081].

Embodiment 84: Another aspect of the invention is a method according to embodiment [0083], wherein the kinase is selected from ephrin and EGFR.

Embodiment 85: Another aspect of the invention is a method of modulating the in vivo activity of a plurality of kinases, the method comprising administering to a subject an effective amount of the compound, and optionally together with a pharmaceutically acceptable carrier, according to any of embodiments [0024]-[0081].

Embodiment 86: Another aspect of the invention is a method according to embodiment [0085], wherein the plurality of kinases comprises at least one of ephrin and EGFR.

Embodiment 87: Another aspect of the invention is a method according to Embodiment [0084], wherein modulating the in vivo activity of the kinase comprises inhibition of said kinase.

Embodiment 88: Another aspect of the invention is a method according to embodiment [0086], wherein modulating the in vivo activity of the plurality of kinases comprises inhibition of at least one of ephrin and EGFR.

Embodiment 89: Another aspect of the invention is a method of treating diseases or disorders associated with uncontrolled, abnormal, and/or unwanted cellular activities, the method comprising administering, to a mammal in need thereof, a therapeutically effective amount of the compound, and optionally together with a pharmaceutically acceptable carrier, as described in any one of embodiments [0024]-[0081].

Definitions

As used in the present specification, the following words and phrases are generally intended to have the meanings as set forth below, except to the extent that the context in which they are used indicates otherwise or they are expressly defined to mean something different.

The atom numbering convention for the quinazoline structure is as follows:

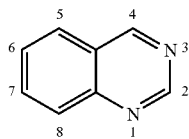

The symbol "—" means a single bond, "=" means a double bond, "≡" means a triple bond. The symbol ∿∿∿refers to a group on a double-bond as occupying either position on the terminus of a double bond to which the symbol is attached; that is, the geometry, E- or Z-, of the double bond is ambiguous. When a group is depicted removed from its parent formula, the "∿" symbol will be used at the end of the bond which was theoretically cleaved in order to separate the group from its parent structural formula.

If a group "R" is depicted as "floating" on a ring system, as for example in the formula:

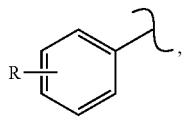

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

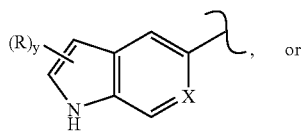

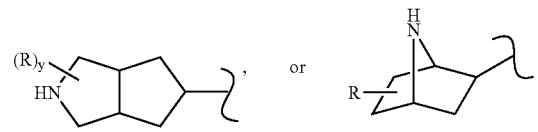

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals —CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

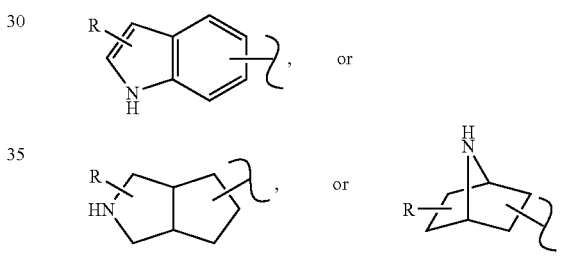

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

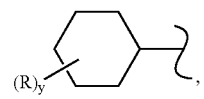

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon). In another example, two R's on the same carbon, including that carbon, may form a ring, thus creating a spirocyclic ring (a "spirocyclyl" group) structure with the depicted ring as for example in the formula:

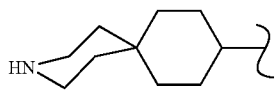

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and "propyl" or "$C_3$ alkyl" each include n-propyl, propenyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH$($C_6H_{13}$)).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond and a double bond can exist between the first carbon of the chain and a carbon atom of the rest of the molecule to which it is attached.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond and a triple bond can exist between the first carbon of the chain and a carbon atom of the rest of the molecule to which it is attached.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —O($CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Aryl" refers to aromatic six- to fourteen-membered carbocyclic rings include, for example, benzene, naphthalene, indane, tetralin, fluorene and the like.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. The aryl, alkylene, alkylidene, or alkylidyne radical portion of an arylalkyl group may be optionally substituted. "Lower arylalkyl" refers to an arylalkyl where the "alkyl" portion of the group has one to six carbons.

"Exo-alkenyl" refers to a double bond that emanates from an annular carbon, and is not within the ring system, for example the double bond depicted in the formula below.

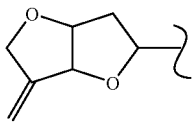

"Fused-polycyclic" or "fused ring system" refers to a polycyclic ring system that contains bridged or fused rings; that is, where two rings have more than one shared atom in their ring structures. Typically, but not necessarily, fused-polycyclics share a vicinal set of atoms. Typically, a spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems, and the nitrogen, phosphorus, carbon or sulfur atoms in the heterocyclyl radical may be optionally oxidized to various oxidation states. In addition, the nitrogen atom may be optionally quaternized; and the ring radical may be partially or fully saturated or aromatic. Examples of such heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl system radical.

"Heteroaryl" refers specifically to an aromatic heterocyclyl system radical.

"Heterocyclylalkyl" refers to a residue in which a heterocyclyl is attached to a parent structure via one of an alkylene, alkylidene, or alkylidyne radical. Examples include (4-methylpiperazin-1-yl)methyl, (morpholin-4-yl)methyl, 2-(oxazolin-2-yl)ethyl, 4-(4-methylpiperazin-1-yl)-2-butenyl, and the like. The heterocyclyl, alkylene, alkylidene, or alkylidyne radical portion of an arylalkyl group may be optionally substituted. "Lower heterocyclylalkyl" refers to an arylalkyl where the "alkyl" portion of the group has one to six carbons.

"Hydrocarbyl" refers to a hydrocarbon residue, generally. The term "hydrocarbyl" can be modified to mean more specific structures, for example "a saturated or mono- or poly-unsaturated $C_3$-$C_{14}$ mono- or fused-polycyclic hydrocarbyl optionally containing one, two, or three annular heteroatoms per ring" means a mono- or polycyclic (for example a bridged bicyclic) ring system, having between three and fourteen-ring atoms, that contains only carbon ring atoms, but optionally can contain up to three heteratoms per ring and/or unsaturation.

"Optional" or "optionally" means that the subsequently described event or circumstance may or may not occur, and that the description includes instances where said event or circumstance occurs and instances in which it does not. It will be understood by those skilled in the art with respect to any group containing one or more substituents that such groups are not intended to introduce any substitution or substitution patterns (for example, substituted alkyl includes optionally substituted cycloalkyl groups, which in turn are defined as including optionally substituted alkyl groups that are sterically impractical and/or synthetically non-feasible. "Optionally substituted" refers to all subsequent modifiers in a term, for example in the term "optionally substituted aryl$C_{1-8}$ alkyl," optional substitution may occur on both the "$C_{1-8}$ alkyl" portion and the "aryl" portion of the molecule; and for example, optionally substituted alkyl includes optionally substituted cycloalkyl groups, which in turn are defined as including optionally substituted alkyl groups. Examples of optional substitution include, but are not limited to alkyl, halogen, alkoxy, hydroxy, oxo, carbamyl, acylamino, sulfonamido, carboxy, alkoxycarbonyl, acyl, alkylthio, alkylsulfonyl, nitro, cyano, amino, alkylamino, cycloalkyl and the like.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, 2,3,3a,4,7,7a-hexahydro-1H-indene, 7-aza-bicyclo[2.2.1]heptane and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, a ring atom of the aforementioned saturated bridged ring system, but not a bridgehead atom, can be a shared atom between the saturated bridged ring system (rings B and B') and a spirocyclyl (ring A) attached thereto, as depicted below. A spirocyclyl can be either carbocyclic or heterocyclic

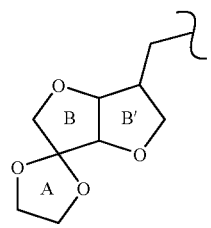

"Substituted" alkyl, aryl, and heterocyclyl, refer respectively to alkyl, aryl, and heterocyclyl, wherein one or more (for example up to about five, in another example, up to about three) hydrogen atoms are replaced by a substituent independently selected from the group: optionally substituted alkyl (for example, fluoroalkyl), optionally substituted alkoxy, alkylenedioxy (for example methylenedioxy), optionally substituted amino (for example, alkylamino and dialkylamino), optionally substituted amidino, optionally substituted aryl (for example, phenyl), optionally substituted arylalkyl (for example, benzyl), optionally substituted aryloxy (for example, phenoxy), optionally substituted arylalkyloxy (for example, benzyloxy), carboxy (—COOH), carboalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heterocyclylalkyl, optionally substituted heterocyclyl, nitro, sulfanyl, sulfinyl, sulfonyl, and thio.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S($O_2$)—H, —S($O_2$)-(optionally substituted alkyl), —S($O_2$)-optionally substituted aryl), —S($O_2$)-(optionally substituted heterocyclyl), —S($O_2$)-(optionally substituted alkoxy), —S($O_2$)-optionally substituted aryloxy), and —S($O_2$)-(optionally substituted heterocyclyloxy).

"Yield" for each of the reactions described herein is expressed as a percentage of the theoretical yield.

In some embodiments, as will be appreciated by those skilled in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are generally named using ACD/Name (available from Advanced Chemistry Development, Inc. of Toronto, Canada). This software derives names from chemical structures according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one skilled in the art would recognize that there can theoretically be some constructs which would not normally be considered as stable compounds. Stable constructs for the saturated bridged ring system as represented by $X^1$, $X^2$, and optionally $X^3$ of formula II include but are not limited to motifs such as: 1) where heteroatoms of a ring or bridge thereon are bonded directly to each other, for example a bridge containing a sulfonamide, 2) where heteroatoms of a ring or bridge thereon are separated by only one carbon, for example a urea, carbamate, acetal, aminal, thioacetal, thioaminal, amidine, guanidine, and the like, 3) where heteroatoms of a ring or bridge thereon are separated by two or more carbons, for example an —$NHCH_2CH_2O$— bridge, and the like, and 4) where heteroatoms in the bridged ring system are separated by more than two carbon atoms, for example wherein the bridged ring system is a decahydro-isoquinoline.

When a particular group with its bonding stucture is denoted as being bonded to two partners, for example a linking group such as —$OCH_2$—, then it is understood that either of the two partners may be bound to the particular group at one end, and the other partner is necessarily bound to the other end of the particular group, unless stated explicitly otherwise.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. When desired, the R- and S-isomers may be resolved by methods known to those skilled in the art, for example by: formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by those skilled in the art.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

Utility of Compounds of the Invention as Screening Agents

To employ the compounds of the invention in a method of screening for candidate agents that bind to, for example ephrin or EGFR receptor kinase, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example ephrin or EGFR protein, may be done in a number of ways. In one example, the candidate agent (the compound of the invention) is labeled, for example, with a fluorescent or radioactive moiety and binding determined directly. For example, thus may be done by attaching all or a portion of ephrin or EGFR protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, for example, radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, ephrin or EGFR protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "Candidate bioactive agent" or "drug candidate" or grammatical equivalents as used herein describe any molecule, for example, protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to ephrin or EGFR.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to ephrin or EGFR, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to ephrin or EGFR for a time sufficient to allow binding, if present. Incubations may be performed at any temperature that facilitates optimal activity, typically between 4° C. and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to ephrin or EGFR and thus is capable of binding to, and potentially modulating, the activity of ephrin or EGFR. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to ephrin or EGFR with a higher affinity. Thus, if the candidate agent is labeled, the presence of the label on the support, coupled with a lack of competitor binding, may indicate the candidate agent is capable of binding to ephrin or EGFR.

It may be of value to identify the binding site of, for example, ephrin or EGFR. This can be done in a variety of ways. In one embodiment, once ephrin or EGFR has been identified as binding to the candidate agent, ephrin or EGFR is fragmented or modified and the assays repeated to identify the necessary components for binding.

Modulation is tested by screening for candidate agents capable of modulating the activity of ephrin or EGFR comprising the steps of combining a candidate agent with ephrin or EGEFR, as above, and determining an alteration in the biological activity of ephrin or EGFR. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to native ephrin or EGFR, but cannot bind to modified ephrin or EGFR.

Positive controls and negative controls may be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, for example, albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Abbreviations and their Definitions

The following abbreviations and terms have the indicated meanings throughout:

Ac=acetyl
ATP=adenosine triphosphate
BNB=4-bromomethyl-3-nitrobenzoic acid
Boc=t-butyloxycarbonyl
br=broad
Bu=butyl
C=degrees Celsius
c-=cyclo
CBZ=carbobenzoxy=benzyloxycarbonyl
d=doublet
dd=doublet of doublet
dt=doublet of triplet
DBU=diazabicyclo[5.4.0]undec-7-ere
DCM=dichloromethane=methylene chloride=$CH_2Cl_2$
DCE=1,2-dichloroethane
DEAD=diethyl azodicarboxylate
DIC=diisopropylcarbodiimide
DIEA=N,N-diisopropylethylamine
DMAP=4-N,N-dimethylaminopyridine
DMP=N,N-dimethylformamide
DMSO=dimethyl sulfoxide
DVB=1,4-divinylbenzene EEDQ=2-ethoxy-1-ethoxycarbonyl-1,2-dihydroquinoline
EI=Electron Impact ionization
Et=ethyl
Fmoc=9-fluorenylmethoxycarbonyl
g=gram(s)
GC=gas chromatography
h or hr=hour(s)
HATU=0-(7-Azabenzotriazol-1-yl)-1,1,3,3-tetramethyluronium hexafluorophosphate
HMDS=hexamethyldisilazane
HOAc=acetic acid
HOBt=hydroxybenzotriazole
HPLC=high pressure liquid chromatography
L=liter(s)
M=molar or molarity
m=multiplet
Me=methyl
mesyl=methanesulfonyl
mg=milligram(s)
MHz=megahertz (frequency)
Min=minute(s)
mL=milliliter(s)
mM=millimolar
mmol=millimole(s)
mol=mole(s)
MS=mass spectral analysis
MTBE=methyl t-butyl ether
N=normal or normality
NBS=N-bromosuccinimide
NCS=N-chlorosuccinimide
nM=nanomolar
NMO=N-methylmorpholine oxide
NMR=nuclear magnetic resonance spectroscopy
PEG=polyethylene glycol
pEY=poly-glutamine, tyrosine
Ph=phenyl
PhOH=phenol
Pfp=pentafluorophenol
PfPy=pentafluoropyridine
PPTS=pyridinium p-toluenesulfonate
Py=pyridine
PyBroP=bromo-tris-pyrrolidino-phosphonium hexafluorophosphate
q=quartet
RT=room temperature
Sat'd=saturated
s=singlet
s-=secondary
t-=tertiary
t or tr=triplet
TBDMS=t-butyldimethylsilyl
TES=triethylsilane
TFA=trifluoroacetic acid
THF=tetrahydrofuran
TMOF=trimethyl orthoformate
TMS=trimethylsilyl
tosyl=p-toluenesulfonyl
Trt=triphenylmethyl
uL=microliter(s)
uM=micromole(s) or micromolar Synthesis of Compounds

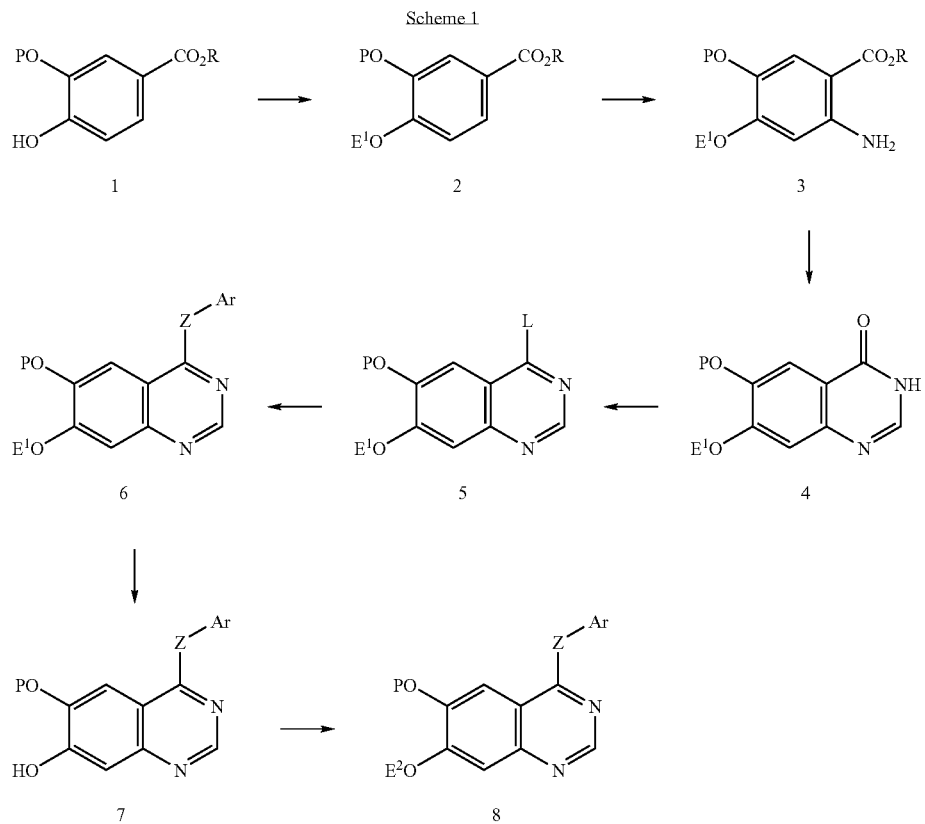

Scheme 1

Scheme 1 depicts a general synthetic route for compounds of the invention and is not intended to be limiting. Specific examples are described subsequently to this general synthetic description. A benzoic ester 1, where R is typically but not necessarily a methyl radical and P is typically but not necessarily an alkyl group, is O-alkylated at the oxygen para to the carboxylate group with an electrophile to afford a substituted derivative 2. P is typically a lower alkyl group, but can be a protecting group that is removed later in a synthesis. When P is a lower allyl group it can possess functionality initially, or be derivitized to contain such functionality at various stages of the synthesis. The group, $E^1$, represents either a protecting group, for example benzyl, or a group that either has moieties present in compounds of the invention or possesses functionality that serve as a precursors to such groups. Aromatic ring nitration and reduction of the corresponding nitro group are carried out in a regio- and chemoselective manner by methods well known in the art to give anthranilate derivative 3. Formation of quinazolin-4-one 4 is carried out by methods well known in the art, for example by heating 3 in formamide solution in the presence of ammonium formate, or for another example by heating directly with formamidine hydrochloride. Introduction of 4-position functionality is carried out by methods known in the art. For example, quinazolin-4-one 4 is converted to an intermediate quinazoline 5, where "V" represents a leaving group, for example chlorine. Quinazoline 5 is then converted to 6 by reaction with a range of nucleophiles, for example amines, alcohols, and thiols. After formation of 6, group "z" is either left "as is" or converted at some subsequent stage to a derivative thereof. For example when Z is —NH—, then the hydrogen on the nitrogen may optionally be replaced with an alkyl group, or when Z is sulfur, then that sulfur atom may be oxidized to, for example, a sulfone. Compound 6 may represent a compound of the invention or, for example when $E^1$ serves as a protecting group, $E^1$ may be removed to provide phenol 7. Introduction of a group $E^2$ is carried out by methods well established in the art, for example alkylation with an appropriately derivatized alkyl halide.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety. Generally, each example set out below describes a multi-step synthesis as outlined above.

Example 1

1,4:3,6-Dianhydro-2-O-[4-[(3-chloro-2-methylphenyl)amino]-6-(methyloxy)quinazolin-7-yl]-5-O-methyl-L-iditol 1,4:3,6-dianhydro-2-O-methyl-5-O-(methylsulfonyl)-D-glucitol: To a solution of 1,4:3,6-dianhydro-2-O-methyl-D-glucitol (1.19 g, 7.4 mmol) in dichloromethane was added pyridine (1 mL, 12.36 mmol) followed by methanesulfonyl chloride (0.69 mL, 8.92 mmol) and the mixture was allowed to stir at room temperature over 12 hours. The solvent was removed and the amorphous residue was partitioned between ethyl acetate and aqueous hydrochloric acid (for example 0.1M HCl). The aqueous phase was extracted once with additional ethyl acetate and the combined organic layers were washed with saturated aqueous sodium chloride then dried over anhydrous magnesium sulfate. Filtration and concentration followed by drying in vacuo afforded 1,4:3,6-dianhydro-2-O-methyl-5-O-(methylsulfonyl)-D-glucitol (1.67 g, 94% yield) as a colorless oil. GCMS calculated for $C_8H_{14}SO_6$: 238 ($M^+$).

4-[(3,4-dichlorophenyl)amino]-6-(methyloxy)quinazolin-7-ol: 4-Chloro-6-(methyl-oxy)-7-[(phenylmethyl)oxy]quinazoline hydrochloride (22.91 g, 67.9 mmol) was suspended in isopropanol followed by addition of 3,4-dichloroaniline (13.2 g, 81.5 mmol) and concentrated aqueous hydrochloric acid (1 mL). The mixture was brought to reflux over 12 hours and diluted with ethyl ether (150 mL). The solid was collected by filtration, washed with additional ethyl ether and dried. The material was then taken into trifluoroacetic acid (150 mL) and brought to reflux over 1 hour. The solution was cooled to room temperature then concentrated in vacuo to give a crystalline residue. The residue was suspended in acetonitrile (100 mL) followed by addition of ethyl ether (100 mL). The solid was collected by filtration and washed with additional ethyl ether then dried in vacuo to give 4-[(3,4-dichlorophenyl)amino]-6-(methyloxy)quinazolin-7-ol (21.49 g, 64% yield) as a tan solid. $^1$H NMR (400 MHz, $d_6$-DMSO): 11.09 (br s, 1H), 8.87 (s, 1H), 8.07 (d, 1H), 8.00 (s, 1H), 7.23 (s, 1H), 3.98 (s, 3H); MS (EI) for $C_{15}H_{11}N_3O_2Cl_2$: 337 ($MH^+$).

1,4:3,6-dianhydro-2-O-[4-[(3-chloro-2-methylphenyl)amino]-6-(methyloxy)quinazolin-7-yl]-5-O-methyl-L-iditol hydrochloride: A suspension of 4[(3,4-dichlorophenyl)amino]-6-(methyloxy)quinazolin-7-ol (1.70 g, 3.78 mmol), 1,4:3,6-dianhydro-2-O-methyl-5-O-(methylsulfonyl)-D-glucitol (1.00 g, 4.20 mmol), and potassium carbonate (2.64 g, 19.10 mmol) in DMF (20 mL) was stirred at 80° C. under nitrogen for 15 h. The reaction mixture was poured into water (100 mL), and extracted with ethyl acetate (3×50 mL). The organic layers were washed with 5% LiCl (2×50 mL), and brine (50 mL) then dried over anhydrous sodium sulfate. Filtration, concentration and column chromatography on silica (97:3 dichloromethane/methanol) gave a solid, which was dissolved in methanol (50 mL), and treated with 4M HCl in 1,4-dioxane (5 mL). The resulting precipitation was filtered, washed with methanol (2×20 mL), and dried to afford 0.99 g (51%) of 1,4:3,6-dianhydro-2-O-[4-[(3-chloro-2-methylphenyl)amino]-6-(methyloxy)quinazolin-7-yl]-5-O-methyl-L-iditol hydrochloride as a yellow solid. $^1$H NMR (400 MHz, $d_6$-DMSO): 11.51 (br s, 1H), 8.91 (s, 1H), 8.38 (s, 1H), 8.16 (d, 1H), 7.82 (dd, 1H), 7.76 (d, 1H), 7.42 (s, 1H), 5.03 (m, 1H), 4.66 (m, 2H), 4.11 (m, 1H), 4.04 (s, 3H), 4.02 (m, 1H), 3.90 (m, 3H), 3.31 (s, 3H); MS (EI) for $C_{22}H_{21}N_3O_5Cl_2$: 478 ($MH^+$).

Using the same or analogous synthetic techniques and/or substituting with alternative reagents, the following compounds of the invention were prepared:

1,4:3,6-dianhydro-2-O-[4-[(4-bromo-3-chloro-2-fluorophenyl)amino]-6-(methyloxy)quinazolin-7-yl]-5-O-methyl-L-iditol: $^1$H NMR (400 MHz, $d_6$-DMSO): 8.76 (s, 1H), 8.09 (s, 1H), 7.79 (dd, 1H), 7.55 (t, 1H), 7.39 (s, 1H), 5.10-5.06 (m, 1H), 4.65 (s, 2H), 4.11 (dd, 1H), 4.04-4.02 (m, 1H), 4.00 (s, 3H), 3.94-3.91 (m, 1H), 3.90-3.87 (m, 2H), 3.31 (s, 3H); MS (EI) for $C_{22}H_{20}BrClFN_3O_5$: 540 ($MH^+$).

1,4:3,6-dianhydro-2-O-[4-[(4-bromo-2,3-dichlorophenyl)amino]-6-(methyloxy)quinazolin-7-yl]-5-O-methyl-L-iditol: $^1$H NMR (400 MHz, $d_6$-DMSO): 8.77 (s, 1H), 8.13 (s, 1H), 7.96 (d, 1H), 7.56 (d, 1H), 7.42 (s, 1H), 5.10-5.06 (m, 1H), 4.66 (s, 2H), 4.12 (dd, 1H), 4.05-4.02 (m, 1H), 4.00 (s, 3H), 3.94-3.91 (m, 1H), 3.90-3.87 (m, 2H), 3.31 (s, 3H); MS (EI) for $C_{22}H_{20}BrCl_2N_3O_5$: 556 ($MH^+$).

1,4:3,6-Dianhydro-2-O-[4-[(3-chloro-2-methylphenyl) amino]-6-(methyloxy)quinazolin-7-yl]-5-O-methyl-L-iditol: $^1$H NMR (400 MHz, d$_6$-DMSO): 9.63 (s, 1H), 8.30 (s, 1H), 7.86 (s, 1H), 7.41 (m, 1H), 7.30 (m, 2H), 7.26 (s, 1H), 5.05 (br s, 1H), 4.63 (dd, 2H), 4.03 (ddd AB, 2H), 3.95 (s, 3H), 3.91 (s, 1H), 3.86 (d, 2H), 3.31 (s, 3H), 2.19 (s, 3H); MS (EI) for $C_{23}H_{24}N_3O_5Cl$: 458 (MH$^+$).

1,4:3,6-Dianhydro-2-O-[4-[(4-bromo-5-chloro-2-fluorophenyl)amino]-6-(methyloxy)quinazolin-7-yl]-5-O-methyl-L-iditol: $^1$H NMR (400 MHz, d$_6$-DMSO): 9.69 (s, 1H), 8.42 (s, 1H), 7.94-7.91 (m, 2H), 7.82 (s, 1H), 7.29 (s, 1H), 5.06 (br s, 1H), 4.63 (dd, 2H), 4.03 (ddd AB, 2H), 3.95 (s, 3H), 3.91-3.86 (m, 3H), 3.31 (s, 3H); MS (EI) for $C_{22}H_{20}N_3O_5BrClF$: 542 (MH$^+$).

1,4:3,6-Dianhydro-2-O-[4-[(3-chloro-2,4-difluorophenyl)amino]-6-(methyloxy)quinazolin-7-yl]-5-O-methyl-L-iditol: $^1$H NMR (400 MHz, d$_6$-DMSO): 11.20 (br s, 1H), 8.81 (s, 1H), 8.06 (s, 1H), 7.68-7.62 (m, 1H), 7.51 (d tr, 1H), 7.43 (s, 1H), 5.09 (br s, 1H), 4.66 (s, 2H), 4.07 (ddd AB 2H), 3.94 (s, 3H), 4.00-3.88 (m, 3H) 3.31 (s, 3H); MS (EI) for $C_{22}H_{20}N_3O_5ClF_2$: 480 (MH$^+$).

1,4:3,6-Dianhydro-2-O-[4-[(4,5-dichloro-2-fluorophenyl)amino]-6-(methyloxy)quinazolin-7-yl]-5-O-methyl-L-iditol: $^1$H NMR (400 MHz, d$_6$-DMSO): 9.69 (s, 1H), 8.42 (s, 1H), 7.94 (d, 1H), 7.84 (d, 1H), 7.82 (s, 1H), 7.29 (s, 1H), 4.63 (m, 2H), 4.03 (ddd AB, 2H), 3.95 (s, 3H), 3.91-3.86 (m, 3H), 3.31 (s, 3H); MS (EI) for $C_{22}H_{20}N_3O_5Cl_2F$: 496 (MH$^+$).

1,4:3,6-Dianhydro-2-O-[4-[(3-chloro-2-fluorophenyl)amino]-6-(methyloxy)quinazolin-7-yl]-5-O-methyl-L-iditol: $^1$H NMR (400 MHz, d$_6$-DMSO): 9.68 (s, 1H), 8.37 (s, 1H), 7.82 (s, 1H), 7.52-7.45 (m, 2H), 7.27 (d tr, 1H), 5.04 (br s, 1H), 4.63 (dd, 2H), 4.02 (ddd AB, 2H), 3.94 (s, 3H), 3.89 (br s, 1H), 3.87 (d 2H), 3.30 (s, 3H); MS (EI) for $C_{22}H_{21}N_3O_5ClF$: 462 (MH$^+$).

1,4:3,6-Dianhydro-2-O-[4-[(4-bromo-3-chlorophenyl)amino]-6-(methyloxy)quinazolin-7-yl]-5-O-methyl-L-iditol: $^1$H NMR (400 MHz, d$_6$-DMSO): 9.58 (s, 1H), 8.52 (s, 1H), 8.23 (d, 1H), 7.82-7.79 (m, 2H) 7.74 (d, 1H), 7.26 (s, 1H) 5.03 (br s, 1H), 4.62 (dd AB, 2H), 4.02 (ddd AB, 2H), 3.96 (s, 3H), 3.89 (br s, 1H), 3.85 (d, 2H) 3.30 (s, 3H); MS (EI) for $C_{22}H_{21}N_3O_5BrCl$: 524 (MH$^+$).

1,4:3,6-Dianhydro-2-O-[4-[(3-bromo-2-methylphenyl)amino]-6-(methyloxy)quinazolin-7-yl]-5-O-methyl-L-iditol: $^1$H NMR (400 MHz, d$_6$-DMSO): 9.65 (s, 1H), 8.30 (s, 1H), 7.86 (s, 1H), 7.57 (dd, 1H), 7.33 (d, 1H), 7.26-7.21 (m, 2H), 5.04 (br s, 1H), 4.63 (dd AB, 2H), 4.03 (ddd AB, 2H), 3.94 (s, 3H), 3.91 (br s, 1H), 3.87 (d, 2H), 3.31 (s, 3H); MS (EI) for $C_{23}H_{24}N_3O_5Br$: 502 (MH$^+$).

1,4:3,6-Dianhydro-2-O-[4-[(3,4-dichlorophenyl)amino]-6-(methyloxy)quinazolin-,7-yl]-2-O-methyl-D-glucitol: MS (EI) for $C_{22}H_{21}N_3O_5Cl_2$: 478 (MH$^+$).

1,4:3,6-Dianhydro-2-O-[4-[(4-bromo-3-chlorophenyl)amino]-6-(methyloxy)quinazolin-7-yl]-5-O-(difluoromethyl)-L-iditol: $^1$NMR (400 MHz, d$_6$-DMSO): 9.64 (s, 1H), 8.56 (s, 1H), 8.26 (d, 1H), 7.86-7.82 (m, 2H), 7.77 (d, 1H), 7.31 (s, 1H), 6.84 (tr, 1H), 5.12 (br s, 1H), 4.74 (m, 2H), 4.06 (ddd AB, 2H), 3.98-3.90 (m, 6H); MS (EI) for $C_{22}H_{19}N_3O_5BrClF_2$: 558 (MH$^{30}$).

1,4:3,6-Dianhydro-2-O-[4-[(4-bromo-3-chlorophenyl)amino]-6-(methyloxy)quinazolin-7-yl]-5-O-ethyl-L-iditol: $^1$H NMR (400 MHz, d$_6$-DMSO): 9.62 (s, 1H), 8.55 (s, 1H), 8.26 (d, 1H), 7.85-7.82 (m, 2H), 7.76 (d, 1H), 5.04 (br s, 1H), 4.62 (dd AB, 2H), 4.15-4.09 (m, 1H), 4.00-3.95 (m, 5H), 3.95-3.82 (m, 2H), 3.57-3.48 (m, 2H), 1.13 (tr, 3H); MS (EI) for $C_{23}H_{23}N_3O_5BrCl$: 536 (MH$^+$).

1,4:3,6-Dianhydro-5-deoxy-2-O-[4-[(4-bromo-3-chlorophenyl)amino]-6-(methyloxy)quinazolin-7-yl]-D-xylohexitol: $^1$H NMR (400 MHz, d$_6$-DMSO): 9.62 (s, 1H), 8.55 (s, 1H), 8.26 (s, 1H), 7.85-7.82 (m, 2H), 7.76 (d, 1H), 7.30 (s, 1H), 4.98 (m, 1H), 4.80 (m, 1H), 4.51 (m, 1H), 4.18-4.14 (m, 1H), 3.97 (s, 3H), 3.92-3.81 (m, 3H), 2.01-1.97 (m, 2H); MS (EI) for $C_{21}H_{19}N_3O_4BrCl$: 492 (MH$^+$).

1,4:3,6-Dianhydro-2-O-methyl-5-O-{6-(methyloxy)-4-[(2,3,4-trichlorophenyl)amino]quinazolin-7-yl}-L-iditol: $^1$H NMR (400 MHz; DMSO-d$_6$): 9.82 (br s, 1H), 8.36 (s, 1H), 8.86 (s, 1H), 7.75-7.73 (d, 1H), 7.60-7.58 (d, 1H), 7.29 (s, 1H), 5.06 (br s, 1H), 5.64-5.62 (m, 2H), 4.10-4.07 (dd, 1H), 4.02-4.01 (d, 1H), 3.97-3.94 (m, 1H), 3.95 (s, 3H), 3.93-3.90 (m, 1H), 3.88 (br m, 1H), 3.31 (s, 3H); MS (EI) for $C_{22}H_{20}Cl_3N_3O_5$: 511.91 (MH$^+$).

1,4:3,6-Dianhydro-2-O-[4-[(3,4-dichloro-2-fluorophenyl)amino]-6-(methyloxy)quinazolin-7-yl]-5-O-methyl-L-iditol hydrochloride: $^1$H NMR (400 MHz; DMSO-d$_6$): 8.75 (s, 1H), 8.03 (s, 1H), 7.70-7.53 (m, 2H), 7.38 (s, 1H), 5.09-5.07 (m, 1H), 4.64-4.63 (br, 1H), 4.13-4.10 (dd, 1H), 4.02-4.01 (d, 1H), 3.99 (s, 3H), 3.93-3.92 (m, 1H), 3.89-3.88 (m, 2H), 3.31 (s, 3H); MS (EI) for $C_{22}H_{20}Cl_2FN_3O_5$: 495.96 (MH$^+$).

Example 2

1,4:3,6-Dianhydro-5-O-[4-[(4-bromo-3-chlorophenyl)amino]-6-(methyloxy)-quinazolin-7-yl]-L-sorbose ethylene glycol acetal 1,4:3,6-dianhydro-5-O-(phenylcarbonyl)-D-fructose ethylene glycol acetal: A solution of 1,4:3,6-dianhydro-5-O-(phenylcarbonyl)-D-fructose (2.00 g, 8.06 mmol), ethylene glycol (5.00 g, 80.6 mmol), and p-toluenesulfonic acid (1.53 g, 8.06 mmol) in benzene (100 mL) was refluxed for 90 min using a Dean-Stark Trap apparatus. The reaction mixture was diluted with ethyl acetate (100 mL), washed with saturated aqueous sodium bicarbonate (2×50 mL) then brine (50 mL), and dried over anhydrous sodium sulfate. Filtration, concentration and column chromatography on silica (1:1 hexane/ethyl acetate) provided 1.44 g (61% yield) of 1,4:3,6-dianhydro-5-O-(phenylcarbonyl)-D-fructose ethylene glycol acetal as a colorless solid. $^1$H NMR (400 MHz; CDCl$_3$): 8.08 (m, 2H), 7.58 (m, 1H), 7.54 (m, 2H), 5.38 (dd, 1H), 4.97 (t, 1H), 4.21-4.02 (m, 7H), 3.86 (d, 1H), 3.75 (d, 1H).

1,4:3,6-dianhydro-D-fructose ethylene glycol acetal: To a solution of 1,4:3,6-dianhydro-5-O-(phenylcarbonyl)-D-fructose ethylene glycol acetal (1.44 g, 4.93 mmol) in methanol (40 mL) was added 50% aqueous sodium hydroxide (0.38 g, 4.75 mmol) and the mixture was stirred at room temperature for 30 minutes. Neutralization with 1M HCl, followed by concentration and column chromatography on silica (1:2 hexane/ethyl acetate) provided 0.74 g (80% yield) of 1,4:3,6-dianhydro-D-fructose ethylene glycol acetal as a colorless solid. $^1$H NMR (400 MHz; CDCl$_3$): 4.60 (t, 1H), 4.32 (m, 1H), 4.14 (d, 1H), 4.05-3.98 (m, 5H), 3.82 (s, 2H), 3.62 (dd, 1H), 2.65 (d, 1H).

1,4:3,6-dianhydro-5-O-(methylsulfonyl)-D-fructose ethylene glycol acetal: To a solution of 1,4:3,6-dianhydro-D-fructose ethylene glycol acetal (0.74 g, 3.93 mmol) and triethylamine (1.20 g, 11.86 mmol) in dichloromethane (40 mL) was added methanesulfonyl chloride (0.90 g, 7.88 mmol) at 0° C. under nitrogen. The solution was warmed to room temperature and stirred for 13 h. Dichloromethane (50 mL) was added, and the organic layer was washed with saturated aqueous sodium bicarbonate (30 mL), water (30 mL), and brine (30 mL) then dried over anhydrous sodium sulfate. Filtration and concentration provided 1.02 g (97%) of 1,4:3, 6-dianhydro-5-O-(methylsulfonyl)-D-fructose ethylene glycol acetal as a yellow oil. $^1$H NMR (400 MHz; CDCl$_3$): 5.08

(m, 1H), 4.82 (t, 1H), 4.13 (dd, 1H), 4.04 (m, 4H), 3.93 (dd, 1H), 3.87 (d, 1H), 3.81 (d, 1H), 3.13 (s, 3H).

1,4:3,6-dianhydro-5-O-[4-[(4-bromo-3-chlorophenyl) amino]-6-(methyloxy)-quinazolin-7-yl]-L-sorbose ethylene glycol acetal: A suspension of 4-[(4-bromo-3-chlorophenyl) amino]-6-(methyloxy)quinazolin-7-ol (235 mg, 0.48 mmol), 1,4:3,6-dianhydro-5-O-(methylsulfonyl)-D-fructose ethylene glycol acetal (190 mg, 0.71 mmol), and potassium carbonate (329 mg, 2.38 mmol) in DMF (10 mL) was stirred at 130° C. under nitrogen for 14 h. The reaction mixture was poured into water (50 mL), and extracted with ethyl acetate (3×30 mL). The organic layers were washed with 5% LiCl (2×25 mL), and brine (25 mL) then dried over anhydrous sodium sulfate and concentrated. Filtration and column chromatography on silica (9:1 dichloromethane/acetone to 7:3 dichloromethane/acetone) gave 77 mg (29%) of 1,4:3,6-dianhydro-5-O-[4-[(4-bromo-3-chlorophenyl)amino]-6-(methyloxy)quinazolin-7-yl]-L-sorbose ethylene glycol acetal as a off-white solid. $^1$H NMR (400 MHz, CDCl$_3$): 8.70 (s, 1H), 8.00 (d, 1H), 7.61 (d, 1H), 7.52 (dd, 1H), 7.31 (s, 1H), 7.14 (s, 1H), 7.00 (s, 1H), 4.98 (m, 1H), 4.86 (d, 1H), 4.42 (d, 1H), 4.32-4.23 (m, 2H), 4.10-4.05 (m, 4H), 4.00 (s, 3H), 3.86 (d, 1H), 3.78 (d, 1H); MS (EI) for C$_{23}$H$_{21}$N$_3$O$_6$BrCl: 550 (MH$^+$).

Example 3

1,4:3,6-Dianhydro-2-O-[4-[(4-bromo-3-chlorophenyl)amino]-6-(methyloxy)-quinazolin-7-yl]-5-deoxy-5-methylidene-D-xylo-hexitol 1,4:3,6-dianhydro-2-deoxy-2-methylidene-D-arabinohexitol: To a solution of 1,4:3,6-dianhydro-2-deoxy-2-methylidene-5-O-(phenylcarbonyl)-D-arabino-hexitol (329 mg, 1.34 mmol) in methanol (10 mL) was added 50% aqueous sodium hydroxide (95 mg, 1.19 mmol) and the mixture was stirred at room temperature for 30 minutes. Neutralization with 4M hydrogen chloride in 1,4-dioxane, followed by concentration and column chromatography on silica (1:1 hexane/ ethyl acetate) provided 141 mg (74%) of 1,4:3,6-dianhydro-2-deoxy-2-methylidene-D-arabino-hexitol as a colorless solid. $^1$H NMR (400 MHz; CDCl$_3$): 5.37 (m, 1H), 5.20 (m, 1H), 4.80 (m, 1H), 4.54 (m, 2H), 4.43 (m, 1H), 4.26 (m, 1H), 3.95 (dd, 1H), 3.54 (dd, 1H), 2.70 (d, 1H).

1,4:3,6-dianhydro-2-deoxy-2-methylidene-5-O-(methylsulfonyl)-D-arabino-hexitol: To a solution of 1,4:3,6-dianhydro-2-deoxy-2-methylidene-D-arabinio-hexitol (135 mg, 0.95 mmol) and triethylamine (288 mg, 2.85 mmol) in dichloromethane (10 mL) was added methanesulfonyl chloride (222 mg, 1.94 mmol) at 0° C. under nitrogen. The solution was warmed to room temperature and stirred for 18 h. Dichloromethane (50 mL) was added and the organic layer was washed with saturated aqueous sodium bicarbonate (2×25 mL), water (25 mL) and brine (25 mL) then dried over anhydrous sodium sulfate. Filtration and concentration provided 213 mg (72%) of 1,4:3,6-dianhydro-2-deoxy-2-methylidene-5-O-(methylsulfonyl)-D-arabino-hexitol as a yellow oil. $^1$H NMR (400 MHz; CDCl$_3$): 5.40 (m, 1H), 5.23 (m, 1H), 5.04 (m, 1H), 4.85 (m, 1H), 4.73 (t, 1H), 4.58 (m, 1H), 4.41 (m, 1H), 4.08 (dd, 1H), 3.86 (dd, 1H), 3.14 (s, 3H).

1,4:3,6-dianhydro-2-O-[4-[(4-bromo-3-chlorophenyl) amino]-6-(methyloxy)-quinazolin-7-yl]-5-deoxy-5-methylidene-D-xylo-hexitol: A suspension of 4-[(4-bromo-3-chlorophenyl)amino]-6-(methyloxy)quinazolin-7-ol (425 mg, 0.86 mmol), 1,4:3,6-dianhydro-2-deoxy-2-methylidene-5-O-(methylsulfonyl)-D-arabino-hexitol (208 mg, 0.94 mmol), and potassium carbonate (594 mg, 4.30 mmol) in DMF (10 mL) was stirred at 130° C. under nitrogen for 15 h. The reaction mixture was poured into water (50 mL), and extracted with ethyl acetate (3×30 mL). The organic layers were washed with 5% LiCl (2×25 mL), and brine (25 mL), dried over anhydrous sodium sulfate then filtered and concentrated. Column chromatography on silica (97:3 dichloromethane/methanol) gave 234 mg (54%) of 1,4:3,6-dianhydro-2-O-[4-[(4-bromo-3-chlorophenyl)amino]-6-(methyloxy)quinazolin-7-yl]-5-deoxy-5-methylidene-D-xylo-hexitol as a yellow solid. $^1$H NMR (400 MHz, CDCl$_3$): 8.70 (s, 1H), 8.01 (d, 1H), 7.61 (d, 1H), 7.51 (dd, 1H), 7.36 (s, 1H), 7.14 (s, 1H), 7.01 (s, 1H), 5.42 (m, 1H), 5.23 (m, 1H), 5.04 (d, 1H), 4.97 (t, 1H), 4.74 (d, 1H), 4.55 (m, 1H), 4.35 (m, 1H), 4.22 (m, 2H), 4.01 (s, 3H); MS (EI) for C$_{22}$H$_{19}$N$_3$O$_4$BrCl: 504 (MH$^+$).

Example 4

Methyl 3,6-anhydro-5-O-[4-[(4-bromo-3-chlorophenyl)amino]-6-(methyloxy) quinazolin-7-yl]-2-O-methyl-α-L-idofuranoside To a mixture of 1,4:3,6-dianhydro-5-O-(phenylcarbonyl)- (D)-glucitol (4.32 g, 17.3 mmol), triethylamine (4.91 mL, 35.3 mmol) and 4-dimethylaminopyridine (0.63 g, 5.2 mmol) in dichloromethane (50 mL) at −10° to −15° was added trifluromethanesulfonic anhydride (3.48 mL, 20.7 mmol) dropwise over ten minutes and the resulting mixture was stirred at this temperature for 3 hours. The mixture was poured into 100 mL of ice-water and extracted with dichloromethane (3×50 mL). The combined organic layers were washed with brine, dried over anhydrous sodium sulfate, filtered then concentrated. The crude triflate was suspended in toluene (50 mL) followed by addition of 1,8-diazabicyclo[4,5,0]undec-7-ene (5.25 mL, 34.6 mmol) and the mixture was stirred at room temperature for 18 hours. The reaction mixture was poured into ice-water and partitioned then the aqueous portion was extracted with dichloromethane (3×50 mL). The combined organic portion was washed with brine, dried over anhydrous sodium sulfate, filtered and concentrated. The residue was purified by flashed chromatography (silica gel, 5-20% ethyl acetate-hexane) to give 1,4:3,6-dianhydro-2-deoxy-5-O-(phenylcarbonyl)-D-arabino-hex-1-enitol, as a white solid, 3.10 g, 77% yield. $^1$H NMR (400 MHz; CDCl$_3$): 8.08-8.06 (m, 2H), 7.61-7.57 (m, 1H), 7.56-7.43 (m, 2H), 6.62-6.61 (d, 1H), 5.48-5.46 (m,1H), 5.32-5.26 (m,1H), 5.13-5.10 (m, 2H), 4.18-4.14 (tr,1H), 3.61-3.56 (tr, 1H).

Methyl 3,6-anhydro-5-O-(phenylcarbonyl)-β-D-glucofuranoside: To a solution of 1,4:3,6-dianhydro-2-deoxy-5-O-(phenylcarbonyl)-D-arabino-hex-1-enitol (1.00 g, 4.3 mmol) in methanol (17 mL) at −4° C. was added 3-chloroperoxybenzoic acid (85%, 1.35 g, 8.6 mmol), and the resulting mixture was slowly warmed to room temperature and stirred for 18 hours. The reaction mixture was concentrated, diluted with dichloromthane (50 mL), washed with saturated aqueous sodium bicarbonate solution, dried over sodium sulfate, filtered and concentrated. The residue was purified by flash chromatography (silica gel, 25-60% ethyl acetate-hexane) to give methyl 3,6-anhydro-5-O -(phenylcarbonyl)-β-D-glucofuranoside as a white solid, 1.03 g, 83% yield. $^1$H NMR (400 MHz; CDCl$_3$): 8.11-8.08 (d, 2H), 7.61-7.56 (tr, 1H), 7.48-7.44 (m, 2H), 5.24-5.17 (m, 2H), 4.96 (s, 1H), 4.57-4.56 (d, 1H), 4.27 (s, 1H), 4.22-4.18 (dd, 1H), 4.08-4.04 (dd, 1H) 3.36 (s, 3H).

Methyl 3,6-anhydro-2-O-methyl-5-O-(phenylcarbonyl)-β-D-glucofuranoside: A mixture of methyl 3,6-anhydro-5-O-(phenylcarbonyl)-β-D-glucofuranoside (1.03 g, 3.7 mmol), silver (1) oxide (0.85 g, 3.7 mmol) and methyl iodide (0.34 mL, 5.5 mmol) in DME (2 mL) was heated at 60° C. for 1 hour. After cooling to room temperature the reaction mixture was diluted with ethyl acetate (50 mL), filtered over celite, adsorbed on silica gel (10 g) and purified by flash chromatography (silica gel, 5-30% ethyl acetate-hexane) to give methyl 3,6-anhydro-2-O-methyl-5-O-(phenylcarbonyl)-β-D-glucofuranoside as a colorless oil, 0.82 g, 76% yield. $^1$H NMR (400 MHz; CDCl$_3$): 8.11-8.09 (d, 2H), 7.60-7.56 (m, 1H), 7.46-7.44 (m, 2H), 5.24-5.20 (m, 1H), 5.18-5.09 (tr, 1H), 4.99 (s, 1H), 4.61-4.60 (d, 1H), 4.21-4.17 (tr, 1H), 4.08-4.03 (tr, 1H), 3.81 (s, 1H), 3.40 (s, 3H), 3.57 (s, 3H).

Methyl 3,6-anhydro-2-O-methyl-β-D-glucofuranoside: A solution of methyl 3,6-anhydro-2-O-methyl-5-O-(phenylcarbonyl)-β-D-glucofuranoside (820 mg, 3.1 mmol) and 50% sodium hydroxide (248 mg, 3.1 mmol) in methanol (10 mL) was stirred at room temperature for 30 minutes. The material was adsorbed on silica gel (5 g) and passed through a short column (15% ethyl acetate in hexanes to 5% methanol in ethyl acetate) to give methyl 3,6-anhydro-2-O-methyl-β-D-glucofuranoside as a colorless oil, 420 mg, 85% yield. $^1$H NMR (400 MHz; CDCl$_3$): 5.04 (s, 1H), 5.84-5.81 (tr, 1H), 4.44-4.42 (tr, 1H), 4.25-4.19 (m, 1H), 3.85-3.75 (m, 1H), 3.49 (s, 3H), 3.43 (s, 3H), 2.75-2.72 (d, 1H).

Methyl 3,6-anhydro-2-O-methyl-5-O-(methylsulfonyl)-β-L-glucofuranoside: Methyl 3,6-anhydro-2-O-methyl-β-D-glucofuranoside (420 mg, 2.6 mmol) was dissolved in dichloromethane (10 mL) and pyridine (0.36 mL, 3.7 mmol) at 0° C. Methanesulfonyl chloride (0.14 mL, 3.1 mmol) was added and the resulting mixture was stirred at 0° C. for 1 hour then at room temperature for 2 hours. The reaction mixture was washed with water and saturated aqueous sodium bicarbonate solution, dried over anhydrous sodium sulfate, filtered and concentrated to give methyl 3,6-anhydro-2-O -methyl-5-O-(methylsulfonyl)-β-D-glucofuranoside as a colorless oil, 669 mg, 95% yield, which was used without further purification.

Methyl 3,6-anhydro-5-O-[4-[(4-bromo-3-chlorophenyl)amino]-6-(methyloxy) quinazolin-7-yl]-2-O-methyl-α-L-idofuranoside: Methyl 3,6-anhydro-2-O-methyl-5-O-(methylsulfonyl)-β-D-glucofuranoside (314 mg, 1.1 mmol) was dissolved in DMF (3 mL). To this solution was added potassium carbonate (404 mg, 2.9 mmol) and 4-[(4-bromo-3-chlorophenyl)amino]-6-methyloxy-7-hydroxyquinazoline trifluoroacetate (280 mg, 0.59 mmol). The resulting mixture was heated at 135° C. for 18 h. After cooling to room temperature the reaction mixture was diluted with ethyl acetate (15 mL), washed with water, dried over anhydrous sodium sulfate, filtered and concentrated. The residue was purified by flash chromatography (silica gel, 2-7% methanol in 1:1 ethyl acetate:hexanes) to give methyl 3,6-anhydro-5-O-[4-[(4-bromo-3-chlorophenyl)amino]-6-(methyloxy)quinazolin-7-yl]-2-O-methyl-α-L-idofuranoside as a white solid, 181 mg, 28% yield. $^1$H NMR (400 MHz; Methanol-d$_4$): 8.75 (s, 1H), 8.04-8.06 (d, 1H), 7.99 (s, 1H), 7.78-7.75 (d, 1H), 7.64-7.61 (d, 1H), 7.35 (s, 1H), 5.16-5.14 (d, 1H), 5.02 (s, 1H), 4.89 (br, 1H), 4.69-4.68 (d, 1H) 4.46-4.42 (dd, 1H), 4.09 (br, 1H), 4.06 (s, 3H), 3.69(s, 1H), 3.48(s, 3H), 3.42 (s, 3H); MS (EI) for C$_{23}$H$_{23}$BrClN$_3$O$_6$: 551.88 (MH$^+$).

Example 6

3,6-Anhydro-5-O-[4-[(4-bromo-3-chlorophenyl)amino]-6-(methyloxy)quinazolin-7-yl]-1,2-O-(1-methylethylidene)-β-D-idofuranose 3,6-Anhydro-1,2-O-(1-methylethylidene)-5-O-(phenylcarbonyl)-α-L-glucofuranose A mixture of 3,6-anhydro-5-O-(phenylcarbonyl)-α-L-glucofuranose (1.00 g), 2,2-dimethoxy propane (0.63 mL), p-toluenesulfonic acid (20 mg) and benzene (10 mL) was heated at reflux for 3 hours. The reaction mixture was cooled then adsorbed on silica gel (10 g) and purified by flash chromatography (silica gel, 5-35% ethyl acetate in hexanes) to give 3,6-anhydro-1,2-O-(1-methylethylidene)-5-O-(phenylcarbonyl)-α-L-glucofuranose as colorless oil, 0.85 g, 74% yield. $^1$H NMR (400 MHz; CDCl$_3$): 8.08-8.06 (d, 2H), 7.59-7.56 (tr, 1H), 7.46-7.42 (m, 2H), 5.99-5.98 (d, 1H), 5.35-5.31 (tr, 1H), 5.10-5.08 (d, 1H), 4.66-4.65 (d, 1H), 4.61-4.60 (d, 1H), 4.20-4.16 (dd, 1H), 3.91-3.74 (tr, 1H), 1.50 (s, 3H), 1.34 (s, 3H).

3,6-Anhydro-1,2-O-(1-methylethylidene)-5-O-(methylsulfonyl)-α-L-glucofuranose: A solution of 3,6-anhydro-1,2-O-(1-methylethylidene)-5-O-(phenylcarbonyl)-α-L-glucofuranose (850 mg) and 50% sodium hydroxide (111 mg) in methanol (10 mL) was stirred at room temperature for 30 minutes. The mixture was then adsorbed on silica gel (5 g) and passed through a short column (15% ethyl acetate in hexanes to 5% methanol in ethyl acetate) and the alcohol intermediate, 390 mg, 70% yield, was used immediately in the next step. The alcohol was dissolved in dichloromethane (10 mL) and pyridine (0.32 mL) at 0° C. Methanesulfonyl chloride (0.12 mL) was added and the resulting mixture was stirred at 0° C. for 1 hour then at room temperature for 2 hours. The reaction mixture was washed with water and saturated aqueous sodium bicarbonate solution, dried over anhydrous sodium sulfate, filtered and concentrated to give 3,6-anhydro-1,2-O-(1-methylethylidene)-5-O-(methylsulfonyl)-α-L glucofuranose as a colorless oil, 485 mg, 90% yield, which was immediately employed in the next step.

3,6-Anhydro-5-O-[4-[(4-bromo-3-chlorophenyl)amino]-6-(methyloxy)quinazolin-7-yl]-1,2-O-(1-methylethylidene)-β-D-idofuranose: 3,6-Anhydro-1,2-O-(1-methylethylidene)-5-O-(methylsulfonyl)-α-L-glucofuranose, (85 mg, 0.30 mmol) was dissolved in DMP (3 mL). To this solution was added potassium carbonate (168 mg, 1.21 mmol) and 4-[(4-bromo-3-chlorophenyl)amino]-6-methyloxy-7-hydroxyquinazoline trifluoroacetate (145 mg, 0.30 mmol). The resulting mixture was heated at 135° C. for 18 h. After cooling to room temperature, the reaction mixture was diluted with ethyl acetate (15 mL), washed with water, dried over anhydrous sodium sulfate, filtered, concentrated. The residue was purified by flash chromatography (silica gel, 2-7% Methanol in 1:1 ethyl acetate:hexanes) to give 3,6-anhydro-5-O-[4-[(4-bromo-3-chlorophenyl)amino]-6-(methyloxy)quinazolin-7-yl]-1,2-O-(1-methylethylidene)-β-D-idofuranose, 121 mg, 77% yield, as a white solid. $^1$H NMR (400 MHz; Methanol-d$_4$): 8.48 (s, 1H), 8.17-8.16 (d, 1H), 7.76 (s, 1H), 7.70-7.61 (m, 2H), 7.19 (s, 1H), 5.95-5.94 (d, 1H), 5.18-5.17 (d, 1H), 4.93-4.91 (m, 1H), 4.70-4.62 (m, 2H), 4.28-4.22 (dd, 1H), 4.08-4.06 (d, 1H), 4.03 (s, 3H), 1.44 (s, 3H), 1.32 (s, 3H); MS (EI) for C$_{24}$H$_{23}$BrClN$_3$O$_6$: 563.83 (MH$^+$).

Example 7

(3S,8aS)-3-(Chloromethyl)hexahydro-1H-pyrrolo[2,1-c][1,4]oxazine and (3R,8aS)-3-(chloromethyl)hexahydro-1H pyrrolo[2,1-c][1,4]oxazine (S)-(+)-Prolinol (6.00 g, 59.3 mmol) was added to epichlorohydrin (47 mL, 600 mmol) at 0° C. The solution was stirred at 40° C. for 0.5 h and then concentrated in vacuo. The residual oil was cooled in an ice bath and concentrated sulfuric acid (18 mL) was added dropwise with stirring. The mixture was heated at 170-180° C. for 1.5 h, poured into ice (300 mL) and then basified with sodium carbonate to pH~8. The mixture was partitioned with ethyl acetate/hexanes and filtered. The filtrate was separated and the aqueous portion was extracted twice with ethyl acetate. The combined organic portion was dried over sodium sulfate, filtered and concentrated in vacuo to afford an oil which was purified by column chromatography (ethyl acetate for less polar product and then 30% methanol in ethyl acetate). (3S,8aS)-3-(Chloromethyl) hexahydro-1H-pyrrolo[2,1-c][1,4]oxazine (less polar product) (1.87 g, 10.7 mmol, 18% yield): $^1$H NMR (400 MHz, CDCl$_3$): 4.06 (dd, 1H), 3.79-3.71 (m, 1H), 3.60-3.48 (m, 2H), 3.36 (dd, 1H), 3.15 (dd, 1H), 3.13-3.06 (m, 1H), 2.21-2.01 (m, 3H), 1.90-1.68 (m, 3H), 1.39-1.24 (m, 1H); MS (EI) for C$_8$H$_{14}$NOCl: 176 (MH$^+$). (3R,8aS)-3-(Chloromethyl)hexahydro-1H-pyrrolo[2,1-c][1,4]oxazine (1.54 g, 8.77 mmol, 15% yield): $^1$H NMR (400 MHz, CDCl$_3$): 3.94-3.77 (m, 4H), 3.55 (dd, 1H), 3.02-2.93 (m, 2H), 2.45 (dd, 1H), 2.29-2.15 (m, 2H), 1.88-1.64 (m, 3H), 1.49-1.38 (m, 1H); MS (EI) for C$_8$H$_{14}$NOCl: 176 (MH$^+$).

Using the same or analogous synthetic techniques and/or substituting with alternative starting materials, the following reagents were prepared:

(3R,8aR)-3-(Chloromethyl)hexahydro-1H-pyrrolo[2,1-c][1,4]oxazine: $^1$H NMR (400 MHz, CDCl$_3$): 4.05 (dd, 1H), 3.79-3.70 (m, 1H), 3.61-3.48 (m, 2H), 3.35 (dd, 1H), 3.15 (dd, 1H), 3.13-3.07 (m, 1H), 2.21-2.01 (m, 3H), 1.89-1.67 (m, 3H), 1.39-1.25 (m, 1H); MS (EI) for C$_8$H$_{14}$NOCl: 176 (MH$^+$).

(3S,8aR)-3-(Chloromethyl)hexahydro-1H-pyrrolo[2,1-c][1,4]oxazine: $^1$H NMR (400 MHz, CDCl$_3$): 3.93-3.77 (m, 4H), 3.55 (dd, 1H), 3.02-2.93 (m, 2H), 2.45 (dd, 1H), 2.30-2.15 (m, 2H), 1.88-1.64 (m, 3H), 1.49-1.37 (m, 1H); MS (EI) for C$_8$H$_{14}$NOCl: 176 (MH$^+$).

Example 8

N-(4-Bromo-2,3-dichlorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride N-(4-bromo-2,3-dichlorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride: (3S,8aS)-3-(Chloromethyl)hexahydro-1H-pyrrolo[2,1-c][1,4]oxazine (115 mg, 0.655 mmol) and 4-[(4-bromo-2,3-dichlorophenyl)amino]-6-(methyloxy)quinazolin-7-ol trifluoroacetic acid salt (347 mg, 0.655 mmol) were dissolved in dimethylacetamide (0.8 mL) and potassium carbonate (452 mg, 3.28 mmol) was added. The mixture was stirred at 130° C. for 36 h. The mixture was cooled to room temperature and the mixture was partitioned between ethyl acetate and water. The aqueous portion was extracted with ethyl acetate and the combined organic portion was washed with brine, dried over sodium sulfate, filtered and concentrated in vacuo to afford a brown oil which was purified by column chromatography (ethyl acetate-ethanol 1:1). The purified material was dissolved in ethanol and treated with 4M solution of HCl in 1,4-dioxane (0.25 mL) and the mixture was concentrated in vacuo. The residue was dissolved in water and lyophilized to afford N-(4-bromo-2,3-dichlorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride as a brown solid (131 mg, 0.222 mmol, 34% yield). $^1$H NMR (400 MHz, d$_6$-DMSO): 11.9-11.5 (m, 2H), 8.79 (s, 1H), 8.34 (s, 1H), 7.96 (d, 1H), 7.54 (d, 1H), 7.41 (s, 1H), 4.47-4.25 (m, 4H), 4.03 (s, 3H) 3.96-3.00 (m, 6H), 2.18-1.88 (m, 3H), 1.73-1.57 (m, 1H); MS (EI) for C$_{23}$H$_{23}$N$_4$O$_3$Cl$_2$Br: 553 (MH$^+$).

Using the same or analogous synthetic techniques and/or substituting with alternative reagents, the following compounds of the invention were prepared:

N-(3,4-Dichlorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride: $^1$H NMR (400 MHz, d$_6$-DMSO): 11.5-11.2 (m, 2H), 8.86 (s, 1H), 8.32 (s, 1H), 8.13 (s, 1H), 7.79 (dd, 1H), 7.73 (d, 1H), 7.37 (s, 1H), 4.45-4.24 (m, 4H), 4.03 (s, 3H) 3.93-3.00 (m, 6H), 2.20-1.90 (m, 3H), 1.74-1.56 (m, 1H); MS (EI) for C$_{23}$H$_{24}$N$_4$O$_3$Cl$_2$: 475 (MH$^+$).

N-(3,4-Dichlorophenyl)-7-{[(3R,8aR)-hexahydro-1H-pyrrolo[2,1-c][1,4]oxazin-3-ylmethyl]oxy}-6-(methyloxy)quinazolin-4-amine hydrochloride: $^1$H NMR (400 MHz, d$_6$-DMSO): 11.6-11.3 (m, 2H), 8.86 (s, 1H), 8.32 (s, 1H), 8.14 (s, 1H), 7.80 (dd, 1H), 7.73 (d, 1H), 7.35 (s, 1H), 4.45-4.25 (m, 4H), 4.03 (s, 3H) 3.96-2.98 (m, 6H), 2.19-1.89 (m, 3H), 1.72-1.57 (m, 1H); MS (EI) for C$_{23}$H$_{24}$N$_4$O$_3$Cl$_2$: 475 (MH$^+$).

N-(3,4-Dichlorophenyl)-7-{[(3R,8aS)-hexahydro-1H-pyrrolo[2,1-c][1,4]oxazin-3-ylmethyl]oxy}-6-(methyloxy)quinazolin-4-amine hydrochloride: $^1$H NMR (400 MHz, d$_6$-DMSO): 11.6-11.4 (m, 2H), 8.89 (s, 1H), 8.42 (s, 1H), 8.18 (d, 1H), 7.84 (dd, 1H), 7.75 (d, 1H), 7.40 (s, 1H), 4.32 (d, 2H), 4.23-4.15 (m, 1H), 4.09-3.95 (m, 2H), 4.05 (s, 3H), 3.70-3.03 (m, 5H), 2.14-2.04 (m, 4H); MS (EI) for C$_{23}$H$_{24}$N$_4$O$_3$Cl$_2$: 475 (MH$^+$).

N-(3,4-Dichlorophenyl)-7-{[(3S,8aR)-hexahydro-1H-pyrrolo[2,1-c][1,4]oxazin-3-ylmethyl]oxy}-6-(methyloxy)quinazolin-4-amine hydrochloride: $^1$H NMR (400 MHz, d$_6$-DMSO): 11.7-11.5 (m, 2H), 8.90 (s, 1H), 8.49 (s, 1H), 8.18 (d, 1H), 7.86 (dd, 1H), 7.75 (d, 1H), 7.42 (s, 1H), 4.31 (d, 2H), 4.24-4.16 (m, 1H), 4.09-3.95 (m, 2H), 4.06 (s, 3H), 3.69-3.04 (m, 5H), 2.14-2.03 (m, 4H); MS (EI) for C$_{23}$H$_{24}$N$_4$O$_3$Cl$_2$: 475 (MH$^+$).

Example 9

N-(3,4-Dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride (3S,8aS)-Hexahydro-1H-pyrrolo[2,1-c][1,4]oxazin-3-ylmethyl acetate: (3S,8aS)-3-(Chloromethyl)hexahydro-1H-pyrrolo[2,1-c][1,4]oxazine (2.30 g, 13.1 mmol) and potassium acetate (12.8 g, 131 mmol) were stirred in dimethylformamide (25 mL) at 140° C. for 20 h. The mixture was partitioned between ethyl acetate and water. The organic portion was washed twice with water, then with brine, dried over sodium sulfate, filtered and concentrated in vacuo to afford (3S,8aS)-hexahydro-1H-pyrrolo[2,1-c][1,4]oxazin-3-ylmethyl acetate as a brown oil (2.53 g, 12.7 mmol, 97% yield). $^1$H NMR (400 MHz, CDCl$_3$): 4.14-4.02 (m, 3H), 3.81-3.72 (m, 1H), 3.37-3.31 (m, 1H), 3.09 (dt, 1H), 3.00 (dd, 1H), 2.21-2.00 (m, 3H), 2.10 (s, 3H), 1.90-1.67 (m, 3H), 1.39-1.24 (m, 1H); MS (EI) for C$_{10}$H$_{17}$NO$_3$: 200 (MH$^+$).

(3S,8aS)-Hexahydro-1H-pyrrolo[2,1-c][1,4]oxazin-3-ylmethanol: (3S,8aS)-Hexahydro-1H-pyrrolo[2,1-c][1,4]oxazin-3-ylmethyl acetate (2.36 g, 11.9 mmol) was treated with sodium methoxide (25 wt % solution in methanol; 2.7 mL) for 0.5 h. The mixture was cooled in an ice bath and a solution of 4M HCl in 1,4-dioxane (3 mL, 12.0 mmol) was added slowly. The mixture was stirred at room temperature for 5 minutes and then was concentrated in vacuo to afford a suspension which was diluted with dichloromethane, filtered and the filtrate was concentrated in vacuo to afford (3S,8aS)-hexahydro-1H-pyrrolo[2,1-c][1,4]oxazin-3-ylmethanol as a brown oil (1.93 g, >100% yield). $^1$H NMR (400 MHz, CDCl$_3$): 4.05 (dd, 1H), 3.73-3.65 (m, 2H), 3.62-3.56 (m, 1H), 3.39-3.34 (m, 1H), 3.10 (dt, 1H), 3.00-2.95 (m, 1H), 2.24-1.98 (m, 4H), 1.97-1.70 (m, 3H), 1.44-1.28 (m, 1H); MS (EI) for C$_8$H$_{15}$NO$_2$: 158 (MH$^+$).

(3S,8aS)-hexahydro-1H-pyrrolo[2,1-c][1,4]oxazin-3-ylmethyl methanesulfonate: (3S,8aS)-Hexahydro-1H-pyrrolo[2,1-c][1,4]oxazin-3-ylmethanol (1.00 g, 6.37 mmol) was dissolved in dichloromethane (10 mL) and triethylamine (2.4 mL, 17.3 mmol) was added at 0° C. followed by dropwise addition of methanesulfonyl chloride (0.93 mL, 12.0 mmol). The solution was warmed to room temperature and stirred for 1.25 h and then was concentrated in vacuo. The residue was partitioned between ethyl acetate and saturated sodium bicarbonate solution. The organic portion was washed with saturated sodium bicarbonate solution. The combined aqueous portion was extracted with ethyl acetate. The combined organic portion was washed with brine, dried over sodium sulfate, filtered and concentrated in vacuo to afford (3S,8aS)-hexahydro-1H-pyrrolo[2,1-c][1,4]oxazin-3-ylmethyl methanesulfonate as an orange-brown oil (1.20 g, 5.1 mmol, 80% yield). MS (EI) for C$_9$H$_{17}$NO$_4$S: 236 (MH$^+$).

N-(3,4-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride: 4-[(3,4-Dichloro-2-fluorophenyl)amino]-6-(methyloxy)quinazolin-7-ol trifluoroacetic acid salt (307 mg, 0.655 mmol) was dissolved in dimethylformamide (1 mL) and potassium carbonate (452 mg, 3.28 mmol) was added followed by (3S,8aS)-hexahydro-1H-pyrrolo[2,1-c][1,4]oxazin-3-ylmethyl methanesulfonate (250 mg, 1.06 mmol). The mixture was stirred at 70° C. for 41 h and then was partitioned between ethyl acetate and water. The aqueous portion was extracted with ethyl acetate. The combined organic portion was dried over sodium sulfate, filtered and concentrated in vacuo to afford an orange oil which was purified by column chromatography (ethyl acetate-ethanol 1:1). The purified material was dissolved in methanol and treated with 4M solution of HCl in 1,4-dioxane (0.1 mL) and the mixture was concentrated in vacuo to afford N-(3,4-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride as a pale yellow solid (66 mg, 0.125 mmol, 19% yield). $^1$H NMR (400 MHz, d$_6$-DMSO): 11.9-11.5 (m, 2H), 8.83 (s, 1H), 8.39-8.35 (m, 1H), 7.69 (dd, 1H), 7.62 (dd, 1H), 7.43 (s, 1H), 4.48-4.24 (m, 4H), 4.04 (s, 3H), 3.97-3.85 (m, 1H), 3.78-2.96 (m, 5H), 2.17-1.90 (m, 3H), 1.72-1.58 (m, 1H); MS (EI) for C$_{23}$H$_{23}$N$_4$O$_3$FCl$_2$: 493 (MH$^+$).

Using the same or analogous synthetic techniques and/or substituting with alternative reagents, the following compounds of the invention were prepared:

N-(3-Chloro-2,4-difluorophenyl)-7-{[(3S,8aS)-hexahydro-1H-pyrrolo[2,1-c][1,4]oxazin-3-ylmethyl]oxy}-6-(methyloxy)quinazolin-4-amine hydrochloride: $^1$H NMR (400 MHz, d$_6$-DMSO): 11.9-11.6 (m, 2H), 8.84 (s, 1H), 8.41-8.37 (m, 1H), 7.67-7.60 (m, 1H), 7.51 (dt, 1H), 7.41 (s, 1H), 4.48-4.24 (m, 4H), 4.04 (s, 3H), 3.97-3.86 (m, 1H), 3.80-2.96 (m, 5H), 2.18-1.90 (m, 3H), 1.72-1.59 (m, 1H); MS (EI) for C$_{23}$H$_{23}$N$_4$O$_3$FCl$_2$: 477 (M$^+$).

N-(4-Bromo-3-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine: $^1$H NMR (400 MHz, CDCl$_3$): 8.70 (s, 1H), 8.49 (dd, 1H), 7.49 (dd, 1H), 7.29 (s, 1H), 6.98 (s, 1H), 4.25 (dd, 1H), 4.17 (dd, 1H), 4.13-4.06 (m, 2H), 4.03 (s, 3H), 3.46-3.38 (m, 1H), 3.20 (dd, 1H), 3.14 (dt, 1H), 2.28-2.17 (m, 2H), 2.17-2.07 (m, 1H), 1.90-1.71 (m, 3H), 1.42-1.30 (m, 1H); MS (EI) for C$_{23}$H$_{23}$N$_4$O$_3$FClBr: 537 (MH$^+$).

N-(4,5-Dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine: $^1$H NMR (400 MHz, CDCl$_3$): 8.91 (d, 1H), 8.71 (s, 1H), 7.29-7.26 (m, 2H), 6.94 (s, 1H), 4.24 (dd, 1H), 4.16 (dd, 1H), 4.11-4.04 (m, 2H), 4.02 (s, 3H), 3.44-3.38 (m, 1H), 3.19 (dd, 1H), 3.13 (dt, 1H), 2.28-2.17 (m, 2H), 2.16-2.07 (m, 1H), 1.91-1.69 (m, 3H), 1.42-1.30 (m, 1H); MS (EI) for C$_{23}$H$_{23}$N$_4$O$_3$FCl$_2$: 493 (MH$^+$).

N-(4-Bromo-5-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine: $^1$H NMR (400 MHz, CDCl$_3$): 8.95 (d, 1H), 8.72 (s, 1H), 7.43 (d, 1H), 7.28 (s, 1H), 6.93 (s, 1H), 4.24 (dd, 1H), 4.15 (dd, 1H), 4.12-4.04 (m, 2H), 4.02 (s, 3H), 3.44-3.37 (m, 1H), 3.19 (dd, 1H), 3.13 (dt, 1H), 2.27-2.16 (m, 2H), 2.16-2.06 (m, 1H), 1.90-1.69 (m, 3H), 1.42-1.28 (m, 1H); MS (EI) for C$_{23}$H$_{23}$N$_4$O$_3$FClBr: 537 (MH$^+$).

Example 10

N-(3,4-Dichloro-2-fluorophenyl)-6-(methyloxy)-7-[(octahydro-2H-quinolizin-3-ylmethyl)oxy]quinazolin-4-amine Octahydro-2H-quinolizin-3-ylmethanol: Ethyl octahydro-2H-quinolizine-3-carboxylate (2.35 g, 11.1 mmol) was added dropwise to a stirred suspension of lithium aluminum hydride (1 M solution in tetrahydrofuran, 33 mL, 33 mmol) in tetrahydrofuran (50 mL) at 0° C. The reaction was stirred at room temperature for 3 h. The mixture was cooled in an ice bath and ethyl acetate (6 mL) was added slowly, followed by water (1.25 mL), 15% aqueous sodium hydroxide solution (5 mL) and water (1.25 mL). The mixture was filtered through a pad of celite and washed with ether. The filtrate was concentrated in vacuo and dried rigorously to afford octahydro-2H-quinolizin-3-ylmethanol as a yellow oil (1.66 g, 9.82 mmol, 88% yield). MS (EI) for C$_{10}$H$_{19}$NO: 170 (MH$^+$).

Octahydro-2H-quinolizin-3-ylmethyl methanesulfonate: Octahydro-2H-quinolizin-3-ylmethanol (600 mg, 3.55 mmol) was dissolved in dichloromethane (8 mL) and triethylamine (1.5 mL, 10.8 mmol) was added at 0° C. followed by dropwise addition of methanesulfonyl chloride (0.56 mL, 7.16 mmol). The solution was warmed to room temperature and stirred for 1.25 h and then was concentrated in vacuo. The residue was partitioned between ethyl acetate and saturated sodium bicarbonate solution. The aqueous portion was extracted with ethyl acetate. The combined organic portion was washed with brine, dried over sodium sulfate, filtered and concentrated in vacuo to afford octahydro-2H-quinolizin-3-ylmethyl methanesulfonate as an orange oil (796 mg, 3.22 mmol, 91% yield). MS (EI) for C$_{11}$H$_{21}$NO$_3$S: 248 (MH$^+$).

N-(3,4-dichloro-2-fluorophenyl)-6-(methyloxy)-7-[(octahydro-2H-quinolizin-3-ylmethyl)oxy]quinazolin-4-amine: 4-[(3,4-Dichloro-2-fluorophenyl)amino]-6-(methyloxy)quinazolin-7-ol hydrochloride (469 mg, 1.20 mmol) was dissolved in dimethylformamide (1 mL) and potassium carbonate (828 mg, 6.00 mmol) was added followed by octahydro-2H-quinolizin-3-ylmethyl methanesulfonate (466 mg, 1.89 mmol) in dimethylformamide (1 mL). The mixture was stirred at 70° C. for 38 h and then was partitioned between ethyl acetate and water. The aqueous portion was extracted with ethyl acetate. The combined organic portion was dried over sodium sulfate, filtered and concentrated in vacuo to afford a brown oil which was purified by column chromatography (15-20% methanol in dichloromethane). The purified material was crystallized from methanol to afford N-(3,4-dichloro-2-fluorophenyl)-6-(methyloxy)-7-[(octahydro-2H-quinolizin-3-ylmethyl)oxy]quinazolin-4-amine as a cream colored solid (83.4 mg, 0.165 mmol, 14% yield). $^1$H NMR (400 MHz, CDCl$_3$): 8.69 (s, 1H), 8.53 (t, 1H), 7.34 (dd, 1H), 7.28-7.22 (m, 1H), 7.23 (s, 1H), 6.98 (s, 1H), 4.06-3.95 (m, 2H), 4.02 (s, 3H), 3.09 (d, 1H), 2.87 (d, 1H), 2.43-2.27 (m, 1H), 2.10-1.97 (m, 1H), 1.95-1.84 (m, 2H), 1.80-1.52 (m, 5H), 1.46-0.95 (m, 5H); MS (EI) for $C_{25}H_{27}N_4O_2FCl_2$: 505 (MH$^+$).

Example 11

(3S,8aS)-3-({[4-[(3,4-Dichloro-2-fluorophenyl)amino]-6-(methyloxy)quinazolin-7-yl]oxy}methyl)-2-methylhexahydropyrrolo[1,2-α]pyrazin-1(2H)-one (3S,8aS)-3-(Hydroxymethyl)hexahydropyrrolo[1,2-α]pyrazin-1(2H)-one: A solution of methyl 1-[(2S)-3-hydroxy-2-({[(phenylmethyl)oxy]carbonyl}amino)propyl]-L-prolinate (3.50 g, 10.4 mmol) in methanol was added to 5% palladium on carbon (50 wt. % in water) in methanol and treated with hydrogen at 40 psi for 1 h. The mixture was filtered and the filtrate was brought to reflux briefly and then cooled and concentrated in vacuo to afford (3S,8aS)-3-(hydroxymethyl)hexahydropyrrolo[1,2-α]pyrazin-1(2H)-one as a colorless solid (1.50 g, 8.83 mmol, 85% yield). $^1$H NMR (400 MHz, CDCl$_3$): 7.28-7.22 (m, 1H), 3.83-3.75 (m, 1H), 3.69 (dd, 1H), 3.56 (dd, 1H), 3.31 (t, 1H), 3.08 (dd, 1H), 2.92 (dt, 1H), 2.76-2.70 (m, 1H), 2.66 (dd, 1H), 2.28-2.16 (m, 1H), 2.02-1.73 (m, 3H); MS (EI) for $C_8H_{14}N_2O_2$: 171 (MH$^+$).

(3S,8aS)-3-({[(1,1-Dimethylethyl)(dimethyl)silyl]oxy}methyl)hexahydropyrrolo [1,2-α]pyrazin-1(2H)-one: To a solution of (3S,8aS)-3-(hydroxymethyl) hexahydropyrrolo[1,2-α]pyrazin-1(2H)-one (1.49 g, 8.82 mmol) in dimethylformamide (20 mL) was added triethylamine (2.45 mL, 17.6 mmol) and 4-dimethylaminopyridine (90 mg, 0.882 mmol). The solution was cooled in an ice bath and tert-butyldimethylsilyl chloride (2.66 g, 17.6 mmol) was added. The mixture was warmed to room temperature and stirred for 14 h. The mixture was concentrated in vacuo and the residue was partitioned between ethyl acetate and water. The aqueous portion was extracted twice with ethyl acetate. The combined organic portion was dried over sodium sulfate, filtered and concentrated in vacuo to afford a pale brown solid which was triturated with ethyl acetate to afford (3S,8aS)-3-({[(1,1-dimethylethyl)(dimethyl)silyl]oxy}methyl) hexahydropyrrolo[1,2-α]pyrazin-1(2H)-one as an off-white solid (1.74 g, 5.84 mmol, 66% yield). $^1$H NMR (400 MHz, CDCl$_3$): 6.09-5.90 (m, 1H), 3.86-3.76 (m, 1H), 3.63 (dd, 1H), 3.44 (dd, 1H), 3.25 (t, 1H), 3.10 (ddd, 1H), 2.98-2.90 (m, 1H), 2.68-2.60 (m, 1H), 2.52 (dd, 1H), 2.28-2.18 (m, 1H), 2.06-1.95 (m, 1H), 1.93-1.74 (m, 2H), 0.90 (s, 9H), 0.07 (s, 6H); MS (EI) for $C_{14}H_{28}N_2O_2Si$: 285 (MH$^+$).

(3S,8aS)-3-({[(1,1-Dimethylethyl)(dimethyl)silyl]oxy}methyl)-2-methylhexahydro pyrrolo[1,2-α]pyrazin-1(2H)-one: (3S,8aS)-3-({[(1,1-Dimethylethyl)(dimethyl)silyl]oxy} methyl)hexahydropyrrolo[1,2-α]pyrazin-1(2H)-one (1.51 g, 5.32 mmol) in dimethylformamide (8 mL) was added to an ice-cooled suspension of sodium hydride (60 wt. % dispersion in oil; 213 mg, 5.32 mmol) in dimethylformamide (8 mL). The mixture was stirred at 0° C. for 0.25 h and then iodomethane (0.332 mL, 5.32 mmol) was added dropwise. The mixture was stirred at room temperature for 0.5 h and then was stirred at 70° C. for 2 h. The mixture was concentrated in vacuo and the residue was partitioned between ethyl acetate and water. The aqueous portion was extracted with ethyl acetate. The combined organic portion was dried over sodium sulfate, filtered and concentrated in vacuo to afford (3S,8aS)-3-({[(1,1-dimethylethyl)(dimethyl)silyl]oxy}methyl)-2-methylhexahydropyrrolo[1,2-α]pyrazin-1(2H)-one as a yellow oil (1.552 g, 5.21 mmol) which was dissolved in tetrahydrofuran (20 mL) and treated with tetrabutylammonium fluoride (1.0M solution in tetrahydrofuran; 10.4 mL, 10.4 mmol) for 2 h at room temperature. The mixture was concentrated in vacuo and purified by column chromatography (10% methanol in dichloromethane) to afford (3S,8aS)-3-(hydroxymethyl)-2-methylhexahydropyrrolo[1,2-α]pyrazin-1(2H)-one as a yellow oil (496 mg, 2.70 mmol, 51% yield from (3S,8aS)-3-({[(1,1-dimethylethyl)(dimethyl)silyl]oxy} methyl)hexahydropyrrolo[1,2-α]pyrazin-1(2H)-one).

$^1$H NMR (400 MHz, CDCl$_3$): 3.98-3.93 (m, 1H), 3.86 (dd, 1H), 3.61-3.55 (m, 1H), 3.29-3.25 (m, 1H), 3.09-3.03 (m, 1H), 3.03-2.97 (m, 1H), 3.02 (s, 3H), 2.93 (dd, 1H), 2.87-2.79 (m, 1H), 2.32-2.21 (m, 1H), 2.00-1.86 (m, 2H), 1.83-1.64 (m, 1H); MS (EI) for $C_9H_{16}N_2O_2$: 185 (MH$^+$).

(3S,8aS)-3-({[4-[(3,4-Dichloro-2-fluorophenyl)amino]-6-(methyloxy)quinazolin-7-yl]oxy}methyl)-2-methylhexahydropyrrolo[1,2-α]pyrazin-1(2H)-one: (3S,8aS)-3-(Hydroxymethyl)-2-methylhexahydropyrrolo[1,2-α]pyrazin-1(2H)-one (505 mg, 2.74 mmol) was dissolved in dichloromethane (10 mL) and triethylamine (0.8 mL, 5.75 mmol) was added at 0° C. followed by dropwise addition of methanesulfonyl chloride (0.45 mL, 5.81 mmol). The solution was warmed to room temperature and stirred for 1.25 h and then was concentrated in vacuo. The residue was partitioned between ethyl acetate and saturated sodium bicarbonate solution. The aqueous portion was extracted with ethyl acetate. The combined organic portion was washed with brine, dried over sodium sulfate, filtered and concentrated in vacuo to afford [(3S,8aS)-2-methyl-1-oxooctahydropyrrolo[1,2-α]pyrazin-3-yl]methyl methanesulfonate as an orange oil (538 mg, 2.05 mmol, 75% yield). 4-[(3,4-Dichloro-2-fluorophenyl)amino]-6-(methyloxy)quinazolin-7-ol hydrochloride (469 mg, 1.20 mmol) was dissolved in dimethylformamide (1 mL) and potassium carbonate (828 mg, 6.00 mmol) was added followed by [(3S,8aS)-2-methyl-1-oxooctahydropyrrolo[1,2-α]pyrazin-3-yl]methyl methanesulfonate (538 mg, 2.05 mmol) in dimethylformamide (1 mL). The mixture was stirred at 70° C. for 34 h and then was concentrated in vacuo. The residue was partitioned between ethyl acetate and water. The aqueous portion was extracted with ethyl acetate. The combined organic portion was dried over sodium sulfate, filtered and concentrated in vacuo to afford a brown oil which was purified by column chromatography (6-8% methanol in dichloromethane) to afford a yellow foam (300 mg, 0.577 mmol, 48% yield). The yellow foam (100 mg) was purified further by column chromatography (ethyl acetate-ethanol 1:1) to afford (3S,8aS)-3-({[4-[(3,4-dichloro-2-fluorophenyl)amino]-6-(methyloxy)quinazolin-7-yl]oxy}methyl)-2-methylhexahydropyrrolo[1,2-α]pyrazin-1(2H)-one as a yellow solid (60 mg). $^1$H NMR (400 MHz, CDCl$_3$): 8.71 (s, 1H), 8.52 (dd, 1H), 7.36-7.32 (m, 2H), 7.01 (s, 1H), 4.49 (dd, 1H), 4.34 (dd, 1H), 4.03 (s, 3H), 3.90-3.84 (m, 1H), 3.47 (t, 1H), 3.13 (s, 3H), 3.05 (dd, 1H), 2.95 (dd, 1H), 2.93-2.83 (m, 2H), 2.29-2.19 (m, 1H), 2.03-

1.84 (m, 2H), 1.83-1.70 (m, 1H); MS (EI) for $C_{24}H_{24}N_5O_3FCl_2$: 520 (MH$^+$).

Example 12

(3S,8aS)-3-({[4-[(3,4-dichloro-2-fluorophenyl) amino]-6-(methyloxy)quinazolin-7-yl]oxy}methyl) hexahydropyrrolo[1,2-α]pyrazin-1(2H)-one 1,2-Dideoxy-1-[(2S)-2-(methoxycarbonyl)-1-pyrrolidinyl]-2-[[(phenylmethoxy) carbonyl]amino]-D-glycero-hexitol: To a solution of 2-deoxy-2-{[(phenylmethyloxy) carbonyl]amino}-D-glycero-hexopyranose (5.0 g, 0.016 mol) in methanol (500 mL) was added L-proline methyl ester hydrochloride (2.8 g, 0.022 mol) and sodium cyanoborohydride (3.4 g, 0.054 mol). The solution was heated to 64° C. for 14 h. After cooling to room temperature, the reaction mixture was concentrated in vacuo to afford 1,2-dideoxy-1-[(2S)-2-(methoxycarbonyl)-1-pyrrolidinyl]-2-[[(phenylmethoxy) carbonyl]amino]-D-glycero-hexitol (6.81 g, 100%) as a clear and colorless oil. MS (EI) for $C_{20}H_{31}N_2O_8$: 427 (MH$^+$).

Methyl 1-[(2S)-3-hydroxy-2-({[(phenylmethyl)oxy] carbonyl}amino)propyl]-L-prolinate: 1,2-dideoxy-1-[(2S)-2-(methoxycarbonyl)-1-pyrrolidinyl]-2-[[(phenylmethoxy) carbonyl]amino]-D-glycero-hexitol (6.81 g, 0.016 mol) was taken into water (100 mL) and the resulting solution was cooled to 0° C. Sodium periodiate (14.8 g, 0.069 mol) dissolved in water was added dropwise and the resulting mixture was stirred at 0° C. for 2 h. The reaction mixture was partitioned with dichloromethane (3×100 mL), dried over anhydrous magnesium sulfate, filtered and concentrated in vacuo. The residue was taken up in methanol (200 mL) and the resulting solution was cooled to 0° C. Sodium borohydride (1.98 g, 0.052 mol) was added and the reaction mixture was stirred for 1 h at 0° C. The reaction mixture was concentrated in vacuo and partitioned with dichloromethane and saturated aqueous ammonium chloride. The organic layer was dried over anhydrous magnesium sulfate, filtered and concentrated in vacuo. The resulting crude product was purified by column chromatography (5% methanol in dichloromethane) to yield methyl 1-[(2S)-3-hydroxy-2-({[(phenylmethyl)oxy] carbonyl}amino)propyl]-L-prolinate (4.9 g, 92%) as a white solid. MS (EI) for $C_{17}H_{25}N_2O_5$: 337 (MH$^+$).

Methyl 1-[(2S)-3-[(methylsulfonyl)oxy]-2-({[(phenylmethyl)oxy]carbonyl}amino) propyl]-L-prolinate: Methyl 1-[(2S)-3-hydroxy-2-({[(phenylmethyl)oxy] carbonyl}amino) propyl]-L-prolinate (200 mg, 0.594 mmol) was dissolved in dichloromethane (5 mL) followed by the addition of 4-(dimethylamino)pyridine (3.6 mg, 0.039 mmol) and triethylamine (0.125 mL, 0.891 mmol) and the resulting mixture was cooled to 0° C. Methanesulfonyl chloride (0.060 mL, 0.773 mmol) was added dropwise and the reaction mixture was stirred for 1 h at 0° C. The mixture was partitioned between dichloromethane and saturated aqueous sodium bicarbonate. The organic layer was dried over anhydrous magnesium sulfate, filtered and concentrated in vacuo to afford methyl 1-[(2S)-3-[(methylsulfonyl)oxy]-2-({[(phenylmethyl)oxy]carbonyl}amino)propyl]-L-prolinate (246 mg, 100%) as a clear and colorless oil. MS (EI) for $C_{18}H_{27}N_2O_7S$: 415 (MH$^+$).

methyl (1R)-2-[(2S)-3-{[4-[(3,4-dichloro-2-fluorophenyl)amino]-6-(methyloxy) quinazolin-7-yl]oxy}-2-({[(phenylmethyl)oxy]carbonyl}amino)propyl]cyclopentane carboxylate: 4-[(3,4-dichloro-2-fluorophenyl)amino-6-(methyloxy)quinazolin-7-ol hydrochloride (400 mg, 1.02 mmol) and methyl 1-[(2S)-3-[(methylsulfonyl)oxy]-2-({[(phenylmethyl)oxy]carbonyl}amino)propyl]-L-prolinate (603 mg, 1.45 mmol) were suspended in DMF (5 mL) and powdered potassium carbonate (705 mg, 5.10 mmol) was added. The mixture was stirred at 70° C. for 12 h. The reaction mixture was filtered and concentrated in vacuo. The crude residue was purified by column chromatography (10% methanol in dichloromethane) to yield methyl (1R)-2-[(2S)-3-{[4-[(3,4-dichloro-2-fluorophenyl)amino]-6-(methyloxy) quinazolin-7-yl]oxy}-2-({[(phenylmethyl)oxy] carbonyl}amino)propyl]cyclopentanecarboxylate (686 mg, 100%) as a yellow oil. MS (EI) for $C_{32}H_{32}Cl_2FN_5O_6$: 672 (M$^+$).

(3S,8aS)-3-({[4-[(3,4-dichloro-2-fluorophenyl)amino]-6-(methyloxy)quinazolin-7-yl]oxy}methyl)hexahydropyrrolo [1,2-α]pyrazin-1(2H)-one: Methyl (1R)-2-[(2S)-3-{[4-[(3,4-dichloro-2-fluorophenyl)amino]-6-(methyloxy)quinazolin-7-yl]oxy}-2-({[(phenylmethyl) oxy]carbonyl}amino)propyl]cyclopentanecarboxylate (686 mg, 1.02 mmol) was diluted with glacial acetic acid (3 mL) and 30 wt % hydrogen bromide in acetic acid (2 mL) was added. The resulting mixture was stirred for 13 h and then concentrated in vacuo. The crude residue was taken up in methanol, (5 mL) followed the addition of powdered potassium carbonate (700 mg, 5.07 mmol) at room temperature. The resulting mixture was stirred for 7 h, filtered, and concentrated in vacuo. The crude residue was purified by column chromatography (10% methanol in dichloromethane) to yield the title compound (181 mg, 35%) as a yellow solid. $^1$H NMR (400 MHz, d$_4$-MeOH): 8.34 (s, 1H), 7.75 (s, 1H), 7.76-7.55 (m, 1H), 7.45-7.40 (dd, 1H), 7.17 (s, 1H), 4.30-4.25 (m, 1H), 4.20-4.15 (m, 2H), 4.03 (s, 3H), 3.78-3.70 (m, 1H), 3.65-3.60 (m, 1H), 3.55-3.50 (m, 1H), 3.32-3.29 (m, 2H), 3.00-2.95 (m, 2H), 2.83-2.78 (m, 2H), 2.25-2.15 (m, 2H); MS (EI) for $C_{23}H_{23}Cl_2FN_5O_3$: 507 (MH$^+$).

Using the same or analogous synthetic techniques and/or substituting with alternative reagents, the following compounds of the invention were prepared:

(3S,8aR)-3-({[4-[(3,4-dichloro-2-fluorophenyl)amino]-6-(methyloxy)quinazolin-7-yl]oxy}methyl)hexahydropyrrolo [1,2-α]pyrazin-1(2H)-one: $C_{23}H_{23}Cl_2FN_5O_3$: 507 (MH$^+$).

(3S,8aS)-3-({[4-[(4-bromo-3-chloro-2-fluorophenyl) amino]-6-(methyloxy)quinazolin-7-yl]oxy}-methyl) hexahydropyrrolo[1,2-a]pyrazin-1-(2H)-one: $^1$H NMR (400 MHz, d$_4$-MeOH): 8.36 (s, 1H), 7.71 (s, 1H). 7.60-7.55 (m, 2H), 7.18 (s, 1H), 4.29-4.22 (m, 1H), 4.19-4.14 (m, 1H), 4.02 (s, 3H), 3.99-3.92 (m, 1H), 3.36-3.30 (m, 1H), 3.32-3.90 (m, 2H), 2.82-2.74 (m, 1H), 2.26-2.10 (m, 1H), 2.19-2.18 (m, 3H), 1.30-1.20 (m, 2H), 0.90-0.80 (m, 1H); MS (EI) for $C_{23}H_{23}BrClN_5O_3$: 551 (MH$^+$).

(3S,9aS)-3-({[4-[(3,4-dichloro-2-fluorophenyl)amino]-6-(methyloxy)quinazolin-7-yl]oxy}methyl)hexahydro-2H-pyrido[1,2-]pyrazin-[(6H)-one: $C_{24}H_{25}Cl_2FN_5O_3$: 521 (MH$^+$).

(3S,9aR)-3-({[4-[(3,4-dichloro-2-fluorophenyl)amino]-6-(methyloxy)quinazolin-7-yl]oxy}methyl)hexahydro-2H-pyrido[1,2-α]pyrazin-[(6H)-one: $C_{24}H_{25}Cl_2FN_5O_3$: 521

Example 13

N-(4-bromo-3-chloro-2-fluorophenyl)-7-({[(3aR,5r,6aS)-2-methyloctahydrocyclo-penta[c]pyrrol-5-yl] methyl}oxy)-6-(methyloxy)quinazolin-4-amine hydrochloride 1,1-Dimethylethyl (3aR,6aS)-5-(hydroxymethyl)hexahydrocyclopenta[c]pyrrole-2(1H)-carboxylate: Under a nitrogen atmosphere, borane tetrahydrofuran complex (1M in THF, 42 mL, 41.9 mmol) was diluted with tetrahydrofuran (42 mL) and cooled with an ice bath. Neat 2,3-dimethylbut- 2-ene (5.0 mL, 41.9 mmol) was added in portions over 0.25 h and the solution was stirred at 0° C. for 3 h. A solution of 1,1-dimethylethyl (3aR,6aS)-5-methylidenehexahydrocyclopenta[c]pyrrole-2(1H)-carboxylate (1.98 g, 8.88 mmol) in tetrahydrofuran (10 mL) was added slowly, and the solution was warmed to room temperature and stirred 12 h. After cooling to 0° C., 10% aqueous sodium hydroxide (17 mL, 41.7 mmol) was added slowly, followed by 30% aqueous hydrogen peroxide (13 mL, 128 mmol) and the solution was warmed to room temperature. The solvent was removed in vacuo and the solution was partitioned between water and diethyl ether. The layers were separated and the aqueous layer was further extracted (3×50 mL diethyl ether). The combined organic layers were dried over anhydrous sodium sulfate, filtered and concentrated in vacuo to provide 2.04 (95%) of 1,1-dimethylethyl (3aR,6aS)-5-(hydroxymethyl)hexahydrocyclopenta[c]pyrrole-2(1H)-carboxylate, which was used without purification. $^1$H NMR (400 MHz, CDCl$_3$): 8.50 (broad s, 1H), 3.66-3.46 (m, 3H), 3.20-3.00 (m, 2H), 2.70-2.59 (m, 2H), 2.37-2.18 (m, 1H), 2.04 (m, 1H), 1.84 (broad s, 1H), 1.70-1.55 (m, 1H), 1.46 (s, 9H), 1.17 (m, 1H), 0.93 (m, 1H).

1,1-Dimethylethyl (3aR,6aS)-5-{[(methylsulfonyl)oxy]methyl}hexahydrocyclo-penta[c]pyrrole-2(1H)-carboxylate Methanesulfonyl chloride (0.2 mL, 2.48 mmol), was added dropwise to a solution of 1,1-dimethylethyl (3aR,6aS)-5-(hydroxymethyl)hexahydro cyclopenta[c] pyrrole-2(1H)-carboxylate (0.40 g, 1.65 mmol) and triethylamine (0.69 mL, 4.95 mmol) in 20 mL dichloromethane at 0° C. and the reaction mixture was stirred for 1 h at room temperature. The solvent was evaporated, the resulting crude mixture was diluted with 100 mL ethyl acetate and washed with water (30 mL), 1M aqueous sodium hydroxide, brine, 1M aqueous hydrochloric acid and brine again. The organic layer was dried over anhydrous sodium sulfate, filtered and concentrated in vacuo. The resulting 1,1-dimethylethyl (3aR,6aS)-5-{[(methylsulfonyl)oxy]methyl}hexahydrocyclopenta[c]pyrrole-2(1H)-carboxylate was used without further purification. MS (EI) for $C_{14}H_{25}NO_5S$: 320 (MH$^+$), 264 (M-tBu).

1,1-Dimethylethyl (3aR,6aS)-5-({[4-[(4-bromo-3-chloro-2-fluorophenyl)amino]-6-(methyloxy)quinazolin-7-yl]oxy}methyl)hexahydrocyclopenta[c]pyrrole-2(1H)-carboxylate: A solution of 4-[(4-bromo-3-chloro-2-fluorophenyl)amino]-6-(methyloxy)quinazolin-7-ol trifluoroacetate (salt) (0.217 g, 0.425 mmol), 1,1-dimethylethyl (3aR,6aS)-5-{[(methylsulfonyl)oxy]methyl}hexahydrocyclopenta[c]pyrrole-2(1H)-carboxylate (0.163 g, 0.510 mmol), potassium carbonate (0.290 g, 2.12 mmol) in N,N-dimethylacetamide (1.6 mL) was heated in a sealed reaction tube at 90° C. for 12 h. The crude reaction mixture was diluted with 100 mL of 10% methanol in ethyl acetate and washed with water (5×30 mL). The organic layer was dried over anhydrous sodium sulfate, filtered and concentrated in vacuo. Column chromatography (SiO$_2$, 3:1 hexanes:acetone) provided 1,1-dimethylethyl (3aR,6aS)-5-({[4-[(4-bromo-3-chloro-2-fluorophenyl)amino]-6-(methyloxy)quinazolin-7-yl]oxy} methyl)hexahydrocyclopenta[c]pyrrole-2(1H)-carboxylate which was used directly in the next step. MS (EI) for $C_{28}H_{31}N_4O_4FClBr$: 623 (MH$^+$).

N-(4-Bromo-3-chloro-2-fluorophenyl)-6-(methyloxy)-7-{[(3aR,5r,6aS)-octahydro-cyclopenta[c]pyrrol-5-ylmethyl]oxy}quinazolin-4-amine hydrochloride: 1,1-Dimethylethyl (3aR,6aS)-5-(I{[[(4-bromo-3-chloro-2-fluorophenyl)amino]-6-(methyl-oxy)quinazolin-7-yl]oxy}methyl) hexahydrocyclopenta[c]pyrrole-2(1H)-carboxylate derivative was taken up in methanol (50 mL) and treated with 4.0M hydrogen chloride in dioxane (excess) and heated briefly to reflux. Concentration in vacuo gave N-(4-bromo-3-chloro-2-fluorophenyl)-6-(methyloxy)-7-{[(3aR,5r,6aS)-octahydrocyclopenta[c]pyrrol-5-ylmethyl]oxy}quinazolin-4-amine hydrochloride which was used directly in the next step. $^1$H NMR (400 MHz, d$_4$-MeOH): 8.70 (s, 1H), 7.97 (s, 1H), 7.68 (d, 1H), 7.49 (t, 1H), 7.28 (s, 1H), 4.25 (m, 2H), 4.08 (s, 3H), 3.57 (m, 1H), 3.02 (m, 4H), 2.80-2.60 (m, 2H), 2.35 (m, 1H), 1.89 (m, 4H), 1.40 (m, 1H). MS (EI) for $C_{23}H_{23}N_4O_2FClBr$: 522 (MH$^+$).

N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine hydrochloride: N-(4-Bromo-3-chloro-2-fluorophenyl)-6-(methyloxy)-7-{[(3aR,5r,6aS)-octahydrocyclopenta-[c]pyrrol-5-ylmethyl]oxy}quinazolin-4-amine hydrochloride was solubilized in formic acid (3.0 mL) and 37% aqueous formaldehyde (0.5 mL, 2.55 mmol) was added. The solution was heated to 95° C. for 12 h and additional formaldehyde (1.0 mL, 5.10 mmol) was added. After heating an additional 12 h, the reaction mixture was concentrated in vacuo. The residue was taken up in methanol and treated with Bio-Rad AG 1-X8 resin hydroxide form until pH 8. The product was filtered, concentrated in vacuo, and purified by HPLC (reverse-phase, water/acetonitrile/0.1% TFA). Upon removal of solvent, the product was taken up in methanol and treated with Bio-Rad AG 1-X8 resin hydroxide form until pH 8. The product was filtered and concentrated in vacuo then taken up in fresh methanol and treated with 4.0 M hydrogen chloride in dioxane (0.05 mL). Removal of solvent in vacuo provided 54.1 mg (24%) of N-(4-bromo-3-chloro-2-fluorophenyl)-7-({[(3aR,5r,6aS)-2-methyloctahydro-cyclopenta[c]pyrrol-5-yl]methyl}oxy)-6-(methyloxy)quinazolin-4-amine hydrochloride. $^1$H NMR (400 MHz, d$_6$-DMSO): 8.83 (d, 1H), 8.33 (s, 1H), 7.80 (d, 1H), 7.56 (t, 1H), 7.40 (s, 1H), 4.16 (m, 2H), 4.01 (s, 3H), 3.80-3.68 (m, 1H), 3.05 (m, 2H), 2.90-2.70 (m, 5H), 2.34 (m, 1H), 2.15 (m, 2H), 1.75 (m, 1H), 1.57 (m, 2H), 1.35 (m, 1H). MS (EI) for $C_{24}H_{25}N_4O_2FClBr$: 537 (MH$^+$).

Using the same or analogous synthetic techniques and/or substituting with alternative reagents, the following compounds of the invention were prepared:

N-(4-bromo-5-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine hydrochloride: $^1$H NMR (400 MHz, d$_6$-DMSO): 8.83 (d, 1H), 8.33 (s, 1H), 8.03 (d, 1H), 7.93 (d, 1H), 7.41 (, 1H), 4.16 (m, 2H), 4.02 (s, 3H), 3.70 (m, 1H), 3.05 (m, 2H), 2.91-2.75 (m, 5H), 2.34 (m, 1H), 2.16 (m, 2H), 1.75 (m, 1H), 1.57 (m, 2H), 1.35 (m, 1H). MS (EI) for $C_{24}H_{25}N_4O_2FClBr$: 537 (MH$^+$).

N-(3-chloro-2,4-difluorophenyl)-7-({[(3aR,5r,6aS)-2-methyloctahydrocyclopenta-[c]pyrrol-5-yl]methyl}oxy)-6-(methyloxy)quinazolin-4-amine hydrochloride: $^1$H NMR (400 MHz, d$_6$-DMSO): 8.81 (d, 1H), 8.39 (d, 1H), 7.61 (m, 1H), 7.47 (m, 1H), 7.42 (s, 1H), 4.17 (m, 2H), 4.02 (s, 3H), 3.67 (m, 1H), 3.05 (m, 2H), 2.91-2.75 (m, 5H), 2.34 (m, 1H), 2.16 (m, 2H), 1.75 (m, 1H), 1.57 (m, 2H), 1.35 (m, 1H). MS (EI) for $C_{24}H_{25}N_4O_2F_2Cl$: 475 (MH$^+$).

Example 14

N-(3,4-dichloro-2-fluorophenyl)-7-({[(3aR,5r,6aS)-2-methyloctahydrocyclopenta-[c]pyrrol-5-yl]methyl}oxy)-6-(methyloxy)quinazolin-4-amine hydrochloride 1,1-Dimethylethyl (3aR,6aS)-5-({[4-[(3,4-dichloro-2-fluorophenyl)amino]-6-(methyloxy)quinazolin-7-yl]

oxy}methyl)hexahydrocyclopenta[c]pyrrole-2(1H)-carboxylate: A solution of 4-[(3,4-dichloro-2-fluorophenyl)amino]-6-(methyloxy)quinazolin-7-ol trifluoroacetate (salt) (0.22 g, 0.47 mmol), 1,1-dimethylethyl (3aR,6aS)-5-{[(methylsulfonyl)oxy]methyl}hexahydrocyclopenta[c]pyrrole-2(1H)-carboxylate (0.16 g, 0.51 mmol), $K_2CO_3$ (0.33 g, 2.36 mmol) in N,N-dimethylacetamide (5 mL) was heated in a sealed reaction tube at 90° C. for 12 h. The crude reaction mixture was diluted with 100 mL 10% methanol in ethyl acetate and washed with saturated aqueous sodium bicarbonate (1×30 mL), water (1×30 mL) and brine (1×30 mL). The organic layer was dried over anhydrous sodium sulfate, filtered and concentrated in vacuo. Column chromatography ($SiO_2$, 3:2 hexanes:acetone) provided 1,1-dimethylethyl (3aR,6aS)-5-({[4-[(3,4-dichloro-2-fluorophenyl)amino]-6-(methyloxy)quinazolin-7-yl]oxymethyl) hexahydrocyclopenta-[c]pyrrole-2(1H)-carboxylate which was used directly in the next step. MS (EI) for $C_{28}H_{31}Cl_2FN_4O_4$: 577, 579 (MH$^+$).

N-(3,4-dichloro-2-fluorophenyl)-6-(methyloxy)-7-{[(3aR,5r,6aS) -octahydrocyclo-penta[c]pyrrol-5-yl]methyl]oxy}quinazolin-4-amine hydrochloride: 1,1-Dimethylethyl (3aR,6aS)-5-({[4-[(3,4-dichloro-2-fluorophenyl)amino]-6-(methyloxy)quinazolin-7-yl]-oxy}methyl)hexahydrocyclopenta[c]pyrrole-2(1H)-carboxylate was taken up in methanol (10 mL) and treated with 4.0M hydrogen chloride in dioxane (excess) and heated briefly to reflux. Concentration in vacuo provided N -(3,4-dichloro-2-fluorophenyl)-6-(methyloxy)-7-{[[(3aR,5r,6aS) -octahydrocyclopenta[c]pyrrol-5-yl]methyl]oxy}quinazolin-4-amine hydro-chloride. MS (EI) for $C_{23}H_{23}Cl_2FN_4O_2$: 477, 479 (MH$^+$).

N-(3,4-Dichloro-2-fluorophenyl)-7-({[(3aR,5r,6aS)-2-methyloctahydrocyclo-penta[c]pyrrol-5-yl]methyl}oxy)-6-(methyloxy)quinazolin-4-amine hydrochloride: N-(3,4-Dichloro-2-fluorophenyl)-6-(methyloxy)-7-{[(3aR,5r,6aS)-octahydrocyclopenta[c]pyrrol-5-yl]methyl]oxy}quinazolin-4-amine hydrochloride was solubilized in formic acid (5.0 mL) and 37% aqueous formaldehyde (1 mL) was added. The solution was heated to 95° C. for 12 h. The reaction mixture was concentrated in vacuo. The residue was taken up in a mixture of 10% methanol in ethyl acetate (100 mL) and washed with saturated aqueous sodium bicarbonate (2×30 mL) and brine. The organic layer was dried over anhydrous sodium sulfate, filtered then concentrated and purified by HPLC (reverse-phase, water/acetonitrile/0.1% TFA). Upon removal of solvent the product was taken up in 10% methanol in ethyl acetate (100 mL) and washed with saturated aqueous sodium bicarbonate (2×30 mL) and brine. The organic layer was dried over anhydrous sodium sulfate, filtered and concentrated then taken up in methanol and treated with 4.0 M hydrogen chloride in dioxane (1 eq.). Removal of solvent in vacuo provided 78.3 mg (25%) of N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine hydrochloride. $^1$H NMR (400 MHz, d$_6$-DMSO): 11.00 (bs, 1H), 8.36 (d, 1H), 8.10 (s, 1H), 7.58 (s, 2H), 7.20 (d, 1H), 4.16 (m, 2H), 4.00 (s, 3H), 3.35 (bs, 3H), 2.50 (m, 2H), 2.21 (m, 3H), 2.03 (m, 2H), 1.60 (m, 2H), 1.12 (m, 2H). MS (EI) for $C_{24}H_{25}Cl_2FN_4O_2$: 491, 493 (MH$^+$).

Using the same or analogous synthetic techniques and/or substituting with alternative reagents, the following compounds of the invention were prepared:

N-(4,5-dichloro-2-fluorophenyl)-7-({[(3aR,5r,6aS)-2-methyloctahydrocyclo-penta[c]pyrrol-5-yl]methyl}oxy)-6-(methyloxy)quinazolin-4-amine hydrochloride: $^1$H NMR (400 MHz, d$_6$-DMSO): 10.9 (bs, 1H), 8.46 (d, 1H), 8.10 (s, 1H), 8.04 (s, 1H), 7.93 (s, 1H), 7.54 (s, 1H), 4.18 (m, 2H), 4.01 (s, 3H), 3.33 (bs, 3H), 2.46 (m, 2H), 2.23 (s, 3H), 2.04 (m, 2H), 1.58 (m, 2H), 1.14 (m, 2H). MS (EI) for $C_{24}H_{25}Cl_2FN_4O_2$: 491 (MH$^+$).

N-(4-bromo-2,3-dichlorophenyl)-7-({[(3aR,5r,6aS)-2-methyloctahydrocyclo-penta[c]pyrrol-5-yl]methyl}oxy)-6-(methyloxy)quinazolin-4-famine hydrochloride: $^1$H NMR (400 MHz, d$_6$-DMSO): 11.0 (bs, 1H), 8.60 (s, 1H), 8.14 (s, 1H), 7.76 (d, 1H), 7.44 (t, 1H), 7.24 (s, 1H), 4.16 (m, 2H), 4.00 (s, 3H), 3.35 (bs, 3H), 2.50 (m, 2H), 2.18 (m, 3H), 2.03 (m, 2H), 1.60 (m, 2H), 1.12 (m, 2H). MS (EI) for $C_{24}H_{25}BrCl_2N_4O_2$: 550, 552 (MH$^+$).

N-(3,4-dichlorophenyl)-7-({[(3aR,5r,6aS)-2-methyloctahydrocyclopenta[c]pyrrol-5-yl]methyl}oxy)-6-(methyloxy)quinazolin-4-amine hydrochloride: $^1$H NMR (400 MHz, d$_6$-DMSO): 10.98 (bs, 1H), 8.88 (s, 1H), 8.41 (s, 1H), 8.20 (d, 1H), 7.86 (d, 1H), 7.75 (s, 1H), 7.46 (s, 1H), 4.08 (m, 2H), 3.98 (s, 3H), 3.28 (m, 2H), 2.54 (m, 2H), 2.20 (s, m, 4H), 2.18 (m, 2H), 1.62 (m, 2H), 1.24 (m, 2H). MS (EI) for $C_{24}H_{26}Cl_2N_4O_2$: 473 (MH$^+$).

Example 15

N-(4-bromo-3-chloro-2-fluorophenyl)-7-({[(3aR,5r,6aS)-2-(1-methylethyl)octahydro-cyclopenta[c]pyrrol-5-yl]methyl}oxy)-6-(methyloxy)quinazolin-4-amine hydrochloride N-(4-bromo-3-chloro-2-fluorophenyl)-7-({[(3aR,5r,6aS)-2-(1-methylethyl)octahydro-cyclopenta[c]pyrrol-5-yl]methyl}oxy)-6-(methyloxy)quinazolin-4-amine hydrochloride: A solution of N-(4-bromo-3-chloro-2-fluorophenyl)-6-(methyloxy)-7-{[(3aR,5r,6aS)-octahydrocyclopenta[c]pyrrol-5-ylmethyl]oxy}quinazolin-4-amine hydrobromide (0.1 g, 0.166 mmol), acetone (0.024 mL, 0.332 mmol), and glacial acetic acid (5 drops) in acetonitrile:water (3:1) was cooled to 0° C. and sodium triacetoxyborohydride (53.0 mg, 0.249 mmol) was added. The solution was warmed to room temperature and stirred 12 h. Additional acetic acid (5 drops), acetone (0.30 mL, 6.54 mmol), sodium triacetoxyborohydride (0.300 g, 1.42 mmol) was added in portions over 12 h. The acetonitrile was removed in vacuo and the aqueous layer was diluted with saturated aqueous sodium bicarbonate and 10% methanol in ethyl acetate then the layers were separated. The aqueous layer was extracted with 10% methanol in ethyl acetate (2×75 mL). The combined organic layers were dried over anhydrous sodium sulfate, filtered and concentrated. Column chromatography ($SiO_2$, gradient of 30-50% methanol in chloroform) followed by concentration and treatment in methanol with 4.0 M hydrogen chloride in dioxane (0.05 mL) and concentration provided N-(4-bromo-3-chloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine hydrochloride (75.7 mg, 76% yield). $^1$H NMR (400 MHz, d$_4$-MeOH): 8.69 (s, 1H), 7.97 (s, 1H), 7.67 (d, 1H), 7.50 (t, 1H), 7.28 (s, 1H), 4.27 (d, 2H), 4.07 (s, 3H), 3.84-3.20 (m, 4H), 3.01 (m, 3H), 2.80 (m, 1H) 2.34 (m, 3H), 1.52 (m, 2H), 1.42 (dd, 6H); MS (EI) for $C_{26}H_{29}N_4O_2FClBr$: 565 (MH$^+$).

Using the same synthetic techniques and/or substituting with alternative reagents, the following compound of the invention was also prepared.

N-(3,4-dichloro-2-fluorophenyl)-7-({[(3aR,5r,6aS)-2-(1-methylethyl)octahydrocyclo-penta[c]pyrrol-5-yl]methyl}oxy)-6-(methyloxy)quinazolin-4-amine hydrochloride: $^1$H NMR (400 MHz, d$_4$-MeOH): 8.68 (broad s, 1H), 7.98 (broad s, 1H), 7.54 (m, 3H), 7.32 (broad s, 1H), 4.27 (d, 2H), 4.07 (s, 3H), 3.84-3.20 (m, 4H), 3.01 (m, 3H), 2.80 (m, 1H) 2.34 (m, 3H), 1.93-1.75 (m, 2H), 1.42 (dd, 6H); MS (EI) for $C_{26}H_{29}N_4O_2FCl_2$: 519 (MH$^+$).

Example 16

N-(4-bromo-3-chloro-2-fluorophenyl)-7-({[(3aR,5r, 6aS)-2-ethyloctahydrocyclo-penta[c]pyrrol-5-yl] methyl}oxy)-6-(methyloxy)quinazolin-4-amine hydrochloride N-(4-Bromo-3-chloro-2-fluorophenyl)-7-({[(3aR,5r, 6aS)-2-ethyloctahydrocyclo-penta[c]pyrrol-5-yl] methyl}oxy)-6-(methyloxy)quinazolin-4-amine hydrochloride: A solution of N-(4-bromo-3-chloro-2-fluorophenyl)-6-(methyloxy)-7-([(3aR,5r,6aS)-octahydrocyclopenta[c] pyrrol-5-ylmethyl]oxy}quinazolin-4-amine hydrobromide (0.1 g, 0.166 mmol) and acetaldehyde (0.010 mL, 0.249 mmol) in 50% methanol in tetrahydrofuran was cooled to 0° C. and sodium cyanoborohydride (1 M in THF, 0.10 mL, 0.200 mmol) was added. The solution was warmed to room temperature and stirred for 1.5 h. The solvents were removed and the residue was partitioned between water and 10% methanol in ethyl acetate. The layers were separated and the aqueous layer was extracted with 10% methanol in ethyl acetate (3×50 mL). The combined organic layers were dried over anhydrous sodium sulfate, filtered and concentrated. Column chromatography (SiO$_2$, gradient of 5-10% methanol in chloroform), followed by treatment in methanol with 4.0 M hydrogen chloride in dioxane (0.05 mL) and concentration provided N-(4-bromo-3-chloro-2-fluorophenyl)-7-({[(3aR, 5r,6aS)-2-ethyloctahydrocyclopenta[c]pyrrol-5-yl] methyl}oxy)-6-(methyloxy) quinazolin-4-amine hydrochloride (37.5 mg, 36% yield). $^1$H NMR (400 MHz, d$_6$-DMSO): 8.75 (d, 1H), 8.21 (broad s, 1H), 7.75 (d, 3H), 7.54 (t, 1H), 7.34 (m, 1H), 7.12 (d, 1H), 4.16 (d, 2H), 4.00 (s, 3H), 3.75 (m, 1H), 3.11-2.65 (m, 3H), 2.40 (m, 1H), 2.15 (m, 2H), 1.61 (m, 2H), 1.26 (m, 5); MS (EI) for $C_{25}H_{27}N_4O_2FClBr$: 551 (MH$^+$).

Using the same synthetic techniques and/or substituting with alternative reagents, the following compound of the invention were prepared:

N-(4-bromo-3-chloro-2-fluorophenyl)-6-(methyloxy)-7-({[(3aR,5r,6aS)-2-(2-methylpropyl)octahydrocyclopenta[c] pyrrol-5-yl]methyl}oxy)quinazolin-4-amine hydrochloride: $^1$H NMR (400 MHz, d$_6$-DMSO): 8.73 (d, 1H), 8.32 (broad s, 1H), 7.76 (d, 1H), 7.54 (t, 1H), 7.41 (m, 1H), 7.22 (d, 1H), 4.18 (d, 2H), 4.01 (s, 3H), 3.74 (m, 1H), 3.11 (m, 1H), 2.94 (m, 5H), 2.65 (m, 1H), 2.40 (m, 1H), 2.13 (m, 2H), 2.00 (m, 1H), 1.69 (m, 1H), 1.36 (m, 1H), 0.98 (t, 6H); MS (EI) for $C_{27}H_{31}N_4O_2FClBr$: 579 (MH$^+$).

N-(3,4-dichloro-2-fluorophenyl)-7-({[(3aR,5r,6aS)-2-ethyloctahydrocyclopenta[c]pyrrol-5-yl]methyl}oxy)-6-(methyloxy)quinazolin-4-amine hydrochloride: $^1$H NMR (400 MHz, d$_6$-DMSO): 8.77 (d, 1H), 8.36 (broad s, 1H), 7.63 (m, 2H), 7.42 (m, 1H), 7.20 (d, 1H), 4.17 (d, 2H), 4.02 (s, 3H), 3.74 (m, 1H), 3.11-2.75 (m, 4H), 2.66 (m, 1H), 2.36 (m, 1H), 2.14 (m, 2H), 1.80 (m, 1H), 1.65 (m, 1H), 1.28 (m, 5H); MS (EI) for $C_{25}H_{27}N_4O_2FCl_2$: 505 (MH$^+$).

N-(3,4-dichloro-2-fluorophenyl)-6-(methyloxy)-7-({[(3aR,5r,6aS)-2-(2-methylpropyl)octahydrocyclopenta[c] pyrrol-5-yl]methyl}oxy)quinazolin-4-amine hydrochloride: $^1$H NMR (400 MHz, d$_6$-DMSO): 8.83 (d, 1H), 8.36 (d, 1H), 7.68 (d, 1H), 7.62 (t, 1H), 7.43 (d, 1H), 7.30 (d, 1H), 4.18 (d, 2H), 4.01 (s, 3H), 3.75 (m, 1H), 3.11 (m, 1H), 2.95 (m, 5H), 2.67 (m, 1H), 2.40 (m, 1H), 2.14 (m, 2H), 2.00 (m, 1H), 1.69 (m, 1H), 1.36 (m, 1H), 0.98 (t, 6H); MS (EI) for $C_{27}H_{31}N_4O_2FCl_2$: 533 (MH$^+$).

Example 17

Ethyl (3aR,5r,6aS)-5-({[4-[(4-bromo-3-chloro-2-fluorophenyl)amino]-6-(methyloxy) quinazolin-7-yl] oxy}methyl)hexahydrocyclopenta[c]pyrrole-2(1H)-carboxylate hydrochloride Ethyl (3aR,5r,6aS)-5-({[4-[(4-bromo-3-chloro-2-fluorophenyl)amino]-6-(methyloxy) quinazolin-7-yl] oxy}methyl)hexahydrocyclopenta[c]pyrrole-2(1H) -carboxylate hydrochloride: A solution of N-(4-bromo-3-chloro-2-fluorophenyl)-6-(methyloxy)-7-{[(3aR,5r,6aS)-octahydrocyclopenta[c]pyrrol-5-ylmethyl]oxy}quinazolin-4-amine hydrobromide (0.050 g, 0.0830 mmol), triethylamine (0.046 mL, 0.0332 mmol) in 2.0 mL dichloromethane was cooled to 0° C. and ethyl chloridocarbonate (0.010 mL, 0.0913 mmol) was added. The solution was stirred for 0.5 h at low temperature and quenched with saturated aqueous sodium bicarbonate. The reaction mixture was then partitioned between dichloromethane and saturated aqueous sodium bicarbonate. The layers were separated and the aqueous layer was extracted with dichloromethane (2×75 mL). The combined organic layers were dried over anhydrous sodium sulfate, filtered and concentrated in vacuo. Column chromatography (SiO$_2$, 5% methanol in dichloromethane), followed by treatment in methanol with 4.0 M hydrogen chloride in dioxane (0.05 mL) and concentration provided ethyl (3aR,5r,6aS) -5-({[4[(4-bromo-3-chloro-2-fluorophenyl)amino]-6-(methyloxy)quinazolin-7-yl]oxy}methyl) hexahydrocyclopenta[c]pyrrole-2(1H)-carboxylate hydrochloride (27.7 mg, 53% yield). $^1$H NMR (400 MHz, d$_4$-MeOH): 8.59 (s, 1H), 7.83 (s, 1H), 7.60 (d, 1H), 7.41 (t, 1H), 7.12 (s, 1H), 4.14 (d, 2H), 4.11 (m, 2H), 4.09 (s, 3H), 3.45 (dd, 2H), 3.30 (dd, 2H), 2.67 (m, 2H), 2.58 (m, 1H), 2.12 (m, 2H), 1.74 (m, 1H), 1.36 (m, 2H), 1.18 (t, 3H); MS (EI) for $C_{26}H_{27}N_4O_4FClBr$: 595 (MH$^+$).

Using the same synthetic techniques and/or substituting with alternative reagents, the following compound of the invention were prepared:

N-(4-bromo-3-chloro-2-fluorophenyl)-6-(methyloxy)-7-({[(3aR,5r,6aS)-2-(methylsulfonyl)octahydrocyclopenta[c] pyrrol-5-yl]methyl}oxy)quinazolin-4-amine hydrochloride: $^1$H NMR (400 MHz, d$_4$-MeOH): 8.70 (s, 1H), 7.94 (s, 1H), 7.69 (d, 1H), 7.49 (t, 1H), 7.23 (s, 1H), 4.24 (d, 2H), 4.18 (m, 2H), 4.09 (s, 3H), 3.45 (dd, 2H), 2.90 (s, 3H), 2.87 (m, 3H), 2.59 (m, 1H), 2.28 (m, 2H), 1.43 (m, 2H); MS (EI) for $C_{24}H_{25}N_4O_4FSClBr$: 601 (MH$^+$).

7-({[(3aR,5r,6aS)-2-acetyloctahydrocyclopenta[c]pyrrol-5-yl]methyl}oxy)-N-(4-bromo-3-chloro-2-fluorophenyl)-6-(methyloxy)quinazolin-4-amine hydrochloride: $^1$H NMR (400 MHz, d$_4$-MeOH): 8.70 (s, 1H), 7.97 (s, 1H), 7.69 (d, 1H), 7.49 (t, 1H), 7.28 (s, 1H), 4.14 (d, 2H), 4.25 (m, 2H), 4.08 (s, 3H), 3.31 (m, 1H), 3.02 (m, 4H), 2.78 (m, 2H), 2.36 (m, 1H), 1.93 (m, 3H), 1.43 (m, 2H); MS (EI) for $C_{25}H_{25}N_4O_3FClBr$: 565 (MH$^+$).

Example 18

N-(3,4-dichlorophenyl)-7-({[(3aR,6aS)-2-methyloctahydrocyclopenta[c]pyrrol-5-yl]oxy)-6-(methyloxy)quinazolin-4-amine hydrochloride 1,1-Dimethylethyl (3aR,6aS)-5-(hydroxy)-hexahydrocyclopenta[c] pyrrole-2(1H)-carboxylate: Sodium borohydride (0.15 g, 4.00 mmol), was added to a solution of 1,1-dimethylethyl (3aR,6aS)-5-oxo-hexahydrocyclopenta[c] pyrrole-2 (1H)-carboxylate (0.45 g, 2.00 mmol) in 10 mL methanol at 0° C. and the reaction mixture was stirred for 1 h at this temperature. The solvent was evaporated, the crude mixture was diluted with 100 mL ethyl acetate and washed with water (30 mL), 1M aqueous hydrochloric acid and brine. The organic layer was dried over anhydrous sodium sulfate, filtered and concentrated to give 1,1-dimethylethyl (3aR,6aS)-5-(hydroxy)-hexahydrocyclopenta[c] pyrrole-2(1H)-carboxylate (0.44 g, 98%). $^1$H NMR (400 MHz, $d_6$-DMSO): 4.08 (m, 1H), 3.40 (m, 2H), 3.30 (m, 2H), 2.50 (m, 2H), 1.98 (m, 2H), 1.40 (s, 9H), 1.30 (m, 2H). MS (EI) for $C_{12}H_{21}NO_3$: 228 (MH$^+$).

1,1-Dimethylethyl (3aR,6aS)-5-{[(methylsulfonyl)oxy]}hexahydrocyclo -penta[c]pyrrole-2(1H)-carboxylate: Methanesulfonyl chloride (0.18 mL, 2.33 mmol), was added dropwise to a solution of 1,1-dimethylethyl (3aR,6aS)-5-(hydroxy)-hexahydrocyclopenta [c] pyrrole-2(1H)-carboxylate (0.44 g, 1.94 mmol) and triethylamine (0.81 mL, 5.81 mmol) in 10 mL dichloromethane at 0° C. and the reaction mixture was stirred for 1 h at room temperature. The solvent was evaporated, the resulting crude mixture was diluted with 100 mL ethyl acetate and washed with water (30 mL), brine, 1M aqueous hydrochloric acid and brine again. The organic layer was dried over anhydrous sodium sulfate, filtered and concentrated. The resulting crude 1,1-dimethylethyl (3aR,6aS)-5-{[(methylsulfonyl)oxy]}hexahydrocyclopenta[c]pyrrole-2(1H)-carboxylate was used without further purification. MS (EI) for $C_{13}H_{23}NO_5S$: 306 (MH$^+$).

1,1-dimethylethyl (3aR,6aS)-5-({[4[(3,4-dichlorophenyl)amino]-6-(methyloxy) quinazolin-7-yl]oxy})hexahydrocyclopenta[c]pyrrole-2(1H)-carboxylate: A solution of 4-[(3,4-dichlorophenyl)amino]-6-(methyloxy)quinazolin-7-ol trifluoroacetate (salt) (0.22 g, 0.49 mmol), 1,1-dimethylethyl (3aR,6aS)-5-{[(methylsulfonyl)oxy]}hexahydro-cyclopenta[c]pyrrole-2(1H)-carboxylate (0.15 g, 0.45 mmol), potassium carbonate (0.34 g, 2.50 mmol) in N,N-dimethylacetamide (5 mL) was heated in a sealed reaction tube at 90° C. for 12 h. The crude reaction mixture was diluted with 100 mL 10% methanol in ethyl acetate and washed with saturated aqueous sodium bicarbonate (1×30 mL), water (1×30 mL) and brine (1×30 mL). The organic layer was dried over anhydrous sodium sulfate, filtered and concentrated. Column chromatography (SiO$_2$, 3:2 hexanes:acetone) provided 1,1-dimethylethyl (3aR,6aS)-5-({[4-[(3,4-dichlorophenyl)amino]-6-(methyloxy)quinazolin-7-yl]oxy})hexahydrocyclopenta[c]pyrrole-2(1H)-carboxylate (0.23 g, 98%). $^1$H NMR (400 MHz, $d_6$-DMSO): 9.57 (s, 1H), 8.52 (s, 1H), 8.24 (d, 1H), 7.88 (dd, 1H), 7.78 (s, 1H), 7.62 (d, 1H), 7.13 (s, 1H), 5.15 (m, 1H), 3.96 (s, 3H), 3.42 (m, 2H), 3.36 (m, 2H), 2.80 (bs, 2H), 2.06 (m, 2H), 1.94 (m, 2H), 1.40 (s, 9H). MS (EI) for $C_{27}H_{30}Cl_2N_4O_4$: 547 (MH$^+$).

N-(3,4-dichloro-phenyl)-6-(methyloxy)-7-{[(3aR,6aS)-octahydrocyclo-penta [c]pyrrol-5-yl]oxy} quinazolin-4-amine hydrochloride: 1,1-Dimethylethyl (3aR,6aS)-5-({[4-[(3,4-dichlorophenyl)amino]-6-(methyloxy)quinazolin-7-yl]oxy})hexahydrocyclo-penta[c]pyrrole-2(1H)-carboxylate (0.23 g, 0.42 mmol) was taken up in methanol (10 mL) and treated with 4.0M hydrogen chloride in dioxane (excess) and heated briefly to reflux. Concentration in vacuo provided N-(3,4-dichloro-phenyl)-6-(methyloxy)-7-{[(3aR,6aS)-octahydrocyclopenta[c]pyrrol-5-yl]oxy} quinazolin-4-amine hydrochloride (0.20 g, 100%). MS (EI) for $C_{22}H_{22}Cl_2N_4O_2$: 445(MH$^+$).

N-(3,4-Dichlorophenyl)-7-({[(3aR,6aS)-2-methyloctahydrocyclopenta [c]pyrrol-5-yl]}oxy)-6-(methyloxy)quinazolin-4-amine hydrochloride: N-(3,4-Dichloro-phenyl)-6-(methyloxy)-7-{[(3aR,6aS) -octahydrocyclopenta-[c]pyrrol-5-yl]oxy}quinazolin-4 amine hydrochloride (0.20 g, 0.42 mmol) was solubilized in formic acid (5.0 mL) and 37% aqueous formaldehyde (1 mL) was added. The solution was heated to 95° C. for 12 h. The reaction mixture was concentrated in vacuo. The residue was taken up in a mixture of 10% methanol in ethyl acetate (100 mL) and washed with saturated aqueous sodium bicarbonate (2×30 mL) and brine. The organic layer was dried over anhydrous sodium sulfate, filtered and concentrated. The residue was purified by HPLC (reverse-phase, acetonitrile/water/0.1% TFA). Upon removal of solvent the product was taken up in a mixture of 10% methanol in ethyl acetate (100 mL) and washed with saturated aqueous sodium bicarbonate (2×30 mL) and brine. The organic layer was dried over anhydrous sodium sulfate, filtered and concentrated then the product was taken up in methanol and treated with 4.0 M hydrogen chloride in dioxane (1 eq.). Removal of solvent in vacuo provided 116 mg (56%) of N-(3,4-dichlorophenyl)-7-({[(3aR,6aS)-2-methyloctahydrocyclopenta[c]pyrrol-5-yl]}oxy)-6-(methyloxy) quinazolin-4-amine hydrochloride. $^1$H NMR (400 MHz, $d_6$-DMSO): 11.05 (bs, 1H), 8.90 (s, 1H), 8.44 (s, 1H), 8.18 (d, 1H), 7.84 (dd, 1H), 7.76 (s, 1H), 7.48 (s, 1H), 5.30 (m, 1H), 4.00 (s, 3H), 3.35 (m, 2H), 2.90 (m, 2H), 2.24 (m, 5H), 2.10 (m, 2H), 1.24 (m, 2H). MS (EI) for $C_{23}H_{24}Cl_2N_4O_2$: 459, 461 (MH$^+$).

Example 19

N-(4-bromo-3-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-anine hydrochloride 3-(Chloromethyl)hexahydro-1H-[1,4]oxazino[3,4-c][1,4]oxazine: A solution of (3R)-morpholin-3-ylmethanol (4.21 g, 36.0 mmol) in 2-(chloromethyl)oxirane (28.2 mL, 0.360 mol) was heated to 40° C. for 3 h and then the solution was concentrated in vacuo. The intermediate was cooled in an ice bath and treated with 30.0 mL of concentrated sulfuric acid. The mixture was heated to 170° C. for 2 h and then allowed to cool to room temperature. The mixture was poured into ice-water and solid sodium bicarbonate was carefully added until the solution was basic. 10% methanol in ethyl acetate was added and the biphasic mixture was filtered. The layers were separated and the aqueous layer was extracted (3×100 mL 10% methanol in ethyl acetate). The combined organic layers were dried over anhydrous sodium sulfate, filtered and concentrated in vacuo. Column chromatography (SiO$_2$, 2:5 hexanes: ethyl acetate) provided 3-(chloromethyl)hexahydro-1H-[1,4]oxazino[3,4-c][1,4]oxazine 2.44 g (35%) as two separated diastereomers. (3R,9aS)-3-(chloromethyl)hexahydro-1H-[1,4]oxazino[3,4-c][1,4]oxazine: (0.886 g, 13% yield): $^1$H NMR (400 MHz, CDCl$_3$): 3.91 (m, 3H), 3.82 (m, 1H), 3.68 (dt, 1H), 3.61 (dd, 1H), 3.47 (dd, 1H), 3.35 (t, 1H), 3.19 (t, 1H), 2.80 (d, 1H), 2.54 (m, 2H), 2.40 (m, 2H); MS (EI) for $C_8H_{14}NO_2Cl$: 192 (MH$^+$). (3S,9aS)-3-(chloromethyl) hexahydro-1H-[1,4]oxazino[3,4-c][1,4]oxazine: (1.55 g, 22% yield): $^1$HNMR (400 MHz, CDCl$_3$): 3.85 (m, 2H), 3.73 (m, 3H), 3.50 (m, 2H), 3.29 (t, 1H), 3.18 (t, 1H), 2.85 (dd, 1H), 2.64 (dd, 1H), 2.40 (m, 2H), 2.17 (t, 1H); MS (EI) for $C_8H_{14}NO_2Cl$: 192 (MH$^+$).

Hexahydro-1H-[1,4]oxazino[3,4-c][1,4]oxazin-3-ylmethyl acetate: A suspension of (3R,9aS)-3-(chloromethyl) hexahydro-1H-[1,4]oxazino[3,4-c][1,4]oxazine (1.97 g, 10.3 mmol) and potassium acetate (10.1 g, 102 mmol) in DMF (20.0 mL) was stirred at 140° C. for 16 h, and then at 150° C. for another 12 h. The reaction mixture was partitioned between water (250 mL) and ethyl acetate (250 mL), the organic layer was washed with 5% lithium chloride (2×100 mL) and brine (100 mL) then dried over anhydrous sodium sulfate and concentrated in vacuo. Column chromatography (SiO$_2$, 1:1 hexane:ethyl acetate, then 100% ethyl acetate) afforded 0.92 g (42%) of hexahydro-1H-[1,4]oxazino[3,4-c][1,4]oxazin-3-ylmethyl acetate as a yellow oil. Distinct diastereomers as described above were converted in this step to give: (3R,9aS)-hexahydro-1H-[1,4]oxazino[3,4-c][1,4]oxazin-3-ylmethyl acetate: $^1$H NMR (400 MHz, CDCl$_3$): 4.18 (dd, 1H), 4.00 (m, 1H), 3.80 (dd, 1H), 3.68 (dt, 1H), 3.60 (dd, 1H), 3.46 (m, 2H), 3.22 (t, 1H), 2.64 (dd, 1H), 2.53 (m, 2H), 2.43-2.35 (m, 2H), 2.10 (s, 3H), and (3S,9aS)-hexahydro-1H-[1,4]oxazino[3,4-c][1,4]oxazin-3-ylmethyl acetate: $^1$H NMR (400 MHz, CDCl$_3$): 4.09 (d, 2H), 3.90-3.82 (m, 2H), 3.75-3.64 (m, 3H), 3.27 (t, 1H), 3.18 (t, 1H), 2.69 (dd, 1H), 2.63 (m, 1H), 2.46-2.33 (m, 2H), 2.16 (t, 1H), 2.10 (s, 3H).

(3R,9aS)-Hexahydro-1H-[1,4]oxazino[3,4-c][1,4]oxazin-3-ylmethyl methanesulfonate: To a solution of (3R,9aS)-hexahydro-1H-[1,4]oxazino[3,4-c][1,4]oxazin-3-ylmethyl acetate (0.922 g, 4.28 mmol) in methanol (14.0 mL) was added 1.03 mL (4.50 mmol) of sodium methoxide (25% wt. in methanol) dropwise at room temperature. After 5 min., 1.6 mL (6.43 mmol) of 4.0M hydrogen chloride in dioxane was added and a pink precipitate formed. The solution was concentrated in vacuo and the pink solid was taken up in 30.0 mL dichloromethane. This slurry was cooled in an ice bath and triethylamine (3.0 mL, 21.5 mmol) was added, followed by methanesulfonyl chloride (0.37 mL, 4.71 mmol). The resultant yellow solution was stirred for 30 minutes at room temperature. The mixture was then partitioned between dichloromethane and saturated aqueous sodium bicarbonate then the aqueous layer was extracted (3×50 mL dichloromethane). The combined organic layers were dried over anhydrous sodium sulfate, filtered and concentrated in vacuo to provide crude (3R,9aS)-hexahydro-1H-[1,4]oxazino[3,4-c][1,4]oxazin-3-ylmethyl methanesulfonate which was taken on to the following reaction without purification.

N-(4-Bromo-3-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine hydrochloride: A solution of (3R,9aS)-hexahydro-1H-[1,4]oxazino[3,4-c][1,4]oxazin-3-ylmethyl methanesulfonate (0.215 g, 0.856 mmol), 4-[(4-bromo-3-chloro-2-fluorophenyl)amino]-6-(methyloxy)quinazolin-7-ol hydrochloride (0.247 g, 0.570 mmol), and potassium carbonate (0.400 g, 2.90 mmol) in DMF (1.9 mL) was heated in a sealed reaction tube at 75° C. for 12 h, then 90° C. for 12 h. The reaction mixture was concentrated in vacuo and the residue was partitioned between 10% methanol in ethyl acetate and saturated aqueous sodium bicarbonate. The layers were separated and the aqueous layer was extracted (3×50 mL 10% methanol in ethyl acetate). The combined organic layers were dried over anhydrous sodium sulfate, filtered and concentrated in vacuo. The crude residue was purified by HPLC (reverse-phase, acetonitrile/water/0.1% TFA). Upon removal of solvent the product was taken up in methanol and treated with Bio-Rad AG 1-X8 resin (hydroxide form) until pH 8. The product was filtered and concentrated in vacuo then taken up in methanol and treated with 4.0 M hydrogen chloride in dioxane (0.10 mL). Removal of solvent in vacuo provided 32.1 mg (10%) of N-(4-bromo-3-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine hydrochloride. MS (EI) for C$_{23}$H$_{23}$N$_4$O$_4$FClBr: 554 (M$^+$).

Using the same or analogous synthetic techniques and/or substituting with alternative reagents, the following compounds of the invention were prepared:

N-(3,4-dichlorophenyl)-7-[(hexahydro-1H-[1,4]oxazino[3,4-c][1,4]oxazin-3-ylmethyl)oxy]-6-(methyloxy)quinazolin-4-amine hydrochloride: $^1$H NMR (400 MHz, d$_6$-DMSO): 8.90 (s, 1H), 8.50 (s, 1H), 8.19 (d, 1H), 7.85 (d, 1H), 7.75 (d, 1H), 7.42 (s, 1H), 4.51 (m, 1H), 4.32 (m, 2H), 4.04 (s, 3H), 4.00-3.62 (m, 4H); MS (EI) for C$_{23}$H$_{24}$N$_4$O$_4$Cl$_2$B: 491 (MH$^+$).

N-(3,4-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine hydrochloride: $^1$H NMR (400 MHz, d$_4$-MeOH): 8.71 (s, 1H), 7.99 (s, 1H), 7.58-7.52 (m, 2H), 7.33 (s, 1H), 4.50 (m, 1H), 4.44 (d, 2H), 4.17-3.94 (m, 4H), 4.09 (s, 3H), 3.82-3.59 (m, 5H), 3.54-3.37 (m, 2H); MS (EI) for C$_{23}$H$_{23}$N$_4$O$_4$Cl$_2$F: 509 (MH$^+$).

N-(4-bromo-3-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine hydrochloride: $^1$H NMR (400 MHz, d$_4$-MeOH): 8.71 (s, 1H), 7.99 (s, 1H), 7.69 (d, 1H), 7.49 (t, 1H), 7.32 (s, 1H), 4.49 (m, 1H), 4.44 (m, 2H), 4.16-3.95 (m, 4H), 4.10 (s, 3H), 3.82-3.58 (m, 5H), 3.54-3.35 (m, 2H); MS (EI) for C$_{23}$H$_{23}$N$_4$O$_4$BrClF: 553 (MH$^+$).

N-(3-chloro-2,4-difluorophenyl)-7-{[(3S,9aS)-hexahydro-1H-[1,4]oxazino[3,4-c][1,4]oxazin-3-ylmethyl]oxy}-6-(methyloxy)quinazolin-4-amine hydrochloride: MS (EI) for C$_{23}$H$_{23}$N$_4$O$_4$ClF$_2$: 493 (MH$^+$).

N-(4,5-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine hydrochloride: $^1$H NMR (400 MHz, d$_4$-MeOH): 8.73 (s, 1H), 7.99 (s, 1H), 7.86 (d, 1H), 7.64 (d, 1H), 7.33 (s, 1H), 4.51 (m, 1H), 4.44 (d, 2H), 4.16-3.94 (m, 4H), 4.10 (s, 3H), 3.84-3.60 (m, 5H), 3.54-3.36 (m, 2H); MS (EI) for C$_{23}$H$_{23}$N$_4$O$_4$ClF$_2$: 509 (MH$^+$).

N-(4-bromo-5-chloro-2-fluorophenyl)-7-{[(3S,9aS)-hexahydro-1H-[c][1,4]oxazino[3,4-c][1,4]oxazin-3-ylmethyl]oxy}-6-(methyloxy)quinazolin-4-amine hydrochloride: $^1$H NMR (400 MHz, d$_4$-MeOH): 8.73 (s, 1H), 7.98 (s, 1H), 7.85 (d, 1H), 7.76 (d, 1H), 7.33 (s, 1H), 4.49 (m, 1H), 4.44 (d, 2H), 4.16-3.94 (m, 4H), 4.09 (s, 3H), 3.82-3.60 (m, 5H), 3.53-3.35 (m, 2H); MS (EI) for C$_{23}$H$_{23}$N$_4$O$_4$BrClF: 553 (MH$^+$).

N-(4-bromo-2,3-dichlorophenyl)-7-{[(3S,9aS)-hexahydro-1H-[1,4]oxazino[3,4-c][1,4]oxazin-3-ylmethyl]oxy}-6-(methyloxy)quinazolin-4-amine hydrochloride: $^1$H NMR (400 MHz, d$_4$-MeOH): 8.67 (s, 1H), 8.00 (s, 1H), 7.84 (d, 1H), 7.48 (d, 1H), 7.34 (s, 1H), 4.51 (m, 1H), 4.44 (d, 2H), 4.09 (s, 3H), 4.15-4.00 (m, 4H), 3.82-3.63 (m, 5H), 3.63-3.38 (m, 2H); MS (EI) for C$_{23}$H$_{23}$N$_4$O$_4$Cl$_2$Br: 570 (MH$^+$).

N-(4-bromo-2,3-dichlorophenyl)-7-{[(3R,9aS)-hexahydro-1H-[1,4]oxazino[3,4-c][1,4]oxazin-3-ylmethyl]oxy}-6-(methyloxy)quinazolin-4-amine hydrochloride: MS (EI) for C$_{23}$H$_{23}$N$_4$O$_4$Cl$_2$Br: 570 (MH$^+$).

N-(3,4-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine hydrochloride: MS (EI) for C$_{23}$H$_{23}$N$_4$O$_4$FCl$_2$: 509 (MH$^+$).

N-(4-bromo-5-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine hydrochloride: MS (EI) for C$_{23}$H$_{23}$N$_4$O$_4$FClBr: 554 (MH$^+$).

N-(4,5-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine hydrochloride: $^1$H NMR (400 MHz, d$_4$-MeOH): 8.74 (s, 1H), 8.00 (s, 1H), 7.86 (d, 1H), 7.64 (d, 1H), 7.35 (broad s, 1H), 4.51 (m, 2H), 4.44 (m, 1H), 4.25-3.95 (m, 4H), 4.09 (s, 3H), 3.82-3.63 (m, 5H), 3.63-3.38 (m, 2H); MS (EI) for C$_{23}$H$_{23}$N$_4$O$_4$FCl$_2$: 509 (MH$^+$).

N-(3-chloro-2,4-difluorophenyl)-7-{[(3R,9aS)-hexahydro-1H-[1,4]oxazino[3,4-c][1,4]oxazin-3-ylmethyl]oxy}-6-(methyloxy)quinazolin-4-amine hydrochloride: MS (EI) for $C_{23}H_{23}N_4O_4F_2Cl$: 493 (MH$^+$).

Example 20

N-(3,4-dichlorophenyl)-7-[(2-{[(3-endo)-8-methyl-8-azabicyclo[3.2.1]oct-3-yl]amino}ethyl)oxy]-6-(methyloxy)quinazolin-4-amine 7-[(2-Aminoethyl)oxy]-N-(3,4-dichlorophenyl)-6-(methyloxy)quinazolin-4-amine hydrochloride: A solution of 4-[(3,4-dichlorophenyl)amino]-6-(methyloxy)quinazolin-7-ol trifluoroacetate (salt) (1.00 g, 2.15 mmol), 1,1-dimethylethyl (2-bromoethyl)carbamate (0.480 g, 2.15 mmol), and potassium carbonate (1.78 g, 12.9 mmol) in N,N-dimethylacetamide (2.2 mL) was heated to 100° C. for 2.5 h. An additional 0.23 g (1.03 mmol) of 1,1-dimethylethyl (2-bromoethyl)carbamate was added and the reaction mixture was further heated to 100° C. for a total of 7 h. The crude reaction mixture was partitioned between water and ethyl acetate and the layers were separated. The aqueous layer was extracted with ethyl acetate (3×100 mL). The combined organic layers were dried over anhydrous sodium sulfate, filtered, and concentrated in vacuo. Column chromatography (SiO$_2$, 3:2 hexanes:acetone) gave N-Boc product, which was then taken up in methanol and treated with 4M hydrogen chloride in dioxane while heating. Dilution with ethyl ether precipitated a pale yellow solid, which was collected by filtration and dried to give 0.761 g (94%) of 7-[(2-aminoethyl)oxy]-N-(3,4-dichlorophenyl)-6-(methyloxy)quinazolin-4-amine hydrochloride. $^1$H NMR (400 MHz, d$_6$-DMSO): 12.01 (s, 1H), 8.94 (s, 1H), 8.67 (s, 1H), 8.35 (broad s, 2H), 8.21 (s, 1H), 7.90 (dd, 1H), 7.75 (d, 1H), 7.53 (s, 1H), 4.43 (t, 2H), 4.08 (s, 3H), 3.36 (m, 2H).

N-(3,4-Dichlorophenyl)-7-[(2-{[(3-endo)-8-methyl-8-azabicyclo[3.2.1]oct-3-yl]amino}ethyl)oxy]-6-(methyloxy)quinazolin-4-amine: To a DMF solution (3.0 mL) of 7-[(2-aminoethyl)oxy]-N-(3,4-dichlorophenyl)-6-(methyloxy)quinazolin-4-amine hydrochloride (56.8 mg, 0.137 mmol) at room temperature, was added glacial acetic acid (3 drops), (1R,5S)-8-methyl-8-azabicyclo[3.2.1]octan-3-one (49.0 mg, 0.137 mmol), and sodium triacetoxyborohydride (43.0 mg, 0.205 mmol). After stirring for 12 h, additional (1R,5S)-8-methyl-8-azabicyclo[3.2.1]octan-3-one (50.0 mg, 0.140 mmol), acetic acid (3 drops) and sodium triacetoxyborohydride were added. The solution was quenched with water, filtered and purified by HPLC (reverse-phase, acetonitrile/water/0.1% TFA). Upon removal of solvent, the product was taken up in methanol and treated with Bio-Rad AG 1-X8 resin (hydroxide form) until pH 8. The product was filtered and concentrated in vacuo, to provide 45.1 mg (66%) of N-(3,4-dichlorophenyl)-7-[(2-{[(3-endo)-8-methyl-8-azabicyclo[3.2.1]oct-3-yl]amino}ethyl)oxy]-6-(methyloxy)quinazolin-4-amine. $^1$H NMR (400 MHz, d$_6$-DMSO): 9.63 (s, 1H), 8.55 (s, 1H), 8.26 (d, 1H), 7.90 (dd, 1H), 7.83 (s, 1H), 7.65 (s, 1H), 7.23 (d, 1H), 4.20 (t, 1H), 4.15 (t, 3H), 3.97 (s, 1H), 3.03 (m, 1H), 2.91 (t, 2H), 2.81 (t, 1H), 2.17 (s, 3H), 2.00-1.84 (m, 6H), 1.67-1.32 (m, 4H); MS (EI) for $C_{25}H_{29}N_5O_2Cl_2$: 502 (MH$^+$).

Example 21

N-(3,4-dichlorophenyl)-7-{[(3-exo)-8-methyl-8-azabicyclo[3.2.1]oct-3-yl]oxy}-6-(methyloxy)quinazolin-4-amine hydrochloride N-(3,4-Dichlorophenyl)-7-{[(3-exo)-8-methyl-8-azabicyclo[3.2.1]oct-3-yl]oxy}-6-(methyloxy)quinazolin-4-amine hydrochloride: A solution of 4-[(3,4-dichlorophenyl)amino]-6-(methyloxy)quinazolin-7-ol trifluoroacetate (salt) (0.150 g, 0.322 mmol), (3-endo)-3-[(methylsulfonyl)oxy]-8-azabicyclo[3.2.1]octane (0.106 g, 0.483 mmol), and potassium carbonate (0.220 g, 1.60 mmol) in N,N-dimethylacetamide (1.1 mL) was heated in a sealed tube at 100° C. for 12 h, followed by 48 h at room temperature. The crude reaction mixture was filtered through celite using methanol eluent, and the solvents were removed in vacuo. The residue was purified by HPLC (reverse-phase, acetonitrile/water/0.1% TFA). Upon removal of solvent, the product was taken up in methanol and treated with Bio-Rad AG 1-X8 resin (hydroxide form) until pH 8. The product was filtered and concentrated in vacuo, then taken up in methanol and treated with 4.0 M hydrogen chloride in dioxane (0.050 mL). Removal of solvent in vacuo provided 48.7 mg (31%) of N-(3,4-dichlorophenyl)-7-{[(3-exo)-8-methyl-8-azabicyclo[3.2.1]oct-3-yl]oxy}-6-(methyloxy)quinazolin-4-amine hydrochloride. $^1$H NMR (400 MHz, d$_6$-DMSO): 10.69 (s, 1H), 8.92 (s, 1H), 8.32 (s, 1H), 8.17 (d, 1H), 7.81 (m, 2H), 7.75 (d, 1H), 5.05 (m, 1H), 4.02 (s, 3H), 2.69 (d, 2H), 2.39 (m, 1H), 2.29-2.18 (m, 6H); MS (EI) for $C_{23}H_{24}N_4O_2Cl_2$: 459 (MH$^+$).

Example 22

N-(3,4-dichlorophenyl)-7-({[(3-endo)-8-methyl-8-azabicyclo[3.2.1]oct-3-yl]methyl}oxy)-6-(methyloxy)quinazolin-4-amine hydrochloride 7-{[(3-endo)-8-Azabicyclo[3.2.1]oct-3-ylmethyl]oxy}-N-(3,4-dichlorophenyl)-6-(methyloxy)quinazolin-4-amine hydrochloride: A solution of 4-[(3,4-dichlorophenyl)amino]-6-(methyloxy)quinazolin-7-ol trifluoroacetate (salt) (0.200 g, 0.429 mmol), 1,1-dimethylethyl (3-endo)-3-{[(methylsulfonyl)oxy]methyl}-8-azabicyclo[3.2.1]octane-8-carboxylate (0.200 g, 0.626 mmol), and potassium carbonate (0.300 g, 2.17 mmol) in N,N-dimethylacetamide (1.4 mL) was heated in a sealed tube at 110° C. for 12 h. Additional mesylate (0.430 g, 1.35 mmol) was added and the mixture was heated for 2 h at 110° C. The crude reaction mixture was partitioned between 10% methanol in ethyl acetate (50 mL) and water (50 mL). The layers were separated and the organic layer was washed with water (2×50 mL) and 1M aqueous sodium hydroxide (1×50 mL). The organic layer was dried over anhydrous sodium sulfate and the solvent was removed in vacuo. The residue was purified by column chromatography (SiO$_2$, 2:1 hexanes:ethyl acetate), followed by HPLC (reverse-phase, acetnitrile/water/0.1% TFA). Solvent was removed in vacuo and the residue partitioned with 10% methanol in ethyl acetate and water. The aqueous layer was made basic with saturated aqueous sodium bicarbonate. The layers were separated and the aqueous layer was further extracted with 10% methanol in ethyl acetate (2×). The combined organic extracts were dried over anhydrous sodium sulfate, filtered and the concentrated in vacuo. The residue was taken up in methanol and treated with 4.0 M hydrogen chloride in dioxane then concentrated to provide 7-{[(3-endo)-8-azabicyclo[3.2.1]oct-3-ylmethyl]oxy}-N-(3,4-dichlorophenyl)-6-(methyloxy)quinazolin-4-amine hydrochloride (0.104 g, 53%). MS (EI) for $C_{23}H_{24}N_4O_2Cl_2$: 459 (MH$^+$).

N-(3,4-Dichlorophenyl)-7-({[(3-endo)-8-methyl-8-azabicyclo[3.2.1]oct-3-yl]methyl}oxy)-6-(methyloxy)quinazolin-4-amine hydrochloride: 7-{[(3-Endo)-8-azabicyclo[3.2.1]oct-3-ylmethyl]oxy}-N-(3,4-dichlorophenyl)-6-(methyloxy)quinazolin-4-amine hydrochloride, (0.104 g, 0.210 mmol) was combined with 37% aqueous formaldehyde (0.10 mL, 1.26 mmol) in formic acid (1.0 mL) and the solution was heated to 110° C. for 12 h. The solvent was removed in vacuo and the residue was taken up in methanol and treated with Bio-Rad AG 1-X8 resin (hydroxide form) until pH 8. The product was filtered and concentrated in vacuo. The residue was purified by HPLC (reverse-phase, acetonitrile/water/0.1% TFA). Upon removal of solvent, the product was taken up in methanol and treated with Bio-Rad AG 1-X8 resin (hydroxide form) until pH 8. The product was filtered and concentrated in vacuo, then taken up in methanol and treated with 4.0 M hydrogen chloride in dioxane (0.10 mL). Removal of solvent in vacuo provided 41.4 mg (39%) of N-(3,4-dichlorophenyl)-7-({[(3-endo)-8-methyl-8-azabicyclo[3.2.1]oct-3-yl]methyl}oxy)-6-(methyloxy)quinazolin-4-amine hydrochloride. $^1$H NMR (400 MHz, d$_6$-DMSO): 8.89 (s, 2H), 8.45 (s, 1H), 8.20 (s, 1H), 7.86 (d, 1H), 7.75 (d, 1H), 7.46 (s, 1H), 4.24 (m, 2H), 4.04 (s, 3H), 3.97 (broad s, 1H), 3.85 (broad s, 1H), 2.65 (d, 1H), 2.25-2.51 (m, 6H), 2.03-1.80 (m, 5H); MS (EI) for $C_{24}H_{26}N_4O_2Cl_2$: 473 (MH$^+$).

Example 23

N-(3,4-dichlorophenyl)-6-(methyloxy)-7-{[(8aR)-tetrahydro-1H-[1,3]thiazolo[4,3-c][1,4]oxazin-6-ylmethyl]oxy}quinazolin-4-amine trifluoroacetate (8aR)-6-(Chloromethyl)tetrahydro-1H-[1,3]thiazolo[4,3-c][1,4]oxazine: A solution of (4R)-1,3-thiazolidin-4-ylmethanol (0.300 g, 2.52 mmol) in 2-(chloromethyl)oxirane (2.0 mL, 25.5 mmol) was heated under nitrogen to 40° C. for 12 h. The solution was then cooled to room temperature and 2-(chloromethyl)oxirane was removed in vacuo. The crude intermediate was cooled in ice, and was taken up in 2.0 mL of concentrated sulfuric acid. The resulting mixture was heated to 200° C. for 0.5 h then poured carefully onto wet ice, which was allowed to melt. The aqueous solution was carefully made basic using solid sodium bicarbonate and the resulting mixture was filtered using water and 10% methanol in ethyl acetate as eluent. The layers were separated and the aqueous layer was extracted with 10% methanol in ethyl acetate. The combined organic layers were dried over anhydrous sodium sulfate, filtered, and concentrated in vacuo to give 11.6 mg (2.4% yield) of crude (8aR)-6-(chloromethyl)tetrahydro-1H-[1,3]thiazolo[4,3-c][1,4]oxazine as a mixture of diastereomers which was directly taken on to the next step.

N-(3,4-Dichlorophenyl)-6-(methyloxy)-7-{[(8aR)-tetrahydro-1H-[1,3]thiazolo[4,3-c][1,4]oxazin-6-ylmethyl]oxy}quinazolin-4-amine trifluoroacetate: A solution of (8aR)-6-(chloromethyl)tetrahydro-1H-[1,3]thiazolo[4,3-c][1,4]oxazine (11.6 mg, 0.0599 mmol), 4-[(3,4-dichlorophenyl)amino]-6-(methyloxy)quinazolin-7-ol trifluoroacetate (salt) (30.0 mg, 0.0644 mmol), and potassium carbonate (45.0 mg, 0.326 mmol) in N,N-dimethylacetamide (1.0 mL) was heated in a sealed tube to 150° C. for 12 h. The crude reaction mixture was directly purified via reverse-phase preparative HPLC (acetonitrile/water/0.1%-TFA). Lyophillization of the pure fractions yielded 3.5 mg (8.9%) of N-(3,4-dichlorophenyl)-6-(methyloxy)-7-{[(8aR)-tetrahydro-1H-[1,3]thiazolo[4,3-c][1,4]oxazin-6-ylmethyl]oxy} quinazolin-4-amine trifluoroacetate. $^1$H NMR (400 MHz, d$_6$-DMSO): 8.80 (s, 1H), 8.11 (s, 1H), 7.99 (s, 1H), 7.74 (s, 2H), 7.29 (s, 1H), 4.29 (d, 2H), 4.11 (m, 2H), 4.00 (s, 3H), 3.96 (m, 1H), 2.99 (m, 2H), 2.56 (t, 1H), 2.367 (m, 1H); MS (EI) for $C_{22}H_{22}N_4O_3SCl_2$: 492 (MH$^+$).

Example 24

N-(3,4-dichlorophenyl)-7-({2-[(3-endo)-8-methyl-8-azabicyclo[3.2.1]oct-3-yl]ethyl}oxy)-6-(methyloxy)quinazolin-4-amine hydrochloride 1,1-Dimethylethyl (3-endo)-3-{2-[(methylsulfonyl)oxy]ethyl}-8-azabicyclo[3.2.1] octane-8-carboxylate: To a solution of 1,1-dimethylethyl (3-endo)-3-(2-hydroxyethyl)-8-azabicyclo[3.2.1]octane-8-carboxylate (30.3 mg, 1.19 mmol) in dichloromethane (4.0 mL), was added triethylamine (0.5 mL, 3.56 mmol) and the solution was cooled to 0° C. under nitrogen. Methanesulfonyl chloride (0.11 mL, 1.42 mmol) was added slowly and mixture was allowed to warm to room temperature and stirred for 1 h. The reaction mixture was partitioned between dichloromethane and water. The aqueous phase was extracted with dichloromethane (2×100 mL). The combined organic layers were dried over anhydrous sodium sulfate, filtered and concentrated in vacuo to provide 35.1 mg (89%) of 1,1-dimethylethyl (3-endo)-3-{2-[(methylsulfonyl)oxy]ethyl}-8-azabicyclo[3.2.1]octane-8-carboxylate, which was carried forward without purification.

1,1-Dimethylethyl (3-endo)-3-(2-{[4-[(3,4-dichlorophenyl)amino]-6-(methyloxy)quinazolin-7-yl]oxy}ethyl)-8-azabicyclo[3.2.1]octane-8-carboxylate: To a solution of 1,1-dimethylethyl (3-endo)-3-{2-[(methylsulfonyl)oxy]ethyl}-8-azabicyclo[3.2.1]octane-8-carboxylate (0.175 g, 0.526 mmol) in N,N-dimethylacetamide (3.5 mL) was added 4-[(3,4-dichlorophenyl)amino]-6-(methyloxy)quinazolin-7-ol trifluoroacetate (salt) (0.490 g, 1.05 mmol) and potassium carbonate (0.728 g, 5.26 mmol), and the reaction was stirred at 110° C. for 18 h. An additional portion of 1,1-dimethylethyl (3-endo)-3-{2-[(methylsulfonyl)oxy]ethyl}-8-azabicyclo[3.2.1]octane-8-carboxylate (0.175 g, 0.526 mmol) was added and the mixture was stirred at 140° C. for 2 h. Another portion of the mesylate (0.300 g, 1.05 mmol) in N,N-dimethylacetamide (4.0 mL) was added and the mixture continued to stir at 140° C. for a further 18 h. The reaction mixture was concentrated in vacuo, and the residue was partitioned between 10% methanol in ethyl acetate and water. The organic layer was washed (3×50 mL water) and the combined aqueous portions were extracted (2×100 mL 10% methanol in ethyl acetate). All organic layers were combined, dried over anhydrous sodium sulfate, filtered and concentrated in vacuo. The residue was purified by HPLC (reverse-phase, acetonitrile/water/0.1% TFA). Upon concentration the remaining aqueous layer was neutralized with solid sodium bicarbonate, extracted (100 mL 10% methanol in ethyl acetate), dried over anhydrous sodium sulfate then filtered and concentrated in vacuo to afford 1,1-dimethylethyl (3-endo)-3-(2-{[4-[(3,4-dichlorophenyl)amino]-6-(methyloxy)quinazolin-7-yl]oxy}ethyl)-8-azabicyclo[3.2.1]octane-8-carboxylate (39.9 mg, 66% yield). $^1$H NMR (400 MHz; d$_6$-DMSO): 9.43 (broad s, 1H), 8.48 (s, 1H), 7.87 (s, 1H), 7.61 (d, 1H), 7.53 (s, 1H), 7.22 (d, 1H), 7.02 (s, 1H), 4.23-3.82 (m, 4H), 3.80 (s, 3H), 2.19 (m, 1H), 1.93 (s, 6H), 1.69-1.42 (m, 3H), 1.36 (s, 9H), 1.22 (m, 1H).

7-({2-[(3-endo)-8-Azabicyclo[3.2.1]oct-3-yl]ethyl}oxy)-N-(3,4-dichlorophenyl)-6-(methyloxy)quinazolin-4-amine hydrochloride: 1,1-Dimethylethyl (3-endo)-3-(2-{[4-[(3,4-dichlorophenyl)amino]-6-(methyloxy)quinazolin-7-yl]

oxy}ethyl)-8-azabicyclo[3.2.1]octane-8-carboxylate was solubilized in methanol (2.3 mL) and treated with 4.0 M hydrogen chloride in dioxane (2.3 mL). The solution was heated to reflux then immediately allowed to cool to room temperature. The solution was then concentrated in vacuo to give 7-({2-[(3-endo)-8-azabicyclo[3.2.1]oct-3-yl]ethyl}oxy)-N-(3,4-dichlorophenyl)-6-(methyloxy) quinazolin-4-amine hydrochloride (34.6 mg, 98% yield). MS (EI) for $C_{24}H_{26}Cl_2N_4O_2$: 473 (MH$^+$).

N-(3,4-Dichlorophenyl)-7-({2-[(3-endo)-8-methyl-8-azabicyclo[3.2.1]oct-3-yl]ethyl}oxy)-6-(methyloxy) quinazolin-4-amine hydrochloride: To a solution of 7-({2-[(3-endo)-8-azabicyclo[3.2.1]oct-3-yl]ethyl}oxy)-N-(3,4-dichlorophenyl)-6-(methyloxy) quinazolin-4-amine hydrochloride (0.346 g, 0.678 mmol) in formic acid (2.7 mL), was added aqueous formaldehyde (37%, 0.27 mL, 4.07 mmol) and the mixture was heated to 110° C. for 5 h, then allowed to cool to room temperature. The solution was concentrated in vacuo and the residue was taken up in methanol and treated with AG 1-X8 resin (hydroxide form) to pH 8. The mixture was filtered and concentrated then the residue purified by HPLC (reverse-phase, acetonitrile/water/0.1% TFA) and the pure fractions lyophillized. The residue was taken up in methanol and neutralized with AG 1-X8 resin (hydroxide form) to pH 8 then filtered and concentrated. The residue was taken into methanol (3 mL) and treated with 4.0 M hydrogen chloride in dioxane to pH 2. Concentration in vacuo afforded the title compound N-(3,4-dichlorophenyl)-7-({2-[(3-endo)-8-methyl-8-azabicyclo[3.2.1]oct-3-yl]ethyl]oxy)-6-(methyloxy)quinazolin-4-amine hydrochloride (12.5 mg, 36% yield). $^1$H NMR (400 MHz; d$_6$-DMSO): 8.86 (s, 2H), 8.40 (s, 1H), 8.16 (t, 1H), 7.82 (d, 1H), 7.73 (d, 1H), 7.38 (s, 1H). 4.22 (m, 2H), 4.03 (s, 3H), 3.92 (broad s, 2H), 2.28 (m, 2H), 2.12-1.91 (m, 6H), 1.88-1.58 (m, 6H); MS (EI) for $C_{25}H_{28}Cl_2N_4O_2$: 485 (MH$^+$).

Example 25

1,4:3,6-Dianhydro-5-O-[4-[(3-chloro-2-fluorophenyl)amino]-6-(methyloxy)quinazolin-7-yl}-2-deoxy-2-fluoro-L-iditol 1,4:3,6-dianhydro-2-O-[4-(methyloxy)carbonyl-2-(methyloxy)phenyl]-5-O-(methylsulfonyl)-D-glucitol: 1,4:3,6-dianhydro-2,5-bis-O-(methylsulfonyl)-D-mannitol (15.6 g, 51.7 mmol) and methyl vanillate (9.40 g, 51.7 mmol) were dissolved in DMF (60 mL) and cesium carbonate (33.7 g, 103 mmol) was added. The mixture was stirred at 100° C. for 2.5 h then cooled to room temperature and filtered. The filtrate was concentrated in vacuo and the residue was partitioned between ethyl acetate and water. Hexanes were added to the biphasic mixture and the precipitate was removed by filtration and discarded. From the filtrate a second crop of precipitate was obtained (8.7 g) and the material was purified by silica gel column chromatography using 30% ethyl acetate in chloroform eluent to afford 1,4:3,6-dianhydro-2-O-[4-(methyloxy)carbonyl-2-(methyloxy)phenyl]-5-O-(methylsulfonyl)-D-glucitol as a colorless solid (3.08 g, 15% yield). $^1$H-NMR (400 MHz, CDCl$_3$): 7.65 (dd, 1H), 7.57 (d, 1H), 6.95 (d, 1H), 5.12 (q, 1H), 4.95 (t, 1H), 4.93-4.90 (m, 1H), 4.67 (d, 1H), 4.28-4.23 (m, 1H), 4.19 (dd, 1H), 4.03 (dd, 1H), 3.95 (dd, 1H), 3.90 (2×s, 6H), 3.15 (s, 3H).

1,4:3,6-dianhydro-2-O-[4-(methyloxy)carbonyl-2-(methyloxy)phenyl]-5-O-(methylsulfonyl)-D-glucitol (4.38 g, 11.3 mmol) was taken into methyl sulfoxide (30 mL) followed by addition of potassium fluoride (7.5 g, 128 mmol) and the mixture was heated to 180° C. over 12 hours. The mixture was cooled to room temperature and partitioned with ethyl acetate and water. The organic layer was washed with water (3×) then brine and dried over anhydrous magnesium sulfate. Filtration and concentration of the organic solution followed by further purification by silica gel column chromatography using hexanes:ethyl acetate (2:1) eluent afforded 1,4:3,6-dianhydro-2-deoxy-2-fluoro-5-O-{2-(methyloxy)$_4$-[(methyloxy)carbonyl]phenyl}-L-iditol (1.5 g, 43% yield) as a colorless oil which was employed in the next step without further purification. GCMS: Calculated for $C_{15}H_{17}O_6F$: 312 (M$^+$).

1,4:3,6-Dianhydro-2-deoxy-2-fluoro-5-O-{2-(methyloxy)-4-[(methyloxy)carbonyl] phenyl}-L-iditol (4.8 g, 15.4 mmol) was taken into dichloromethane (45 mL) and the solution cooled to 0° C. Fuming nitric acid (90% reagent, 1.3 mL) was added dropwise to the solution followed by addition of concentrated sulfuric acid (0.3 mL). Two additional aliquots of both acids were added at ten minute intervals and the mixture was allowed to warm to room temperature with stirring an additional 20 minutes. An excess of ethyl acetate (100 mL) was added to the mixture followed by water (50 mL) and the organic layer subsequently washed with water (1×), saturated aqueous sodium bicarbonate (2×) and brine then dried over anhydrous magnesium sulfate, filtered and concentrated to give 1,4:3,6-dianhydro-2-deoxy-2-fluoro-5-O-{2-(methyloxy)-4-[(methyloxy)carbonyl]-5-nitrophenyl]-L-iditol (5.0 g, 91% yield) as a yellow amorphous residue. The material was hydrogenated at 50 psi hydrogen gas pressure in a Parr apparatus in methanol solution (50 mL) using 10% Pd/C catalyst (1.0 g) over 12 hours. Filtration of the catalyst and concentration of the organic solution afforded 5-O-{5-amino-2-(methyloxy)-4-[(methyloxy)carbonyl]phenyl}-1,4:3,6-dianhydro-2-deoxy-2-fluoro-L-iditol (4.5 g, 90% overall yield) as a solid. $^1$H-NMR (400 MHz, CDCl$_3$): 7.32 (s, 1H), 6.24 (s, 1H), 5.55-5.62 (br s, 2H), 5.10 (dd, 1H), 4.82 (d, 2H), 4.79 (m, 1H), 4.81-4.03 (m, 4H), 3.93 (dd, 1H), 3.85 (s, 3H), 3.78 (s, 3H). MS (EI) for $C_{15}H_{18}NO_6F$: 328 (MH$^+$).

5-O-{5-Amino-2-(methyloxy)-4-[(methyloxy)carbonyl]phenyl}-1,4:3,6-dianhydro-2-deoxy-2-fluoro-L-iditol (4.5 g 13.7 mmol.) was taken into formamide (40 mL) followed by addition of ammonium formate (1.7 g, 27.5 mmol.) and the mixture was heated to 165° C. for 2.5 hours. The mixture was then cooled to room temperature and partitioned with ethyl acetate:hexanes (1:1) and water to give a biphasic suspension. The residue was collected by filtration, washed with water then ethyl ether and dried in vacuo to give 1,4:3,6-dianhydro-2-deoxy-2-fluoro-5-O-[6-(methyloxy)$_4$-oxo-3,4-dihydro-quinazolin-7-yl]-L-iditol (3.61 g, 82% yield) as a tan solid. MS (EI) for $C_{15}H_{15}N_2O_5F$: 323 (MH$^+$).

1,4:3,6-Dianhydro-2-deoxy-2-fluoro-5-O-[6-(methyloxy)$_4$-oxo-3,4-dihydro-quinazolin-7-yl]-L-iditol (3.61 g, 11.2 mmol.) was suspended in chloroform (50 mL) followed by addition of DMF (1.0 mL) and oxalyl chloride (2.0 mL) then the mixture was brought to reflux for 10 minutes then cooled followed by addition of DMF (0.5 mL) and oxalyl chloride (1.0 mL) and the mixture was brought to reflux an additional hour. The mixture was again allowed to cool to room temperature and neutralized by slow addition of saturated aqueous sodium bicarbonate. The mixture was extracted with chloroform (2×) then ethyl acetate (1×) and the combined organic layers were dried over anhydrous magnesium sulfate, filtered and concentrated to give 1,4:3,6-dianhydro-5-O-[4-chloro-6-(methyloxy)quinazolin-7-yl]-2-deoxy-2-fluoro-L-iditol (3.34 g, 88% yield). $^1$H-NMR (400 MHz, d$_6$-DMSO): 8.91 (s, 1H), 7.57 (s, 1H), 7.45 (s, 1H), 5.24 (dd, 1H), 5.24 (br s, 1H), 4.84-4.79 (m, 2H), 4.17-3.87 (m, 4H), 4.01 (s, 3H). MS (EI) for $C_{15}H_{14}N_2O_4FCl$: 341 (MH$^+$).

1,4:3,6-Dianhydro-5-O-[4-chloro-6-(methyloxy)quinazolin-7-yl]-2-deoxy-2-fluoro-L-iditol (3.34 g, 9.8 mmol.) and 3-chloro-2-fluoroaniline hydrochloride (2.0 g, 10.8 mmol.) were taken into acetonitrile (50 mL) and the mixture was brought to reflux for 2.5 hours. The resulting suspension was cooled to room temperature and diluted with an excess of ethyl ether. The solid product was collected by filtration and recrystallized from a minimum of warm methanol with addition of ethyl ether. The solid was collected by filtration and dried in vacuo to give 1,4:3,6-dianhydro-5-O-{4-[(3-chloro-2-fluorophenyl)amino]-6-(methyloxy)quinazolin-7-yl)-2-deoxy-2-fluoro-L-iditol (4.2 g, 95% yield) as an off white solid. $^1$H-NMR (400 MHz, $d_6$-DMSO): 12.11 (s, 1H), 8.84 (s, 1H), 8.52 (s, 1H), 7.64 (tr, 1H), 7.53 (tr, 1H), 7.50 (s, 1H), 7.35 (tr, 1H), 5.24 (dd, 1H), 5.11 (tr, 1H), 4.16-3.89 (m, 4H), 4.02 (s, 3H). MS (EI) for $C_{21}H_{18}N_3O_4F_2Cl$: 450 (MH$^+$).

Example 26

N-(3,4-dichlorophenyl)-7-{[(4-methylmorpholin-2-yl)methyl]oxy}-6-(methyloxy) quinazolin-4-amine A solution of 2-(chloromethyl)-4-(phenylmethyl)morpholine (498 mg, 2.21 mmol) in methanol (20 mL) was hydrogenated over 10% Pd—C (120 mg) for 17 h. The catalyst was filtered off, and the filtrate was concentrated to give 2-(chloromethyl)morpholine as a colorless oil. To a solution of this oil in methanol (20 mL) was added di-tert-butyl dicarbonate (425 mg, 1.95 mmol), and the reaction mixture was stirred at room temperature for 5 h. Concentration and purification by column chromatography on silica (9:1 hexanes/ethyl acetate) provided 1,1-dimethylethyl 2-(chloromethyl)morpholine-2-carboxylate 283 mg (54%) as a colorless solid. $^1$H NMR (400 MHz, $d_4$-MeOH): 4.02 (d, 1H), 3.88 (d, 1H), 3.81 (m, 1H), 3.61-3.47 (m, 4H), 2.95 (br. s, 1H), 2.75 (br. s, 1H), 1.46 (s, 9H).

To a solution of 4-[(3,4-dichlorophenyl)amino]-6-(methyloxy)quinazolin-7-ol (12.95 g, 38.52 mmol) in dimethylacetamide (80 mL) was added 1,1-dimethylethyl 2-(chloromethyl)morpholine-2-carboxylate (11.94 g, 50.66 mmol) and potassium carbonate (15.97 g, 115.55 mmol), and the reaction mixture was stirred at 130° C. under nitrogen for 13 h. After cooling to room temperature, the mixture was partitioned between water (500 mL) and ethyl acetate (250 mL). The layers were separated, the organic layer diluted with hexanes (250 mL) and washed with water (200 mL). The combined aqueous layers were further extracted with ethyl acetate (2×200 mL). Some product precipitated from the combined organic layers and was filtered. The solid was washed with methanol (2×50 mL) and dried to give 4.77 g (25%) of 1,1-dimethylethyl 2-({[4-[(3,4-dichlorophenyl)amino]-6-(methyloxy)quinazoin-7-yl]oxy}morpholine-4-carboxylate as a tan solid. The methanol washes were concentrated, combined with the filtrate, washed with 5% lithium chloride (2×200 mL) and brine (200 mL), dried over sodium sulfate and concentrated. Crystallization from methanol gave another 6.86 g (36%). $^1$H NMR (400 MHz, $d_4$-MeOH): 8.47 (s, 1H), 8.15 (d, 1H), 7.74 (dd, 1H), 7.70 (s, 1H), 7.49 (d, 1H), 7.15 (s, 1H), 4.24-4.06 (m, 3H), 4.02 (s, 3H), 3.98-3.82 (m, 3H), 3.59 (m, 1H), 3.00 (br. s, 2H), 1.48 (s, 9H); MS (EI) for $C_{25}H_{28}N_4O_5Cl_2$: 535 (MH$^+$).

To a suspension of 1,1-dimethylethyl 2-({[4-[(3,4-dichlorophenyl)amino]-6-(methoxy)quinazolin-7-yl]oxy}morpholine-4-carboxylate (4.77 g, 8.91 mmol) in methanol (50 mL) was added a 4M solution of HCl in 1,4-dioxane (50 mL), and the reaction mixture was refluxed for 5 min. After cooling to room temperature, diethyl ether (100 mL) was added and the precipitate was filtered and dried. The solid was dissolved in methanol (200 mL) and treated with Bio-Rad 1-X8 resin hydroxide form until pH 8. Filtration and concentration in vacuo provided 3.32 g (86%) of N-(3,4-dichlorophenyl)-6-(methyloxy)-7-[(morpholin-2-ylmethyl)oxy]quinazolin-4-amine as a brown solid. $^1$H NMR (400 MHz, $d_4$-MeOH): 8.47 (s, 1H), 8.14 (d, 1H), 7.73 (m, 2H), 7.49 (d, 1H), 7.15 (s, 1H), 4.24-4.13 (m, 2H), 4.09-3.97 (m, 5H), 3.76 (m, 1H), 3.22 (dd, 1H), 3.02-2.90 (m, 3H); MS (EI) for $C_{20}H_{20}N_4O_3Cl_2$: 435 (MH$^+$).

To a solution of N-(3,4-chlorophenyl)-6-(methyloxy)-7-[(morpholin-2-ylmethyl)oxy]quinazolin-4-amine (3.32 g, 7.7 mmol) in formic acid (33.2 mL) was added a 37 wt % solution of formaldehyde in water (3.32 mL), and the reaction mixture was heated at 95° C. for 2.5 h. After cooling to room temperature, the reaction mixture was concentrated. The residue was dissolved in methanol and treated with Bio-Rad AG®1-X8 hydroxide form resin until pH 8. Filtration and concentration in vacuo afforded 3.11 g (91%) of the title compound as a yellow-brown solid. $^1$H NMR (400 MHz, $d_4$-MeOH): 8.46 (s, 1H), 8.14 (d, 1H), 7.73 (dd, 1H), 7.68 (s, 1H), 7.48 (d, 1H), 7.13 (s, 1H), 4.21-4.09 (m, 2H), 4.02 (s, 3H), 4.01-3.91 (m, 3H), 2.96 (m, 1H), 2.75 (m, 1H), 2.35 (s, 3H), 2.22 (m, 1H), 2.11 (t, 1H); MS (EI) for $C_{21}H_{22}N_4O_3Cl_2$: 449 (MH$^+$).

Using the same or analogous synthetic techniques and/or substituting with alternative reagents, the following compounds of the invention were prepared:

N-(3,4-dichlorophenyl)-6-(methyloxy)-7-({[4-(phenylmethyl)morpholin-2-yl]methyl}oxy)quinazolin-4-amine: $^1$H NMR (400 MHz, $d_4$-MeOH): 8.48 (s, 1H), 8.15 (d, 1H), 7.74 (m, 2H), 7.50 (d, 1H), 7.38-7.24 (m, 5H), 7.16 (s, 1H), 4.21-4.09 (m, 2H), 4.06-3.99 (m, 4H), 3.91 (m, 1H), 3.72 (m, 1H), 3.58 (s, 2H), 2.96 (m, 1H), 2.73 (m, 1H), 2.25 (m, 1H), 2.16 (t, 1H); MS (EI) for $C_{27}H_{26}N_4O_3Cl_2$: 525 (MH$^+$).

N-(3,4-dichlorophenyl)-6-(methyloxy)-7-[(1,4-oxazepan-2-ylmethyl)oxy]quinazolin-4-amine: $^1$H NMR (400 MHz, $d_4$-MeOH): 8.47 (s, 1H), 8.14 (d, 1H), 7.73 (m, 2H), 7.49 (d, 1H), 7.15 (s, 1H), 4.20-4.00 (m, 7H), 3.80 (m, 1H), 3.21 (dd, 1H), 2.95 (m, 3H), 1.91 (m, 2H); MS (EI) for $C_{21}H_{22}N_4O_3Cl_2$: 449 (MH$^+$).

N-(3,4-dichlorophenyl)-7-{[(4-methyl-1,4-oxazepan-2-yl)methyl]oxy}-6-(methyloxy)quinazolin-4-amine: $^1$H NMR (400 MHz, $d_4$-MeOH): 8.46 (s, 1H), 8.14 (d, 1H), 7.73 (dd, 1H), 7.70 (s, 1H), 7.49 (d, 1H), 7.14 (s, 1H), 4.23-4.13 (m, 2H), 4.09-3.93 (m, 5H), 3.87 (m, 1H), 3.08 (d, 1H), 2.88 (m, 1H), 2.65 (m, 2H), 2.46 (s, 3H), 2.05 (m, 1H), 1.92 (m, 1H); MS (EI) for $C_{22}H_{24}N_4O_3Cl_2$: 463 (MH$^+$).

N-(3,4-dichlorophenyl)-7-{[(4-ethyl-1,4-oxazepan-2-yl)methyl]oxy}-6-(methyloxy)quinazolin-4-amine hydrochloride: $^1$H NMR (400 MHz, $d_4$-MeOH): 8.77 (s, 1H), 8.06-8.05 (m, 2H), 7.72 (dd, 1H), 7.60 (d, 1H), 7.31 (s, 1H), 4.62-4.32 (m, 3H), 4.30 (s, 3H), 4.04-3.36 (m, 8H), 2.40-2.08 (m, 2H), 1.45 (tr, 3H); MS (EI) for $C_{23}H_{26}N_4O_3Cl_2$: 477 (MH$^+$).

N-(3,4-dichlorophenyl)-6-(methyloxy)-7-[(tetrahydro-2H-pyran-2-ylmethyl)oxy]quinazolin-4-amine: $^1$H NMR (400 MHz, $d_6$-DMSO): 9.55 (s, 1H), 8.51 (s, 1H), 8.24 (d, 1H), 7.88 (dd, 1H), 7.77 (s, 1H), 7.61 (d, 1H), 7.17 (s, 1H), 4.05 (m, 2H), 3.97 (s, 3H), 3.92-3.88 (m, 1H), 3.73-3.65 (m, 1H), 3.42-3.38 (m, 2H), 1.88-1.81 (m, 1H), 1.70-1.64 (m, 1H), 1.53-1.35 (m, 3H); MS (EI) for $C_{21}H_{20}N_3O_3Cl_2$: 434 (MH$^+$).

Example 27

N-(3,4-dichlorophenyl)-7-[({2-[(dimethylamino)methyl]-1,3-thiazol-4-yl}methyl)oxy]-6-(methyloxy)quinazolin-4-amine (Dimethylamino)acetonitrile (1.16 mL, 11.9 mmol) was added to a mixture of DMF (5 mL) and triethylamine (2 mL). Hydrogen sulfide gas was bubbled into the solution until the solution was dark green. The solution was then heated at 70° C. for 0.5 h. Excess hydrogen sulfide was removed from the system by bubbling nitrogen into the solution and then the volatiles were removed in vacuo. to afford 2-(dimethylamino)ethanethioamide as burgundy crystals (0.660 g, 5.59 mmol, 47% yield). $^1$H NMR (400 MHz; CDCl$_3$): 2.30 (s, 6H); 3.37 (s, 2H); 7.80 (br s, 1H); 8.80 (br s, 1H); GCMS for C$_4$H$_{10}$N$_2$S: 118 (M$^+$).

2-(Dimethylamino)ethanethioamide (0.382 g, 3.24 mmol), 1,3-dichloroacetone (0.453 g, 3.56 mmol) and sodium bicarbonate (0.301 g, 3.56 mmol) was stirred in 1,2-dichloroethane (4 mL) at room temperature for 24 h. The reaction mixture was filtered and the filter cake was washed with 1,2-dichloroethane. The filtrate was added dropwise to a cooled (ice bath) solution of thionyl chloride (0.260 mL, 3.56 mmol) in 1,2-dichloroethane (2 mL). The solution was stirred at 70° C. for 0.5 h and then cooled to room temperature. The brown mixture was filtered and washed with 1,2-dichloroethane to afford N-{[4-(chloromethyl)-1,3-thiazol-2-yl]methyl}-N,N-dimethylamine hydrochloride as a brown solid (0.550 g, 2.42 mmol, 75% yield). $^1$H NMR (400 MHz; D$_2$O): 2.79 (s, 6H); 4.52 (s, 2H); 4.61 (s, 2H); 7.60 (s, 1H).

N-{[4-(Chloromethyl)-1,3-thiazol-2-yl]methyl}-N,N-dimethylamine hydrochloride hydrochloride (0.050 g, 0.220 mmol) and 4-[(3,4-dichlorophenyl)amino]-6-(methoxy)quinazolin-7-ol (0.074 g, 0.220 mmol) were suspended in DMP (4 mL) and potassium carbonate (0.152 g, 1.10 mmol) was added. The mixture was stirred at room temperature for 50 h and then at 70° C. for 3.5 h. An additional portion of N-{[4-(chloromethyl)-1,3-thiazol-2-yl]methyl}-N,N-dimethylamine hydrochloride hydrochloride (0.019 g, 0.084 mmol) was added and the mixture was stirred at 70° C. for a further 25 h. The reaction mixture was concentrated in vacuo. and the residue was partitioned between ethyl acetate and brine. The organic portion was washed with 1 N aqueous sodium hydroxide, brine, dried over sodium sulfate, filtered and concentrated in vacuo. to afford a brown solid. Recrystallization from ethyl acetate/diethyl ether afforded the title compound as a pale brown solid (0.016 g, 0.033 mmol, 15% yield). $^1$H NMR (400 MHz; CDCl$_3$): 2.37 (s, 6H); 3.79 (s, 2H); 4.00 (s, 3H); 5.34 (s, 2H); 7.00 (s, 1H); 7.15 (br s, 1H); 7.34-7.37 (m, 2H); 7.55 (d, 1H); 7.57 (d, 1H); 7.96 (d, 1H); 8.66 (s, 1H); MS (EI) for C$_{22}$H$_{21}$Cl$_2$N$_5$O$_2$S: 490 (MH$^+$).

Example 28

N-(3,4-dichlorophenyl)-6-(methyloxy)-7-({[2-(morpholin-4-ylmethyl)-1,3-thiazol-4-yl]methyl}oxy)quinazolin-4-amine Morpholin-4-ylacetonitrile (1.03 g, 8.17 mmol) was added to a mixture of DMF (3.5 mL) and triethylamine (1.4 mL). Hydrogen sulfide gas was bubbled into the solution until the solution was light green. The solution was then heated at 70° C. for 0.5 h. Excess hydrogen sulfide was removed from the system by bubbling nitrogen into the solution and then the volatiles were removed in vacuo to afford brown crystals. These crystals were triturated with ethanol to afford 2-morpholin-4-ylethanethioamide as very pale brown crystals (0.525 g, 3.28 mmol, 40% yield). $^1$H NMR (400 MHz; CDCl$_3$): 2.53-2.58 (m, 4H); 3.44 (s, 2H); 3.70-3.74 (m, 4H); 7.74 (br s, 1H); 8.70 (br s, 1H); GCMS for C$_6$H$_{12}$N$_2$OS: 160 (M$^+$).

2-Morpholin-4-ylethanethioamide (0.403 g, 2.52 mmol), 1,3-dichloroacetone (0.353 g, 2.77 mmol) and sodium bicarbonate (0.234 g, 2.77 mmol) was stirred in 1,2-dichloroethane (4 mL) at room temperature for 74 h at which point 1,4-dioxane was added in an attempt to improve solubility and the mixture was stirred for a further 30 h. The reaction mixture was filtered and the filter cake was washed with 1,2-dichloroethane. The filtrate was added dropwise to a cooled (ice bath) solution of thionyl chloride (0.202 mL, 2.77 mmol) in 1,2-dichloroethane (3 mL). The solution was stirred at 70° C. for 0.5 h and then cooled to room temperature. The brown mixture was filtered and washed with 1,2-dichloroethane to afford 4-{[4-(chloromethyl)-1,3-thiazol-2-yl]methyl}morpholine hydrochloride as a very pale brown solid (0.024 g, 0.091 mmol, 4% yield). $^1$H NMR (400 MHz; D$_2$O): 3.29-3.39 (m, 4H); 3.78-3.92 (m, 4H); 4.63 (s, 2H); 4.67 (s, 2H); 7.67 (s, 1H); MS (EI) for C$_9$H$_{13}$ClN$_2$OS: 233 (MH$^+$).

4-([4-(Chloromethyl)-1,3-thiazol-2-yl]methyl}morpholine hydrochloride (0.024 g, 0.089 mmol) and 4-[(3,4-dichlorophenyl)amino]-6-(methyloxy)quinazolin-7-ol (0.030 g, 0.089 mmol) were suspended in DMP (2 mL) and potassium carbonate (0.062 g, 0.449 mmol) was added. The mixture was stirred at 70° C. for 21 h. The reaction mixture was concentrated in vacuo and the residue was purified by reverse phase HPLC to afford the title compound as a colorless solid (0.026 g, 0.049 mmol, 54% yield). $^1$H NMR (400 MHz; CDCl$_3$): 2.50 (br s, 1H); 2.57-2.64 (m, 4H); 3.75 (t, 4H); 3.84 (s, 2H); 3.96 (s, 3H); 5.28 (s, 2H); 7.09 (s, 1H); 7.31 (s, 1H); 7.37 (s, 1H); 7.43 (d, 1H); 7.60 (dd, 1H); 7.97 (d, 1H); 8.61 (s, 1H); MS (EI) for C$_{24}$H$_{23}$Cl$_2$N$_5$O$_3$S: 532 (MH$^+$).

Example 29

N-(3,4-dichlorophenyl)-6-(methyloxy)-7-({[2-[(4-methylpiperazin-1-yl)methyl]-1,3-thiazol-4-yl]methyl}oxy)quinazolin-4-amine (4-Methylpiperazin-1-yl)acetonitrile (1.03 g, 7.42 mmol) was added to a mixture of DMF (5 mL) and triethylamine (2 mL). Hydrogen sulfide gas was bubbled into the solution until the solution was dark green. The solution was then heated at 70° C. for 1 h. Excess hydrogen sulfide was removed from the system by bubbling nitrogen into the solution and then the volatiles were removed in vacuo to afford brown crystals. These crystals were triturated with ethanol to afford 2-(4-methylpiperazin-1-yl)ethanethioamide as very pale brown crystals (0.455 g, 2.63 mmol, 35% yield). $^1$H NMR (400 MHz; CDCl$_3$): 2.29 (s, 3H); 2.38-2.66 (m, 8H); 3.44 (s, 2H); 7.72 (br s, 1H); 8.76 (br s, 1H); GCMS for C$_7$H$_{15}$N$_3$S: 173 (M$^+$).

2-(4-Methylpiperazin-1-yl)ethanethioamide (0.438 g, 2.53 mmol), 1,3-dichloroacetone (0.355 g, 2.78 mmol) and sodium bicarbonate (0.236 g, 2.78 mmol) was stirred in chloroform (4 mL) at room temperature for 48 h. The reaction mixture was filtered and the filter cake was washed with chloroform. The filtrate was added dropwise to a cooled (ice bath) solution of thionyl chloride (0.205 mL, 2.78 mmol) in chloroform (2 mL). The solution was stirred at 60° C. for 0.5 h and then cooled to room temperature. The brown mixture was filtered and washed with chloroform to afford 1-{[4-(chloromethyl)-1,3-thiazol-2-yl]methyl}-4-methylpiperazine hydrochloride as a brown solid (0.421 g, 1.49 mmol, 59% yield). $^1$H NMR (400 MHz; D$_2$O): 2.89 (s, 3H); 3.18-3.43 (m, 4H); 3.56-3.78 (m, 4H); 4.56 (s, 2H); 4.67 (s, 2H); 7.66 (s, 1H); MS (EI) for C$_{10}$H$_{16}$ClN$_3$S: 246 (MH$^+$).

1-{[4-(Chloromethyl)-1,3-thiazol-2-yl]methyl}-4-methylpiperazine hydrochloride (0.067 g, 0.238 mmol) and 4-[(3,4-dichlorophenyl)amino]-6-(methoxy)quinazolin-7-ol (0.080 g, 0.238 mmol) were suspended in DMF (4 mL) and potassium carbonate (0.164 g, 1.19 mmol) was added. The mixture was stirred at 70° C. for 21 h. The reaction mixture was concentrated in vacuo and the residue was purified by reverse phase HPLC to afford the title compound as a colorless solid (0.025 g, 0.046 mmol, 19% yield). $^1$H NMR (400 MHz; CDCl$_3$): 2.08 (s, 5H); 2.39 (s, 3H); 2.59-2.74 (m, 6H); 3.44-3.78 (m, 5H); 3.86 (s, 2H); 3.98 (s, 3H); 5.30 (s, 2H); 7.10 (s, 1H); 7.33 (s, 1H); 7.37 (s, 1H); 7.43 (d, 1H); 7.61 (dd, 1H); 7.99 (d, 1H); 8.60 (s, 1H); MS (EI) for C$_{25}$H$_{26}$Cl$_2$N$_6$O$_2$S: 545 (MH$^+$).

Example 30

N-(3,4-dichlorophenyl)-6-(methyloxy)-7-([5-(1-methylpiperidin-4-yl)-1,2,4-oxadiazol-3-yl]methyl}oxy)quinazolin-4-amine (Method 1)

Bromoacetonitrile (2.1 ml, 30.1 mmol) was added to a mixture of 4-[(3,4-dichlorophenyl)amino]-6-(methyloxy)quinazolin-7-ol (10.12 g; 30.1 mmol) and potassium carbonate (16.6 g; 120.1 mmol) in DMF (200 ml). The mixture was stirred at room temperature overnight. The solvent was removed under high vacuum and the residue was triturated with water, filtered, washed with a mixture of hexane and ether (1/1) and dried under vacuum to give {[4-[(3,4-dichlorophenyl)amino]-6-(methyloxy)quinazolin-7-yl]oxy}acetonitrile (9.6 g; 91% yield). $^1$H NMR (400 MHz; DMSO-d$_6$): 3.99 (s, 3H), 5.40 (s, 2H), 7.41 (s, 1H), 7.64 (d, 1H), 7.87 (dd, 1H), 7.90 (s, 1H), 8.23 (d, 1H), 8.57 (s, 1H), 9.69 (s, 1H); MS (EI) for C$_{17}$H$_{12}$Cl$_2$N$_4$O$_2$: 375.06 (MH$^+$).

To a suspension of {[4-[(3,4-dichlorophenyl)amino]-6-(methyloxy)quinazolin-7-yl]oxy}acetonitrile (14.7 g; 39.3 mmol) in EtOH (600 ml) was added a 50% aqueous solution of NH$_2$OH (24.1 ml; 393 mmol) and the reaction mixture was refluxed for 2 hours. The solvent was evaporated off and the residue was triturated with ether, collected by filtration and dried under vacuum to give 2-{[4-[(3,4-dichlorophenyl)amino]-6-(methyloxy)quinazolin-7-yl]oxy}-N-hydroxyethanimidamide (14.5 g; 90% yield). $^1$H NMR (400 MHz; DMSO-d$_6$): 3.98 (s, 3H), 4.58 (s, 2H), 5.70 (s, 2H), 7.38 (s, 1H), 7.65 (d, 1H), 7.84 (s, 1H), 7.89 (dd, 1H), 8.26 (d, 1H), 8.55 (s, 1H), 9.41 (s, 1H), 9.64 (s, 1H); MS (EI) for C$_{17}$H$_{15}$Cl$_2$N$_5$O$_3$: 408.05 (MH$^+$).

To a solution of Boc-isonipecotic acid (4.72 g; 20.6 mmol) and 4-methylmorpholine (5.7 ml; 51.5 mmol) in DMF (200 ml) were added HOBT (3.06 g; 22.7 mmol) and EDCI (4.35 g; 22.7 mmol) and the solution was stirred at room temperature for 30 minutes. To the reaction mixture 2-{[4-[(3,4-dichlorophenyl)amino]-6-(methyloxy)quinazolin-7-yl]oxy)-N-hydroxyethanimidamide (7 g; 17.1 mmol) was added and the solution was stirred at room temperature overnight. The solvent was removed under vacuum and the residue was dissolved in ethyl acetate. The organic layer was washed with saturated aqueous NaHCO$_3$, brine, dried over NaSO$_4$ and concentrated.

Procedure a) To the residue was added p-xylene (200 ml) and the suspension was refluxed for two hours. The solvent was removed under vacuum and the residue was purified by column chromatography (SiO$_2$, hexanes/acetone from 4/1 to 1/1) to give 1,1-dimethylethyl 4-[3-({[4-[(3,4-dichlorophenyl)amino]-6-(methyloxy)quinazolin-7-yl]oxy}methyl)-1,2,4-oxadiazol-5-yl]piperidine-1-carboxylate (8.3 g; 81% yield over two steps)

Procedure b) The residue was dissolved in THF (400 ml) and n-Bu$_4$NF (1M in THF; 17.1 ml; 17.1 mmol) was added. The reaction mixture was stirred at room temperature for 2 h. The solvent was evaporated off and the residue was dissolved in ethyl acetate; the organic layer was washed with H$_2$O, brine, dried over Na$_2$SO$_4$ and concentrated in vacuo. The residue was purified by column chromatography (SiO$_2$, hexanes/acetone) to give 1,1-dimethylethyl 4-[3-({[4-[(3,4-dichlorophenyl)amino]-6-(methyloxy)quinazolin-7-yl]oxy}methyl)-1,2,4-oxadiazol-5-yl]piperidine-1-carboxylate (6.9 g; 66% overall yield). $^1$H NMR (400 MHz; DMSO-d$_6$): 1.40 (s, 9H), 1.55-1.67 (m, 2H), 2.01-2.08 (m, 2H), 2.83-3.05 (br s, 2H), 3.33 (m, 1H), 3.88-3.96 (m, 2H), 3.99 (s, 3H), 5.53 (s, 2H), 7.43 (s, 1H), 7.73 (s, 2H), 8.02 (s, 1H), 8.1 (s, 1H), 8.81 (s, 1H), 10.74 (br s, 1H); MS (EI) for C$_{28}$H$_{30}$Cl$_2$N$_6$O$_5$: 601.09 (MH$^+$)

1,1-Dimethylethyl 4-[3-({[4-[(3,4-dichlorophenyl)amino]-6-(methyloxy)quinazolin-7-yl]oxy}methyl)-1,2,4-oxadiazol-5-yl]piperidine-1-carboxylate (12.3 g, 20.4 mmol) was dissolved in MeOH (100 ml) and HCl (4M in dioxane; 65 ml) was added. The solution was stirred at room temperature for 10 min and concentrated to half the initial volume. Ethyl ether was added to the suspension obtained and the precipitate was collected by filtration, washed with ether and concentrated to dryness to give 8 g of N-(3,4-dichlorophenyl)-6-(methyloxy)-7-{[(5-piperidin-4-yl-1,2,4-oxadiazol-3-yl)methyl]oxy}quinazolin-4-amine (78% yield). $^1$H NMR (400 MHz; DMSO-d$_6$): 1.61 (qd, 2H), 1.94 (m, 2H), 2.07-2.19 (br s, 1H), 2.57 (td, 2H), 2.95 (dt, 2H), 3.17 (m, 1H), 3.97 (s, 3H), 5.44 (s, 2H), 7.40 (s, 1H), 7.63 (d, 1H), 7.85 (s, 1H), 7.87 (dd, 1H), 8.23 (d, 1H), 8.54 (s, 1H), 9.64 (s, 1H); MS (EI) for C$_{23}$H$_{22}$Cl$_2$N$_6$O$_3$: 501.07 (MH$^+$)

Aqueous formaldehyde (37%, 894 ml, 12.0 mmol) was added to a solution of N-(3,4-dichlorophenyl)-6-(methyloxy)-7-{[(5-piperidin-4-yl-1,2,4-oxadiazol-3-yl)methyl]oxy}quinazolin-4-amine (1 g, 2.0 mmol) in formic acid (2 ml). The mixture was heated at 95° C. for two hours. The volatiles were removed under vacuum, the residue was dissolved in CH$_3$OH and the pH of the solution was adjusted to 9 by addition of Biorad AG® 1-X8 hydroxide form resin. The solution was filtered, concentrated in vacuo and the residue was crystallized from MeOH/H$_2$O to give N-(3,4-dichlorophenyl)-6-(methyloxy)-7-({[5-(1-methylpiperidin-4-yl)-1,2,4-oxadiazol-3-yl]methyl}oxy)quinazolin-4-amine (714 mg; 69% yield). $^1$H NMR (400 MHz; DMSO-d$_6$): 1.69-1.82 (m, 2H), 1.97-2.05 (m, 4H), 2.16 (s, 3H), 2.71-2.78 (m, 2H), 2.98-3.10 (m, 1H), 3.96 (s, 3H), 5.44 (s, 2H), 7.39 (s, 1H), 7.62 (d, 1H), 7.83 (s, 1H), 7.87 (dd, 1H), 8.22 (d, 1H), 8.53 (s, 1H), 9.63 (s, 1H); MS (EI) for C$_{24}$H$_{24}$Cl$_2$N$_6$O$_3$: 515.07 (MH$^+$)

Using the same or analogous synthetic techniques and/or substituting with alternative reagents, the following compounds of the invention were prepared:

N-(3,4-dichlorophenyl)-7-[({5-[(dimethylamino)methyl]-1,2,4-oxadiazol-3-yl}methyl)oxy]-6-(methyloxy)quinazolin-4-amine: $^1$H NMR (400 MHz; DMSO-d$_6$): 2.26 (s, 6H), 3.87 (s, 2H), 3.97 (s, 3H), 5.49 (s, 2H), 7.39 (s, 1H), 7.85-7.90 (m, 2H), 8.23 (d, 1H), 8.53 (s, 1H), 9.67 (s, 1H); MS (EI) for C$_{21}$H$_{20}$Cl$_2$N$_6$O$_3$: 475.06 (MH$^+$).

N-(3,4-dichlorophenyl)-6-(methyloxy)-7-{[(5-piperidin-3-yl-1,2,4-oxadiazol-3-yl)methyl]oxy}quinazolin-4-famine: $^1$H NMR (400 MHz; DMSO-d): 1.37-1.82 (m, 4H), 2.04-2.14 (m, 1H), 2.20-2.34 (m, 1H), 2.70-2.87 (m, 2H), 3.07-3.22 (m, 2H), 3.97 (s, 3H), 5.44 (s, 2H), 7.40 (s, 1H), 7.63 (d, 1H), 7.85

(s, 1H), 7.87 (dd, 1H), 8.23 (d, 1H), 8.54 (s, 1H), 9.64 (s, 1H); MS (EI) for $C_{23}H_{22}Cl_2N_6O_3$: 501.03 (MH$^+$).

N-(3,4-dichlorophenyl)-6-(methyloxy)-7-({[5-(1-methylpiperidin-3-yl)-1,2,4-oxadiazol-3-yl]methyl}oxy)quinazolin-4-amine: $^1$H NMR (400 MHz; DMSO-d$_6$): 1.51-1.76 (m, 4H), 1.92-2.12 (m, 2H), 2.18 (s, 3H), 2.30-2.40 (m, 1H), 2.51-2.58 (m, 1H), 2.87-2.94 (m, 1H) 3.97 (s, 3H), 5.44 (s, 2H), 7.40 (s, 1H), 7.63 (d, 1H), 7.83-7.90 (m, 2H), 8.23 (d, 1H), 8.54 (s, 1H), 9.64 (s, 1H); MS (EI) for $C_{24}H_{24}Cl_2N_6O_3$: 515.06 (MH$^+$).

N-(3,4-dichlorophenyl)-6-(methyloxy)-7-({[5-(piperidin-2-yl)-1,2,4-oxadiazol-3-yl]methyl}oxy)quinazolin-4-amine: $^1$H NMR (400 MHz; DMSO-d$_6$): 1.26-1.50 (m, 4H), 1.52-1.72 (m, 2H), 1.82-1.90 (m, 1H), 2.50-2.64 (m, 1H), 2.80-2.90 (m, 1H), 3.91 (s, 3H), 5.41 (s, 2H), 7.35 (s, 1H), 7.58 (d, 1H), 7.80-7.86 (m, 2H), 8.19 (d, 1H), 8.49 (s, 1H), 9.60 (s, 1H); MS (EI) for $C_{23}H_{22}Cl_2N_6O_3$: 501.11 (MH$^+$).

N-(3,4-dichlorophenyl)-6-(methyloxy)-7-({[5-(1-methylpiperidin-2-yl)-1,2,4-oxadiazol-3-yl]methyl}oxy)quinazolin-4-amine hydrochloride: $^1$H NMR (400 MHz; DMSO-d$_6$): 1.61 (br m, 1H), 1.75-1.88 (br m, 3H), 2.08 (br m, 1H), 2.28 (br d, 1H), 2.75 (s, 3H), 3.24 (br m, 1H), 3.49 (br m, 2H), 4.05 (s, 3H), 5.08 (br s, 1H), 5.64 (s, 2H), 7.62 (s, 1H), 7.71 (d, 1H), 7.87 (dd, 1H), 8.18 (d, 1H), 8.65 (s, 1H), 8.88 (s, 1H), 11.95 (s, 1H); MS (EI) for $C_{24}H_{24}Cl_2N_6O_3$: 515.11 (MH$^+$).

N-(3,4-dichlorophenyl)-6-(methyloxy)-7-({[5-(1-ethylpiperidin-2-yl)-1,2,4-oxadiazol-3-yl]methyl}oxy)quinazolin-4-amine hydrochloride: $^1$H NMR (400 MHz; DMSO-d$_6$): 11.80 (br s, 1H), 8.87 (s, 1H), 8.56 (s, 1H), 8.18 (d, 1H), 7.85 (dd, 1H), 7.73 (d, 1H), 7.60 (s, 1H), 5.65 (s, 2H), 5.10 (br s, 1H), 4.05 (s, 3H), 3.80-3.50 (br m, 4H), 3.20-3.00 (br m, 2H), 2.30-2.00 (br m, 1H), 1.95 (br m, 2H), 1.65 (br m, 1H), 1.20 (br m, 3H); MS (EI) for $C_{25}H_{26}Cl_2N_6O_3$: 529 (MH$^+$).

Example 31

N-(3,4-dichlorophenyl)-6-(methyloxy)-7-([(5-piperidin-2-yl-1,2,4-oxadiazol-3-yl)methyl]oxy}quinazolin-4-amine hydrochloride (Method 2)

To a suspension of 50.0 g (0.41 mol) benzoic acid in 150 mL N,N-dimethylformamide 70.0 g (0.50 mol) potassium carbonate was added and the mixture was stirred until the evolution of gas has ceased. The reaction mixture was cooled to 0° C. and a solution of 29.0 mL (0.41 mol) bromoacetonitrile in 50 mL N,N-dimethylformamide was added dropwise. The reaction mixture was stirred overnight at room temperature. The solvent was evaporated and the residue was dissolved in 500 mL ethyl acetate. It was washed with water (3×150 mL), saturated aqueous sodium hydrogencarbonate (150 mL) and brine. The organic layer was separated and dried over anhydrous sodium sulfate. The drying agent was filtered off and the solvent was evaporated. The resulting crude product was purified by column chromatography (hexane-ethyl acetate 9:1 to 4:1) to yield cyanomethyl benzoate 62.6 g (95%). $^1$H-NMR (400 MHz; DMSO-d$_6$): 7.98 (m, 2H), 7.69 (m, 1H), 7.54 (m, 2H), 5.20 (s, 2H); GCMS for $C_9H_7NO_2$: 161 (MH$^+$).

Cyanomethyl benzoate (22.2 g, 138 mmol) was dissolved in ethanol (250 mL) followed by addition of 50% aqueous hydroxylamine (16.9 mL, 276 mmol) and the mixture was stirred for 15 minutes at room temperature. Concentration followed by addition of water (250 mL) afforded a colorless crystalline solid that was collected by filtration and washed with additional water then dried in vacuo to give 2-(hydroxyamino)-2-iminoethyl benzoate (23.69 g, 88% yield). $^1$H-NMR (400 MHz; DMSO-d$_6$): 9.37 (s, 1H), 7.98 (m, 2H), 7.65 (m, 1H), 7.54 (tr, 2H), 5.69 (br s, 2H), 4.64 (s, 2H).

Example 32

N-(3,4-dichlorophenyl)-6-(methyloxy)-7-[({3-[(4-methylpiperazin-1-yl)methyl]-1,2,4-oxadiazol-5-yl}methyl)oxy]quinazolin-4-amine A mixture of 4-[(3,4-dichlorophenyl)amino]-6-(methyloxy)quinazolin-7-ol (3.67 g), methyl bromoacetate (0.81 mL), and potassium carbonate (4.66 g) in DMF (21 mL) was stirred at room temperature for 18 hours. The reaction mixture was diluted with ethyl acetate and filtered. The solid was combined with the filtrate and washed with water, dried over sodium sulfate and evaporated to give a brown solid which was recrystallized in methanol to give methyl {[4-[(3,4-dichlorophenyl)amino]-6-(methyloxy)quinazolin-7-yl]oxy}acetate (2.80 g). $^1$H-NMR (400 MHz; DMSO-d$_6$): 9.62 (s,1H), 8.46 (s, 1H), 8.24 (s, 1H), 7.94-7.85 (m, 2H), 7.63 (d, 1H), 7.17 (s, 1H), 5.04 (s, 2H), 4.00 (s, 3H), 3.72 (s, 3H); MS (EI) for $C_{18}H_{15}N_3O_4Cl_2$: 408 (MH$^+$).

A mixture (4-methylpiperazin-1-yl)acetonitrile (400 mg), hydroxylamine (50% aqueous solution, 2.0 mL) and ethanol (10.0 mL), was stirred at room temperature for 18 hours. The reaction mixture was evaporated to dryness to give a crystalline solid that was washed with hexane and dried under vacuum to give N-hydroxy-2-(4-methylpiperazin-1-yl)ethanimidamide (405 mg). $^1$H-NMR (400 MHz; CDCl$_3$): 5.19 (br s, 3H), 3.00 (s, 2H), 2.75-2.28 (br m, 8H), 2.70 (s, 3H).

Sodium hydride (60% oil dispersion, 30 mg) was added to a mixture of N-hydroxy-2-(4-methylpiperazin-1-yl)ethanimidamide (50 mg) and 3 A molecular sieves (110 mg) in 1 mL of DMF. After the initial hydrogen evolution had stopped, the mixture was heated at 60° C. for 30 minutes. {[4-[(3,4-Dichlorophenyl)amino]-6-(methyloxy)quinazolin-7-yl]oxy}acetate (50 mg) was added to the reaction mixture and the heating was continued at 90° C. for one hour. The reaction was cooled to room temperature, diluted with methanol, and filtered. The filtrate was purified by reverse phase HPLC, and the eluent containing the expected product was concentrated to dryness and isolated as the TFA salt. The salt was taken into methanol and treated with Biorad AG® 1-X8 hydroxide form resin then filtered and the filtrate concentrated and dried in vacuo to give the title compound (25.0 mg) $^1$H-NMR (400 MHz, DMSO-d$_6$): 10.60 (br s, 1H), 8.78 (s, 1H), 8.17 (s, 1H), 8.02 (s, 1H), 7.79 (d, 1H), 7.70 (d, 1H), 7.22 (s, 1H), 5.78 (s, 2H), 4.00 (s, 3H), 3.82 (s, 2H), 3.15-2.90 (br m, 4H), 2.80 (s, 3H), 2.60-2.45 (br m, 4H); MS (EI) for $C_{24}H_{25}N_7O_3Cl_2$: 530 (MH$^+$).

Using the same or analogous synthetic techniques and/or substituting with alternative reagents, the following compounds of the invention were prepared:

N-(3,4-dichlorophenyl)-7-[({3-[(dimethylamino)methyl]-1,2,4-oxadiazol-5-yl}methyl)oxy]-6-(methyloxy)quinazolin-4-amine: $^1$H-NMR (400 MHz; DMSO-d$_6$): 10.48 (br s,1H), 8.75 (s, 1H), 8.20 (s, 1H), 8.05 (s, 1H), 7.81 (d, 1H), 7.72 (d, 1H), 7.25 (s, 1H), 5.85 (s, 2H), 4.85 (s, 2H), 4.00 (s, 3H), 2.88 (s, 6H); MS (EI) for $C_{21}H_{20}N_6O_3Cl_2$: 475 (MH$^+$).

N-(3,4-dichlorophenyl)-6-(methyloxy)-7-({[3-(morpholinyl-4-methyl)-1,2,4-oxadiazol-5-yl]methyl}oxy)quinazolin-4-amine: $^1$H-NMR (400 MHz, DMSO-d$_6$): 10.50 (br s, 1H), 8.78 (s, 1H), 8.18 (s, 1H), 8.04 (s, 1H), 7.79 (d, 1H), 7.70 (d, 1H), 7.22 (s, 1H), 5.82 (s, 2H), 4.37 (s, 2H), 4.00 (s, 3H), 3.78-3.70 (br m, 4H), 2.15-2.95 (br m, 4H); MS (EI) for $C_{24}H_{25}N_7O_3Cl_2$: 517 (MH$^+$).

Example 33

N-(3,4-dichlorophenyl)-6-(methyloxy)-7-({[3-(4-methylpiperazin-1-yl)-1,2,4-oxadiazol-5-yl]methyl}oxy)quinazolin-4-amine 1,1-Dimethylethyl 1-piperazinecarboxylate (25 g, 134.2 mmol) was taken into THF (100 mL) followed by addition of triethylamine (25 mL, 178 mmol). The solution was cooled to 0° C. follwed by addition dropwise addition of cyanogen bromide (15.6 g, 147.6 mmol) in THF (100 mL) and the resulting mixture was allowed to warm to room temperature then stirred an additional 12 hours. The reaction mixture was concentrated in vacuo and partitioned with ethyl ether and water. The organic layer was washed once with saturated aqueous NaCl then dried over anhydrous magnesium sulfate followed by concentration to afford 1,1-dimethylethyl 4-cyanopiperazine-1-carboxylate (24.5 g, 86% yield) as a colorless crystalline solid. $^1$H-NMR (400 MHz, CDCl$_3$): 3.51 (tr, 4H), 3.19 (tr, 4H), 1.46 (s, 9H).

1,1-Dimethylethyl 4-cyanopiperazine-1-carboxylate (10 g, 47.1 mmol) was taken into ethanol (100 mL) and the resulting solution was cooled to 0° C. Hydroxylamine (50% aqueous solution, 3.5 mL, 56.5 mmol) was added and the mixture was allowed to warm to room temperature then stirred an additional hour. The mixture was then concentrated in vacuo to a paste and suspended in 1:1 ethyl ether/hexane (100 mL) and the solid product collected by filtration. The solid was washed with an additional portion of ethyl ether/hexane then dried to give 1,1-dimethylethyl 4-[(hydroxyamino)(imino)methyl]piperazine-1-carboxylate (9.64 g, 83% yield) as a white solid. $^1$H-NMR (400 MHz, DMSO-d$_6$): 8.34 (s, 1H), 5.19 (s, 2H), 3.30 (tr, 4H), 2.91 (tr, 4H), 1.39 (s, 9H).

1,1-Dimethylethyl 4-[(hydroxyamino)(imino)methyl]piperazine-1-carboxylate (3.58 g, 14.6 mmol) was suspended in THF (50 mL) followed by the addition of diisopropylethylamine (3.0 mL, 17.5 mmol) and the mixture was cooled to 0° C. Acetoxyacetyl chloride (1.6 mL, 14.6 mmol) was added by syringe and the mixture was allowed to stir an additional 30 minutes at 0° C. The resulting homogeneous solution was allowed to warm to room temperature then concentrated in vacuo to afford a white solid residue. The material was suspended in water (50 ml) and the solid product was collected by filtration, washed with additional water then hexanes and dried in vacuo. The intermediate O-acyl derivative was then suspended in THF (50 mL) followed by addition of TBAF (1.0M in THF, 3.5 mL) and the mixture was stirred for 30 minutes at room temperature. The homogeneous solution obtained was concentrated in vacuo and the residue partitioned with ethyl ether and water. The organic layer was washed twice with additional water then with saturated aqueous sodium chloride and dried over anhydrous magnesium sulfate. Filtration and concentration gave 1,1-dimethylethyl 4-{5-[(acetoxy)methyl]-1,2,4-oxadiazol-3-yl}piperazine-1-carboxylate (3.6 g, 76% yield) as a colorless crystalline solid. $^1$H-NMR (400 MHz, CDCl$_3$): 5.14 (s, 2H), 3.51 (tr, 4H), 3.42 (tr, 4H), 2.18 (s, 3H), 1.48 (s, 9H).

1,1-Dimethylethyl 4-{5-[(acetoxy)methyl]-1,2,4-oxadiazol-3-yl}piperazine-1-carboxylate (13.57 g, 41.6 mmol) was dissolved in methanol (100 mL) followed by addition of aqueous sodium hydroxide (4M, 10.4 mL) and the mixture was stirred for 30 minutes at room temperature. The reaction mixture was concentrated in vacuo and the residue partitioned with ethyl acetate and 0.1M aqueous hydrochloric acid. The organic layer was then washed with saturated aqueous sodium chloride then dried over anhydrous magnesium sulfate. Filtration and concentration afforded 1,1-dimethylethyl 4-[5-(hydroxymethyl)-1,2,4-oxadiazol-3-yl]piperazine-1-carboxylate (10.51 g, 89% yield) as a colorless crystalline solid. $^1$H-NMR (400 MHz, CDCl$_3$): 4.75 (s, 2H), 3.53-3.50 (m, 4H), 3.44-3.42 (m, 4H), 3.20 (br s, 1H), 1.48 (s, 9H).

1,1-Dimethylethyl 4-[5-(hydroxymethyl)-1,2,4-oxadiazol-3-yl]piperazine-1-carboxylate (7.4 g, 26 mmol) was taken into dichloromethane (100 mL) followed by addition of pyridine (5.3 mL, 65 mmol) and the solution was cooled to 0° C. Thionyl chloride (2.3 mL, 31.2 mmol) was added by syringe and the mixture was allowed to warm to room temperature and stirred an additional 12 hours. The mixture was then concentrated in vacuo and the residue partitioned with ethyl acetate and water. The aqueous phase was extracted twice with ethyl acetate and the combined organic layers were washed once with 0.1M aqueous hydrochloric acid then saturatedaqueous sodium chloride and dried over anhydrous magnesium sulfate. Filtration, concentration and purification of the residue by silica gel flash chromatography using 3:1 hexanes:ethyl acetate provided 1,1-dimethylethyl 4-[5-(chloromethyl)-1,2,4-oxadiazol-3-yl]piperazine-1-carboxylate (4.82 g, 61% yield) as a slightly yellow crystalline solid. $^1$H-NMR (400 MHz, CDCl$_3$): 4.53 (s, 2H), 3.51 (tr, 4H), 3.43 (tr, 4H), 1.48 (s, 9H).

1,1-dimethylethyl 4-[5-(chloromethyl)-1,2,4-oxadiazol-3-yl]piperazine-1-carboxylate (173.6 mg, 0.57 mmol), 4-[(3,4-dichlorophenyl)amino]-6-(methyloxy)quinazolin-7-ol (154 mg, 0.46 mmol) and potassium carbonate (315 mg, 2.85 mmol) were taken into DMF (2 mL) and the mixture was heated to 50° C. for one hour. The mixture was then cooled to room temperature and partitioned with ethyl acetate and water. The organic layer was washed once more with water and the organic layer was partitioned again with water. A precipitate forms in the organic layer at this point and hexanes was added to the biphasic mixture in portions until formation of the precipitate is complete. The solid product was then collected by filtration. The solid residue was suspended in hot methanol and diluted with water followed by collection of the solid by filtration. The solid was washed with ethyl ether and dried in vacuo to give 1,1-dimethylethyl 4-[5-({[4-[(3,4-dichlorophenyl)amino]-6-(methyloxy)quinazolin-7-yl]oxy}methyl)-1,2,4-oxadiazol-3-yl]piperazine-1-carboxylate (170.7 mg, 62% yield) as a tan solid. $^1$H-NMR (400 MHz, DMSO-d$_6$): 9.65 (s, 1H), 8.54 (s, 1H), 8.23 (d, 1H), 7.88-7.86 (m, 2H), 7.63 (d, 1H), 7.32 (s, 1H), 5.58 (s, 2H), 3.98 (s, 3H), 3.43-3.40 (m, 4H), 3.34-3.32 (m, 4H), 1.41 (s, 9H); MS (EI) for C$_{27}$H$_{29}$Cl$_2$N$_7$O$_5$: 602 (MH$^+$).

1,1-dimethylethyl 4-[5-({[4-[(3,4-dichlorophenyl)amino]-6-(methyloxy)quinazolin-7-yl]oxy}methyl)-1,2,4-oxadiazol-3-yl]piperazine-1-carboxylate (170 mg, 0.28 mmol) was taken into methanol (2.5 mL) followed by addition of anhydrous hydrogen chloride in dioxane (4M, 2.5 mL) and the mixture was brought to reflux then immediately allowed to cool to room temperature over 5 minutes. The mixture was then concentrated in vacuo to a slurry followed by addition of excess ethyl ether. The solid residue was collected by filtration and dried in vacuo to give N-(3,4-dichlorophenyl)-6-(methyloxy)-7-{[(3-piperazin-1-yl-1,2,4-oxadiazol-5-yl)methyl}oxyquinazolin-4-amine hydrochloride (145 mg, 100% yield) as a tan solid. $^1$H-NMR (400 MHz, DMSO-d$_6$): (hydrochloride) 11.98 (s, 1H), 9.54 (br s, 2H), 8.87 (s, 1H), 8.66 (s, 1H), 8.17 (d, 1H), 7.86 (dd, 1H), 7.70 (d, 1H), 7.47 (s, 1H), 5.66 (s, 2H), 4.06 (s, 3H), 3.64-3.61 (m, 4H), 3.19-3.16 (m, 4H); (free base) 9.69 (s, 1H), 8.53 (s, 1H), 8.24 (d, 1H), 7.90-7.87 (m, 2H), 7.62 (d, 1H), 7.31 (s, 1H), 5.56 (s, 2H), 3.99 (s, 3H), 3.31-3.29 (m, 4H), 2.81-2.79 (m, 4H); MS (EI) for $C_{22}H_{21}Cl_2N_7O_3$: 502 (MH$^+$).

N-(3,4-dichlorophenyl)-6-(methyloxy)-7-{[(3-piperazin-1-yl)-1,2,4-oxadiazol-5-yl]methyl}oxyquinazolin-4-amine hydrochloride (66 mg, 0.12 mmol) was suspended in methanol (5 mL) followed by addition of Bio-Rad AG®1-X8 hydroxide form resin until pH 8. The resin was then removed by filtration and the methanol solution was concentrated in vacuo. The residue was taken into formic acid (2 mL) and 37 W% aqueous formaldehyde (50 uL, 0.6 mmol) was added. The mixture was heated to 90° C. for 2.5 hours then concentrated in vacuo. The residue was taken into 1 mL of methanol and the solution acidified by addition of 4M anhydrous hydrogen chloride in dioxane to pH 2. Portionwise addition of ethyl ether afforded a crystalline solid that was collected by filtration and dried to give N-(3,4-dichlorophenyl)-6-(methyloxy)-7-({[3-(4-methylpiperazin-1-yl)-1,2,4-oxadiazol-5-yl]methyl}oxy)quinazolin-4-amine hydrochloride (53.9 mg, 80% yield) as a tan solid. $^1$H-NMR (400 MHz, DMSO-d): 11.98 (s, 1H), 11.39 (s, 1H), 8.87 (s, 1H), 8.65 (s, 1H), 8.17 (d, 1H), 7.86 (dd, 1H), 7.69 (d, 1H), 7.48 (s, 1H), 5.67 (s, 2H), 4.06 (s, 3H), 3.95 (br d, 2H), 3.49-3.46 (m, 4H), 3.15 (br m, 2H), 2.78 (s, 3H); MS (EI) for $C_{23}H_{23}Cl_2N_7O_3$: 516 (MH$^+$).

Using the same or analogous synthetic techniques and/or substituting with alternative reagents, the following compounds of the invention were prepared:

N-(3,4-dichlorophenyl)-6-(methyloxy)-7-({[3-(4-ethylpiperazin-1-yl)-1,2,4-oxadiazol-5-yl]methyl}oxy)quinazolin-4-amine hydrochloride: $^1$H-NMR (400 MHz, DMSO-d$_6$):

Example 34

N-(3,4-dichlorophenyl)-6-(methyloxy)-7-{[(5-methyl-4,5,6,7-tetrahydro[1,3] thiazolo[5,4-c]pyridin-2-yl)methyl]oxy}quinazolin-4-amine hydrochloride To a solution of {[4-[3,4-dichlorophenyl)amino]-6-(methyloxy)quinazolin-7-yl]oxy}acetonitrile (0.450 g, 1.20 mmol) in DMF (2 mL) was added NEt$_3$ (0.30 mL, 2.2 mmol). Hydrogen sulfide (g) was bubbled through the solution until saturation (5 min.). The solution was then heated to 70° C. and it turned dark green. After 0.5 h, the solution was cooled to room temperature, 0.20 mL NEt$_3$ (1.4 mmol) was added, and H$_2$S (g) was bubbled through for 5 min. The solution was again heated to 70° C. for 1.5 h. The solvent was removed in vacuo and the product was crystallized from MeOH to yield 0.459 g (94%) of 2-{[4-[(3,4-dichlorophenyl)amino]-6-(methyloxy)quinazolin-7-yl]oxy}ethanethioamide as a yellow solid. $^1$H NMR (400 MHz, d$_6$-DMSO): 10.07 (s, 1H), 9.68 (s, 1H), 9.29 (s, 1H), 8.55 (s, 1H), 8.26 (d, 1H), 7.91 (m, 2H), 7.66 (d, 1H), 7.10 (s, 1H), 4.96 (s, 1H), 4.01 (s, 3H), 2.73 (d, 2H); MS (EI) for $C_{17}H_{14}N_4O_2SCl_2$: 409 (MH$^+$).

To a solution of 2-{[4-[(3,4-dichlorophenyl)amino]-6-(methyloxy)quinazolin-7-yl]oxy}ethanethioamide (0.300 g, 0.733 mmol) in DMF (5 mL) was added 1,1-dimethylethyl 3-bromo-4-oxopiperidine-1-carboxylate (0.310 g, 1.11 mmol). The solution was stirred at 60° C. for 72 h. An additional 0.100 g (0.360 mmol) of 1,1-dimethylethyl 3-bromo-4-oxopiperidine-1-carboxylate was added to the reaction mixture, which was then heated at 60° C. for an additional 24 h. The solvent was removed in vacuo and the crude reaction mixture was purified via column chromatography (SiO$_2$, 50% hexanes/ethyl acetate). This intermediate was then subjected to 10% TFA in CH$_2$Cl$_2$ at room temperature. After removal of the solvent, the crude amine salt was taken up in fresh MeOH and treated with Bio-Rad AG 1-X8 resin hydroxide form until pH 8. Filtration and concentration in vacuo provided 0.247 g (69%) of N-(3,4-dichlorophenyl)-6-(methyloxy)-7-[(4,5,6,7-tetrahydro[1,3]thiazolo[5,4-c]pyridin-2-ylmethyl)oxy]quinazolin-4-amine as a brown oil.

$^1$H NMR (400 MHz, d$_6$-DMSO): 9.68 (s, 1H), 8.43 (s, 1H), 8.24 (d, 1H), 7.89 (d, 1H), 7.87 (d, 1H), 7.62 (d, 1H), 7.37 (s, 1H), 5.54 (s, 2H), 3.98 (s, 3H), 3.87 (s, 2H), 2.97 (t, 2H), 2.66 (t, 2H); MS (EI) for $C_{22}H_{19}N_5O_2SCl_2$: 488 (M$^+$)

N-(3,4-Dichlorophenyl)-6-(methyloxy)-7-[(4,5,6,7-tetrahydro[1,3]thiazolo[5,4-c]pyridin-2-ylmethyl)oxy]quinazolin-4-amine (0.247 g, 0.506 mmol) was combined with 37% aqueous formaldehyde (0.23 mL, 3.1 mmol) in formic acid (2 mL) and the solution was heated at 95° C. for 1 h. The solvent was removed in vacuo and the residue was purified via HPLC (reverse-phase, CH$_3$CN/H$_2$O with 0.1% TFA). Upon removal of CH$_3$CN/H$_2$O, the product was taken up in MeOH and treated with Bio-Rad AG 1-X8 resin hydroxide form until pH 8. The product was filtered and concentrated in vacuo, then taken up in fresh MeOH and treated with 4.0 M HCl/dioxane (0.050 mL). Removal of solvent in vacuo provided 0.085 g (31%) of N-(3,4-dichlorophenyl)-6-(methyloxy)-7-{[(5-methyl-4,5,6,7-tetrahydro[1,3]thiazolo[5,4-c]pyridin-2-yl)methyl]oxy}quinazolin-4-amine hydrochloride as a pale yellow solid. $^1$H NMR (400 MHz, d$_6$-DMSO): 8.69 (s, 1H), 8.24 (d, 1H), 8.11 (s, 1H), 7.89 (dd, 1H), 7.70 (d, 1H), 7.42 (s, 1H), 5.65 (s, 3H), 4.65 (m, 1H), 4.40 (m, 1H), 4.02 (s, 3H), 3.70 (m, 1H), 3.12 (m, 2H), 2.94 (s, 4H); MS (EI) for $C_{23}H_{21}N_5O_2SCl_2$: 502 (M$^+$).

Example 35

N-(3,4-dichlorophenyl)-7-{[(5-ethyl-4,5,6,7-tetrahydro[1,3]thiazolo[5,4-c]pyridin-2-yl)methyl]oxy}-6-(methyloxy)quinazolin-4-amine hydrochloride N-(3,4-Dichlorophenyl)-6-(methyloxy)-7-[(4,5,6,7-tetrahydro[1,3]thiazolo[5,4-c]pyridin-2-ylmethyl)oxy]quinazolin-4-amine (0.249 g, 0.510 mmol) was taken up in 50% THF/MeOH (10 mL) and the solution was cooled with an ice bath. Acetaldehyde (0.057 mL, 1.0 mmol), followed by NaCNBH$_3$ (0.038 g, 0.61 mmol) were added. The solution was allowed to warm to room temperature. After 4 h, additional acetaldehyde (0.050 mL, 0.89 mmol) and NaCNBH$_3$ (0.040 g, 0.64 mmol) were added and the solution was stirred for 12 h. An additional 0.050 mL (0.89 mmol) of acetaldehyde and NaCNBH$_3$ (0.020 g, 0.32 mmol) were added. The solution was poured into 10% MeOH/ethyl acetate (100 mL) and washed once with H$_2$O (100 mL). The organic layer was dried (Na$_2$SO$_4$); filtered and the solvent was removed in vacuo. The crude product was purified via preparative HPLC (reverse phase, CH$_3$CN/H$_2$O/NH$_4$OAc/AcOH). The solvents were removed, the product was taken up in MeOH and treated with 4.0M HCl/dioxane (0.025 mL), and lyophilized to provide 0.036 g (12%) of N-(3,4-dichlorophenyl)-7-{[(5-ethyl-4,5,6,7-tetrahydro[1,3]thiazolo[5,4-c]pyridin-2-yl)methyl]oxy}-6-(methyloxy)quinazolin-4-amine hydrochloride as a yellow solid.

$^1$H NMR (400 MHz, d$_6$-DMSO): 9.56 (broad s, 1H), 8.85 (s, 1H), 8.37 (broad s, 1H), 8.15 (d, 1H), 7.81 (dd, 1H), 7.73 (d, 1H), 7.48 (s, 1H), 5.66 (s, 2H), 4.71 (d, 1H), 4.36 (m, 1H), 4.04 (s, 3H), 3.74 (m, 1H), 3.13 (m, 3H), 1.32 (t, 3H); MS (EI) for $C_{24}H_{23}N_5O_2SCl_2$: 516 (M$^+$).

Example 36

N-(3,4-dichlorophenyl)-6-(methyloxy)-7-({[2-(1-methylpiperidin-4-yl)-1,3-thiazol-4-yl]methyl}oxy)quinazolin-4-amine hydrochloride 1,1-Dimethylethyl 4-(aminocarbonothioyl)piperidine-1-carboxylate (1.50 g, 6.14 mmol), NaHCO$_3$ (0.570 g, 6.78 mmol) and 1,3-dichloroacetone (0.860 g, 6.77 mmol) were combined in 1,2-dichloroethane (4 mL) and the reaction mixture was stirred at room temperature for 12 h. The crude reaction mixture was filtered using CH$_2$Cl$_2$ and the filtrate was concentrated in vacuo until approximately 30 mL of solvent remained. To this solution was added pyridine (0.75 mL, 9.2 mmol), and the solution was cooled with an ice bath. Thionyl chloride (0.49 mL, 6.8 mmol) was added and the solution was allowed to warm slowly to room temperature. The solvent was removed in vacuo and the residue was taken up in 10% MeOH/ethyl acetate (100 mL). The organic layer was washed with H$_2$O (100 mL) and brine (100 mL), dried (Na$_2$SO$_4$), filtered, and concentrated in vacuo to yield 2.24 g (>100%) of crude 1,1-dimethylethyl 4-[4-(chloromethyl)-1,3-thiazol-2-yl]piperidine-1-carboxylate as a colorless oil. $^1$H NMR (400 MHz, d$_6$-DMSO): 7.62 (s, 1H), 4.60 (s, 2H), 3.98 (m, 1H), 3.63 (dd, 2H), 3.16 (m, 1H), 2.90 (broad s, 2H), 2.01 (dd, 1H), 1.51 (m, 2H), 1.40 (s, 9H). MS (EI) for C$_{14}$H$_{21}$N$_2$O$_2$SCl: 261 (M-tBu).

To a solution of 4-[3,4-dichlorophenyl)amino]-6-(methyloxy)quinazolin-7-ol (1.00 g, 2.97 mmol) in DMP (10 mL) was added 1,1-dimethylethyl 4-[4-(chloromethyl)-1,3-thiazol-2-yl]piperidine-1-carboxylate (1.04 g, 3.28 mmol) and K$_2$CO$_3$ (2.06 g, 14.9 mmol). The solution was heated to 70° C. for 12 h, and then the solvent was removed in vacuo. The residue was taken up in 10% MeOH/ethyl acetate (100 mL) and washed with H$_2$O (100 mL). The organic layer was dried (Na$_2$SO$_4$), filtered and concentrated in vacuo. Column chromatography (SiO$_2$, 50% hexanes/acetone) yielded 0.642 g (35%) of crude 1,1-dimethylethyl 4-[4-({[4-[(3,4-dichlorophenyl)amino]-6-(methyloxy)quinazolin-7-yl]oxy}methyl)-1,3-thiazol-2-yl]piperidine-1-carboxylate. Half of this intermediate (0.300 g) was then subjected to 10% TFA in CH$_2$Cl$_2$ at room temperature for 1 h, then concentrated in vacuo. The residue was dissolved in MeOH (50 mL) and treated with Bio-Rad AG 1-X8 resin hydroxide form to pH 8. Filtration and concentration in vacuo provided 0.230 g (92% from 1,1-dimethylethyl 4-[4-({[4-[(3,4-dichlorophenyl)amino]-6-(methyloxy)quinazolin-7-yl]oxy}methyl)-1,3-thiazol-2-yl]piperidine-1-carboxylate) of N-(3,4-dichlorophenyl)-6-(methyloxy)-7-{[(2-piperidin-4-yl-1,3-thiazol-4-yl)methyl]oxy}quinazolin-4-amine as a brown oil. MS (EI) for C$_{24}$H$_{23}$N$_5$O$_2$SCl$_2$: 516 (M$^+$).

N-(3,4-Dichlorophenyl)-6-(methyloxy)-7-{[(2-piperidin-4-yl-1,3-thiazol-4-yl)methyl]oxy}quinazolin-4-amine (0.078 g, 0.15 mmol) was combined with 37% aqueous formaldehyde (0.025 mL, 0.34 mmol) in formic acid (2 mL) and the solution was heated to 95° C. for 1 h. The solvent was removed in vacuo and the residue was taken up in 10% MeOH/ethyl acetate (100 mL) and washed with saturated NaHCO$_3$ (aq) (100 mL). The organic layer was dried (Na$_2$SO$_4$), filtered, and concentrated in vacuo. Trituration from MeOH and treatment of the resultant yellow solid with 4.0 M HCl/dioxane (0.050 mL) in MeOH, followed by lyophilization, provided 0.032 g (37%) of N-(3,4-dichlorophenyl)-6-(methyloxy)-7-({[2-(1-methylpiperidin-4-yl)-1,3-thiazol-4-yl]methyl}oxy)quinazolin-4-amine hydrochloride as a pale yellow solid. $^1$H NMR (400 MHz, d$_6$-DMSO): 8.55 (s, 1H), 8.25 (d, 1H), 7.89 (dd, 2H), 7.76 (s, 1H), 7.63 (d, 1H), 7.41 (s, 1H), 5.30 (s, 2H), 3.96 (s, 3H), 3.52 (d, 2H), 3.29 (m, 2H), 3.08 (m, 1H), 2.79 (s, 3H), 2.29 (d, 2H), 1.95 (m, 2H); MS (EI) for C$_{26}$H$_{25}$N$_5$O$_2$SCl$_2$: 530 (MH$^+$).

Example 37

N-(3,4-dichlorophenyl)-7-({[2-(1-ethylpiperidin-4-yl)-1,3-thiazol-4-yl]methyl}oxy)-6-(methyloxy)quinazolin-4-amine hydrochloride N-(3,4-Dichlorophenyl)-6-(methyloxy)-7-{[(2-piperidin-4-yl-1,3-thiazol-4-yl)methyl]oxy}quinazolin-4-amine (0.230 g, 0.445 mmol) was taken up in 50% MeOH/THF (10 mL) and cooled with an ice bath. Acetaldehyde (0.050 mL, 0.89 mmol) was added, followed by NaCNBH$_3$ (0.034 g, 0.54 mmol) and the solution was allowed to warm to room temperature. After 1.5 h, 0.016 g (0.25 mmol) of additional NaCNBH$_3$ was added and the solution was stirred for 12 h. The reaction mixture was poured into ethyl acetate (100 mL), washed with saturated NaHCO$_3$ (aq) (50 mL) and dried (Na$_2$SO$_4$). Filtratation and concentration in vacuo was followed by preparative HPLC (reverse-phase, CH$_3$CN/H$_2$O with 0.01% TFA). This product was neutralized (NaHCO$_3$) to give 0.167 g (0.306 mmol) of free amine, which was taken up in MeOH (50 mL) and treated with 4.0 M HCl/dioxane (0.077 mL, 0.31 mmol). Lyophilization provided 0.105 g (41%) of N-(3,4-dichlorophenyl)-7-({[2-(1-ethylpiperidin-4-yl)-1,3-thiazol-4-yl]methyl}oxy)-6-(methyloxy)quinazolin-4-amine hydrochloride as a pale yellow solid. $^1$H NMR (400 MHz, d$_6$-DMSO): 8.65 (broad s, 1H), 8.23 (d, 1H), 8.08 (broad s, 1H), 7.88 (d, 1H), 7.78 (s, 1H), 7.66 (d, 1H), 7.47 (s, 1H), 5.32 (s, 2H), 3.98 (s, 3H), 3.55 (d, 2H), 3.01-3.11 (m, 5H), 2.29 (m, 2H), 2.04 (m, 2H), 1.26 (t, 3H); MS (EI) for C$_{26}$H$_{27}$N$_5$O$_2$SCl$_2$: 544 (M$^+$).

Assays

Generally for assay of activity, either ephrin, EGFR, or a compound according to the invention is non-diffusably bound to an insoluble support having isolated sample-receiving areas (for example, a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (for example, polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Exemplary methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

One measure of inhibition is K$_i$. For compounds with IC$_{50}$'s less than 1 µM, the K$_i$ or K$_d$ is defined as the dissociation rate constant for the interaction of the agent with ephrin or EGFR. Exemplary compositions have $K_i$'s of, for example, less than about 100 μM, less than about 10 μM, less than about 1 μM, and further for example having $K_i$'s of less than about 100 μM, and still further, for example, less than about 10 μM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + K_d) - \sqrt{(E_0 + I_0 + K_d)^2 - 4E_0 I_0}}{2E_0}\right]$$

Where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Exemplary compounds have $GI_{50}$'s of, for example, less than about 1 mM, less than about 10 μM, less than about 1 μM, and further, for example, having $GI_{50}$'s of less than about 100 nM, still further having $GI_{50}$'s of less than about 10 nM. Measurement of $GI_{50}$ is done using a cell proliferation assay.

Tyrosine kinase activity is determined by 1) measurement of kinase-dependent ATP consumption by in the presence of a generic substrate such as polyglutamine, tyrosine (pEY), by luciferase/luciferin-mediated chemiluminescence or; 2) incorporation of radioactive phosphate derived from $^{33}$P-ATP into a generic substrate which has been adsorbed onto the well surface of polystyrene microtiter plates. Phosphorylated substrate products are quantified by scintillation spectrometry.

Materials and Methods

Kinase activity and compound inhibition are investigated using one or more of the three assay formats described below. A brief summary of assay conditions is listed in Table 2. The ATP concentrations are selected near its Michaelis-Menten constant ($K_M$) for each individual kinase. Dose-response experiments are performed at ten different inhibitor concentrations in a 384-well plate format. The data are fitted to a standard four-parameter equation listed below:

$$Y = Min + (Max - Min)/(1 + (X/IC_{50})^H)$$

where Y is the observed signal, X is the inhibitor concentration, Min is the background signal in the absence of enzyme (0% enzyme activity), Max is the signal in the absence of inhibitor (100% enzyme activity), $IC_{50}$ is the inhibitor concentration at 50% enzyme inhibition and H represents the empirical Hill's slope to measure the cooperativity. Typically H is close to unity. These parameters are obtained by nonlinear regression algorithm built into ActivityBase software (available from ID Business Solutions Ltd., of Guildford, Surrey, UK).

$^{33}$P Phosphoryl Transfer Assay (Radiometric)

Greiner 384-well white clear bottom high binding plates (available from Greiner Bio-One, Inc., of Longwood, Fla.) are coated with 2 μg/well of protein or peptide substrate in a 50 μL volume overnight at ambient temperature. The coating buffer contains 40 μg/mL substrate, 22.5 mM $Na_2CO_3$, 27.5 mM $NaHCO_3$, 150 mM NaCl and 3 mM $NaN_3$. The coating solution is aspirated and the plates are washed once with 50 μL of assay buffer and padded dry. Subsequently compounds and enzymes are mixed with $\gamma^{33}$P-ATP (3.3 μCi/nmol) in a total volume of 20 uL in suitable assay buffers (see Table 2). For example the final EphB4 reaction solution contains 20 mM Tris HCl, pH 7.5, 10 mM $MgCl_2$, 0.01% Triton X-100, 0.1 mM $NaVO_3$, 5 μM EphB4 enzyme and 5 μM ATP. The mixture is incubated at ambient temperature for 1.5-2.5 hrs as indicated in Table 2 and stopped by aspirating using an EMBLA 96-head washer. The plates are subsequently washed 6-12 times with PBST or TBS buffer. Scintillation fluid (50 μl/well) is then added, the plates are sealed and activity assessed by liquid scintillation spectrometry on a Perkin Elmer MicroBeta TriLux (available from PerkinElmer Life and Analytical Sciences, Inc., of Boston Mass.).

Luciferase-Coupled Chemiluminescent Assay (LCCA)

In the LCCA assays, kinase activity is measured by the ATP consumption that is accurately measured by luciferase-coupled chemiluminescence. Greiner 384-well white clear bottom medium binding plates are used for LCCA. Briefly the kinase reaction is initiated by mixing compounds, ATP and kinases in a 20 μL volume. The mixture is incubated at ambient temperature for 2-4 hrs as indicated in Table 2. At the end of the kinase reaction, a 20 μL luciferase-luciferin mix is added and the chemiluminescent signal is read on a Wallac Victor$^2$ reader. The luciferase-luciferin mix consists of 50 mM HEPES, pH 7.8, 8.5 ug/mL oxalic acid (pH 7.8), 5 (or 50) mM DTT, 0.4% Triton X-100, 0.25 mg/mL coenzyme A, 63 μM AMP, 28 ug/mL luciferin and 40,000 units of light/mL luciferase. For the LCCA assays, the ATP consumption has been kept at 25-45%, where the decrease in substrate concentration has less than 35% effect on $IC_{50}$ values compared to the "theoretical" values with no substrate turnover. The $IC_{50}$ values correlates well with those of radiometric assays.

AlphaScreen

In AlphaScreen, when the donor and acceptor beads are close in proximity, a series of photochemical events will give rise to a fluorescent signal upon light activation. Here we use biotinylated poly-(Glu, Tyr) 4:1 as the kinase substrate, streptavidin-coated donor beads and anti-phosphortyrosine antibody PY100-coated acceptor beads. Upon phosphorylation, the peptide substrate can bind to both donor and acceptor beads, thus gives rise to fluorescence. Compounds, ATP, biotinylated poly-(Glu, Tyr) and kinases are mixed in a volume of 20 μL for 1 hr at ambient temperature using Greiner 384-well white clear bottom medium binding plates. Then 10 uL solution containing 15-30 mg/mL AlphaScreen beads, 75 mM Hepes, pH 7.4, 300 mM NaCl, 120 mM EDTA, 0.3% BSA and 0.03% Tween-20 is added to each well. After 2-16 hr incubation of the beads, plates are read in a Perkin Elmer AlphaQuest reader (available from PerkinElmer Life and Analytical Sciences, Inc., of Boston Mass.). The $IC_{50}$ values correlate well with those of radiometric assays.

Enzymes were purchased from Proqinase (of Freiburg, Germany) and Panvera (of Madison, Wis.).

TABLE 2

| Enzyme | Assay format | [E] | [ATP] | Substrate | [Substrate] | Incubation Time (min) | Assay Buffer | Enzyme Construct/Preparation | Enzyme Source |
|---|---|---|---|---|---|---|---|---|---|
| EphB4 | Radiometric | 5 nM | 5 µm | poly-AEKY | 2 µg/well | 150 | 20 mM TrisHCl, pH 7.5, 10 mM MgCl$_2$, 0.1 mM NaVO$_3$, 0.01% Triton | Kinase domain E605-E890 with N-termianl His6 tag is expressed in baculovirus and purified by IMAC chromatography. | PanVera |
| EphA2 | LCCA | 20 nM | 3 µM | poly-EY | 1.6 µM | 180 | 20 mM TrisHCl, pH 7.5, 10 mM MgCl$_2$, 3 mM MnCl$_2$, 0.01% Triton | N598-R890 with N-termial His6 tag is expressed in baculovirus and purified by IMAC chromatography. | PanVera |
| EGFR | LCCA | 7 nM 11 nM | 3 µM | poly-EY | 1.6 µM | 210 | 20 mM TrisHCl, pH 7.5, 10 mM MgCl$_2$, 3 mM MnCl$_2$, 1 mM DTT, 0.01% Triton | amino acids H672-A1210, N-terminally fused to GST-HIS6-Thrombin cleavage site, expressed in baculovirus, one-step affinity purification using GSH-agarose | ProQinase |
| ErbB2 | Alphascreen | 1 nM | 3 µM | poly-EY | 5 nM | 60 | 20 mM TrisHCl, pH 7.5, 10 mM MgCl$_2$, 3 mM MnCl$_2$, 1 mM DTT, 0.01% Triton | Kinase domain Q679-V1255 with N-terminal GST-HIS6 tag is expressed in baculovirus infected Sf9 cells and purified by GSH-agarose | ProQinase |
| KDR | LCCA | 5 nM 6 nM | 3 µM | poly-EY | 1.6 µM | 240 | 20 mM TrisHCl, pH 7.5, 10 mM MgCl$_2$, 3 mM MnCl$_2$, 1 mM DTT, 0.01% Triton | Human KDR c-DNA, Amino Acids D807-V1356, N-terminally fused to GST. One-step affinity purification using GSH-agarose | ProQinase |
| Flt-1 | Radiometric | 6 nM | 5 µM | poly-EY | 2 µg/well | 120 | 20 mM TrisHCl, pH 7.5, 10 mM MgCl$_2$, 3 mM MnCl$_2$, 1 mM DTT, 0.01% Triton | Human VEGF-R1 cDNA, cytoplasmic domain, N-terminally fused to GST-Factor X cleavage site. One-step affinity puricication using GSH-agarose | ProQinase |

Structure Activity Relationships

Tables 3-6 show structure activity relationship data for selected compounds of the invention. As the data indicates, compounds of the invention fall into different classes; some are "spectrum selective" (supra), some are selective for Ephrin, some selective for EGFR, and some inhibit Ephrin and EGFR selectively, for example. Inhibition is indicated as IC$_{50}$ with the following key: A=IC$_{50}$ less than 50 µM, B=IC$_{50}$ greater than 50 µM, but less than 1000 µM, C=IC$_{50}$ greater than 1000 µM, but less than 20,000 µM, and D=IC$_{50}$ greater than 20,000 µM. Abbreviations for enzymes listed in Tables 3-6 are defined as follows: EphB4 and EphA2 refer to ephrin receptor tyrosine kinase family members ephrin B4 and A2; KDR, kinase insert domain receptor tyrosine kinase, and Flt-1, fms-like tyrosine kinase-1, are representative of the FLK family or receptor tyrosine kinases; EGFR, epidermal growth factor receptor tyrosine kinase, and ErbB2 are representative of the HER family of receptor tyrosine kinases.

TABLE 3

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 1 | N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine | A | A | A | B | A | A |
| 2 | N-(4-bromo-3-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine | A | A | A | B | A | A |
| 3 | N-(3-chloro-2,4-difluorophenyl)-7-({[(3aR,5s,6aS)-2-methyloctahydrocyclopenta[c]pyrrol-5-yl]methyl}oxy)-6-(methyloxy)quinazolin-4-amine | A | A | A | B | A | A |
| 4 | N-(4,5-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine | A | A | A | B | A | A |
| 5 | N-(4-bromo-5-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine | A | A | A | B | A | A |
| 6 | N-(4-bromo-2,3-dichlorophenyl)-7-({[(3aR,5s,6aS)-2-methyloctahydrocyclopenta[c]pyrrol-5-yl]methyl}oxy)-6-(methyloxy)quinazolin-4-amine | A | A | A | C | A | B |

TABLE 3-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 7 | N-(3,4-dichlorophenyl)-7-({[(3aR,5s,6aS)-2-methyloctahydrocyclopenta[c]pyrrol-5-yl]methyl}oxy)-6-(methyloxy)quinazolin-4-amine | A | A | A | B | A | A |
| 8 | N-(4-bromo-2,3-dichlorophenyl)-7-{[(3R,9aS)-hexahydro-1H-[1,4]oxazino[3,4-c][1,4]oxazin-3-ylmethyl]oxy}-6-(methyloxy)quinazolin-4-amine | B | B | B | C | A | C |
| 9 | N-(4,5-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine | B | B | B | B | A | B |
| 10 | N-(4-bromo-5-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine | B | B | B | B | A | B |
| 11 | N-(3-chloro-2,4-difluorophenyl)-7-{[(3R,9aS)-hexahydro-1H-[1,4]oxazino[3,4-c][1,4]oxazin-3-ylmethyl]oxy}-6-(methyloxy)quinazolin-4-amine | B | B | B | B | A | B |
| 12 | N-(3,4-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine | A | A | A | A | A | A |
| 13 | N-(4-bromo-3-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine | A | A | A | A | A | A |
| 14 | N-(3-chloro-2,4-difluorophenyl)-7-{[(3S,9aS)-hexahydro-1H-[1,4]oxazino[3,4-c][1,4]oxazin-3-ylmethyl]oxy}-6-(methyloxy)quinazolin-4-amine | A | B | B | B | A | B |
| 15 | N-(3,4-dichlorophenyl)-7-[(hexahydro-1H-[1,4]oxazino[3,4-c][1,4]oxazin-3-ylmethyl)oxy]-6-(methyloxy)quinazolin-4-amine | A | B | A | B | A | A |
| 16 | N-(4,5-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine | A | B | B | B | A | B |
| 17 | N-(4-bromo-2,3-dichlorophenyl)-7-{[(3S,9aS)-hexahydro-1H-[1,4]oxazino[3,4-c][1,4]oxazin-3-ylmethyl]oxy}-6-(methyloxy)quinazolin-4-amine | A | B | B | B | A | C |
| 18 | N-(4-bromo-5-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine | A | B | B | B | A | B |
| 19 | N-(3,4-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine | A | B | A | B | A | B |
| 20 | N-(4-bromo-3-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine | B | B | A | B | A | B |
| 21 | N-(3,4-dichlorophenyl)-7-{[(3R,8aR)-hexahydro-1H-pyrrolo[2,1-c][1,4]oxazin-3-ylmethyl]oxy}-6-(methyloxy)quinazolin-4-amine | A | B | A | B | A | B |
| 22 | N-(4-bromo-5-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine | A | A | A | B | A | B |
| 23 | N-(3,4-dichlorophenyl)-7-{[(3S,8aR)-hexahydro-1H-pyrrolo[2,1-c][1,4]oxazin-3-ylmethyl]oxy}-6-(methyloxy)quinazolin-4-amine | A | A | A | B | A | A |
| 24 | N-(3,4-dichlorophenyl)-7-{[(3S,8aS)-hexahydro-1H-pyrrolo[2,1-c][1,4]oxazin-3-ylmethyl]oxy}-6-(methyloxy)quinazolin-4-amine | A | A | A | B | A | B |
| 25 | N-(3,4-dichlorophenyl)-7-{((3R,8aS)-hexahydro-1H-pyrrolo[2,1-c][1,4]oxazin-3-ylmethyl)oxy}-6-(methyloxy)quinazolin-4-amine | A | A | A | B | A | A |
| 26 | N-(3,4-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine | A | A | A | B | A | B |
| 27 | N-(4-bromo-3-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine | A | A | A | A | A | B |
| 28 | N-(3-chloro-2,4-difluorophenyl)-7-{[(3S,8aS)-hexahydro-1H-pyrrolo[2,1-c][1,4]oxazin-3-ylmethyl]oxy}-6-(methyloxy)quinazolin-4-amine | A | A | B | B | A | B |
| 29 | N-(4-bromo-2,3-dichlorophenyl)-7-{[(3S,8aS)-hexahydro-1H-pyrrolo[2,1-c][1,4]oxazin-3-ylmethyl]oxy}-6-(methyloxy)quinazolin-4-amine | A | A | A | B | A | B |
| 30 | N-(4,5-dichloro-2-fluorophenyl)-7-{((3S,8aS)-hexahydro-1H-pyrrolo[2,1-c][1,4]oxazin-3-ylmethyl)oxy}-6-(methyloxy)quinazolin-4-amine | A | A | A | B | A | B |
| 31 | 1,4:3,6-dianhydro-5-({[4-[(4-bromo-5-chloro-2-fluorophenyl)amino]-6-(methyloxy)quinazolin-7-yl]oxy}methyl)-5-deoxy-2-O-methyl-D-xylo-hexitol | B | B | B | C | A | B |

TABLE 3-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 32 | 1,4:3,6-dianhydro-5-deoxy-5-({[4-[(3,4-dichlorophenyl)amino]-6-(methyloxy)quinazolin-7-yl]oxy}methyl)-2-O-methyl-D-glucitol | B | C | B | C | A | B |
| 33 | 1,4:3,6-dianhydro-5-deoxy-5-({[4-[(3,4-dichloro-2-fluorophenyl)amino]-6-(methyloxy)quinazolin-7-yl]oxy}methyl)-2-O-methyl-D-xylo-hexitol | A | B | B | C | A | B |
| 34 | 1,4:3,6-dianhydro-5-({[4-[(4-bromo-3-chloro-2-fluorophenyl)amino]-6-(methyloxy)quinazolin-7-yl]oxy}methyl)-5-deoxy-2-O-methyl-D-xylo-hexitol | A | B | B | C | A | B |
| 35 | 1,4:3,6-dianhydro-5-({[4-[(3-chloro-2,4-difluorophenyl)amino]-6-(methyloxy)quinazolin-7-yl]oxy}methyl)-5-deoxy-2-O-methyl-D-xylo-hexitol | A | B | C | C | A | B |
| 36 | 1,4:3,6-dianhydro-5-({[4-[(4-bromo-2,3-dichlorophenyl)amino]-6-(methyloxy)quinazolin-7-yl]oxy}methyl)-5-deoxy-2-O-methyl-D-glucitol | A | C | B | C | A | C |
| 37 | 1,4:3,6-dianhydro-2-deoxy-2-({[4-[(3,4-dichlorophenyl)amino]-6-(methyloxy)quinazolin-7-yl]oxy}methyl)-5-O-methyl-D-threo-hexitol | B | B | B | C | A | C |
| 38 | 1,4:3,6-dianhydro-5-deoxy-5-({[4-[(4,5-dichloro-2-fluorophenyl)amino]-6-(methyloxy)quinazolin-7-yl]oxy}methyl)-2-O-methyl-D-glucitol | B | B | B | C | A | B |
| 39 | (3S,9aS)-3-({(4-[(3,4-dichloro-2-fluorophenyl)amino]-6-(methyloxy)quinazolin-7-yl]oxy}methyl)hexahydro-2H-pyrido[1,2-a]pyrazin-1(6H)-one | A | A | A | B | A | C |
| 40 | (3S,9aR)-3-({[4-[(3,4-dichloro-2-fluorophenyl)amino]-6-(methyloxy)quinazolin-7-yl]oxy}methyl)hexahydro-2H-pyrido[1,2-a]pyrazin-1(6H)-one | A | B | B | B | A | C |
| 41 | (3S,8aS)-3-({[4-((3,4-dichloro-2-fluorophenyl)amino]-6-(methyloxy)quinazolin-7-yl]oxy}methyl)hexahydropyrrolo[1,2-a]pyrazin-1(2H)-one | A | B | A | B | A | B |
| 42 | (3S,8aR)-3-({(4-[(3,4-dichloro-2-fluorophenyl)amino]-6-(methyloxy)quinazolin-7-yl]oxy}methyl)hexahydropyrrolo[1,2-a]pyrazin-1(2H)-one | A | A | A | B | A | C |
| 43 | (3S,8aS)-3-({[4-[(4-bromo-3-chloro-2-fluorophenyl)amino]-6-(methyloxy)quinazolin-7-yl]oxy}methyl)hexahydropyrrolo[1,2-a]pyrazin-1(2H)-one | A | B | A | B | A | C |
| 44 | (3S,8aS)-3-({[4-[(3,4-dichloro-2-fluorophenyl)amino]-6-(methyloxy)quinazolin-7-yl]oxy}methyl)-2-methylhexahydropyrrolo[1,2-a]pyrazin-1(2H)-one | A | B | B | B | A | C |
| 45 | N-(3,4-dichlorophenyl)-7-({2-[(8-methyl-8-azabicyclo[3.2.1]oct-3-yl)amino]ethyl}oxy)-6-(methyloxy)quinazolin-4-amine | A | B | A | B | A | A |
| 46 | N-(3,4-dichlorophenyl)-6-(methyloxy)-7-{[(8aR)-tetrahydro-1H-[1,3]thiazolo[4,3-c][1,4]oxazin-6-ylmethyl]oxy}quinazolin-4-amine | A | B | B | B | A | B |
| 47 | N-(3,4-dichlorophenyl)-7-{[2-(8-methyl-8-azabicyclo[3.2.1]oct-3-yl)ethyl]oxy}-6-(methyloxy)quinazolin-4-amine | B | B | B | C | A | A |
| 48 | N-(3,4-dichlorophenyl)-7-{[(8-methyl-8-azabicyclo[3.2.1]oct-3-yl)methyl]oxy}-6-(methyloxy)quinazolin-4-amine | B | B | B | C | A | B |
| 49 | N-(3,4-dichlorophenyl)-7-{[(3aR,6aS)-2-methyloctahydrocyclopenta[c]pyrrol-5-yl]oxy}-6-(methyloxy)quinazolin-4-amine | B | B | B | C | A | B |
| 50 | N-(3,4-dichlorophenyl)-7-[(8-methyl-8-azabicyclo[3.2.1]oct-3-yl)oxy]-6-(methyloxy)quinazolin-4-amine | C | C | C | C | A | C |
| 51 | 1,4:3,6-dianhydro-2-O-[4-[(4-bromo-5-chloro-2-fluorophenyl)amino]-6-(methyloxy)quinazolin-7-yl]-5-O-methyl-L-iditol | B | C | C | C | A | C |
| 52 | 1,4:3,6-dianhydro-2-O-[4-[(3,4-dichloro-2-fluorophenyl)amino]-6-(methyloxy)quinazolin-7-yl]-5-O-methyl-L-iditol | A | C | C | C | A | B |
| 53 | 1,4:3,6-dianhydro-2-O-[4-[(4-bromo-3-chloro-2-fluorophenyl)amino]-6-(methyloxy)quinazolin-7-yl]-5-O-methyl-L-iditol | B | C | B | C | A | B |
| 54 | 1,4:3,6-dianhydro-2-O-methyl-5-O-{6-(methyloxy)-4-[(2,3,4-trichlorophenyl)amino]quinazolin-7-yl}-L-iditol | B | C | C | C | A | C |
| 55 | 1,4:3,6-dianhydro-5-O-[4-[(3,4-dichlorophenyl)amino]-6-(methyloxy)quinazolin-7-yl]-2-O-methyl-D-xylo-hexitol | B |   | B | C | A | B |
| 56 | 1,4:3,6-dianhydro-2-O-[4-[(4-bromo-2,3-dichlorophenyl)amino]-6-(methyloxy)quinazolin-7-yl]-5-O-methyl-L-iditol | B | C | C | C | A | B |
| 57 | dianhydro-5-O-[4-[(4-bromo-3-chlorophenyl)amino]-6-(methyloxy)quinazolin-7-yl]-L-sorbose ethylene glycol acetal | B | C | C | C | A | B |

TABLE 3-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 58 | 1,4:3,6-dianhydro-2-O-[4-[(3-chloro-2,4-difluorophenyl)amino]-6-(methyloxy)quinazolin-7-yl]-5-O-methyl-L-iditol | B | C | C | C | A | C |
| 59 | 1,4:3,6-dianhydro-2-O-[4-[(4,5-dichloro-2-fluorophenyl)amino]-6-(methyloxy)quinazolin-7-yl]-5-O-methyl-L-iditol | B | C | C | C | A | C |
| 60 | 1,4:3,6-dianhydro-2-O-[4-[(4-bromo-3-chlorophenyl)amino]-6-(methyloxy)quinazolin-7-yl]-5-O-(difluoromethyl)-L-iditol | B | C | C | B | A | B |
| 61 | 1,4:3,6-dianhydro-2-O-[4-[(3-chloro-2-fluorophenyl)amino]-6-(methyloxy)quinazolin-7-yl]-5-O-methyl-L-iditol | B | C | C | C | A | B |
| 62 | 1,4:3,6-dianhydro-2-O-[4-[(3,4-dichlorophenyl)amino]-6-(methyloxy)quinazolin-7-yl]-5-O-methyl-L-iditol | B | C | C | C | A | B |
| 63 | 1,4:3,6-dianhydro-2-O-[4-[(4-bromo-3-chlorophenyl)amino]-6-(methyloxy)quinazolin-7-yl]-5-O-methyl-L-iditol | B | C | C | D | A | B |
| 64 | 1,4:3,6-dianhydro-2-O-[4-[(4-bromo-3-chlorophenyl)amino]-6-(methyloxy)quinazolin-7-yl]-5-O-ethyl-L-iditol | B | C | C | B | A | B |
| 65 | 1,4:3,6-dianhydro-2-O-[4-[(3-bromo-2-methylphenyl)amino]-6-(methyloxy)quinazolin-7-yl]-5-O-methyl-L-iditol | C | C | D | D | A | C |
| 66 | 1,4:3,6-dianhydro-2-O-[4-[(3-chloro-2-methylphenyl)amino]-6-(methyloxy)quinazolin-7-yl]-5-O-methyl-L-iditol | C | C | D | D | A | C |
| 67 | 1,4:3,6-dianhydro-2-O-[4-[(4-bromo-3-chlorophenyl)amino]-6-(methyloxy)quinazolin-7-yl]-5-deoxy-D-xylo-hexitol | C | C | C | C | A | B |
| 68 | 1,4:3,6-dianhydro-2-O-[4-[(4-bromo-3-chlorophenyl)amino]-6-(methyloxy)quinazolin-7-yl]-5-O-methyl-D-glucitol | C | C | C | C | A | C |

TABLE 4

| Entry | Nomenclature | EGFR IC$_{50}$ | EphB4 IC$_{50}$ | KDR IC$_{50}$ | Flt1 IC$_{50}$ |
|---|---|---|---|---|---|
| 1 | 1,4:3,6-dianhydro-2-deoxy-2-fluoro-5-O-{6-(methyloxy)-4-[(2,3,4-trifluorophenyl)amino]quinazolin-7-yl}-D-iditol | A | B | C | C |
| 2 | 1,4:3,6-dianhydro-5-O-[4-[(2-chloro-4-fluorophenyl)amino]-6-(methyloxy)quinazolin-7-yl]-2-deoxy-2-fluoro-D-iditol | A | C | C | C |
| 3 | 1,4:3,6-dianhydro-5-O-[4-[(2-bromo-4-fluorophenyl)amino]-6-(methyloxy)quinazolin-7-yl]-2-deoxy-2-fluoro-D-iditol | A | C | C | C |
| 4 | 1,4:3,6-dianhydro-2-deoxy-5-O-[4-[(2,6-difluorophenyl)amino]-6-(methyloxy)quinazolin-7-yl]-2-fluoro-D-iditol | A | C | C | C |
| 5 | 1,4:3,6-dianhydro-5-O-[4-[(3-chloro-2-fluorophenyl)amino]-6-(methyloxy)quinazolin-7-yl]-2-deoxy-2-fluoro-D-iditol | A | B | C | C |
| 6 | 1,4:3,6-dianhydro-2-deoxy-2-fluoro-5-O-[4-{[4-fluoro-3-(trifluoromethyl)phenyl]amino}-6-(methyloxy)quinazolin-7-yl]-D-iditol | A | C | C | C |
| 7 | 1,4:3,6-dianhydro-2-deoxy-5-O-[4-[(2,4-difluorophenyl)amino]-6-(methyloxy)quinazolin-7-yl]-2-fluoro-D-iditol | A | C | C | C |
| 8 | 1,4:3,6-dianhydro-2-deoxy-5-O-[4-[(2,5-difluorophenyl)amino]-6-(methyloxy)quinazolin-7-yl]-2-fluoro-D-iditol | A | C | C | C |
| 9 | 1,4:3,6-dianhydro-2-deoxy-5-O-[4-[(2,3-difluorophenyl)amino]-6-(methyloxy)quinazolin-7-yl]-2-fluoro-D-iditol | A | C | C | C |
| 10 | 1,4:3,6-dianhydro-5-O-[4-[(5-chloro-2-fluorophenyl)amino]-6-(methyloxy)quinazolin-7-yl]-2-deoxy-2-fluoro-D-iditol | A | C | C | C |
| 11 | 1,4:3,6-dianhydro-2-deoxy-5-O-[4-[(3,5-difluorophenyl)amino]-6-(methyloxy)quinazolin-7-yl]-2-fluoro-D-iditol | A | B | C | C |
| 12 | 1,4:3,6-dianhydro-5-O-(4-[(3-chloro-4-fluorophenyl)amino]-6-(methyloxy)quinazolin-7-yl]-2-deoxy-2-fluoro-D-iditol | A | B | C | C |
| 13 | 1,4:3,6-dianhydro-5-O-(4-[(4-bromo-2-chlorophenyl)amino]-6-(methyloxy)quinazolin-7-yl]-2-deoxy-2-fluoro-D-iditol | A | C | C | C |
| 14 | 1,4:3,6-dianhydro-2-deoxy-5-O-[4-[(3,4-dichloro-2-fluorophenyl)amino]-6-(methyloxy)quinazolin-7-yl]-2-fluoro-D-iditol | A | B | C | C |

TABLE 4-continued

| Entry | Nomenclature | EGFR IC$_{50}$ | EphB4 IC$_{50}$ | KDR IC$_{50}$ | Flt1 IC$_{50}$ |
|---|---|---|---|---|---|
| 15 | 1,4:3,6-dianhydro-5-O-[4-[(4-bromo-5-chloro-2-fluorophenyl)amino]-6-(methyloxy)quinazolin-7-yl]-2-deoxy-2-fluoro-D-iditol | A | B | C | C |
| 16 | 1,4:3,6-dianhydro-2-deoxy-2-fluoro-5-O-{6-(methyloxy)-4-[(2,4,5-trifluorophenyl)amino]quinazolin-7-yl}-D-iditol | A | C | C | C |
| 17 | 1,4:3,6-dianhydro-2-deoxy-2-fluoro-5-O-{6-(methyloxy)-4-[(2,4,6-trifluorophenyl)amino]quinazolin-7-yl}-D-iditol | A | C | C | C |
| 18 | 1,4:3,6-dianhydro-5-O-[4-((4-[(4-chlorophenyl)oxy]-3,5-difluorophenyl}amino)-6-(methyloxy)quinazolin-7-yl]-2-deoxy-2-fluoro-D-iditol | A | C | C | C |
| 19 | 1,4:3,6-dianhydro-5-O-[4-[(4-bromo-3-chloro-2-fluorophenyl)amino]-6-(methyloxy)quinazolin-7-yl]-2-deoxy-2-fluoro-D-iditol | A | B | B | C |
| 20 | 1,4:3,6-dianhydro-5-O-[4-[(4-bromo-2,3-dichlorophenyl)amino]-6-(methyloxy)quinazolin-7-yl]-2-deoxy-2-fluoro-D-iditol | A | B | C | C |
| 21 | 1,4:3,6-dianhydro-5-O-[4-[(4-bromo-3-chloro-5-fluorophenyl)amino]-6-(methyloxy)quinazolin-7-yl]-2-deoxy-2-fluoro-D-iditol | A | B | C | C |
| 22 | 1,4:3,6-dianhydro-2-deoxy-5-O-[4-[(4,5-dichloro-2-fluorophenyl)amino]-6-(methyloxy)quinazolin-7-yl]-2-fluoro-D-iditol | A | B | C | C |
| 23 | 1,4:3,6-dianhydro-2-deoxy-2-fluoro-5-O-{6-(methyloxy)-4-[(2,3,4-trichlorophenyl)amino]quinazolin-7-yl}-D-iditol | A | B | C | C |
| 24 | 1,4:3,6-dianhydro-2-deoxy-2-fluoro-5-O-{6-(methyloxy)-4-[(3,4,5-trichlorophenyl)amino]quinazolin-7-yl}-D-iditol | A | C | C | C |
| 25 | 1,4:3,6-dianhydro-5-O-[4-[(4-bromo-2-fluorophenyl)amino]-6-(methyloxy)quinazolin-7-yl]-2-deoxy-2-fluoro-D-iditol | A | C | C | C |
| 26 | 1,4:3,6-dianhydro-5-O-[4-[(4-chloro-2-fluorophenyl)amino]-6-(methyloxy)quinazolin-7-yl]-2-deoxy-2-fluoro-D-iditol | A | C | C | C |
| 27 | 1,4:3,6-dianhydro-5-O-[4-[(3-chloro-2-methylphenyl)amino]-6-(methyloxy)quinazolin-7-yl]-2-deoxy-2-fluoro-D-iditol | A | B | C | C |
| 28 | 1,4:3,6-dianhydro-2-deoxy-5-O-(4-[(3,4-difluorophenyl)amino]-6-(methyloxy)quinazolin-7-yl]-2-fluoro-D-iditol | A | C | C | C |
| 29 | 1,4:3,6-dianhydro-5-O-[4-[(2-chlorophenyl)amino]-6-(methyloxy)quinazolin-7-yl]-2-deoxy-2-fluoro-D-iditol | A | C | C | C |
| 30 | 1,4:3,6-dianhydro-2-deoxy-2-fluoro-5-O-[4-[(2-fluorophenyl)amino]-6-(methyloxy)quinazolin-7-yl]-D-iditol | A | C | C | C |
| 31 | 1,4:3,6-dianhydro-5-O-[4-[(3-chlorophenyl)amino]-6-(methyloxy)quinazolin-7-yl]-2-deoxy-2-fluoro-D-iditol | A | C | C | C |
| 32 | 1,4:3,6-dianhydro-2-deoxy-2-fluoro-5-O-[4-[(4-fluorophenyl)amino]-6-(methyloxy)quinazolin-7-yl]-D-iditol | A | C | C | C |
| 33 | 1,4:3,6-dianhydro-5-O-[4-[(4-chlorophenyl)amino]-6-(methyloxy)quinazolin-7-yl]-2-deoxy-2-fluoro-D-iditol | A | C | C | C |
| 34 | 1,4:3,6-dianhydro-2-deoxy-5-O-[4-[(2,4-dichlorophenyl)amino]-6-(methyloxy)quinazolin-7-yl]-2-fluoro-D-iditol | A | C | C | C |
| 35 | 1,4:3,6-dianhydro-2-deoxy-5-O-[4-[(2,5-dichlorophenyl)amino]-6-(methyloxy)quinazolin-7-yl]-2-fluoro-D-iditol | A | C | C | C |
| 36 | 1,4:3,6-dianhydro-2-deoxy-5-O-[4-[(3,4-dichlorophenyl)amino]-6-(methyloxy)quinazolin-7-yl]-2-fluoro-D-iditol | A | B | C | C |
| 37 | 1,4:3,6-dianhydro-5-O-[4-[(2-bromo-4,6-difluorophenyl)amino]-6-(methyloxy)quinazolin-7-yl]-2-deoxy-2-fluoro-D-iditol | A | C | C | C |
| 38 | 1,4:3,6-dianhydro-5-O-[4-{[4-chloro-3-(trifluoromethyl)phenyl]amino}-6-(methyloxy)quinazolin-7-yl]-2-deoxy-2-fluoro-D-iditol | A | C | C | C |
| 39 | 1,4:3,6-dianhydro-5-O-[4-{[2-chloro-5-(trifluoromethyl)phenyl]amino}-6-(methyloxy)quinazolin-7-yl]-2-deoxy-2-fluoro-D-iditol | A | C | C | C |
| 40 | 1,4:3,6-dianhydro-2-deoxy-2-fluoro-5-O-[4-{[2-fluoro-3-(trifluoromethyl)phenyl]amino}-6-(methyloxy)quinazolin-7-yl]-D-iditol | A | C | C | C |
| 41 | 1,4:3,6-dianhydro-5-O-[4-{[2-bromo-5-(trifluoromethyl)phenyl]amino}-6-(methyloxy)quinazoun-7-yl]-2-deoxy-2-fluoro-D-iditol | A | C | C | C |

TABLE 4-continued

| Entry | Nomenclature | EGFR IC$_{50}$ | EphB4 IC$_{50}$ | KDR IC$_{50}$ | Flt1 IC$_{50}$ |
|---|---|---|---|---|---|
| 42 | 1,4:3,6-dianhydro-5-O-[4-{[2-bromo-4-(trifluoromethyl)phenyl]amino}-6-(methyloxy)quinazolin-7-yl]-2-deoxy-2-fluoro-D-iditol | A | C | C | C |
| 43 | 1,4:3,6-dianhydro-2-deoxy-2-fluoro-5-O-[4-{[4-fluoro-2-(trifluoromethyl)phenyl]amino}-6-(methyloxy)quinazolin-7-yl]-D-iditol | A | C | C | C |
| 44 | 1,4:3,6-dianhydro-5-O-[4-{[3-bromo-5-(trifluoromethyl)phenyl]amino}-6-(methyloxy)quinazolin-7-yl]-2-deoxy-2-fluoro-D-iditol | A | C | C | C |
| 45 | 1,4:3,6-dianhydro-5-O-[4-[(2-bromophenyl)amino]-6-(methyloxy)quinazolin-7-yl]-2-deoxy-2-fluoro-D-iditol | A | C | C | C |
| 46 | 1,4:3,6-dianhydro-5-O-[4-[(3-bromophenyl)amino]-6-(methyloxy)quinazolin-7-yl]-2-deoxy-2-fluoro-D-iditol | A | C | C | C |
| 47 | 1,4:3,6-dianhydro-5-O-[4-[(4-bromophenyl)aminol-6-(methyloxy)quinazolin-7-yl]-2-deoxy-2-fluoro-D-iditol | A | C | C | C |
| 48 | 1,4:3,6-dianhydro-5-O-[4-[(3-bromo-4-methylphenyl)amino]-6-(methyloxy)quinazolin-7-yl]-2-deoxy-2-fluoro-D-iditol | A | B | C | C |
| 49 | 1,4;3,6-dianhydro-5-O-[4-[(5-chloro-2-methylphenyl)amino]-6-(methyloxy)quinazolin-7-yl]-2-deoxy-2-fluoro-D-iditol | A | C | C | C |
| 50 | 1,4:3,6-dianhydro-2-deoxy-5-O-[4-[(3,5-dimethylphenyl)amino]-6-(methyloxy)quinazolin-7-yl]-2-fluoro-D-iditol | A | C | C | C |
| 51 | 1,4:3,6-dianhydro-5-O-[4-{[2,5-bis(methyloxy)phenyl]amino}-6-(methyloxy)quinazolin-7-yl]-2-deoxy-2-fluoro-D-iditol | A | C | C | C |
| 52 | 1,4:3,6-dianhydro-5-O-[4-{[5-chloro-2,4-bis(methyloxy)phenyl]amino}-6-(methyloxy)quinazolin-7-yl]-2-deoxy-2-fluoro-D-iditol | A | C | C | C |
| 53 | 1,4:3,6-dianhydro-5-O-[4-{[4-chloro-2,5-bis(methyloxy)phenyl]amino}-6-(methyloxy)quinazolin-7-yl]-2-deoxy-2-fluoro-D-iditol | A | C | C | C |
| 54 | 1,4:3,6-dianhydro-5-O-[4-[(3-chloro-2,4-difluorophenyl)amino]-6-(methyloxy)quinazolin-7-yl]-2-deoxy-2-fluoro-D-iditol | A | B | C | C |

TABLE 5

| Entry | Name | EphB4 IC$_{50}$ |
|---|---|---|
| 1 | N-(3,4-dichlorophenyl)-6-(methytoxy)-7-[(tetrahydro-2H-pyran-2-ylmethyl)oxy]quinazolin-4-amine | A |
| 2 | N-(3,4-dichlorophenyl)-7-[({5-[(dimethylamino)methyl]-1,2,4-oxadiazol-3-yl}methyl)oxy]-6-(methyloxy)quinazolin-4-amine | A |
| 3 | N-(3,4-dichlorophenyl)-7-[({3-[(dimethylamino)methyl]-1,2,4-oxadiazol-5-yl}methyl)oxy]-6-(methyloxy)quinazolin-4-amine | B |
| 4 | N-(3,4-dichlorophenyl)-6-(methyloxy)-7-[({3-[(4-methylpiperazin-1-yl)methyl]-1,2,4-oxadiazol-5-yl}methyl)oxy]quinazolin-4-amine | B |
| 5 | N-(3,4-dichlorophenyl)-6-(methyloxy)-7-{[(5-piperidin-4-yl-1,2,4-oxadiazol-3-yl)methyl]oxy}quinazolin-4-amine | A |
| 6 | N-(3,4-dichlorophenyl)-6-(methyloxy)-7-({[5-(1-methylpiperidin-4-yl)-1,2,4-oxadiazol-3-yl]methyl}oxy)quinazolin-4-amine | A |
| 7 | N-(3,4-dichlorophenyl)-6-(methyloxy)-7-[{(3-(morpholin-4-ylmethyl)-1,2,4-oxadiazol-5-yl]methyl}oxy)quinazolin-4-amine | B |
| 8 | N-(3,4-dichlorophenyl)-6-(methyloxy)-7-[(morpholin-2-ylmethyl)oxy]quinazolin-4-amine | A |
| 9 | N-(3,4-dichlorophenyl)-6-(methyloxy)-7-{[(5-piperidin-2-yl-1,2,4-oxadiazol-3-yl)methyl]oxy}quinazolin-4-amine | A |
| 10 | N-(3,4-dichlorophenyl)-7-[({2-[(dimethylamino)methyl]-1,3-thiazol-4-yl]methyl)oxy]-6-(methyloxy)quinazolin-4-amine | B |
| 11 | N-(3,4-dichlorophenyl)-6-(methyloxy)-7-({[4-(phenylmethyl)morpholin-2-yl]methyl}oxy)quinazolin-4-amine | B |
| 12 | 1,1-dimethylethyl 2-({[4-[(3,4-dichlorophenyl)amino]-6-(methyloxy)quinazolin-7-yl]oxy}methyl)morpholine-4-carboxylate | B |
| 13 | N-(3,4-dichlorophenyl)-6-(methyloxy)-7-({[2-(morpholin-4-ylmethyl)-1,3-thiazol-4-yl]methyl}oxy)quinazolin-4-amine | B |
| 14 | N-(3,4-dichlorophenyl)-6-(methyloxy)-7-[({2-[(4-methylpiperazin-1-yl)methyl]-1,3-thiazol-4-yl}methyl)oxy]quinazolin-4-amine | A |
| 15 | N-(3,4-dichlorophenyl)-7-{[(4-methylmorpholin-2-yl)methyl]oxy}-6-(methyloxy)quinazolin-4-amine | A |

TABLE 5-continued

| Entry | Name | EphB4 IC$_{50}$ |
|---|---|---|
| 16 | N-(3,4-dichlorophenyl)-6-(methyloxy)-7-[(1,4-oxazepan-2-ylmethyl)oxy]quinazolin-4-amine | A |
| 17 | N-(3,4-dichlorophenyl)-6-(methyloxy)-7-{[(5-piperidin-3-yl-1,2,4-oxadiazol-3-yl]methyl]oxy}quinazolin-4-amine | A |
| 18 | N-(3,4-dichlorophenyl)-6-(methyloxy)-7-({[5-(1-methylpiperidin-2-yl)-1,2,4-oxadiazol-3-yl]methyl}oxy)quinazolin-4-amine | A |
| 19 | N-(3,4-dichlorophenyl)-7-{[(4-methyl-1,4-oxazepan-2-yl)methyl]oxy}-6-(methyloxy)quinazolin-4-amine | A |
| 20 | N-(3,4-dichlorophenyl)-6-(methyloxy)-7-({[5-(1-methylpiperidin-3-yl)-1,2,4-oxadiazol-3-yl]methyl}oxy)quinazolin-4-amine | A |

TABLE 6

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 1 | N-(3,4-dichlorophenyl)-6-(methyloxy)-7-[(1,3-thiazol-4-ylmethyl)oxy]quinazolin-4-amine | B | B | B | B | A | — |
| 2 | N-(3,4-dichlorophenyl)-6-(methyloxy)-7-[(pyridin-3-ylmethyl)oxy]quinazolin-4-amine | — | B | B | B | — | — |
| 3 | 7-[(cyclopropylmethyl)oxy]-N-(3,4-dichlorophenyl)-6-(methyloxy)quinazolin-4-amine | A | B | B | — | A | B |
| 4 | N-(3,4-dichlorophenyl)-6-(methyloxy)-7-[(tetrahydrofuran-2-ylmethyl)oxy]quinazolin-4-amine | A | B | B | — | A | — |
| 5 | 7-(cyclopentyloxy)-N-(3,4-dichlorophenyl)-6-(methyloxy)quinazolin-4-amine | B | B | C | — | A | — |
| 6 | methyl 6-O-[4-[(3,4-dichlorophenyl)amino]-6-(methyloxy)quinazolin-7-yl]-alpha-D-glucopyranoside | A | B | B | — | A | B |
| 7 | N-(3,4-dichlorophenyl)-6-(methyloxy)-7-[(2-morpholin-4-yl-2-oxoethyl)oxy]quinazolin-4-amine | C | B | C | — | A | — |
| 8 | 1,1-dimethylethyl 2-[3-({[4-[(3,4-dichlorophenyl)amino]-6-(methyloxy)quinazolin-7-yl]oxy}methyl)-1,2,4-oxadiazol-5-yl]piperidine-1-carboxylate | B | C | C | — | A | — |
| 9 | 1,1-dimethylethyl 4-[3-({[4-[(3,4-dichlorophenyl)amino]-6-(methyloxy)quinazolin-7-yl]oxy}methyl)-1,2,4-oxadiazol-5-yl]piperidine-1-carboxylate | B | B | B | — | A | — |
| 10 | N-(3,4-dichlorophenyl)-6-(methyloxy)-7-({[4-(4-pyrrolidin-1-ylphenyl)-1,3-thiazol-2-yl]methyl}oxy)quinazolin-4-amine | C | C | C | — | A | — |
| 11 | N-(3,4-dichlorophenyl)-7-[({4-[4-(diethylamino)phenyl]-1,3-thiazol-2-yl}methyl)oxy]-6-(methyloxy)quinazolin-4-amine | C | C | C | — | A | — |
| 12 | 5-[2-({[4-[(3,4-dichlorophenyl)amino]-6-(methyloxy)quinazolin-7-yl]oxy}methyl)-1,3-thiazol-4-yl]-2-hydroxybenzamide | C | C | C | — | A | — |
| 13 | 7-[(2-cyclohexylethyl)oxy]-N-(3,4-dichlorophenyl)-6-(methyloxy)quinazolin-4-amine | C | C | C | — | A | — |
| 14 | 7-[(cyclohexylmethyl)oxy]-N-(3,4-dichlorophenyl)-6-(methyloxy)quinazolin-4-amine | B | C | C | — | A | — |
| 15 | 7-[(cyclobutylmethyl)oxy]-N-(3,4-dichlorophenyl)-6-(methyloxy)quinazolin-4-amine | B | C | C | — | A | — |
| 16 | N-(3,4-dichlorophenyl)-7-{[2-(1,3-dioxolan-2-yl)ethyl]oxy}-6-(methyloxy)quinazolin-4-amine | B | B | B | — | A | — |
| 17 | N-(3,4-dichlorophenyl)-7-{[2-(1,3-dioxan-2-yl)ethyl]oxy}-6-(methyloxy)quinazolin-4-amine | B | B | B | — | A | — |
| 18 | N-(3,4-dichlorophenyl)-6-(methyloxy)-7-[(2-morpholin-4-ylethyl)oxy]quinazolin-4-amine | B | B | B | — | A | — |
| 19 | N-(3,4-dichlorophenyl)-6-(methyloxy)-7-[(2-pyrrolidin-1-ylethyl)oxy]quinazolin-4-amine | B | B | B | — | A | — |
| 20 | N-(3,4-dichlorophenyl)-6-(methyloxy)-7-[(2-piperidin-1-ylethyl)oxy]quinazolin-4-amine | B | B | B | — | A | — |
| 21 | 2-(2-{[4-[(3,4-dichlorophenyl)amino]-6-(methyloxy)quinazolin-7-yl]oxy}ethyl)-1H-isoindole-1,3(2H)-dione | A | B | B | — | A | B |
| 22 | N-(3,4-dichlorophenyl)-6-(methyloxy)-7-{[(4-pyridin-3-yl-1,3-thiazol-2-yl)methyl]oxy}quinazolin-4-amine | C | C | C | — | A | — |
| 23 | N-(3,4-dichlorophenyl)-6-(methyloxy)-7-{[(4-pyridin-2-yl-1,3-thiazol-2-yl)methyl]oxy}quinazolin-4-amine | C | C | C | — | A | — |
| 24 | N-(3,4-dichlorophenyl)-6-(methyloxy)-7-{[(4-pyridin-4-yl-1,3-thiazol-2-yl)methyl]oxy}quinazolin-4-amine | C | C | C | — | A | — |
| 25 | N-(3,4-dichlorophenyl)-6-(methyloxy)-7-{[(2-morpholin-4-yl-1,3-thiazol-4-yl)methyl]oxy}quinazolin-4-amine | — | C | C | — | A | C |
| 26 | N-(3,4-dichlorophenyl)-6-(methyloxy)-7-{[(3-morpholin-4-yl-1,2,4-oxadiazol-5-yl)methyl]oxy}quinazolin-4-amine | — | C | C | — | A | — |
| 27 | N-(3,4-dichlorophenyl)-7-({[3-(dimethylamino)-1,2,4-oxadiazol-5-yl]methyl}oxy)-6-(methyloxy)quinazolin-4-amine | A | C | C | — | A | — |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 28 | N-(3,4-dichlorophenyl)-6-(methyloxy)-7-[({4-[(4-methylpiperazin-1-yl)methyl]-1,3-thiazol-2-yl}methyl)oxy]quinazolin-4-amine | B | B | B | — | A | — |
| 29 | N-(3,4-dichlorophenyl)-6-(methyloxy)-7-[(4,5,6,7-tetrahydro[1,3]thiazolo[5,4-c]pyridin-2-ylmethyl)oxy]quinazolin-4-amine | B | B | B | — | A | B |
| 30 | N-(3,4-dichlorophenyl)-6-(methyloxy)-7-({[4-(morpholin-4-ylmethyl)-1,3-thiazol-2-yl]methyl}oxy)quinazolin-4-amine | B | B | B | — | A | |
| 31 | N-(3,4-dichlorophenyl)-7-[({4-[(4-methyl-1,4-diazepan-1-yl)methyl]-1,3-thiazol-2-yl}methyl)oxy]-6-(methyloxy)quinazolin-4-amine | A | A | A | — | A | — |
| 32 | N-(3,4-dichlorophenyl)-6-(methyloxy)-7-{[(5-{[(phenylmethyl)oxy]methyl}-1,2,4-oxadiazol-3-yl)methyl]oxy}quinazolin-4-amine | B | C | B | — | A | — |
| 33 | N-(3,4-dichlorophenyl)-7-{[(4-ethylmorpholin-2-yl)methyl]oxy}-6-(methyloxy)quinazolin-4-amine | A | B | A | — | A | B |
| 34 | N-(3,4-dichlorophenyl)-6-(methyloxy)-7-{[(2-piperidin-4-yl-1,3-thiazol-4-yl)methyl]oxy}quinazolin-4-amine | B | B | B | — | A | A |
| 35 | N-(3,4-dichlorophenyl)-6-(methyloxy)-7-({[2-(1-methylpiperidin-4-yl)-1,3-thiazol-4-yl]methyl}oxy)quinazolin-4-amine | B | B | A | — | A | B |
| 36 | 1,1-dimethylethyl 4-[5-({[4-[(3,4-dichlorophenyl)amino]-6-(methyloxy)quinazolin-7-yl]oxy}methyl)-1,2,4-oxadiazol-3-yl]piperazine-1-carboxylate | C | C | C | — | A | — |
| 37 | N-(3,4-dichlorophenyl)-6-(methyloxy)-7-{[(3-piperazin-1-yl-1,2,4-oxadiazol-5-yl)methyl]oxy}quinazolin-4-amine | B | A | A | — | A | A |
| 38 | N-(3,4-dichlorophenyl)-6-(methyloxy)-7-({[3-(4-methylpiperazin-1-yl)-1,2,4-oxadiazol-5-yl]methyl}oxy)quinazolin-4-amine | B | A | A | — | A | A |
| 39 | N-(3,4-dichlorophenyl)-7-({[5-(1-ethylpiperidin-2-yl)-1,2,4-oxadiazol-3-yl]methyl}oxy)-6-(methyloxy)quinazolin-4-amine | A | B | A | — | A | A |
| 40 | N-(3,4-dichlorophenyl)-7-({[3-(4-ethylpiperazin-1-yl)-1,2,4-oxadiazol-5-yl]methyl}oxy)-6-(methyloxy)quinazolin-4-amine | A | A | A | — | A | — |
| 41 | N-(3,4-dichlorophenyl)-6-(methyloxy)-7-[({5-[4-(methyloxy)phenyl]-1,2,4-oxadiazol-3-yl}methyl)oxy]quinazolin-4-amine | C | C | C | — | A | — |
| 42 | N-(3,4-dichlorophenyl)-6-(methyloxy)-7-[({2-[4-(trifluoromethyl)phenyl]-1,3-thiazol-4-yl}methyl)oxy]quinazolin-4-amine | C | C | C | — | B | — |
| 43 | 7-({[2-(4-chlorophenyl)-1,3-thiazol-4-yl]methyl}oxy)-N-(3,4-dichlorophenyl)-6-(methyloxy)quinazolin-4-amine | C | C | C | — | B | — |
| 44 | N-(3,4-dichlorophenyl)-7-({[5-(3,5-dimethylisoxazol-4-yl)-1,2,4-oxadiazol-3-yl]methyl}oxy)-6-(methyloxy)quinazolin-4-amine | C | C | C | — | A | — |
| 45 | 7-{[(5-chloro-1-benzothien-3-yl)methyl]oxy}-N-(3,4-dichlorophenyl)-6-(methyloxy)quinazolin-4-amine | C | C | C | — | B | — |
| 46 | N-(3,4-dichlorophenyl)-7-[({3-[4-(1,1-dimethylethyl)phenyl]-1,2,4-oxadiazol-5-yl}methyl)oxy]-6-(methyloxy)quinazolin-4-amine | C | C | C | — | B | — |
| 47 | N-(3,4-dichlorophenyl)-6-(methyloxy)-7-[({5-[2-(methyloxy)phenyl]-1,2,4-oxadiazol-3-yl}methyl)oxy]quinazolin-4-amine | C | C | C | — | A | — |
| 48 | N-(3,4-dichlorophenyl)-6-(methyloxy)-7-({[5-(4-methylphenyl)-1,3,4-oxadiazol-2-yl]methyl}oxy)quinazolin-4-amine | C | C | C | — | A | — |
| 49 | N-(3,4-dichlorophenyl)-6-(methyloxy)-7-({[1-(phenylmethyl)-1H-imidazol-2-yl]methyl}oxy)quinazolin-4-amine | C | C | C | — | A | — |
| 50 | N-(3,4-dichlorophenyl)-7-({[3-(2,6-dichlorophenyl)-5-methylisoxazol-4-yl]methyl}oxy)-6-(methyloxy)quinazolin-4-amine | C | C | C | — | B | — |
| 51 | N-(3,4-dichlorophenyl)-7-{[(6-fluoro-4H-1,3-benzodioxin-8-yl)methyl]oxy}-6-(methyloxy)quinazolin-4-amine | C | C | C | — | A | — |
| 52 | 7-{[(3,5-dibromophenyl)methyl]oxy}-N-(3,4-dichlorophenyl)-6-(methyloxy)quinazolin-4-amine | C | C | C | — | B | — |
| 53 | N-(3,4-dichlorophenyl)-7-{[(2,6-difluorophenyl)methyl]oxy}-6-(methyloxy)quinazolin-4-amine | B | C | C | — | A | — |
| 54 | N-(3,4-dichlorophenyl)-6-(methyloxy)-7-[({3-[(pyridin-2-ylsulfonyl)methyl]-1,2,4-oxadiazol-5-yl}methyl)oxy]quinazolin-4-amine | B | B | B | — | A | — |
| 55 | N-(3,4-dichlorophenyl)-6-(methyloxy)-7-{[(5-phenyl-1,2,4-oxadiazol-3-yl)methyl]oxy}quinazolin-4-amine | C | C | C | — | A | — |
| 56 | 7-({[4-chloro-2-(trifluoromethyl)quinolin-6-yl]methyl}oxy)-N-(3,4-dichlorophenyl)-6-(methyloxy)quinazolin-4-amine | C | C | C | — | B | — |
| 57 | N-(3,4-dichlorophenyl)-6-(methyloxy)-7-{[2-(1-methylpyrrolidin-2-yl)ethyl]oxy}quinazolin-4-amine | B | B | B | — | A | — |
| 58 | N-(3,4-dichlorophenyl)-7-({[5-(1-ethylpiperidin-4-yl)-1,2,4-oxadiazol-3-yl]methyl}oxy)-6-(methyloxy)quinazolin-4-amine | A | A | A | — | A | A |
| 59 | N-(3,4-dichlorophenyl)-7-({[5-(1-ethylpiperidin-3-yl)-1,2,4-oxadiazol-3-yl]methyl}oxy)-6-(methyloxy)quinazolin-4-amine | A | A | A | — | A | A |
| 60 | N-(3,4-dichlorophenyl)-7-({[2-(dimethylamino)-1,3-thiazol-4-yl]methyl}oxy)-6-(methyloxy)quinazolin-4-amine | C | C | C | — | A | — |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 61 | N-(3,4-dichlorophenyl)-7-{[(4-ethyl-1,4-oxazepan-2-yl)methyl]oxy}-6-(methyloxy)quinazolin-4-amine | A | A | A | — | A | B |
| 62 | N-(3,4-dichlorophenyl)-7-({[2-(1-ethylpiperidin-4-yl)-1,3-thiazol-4-yl]methyl}oxy)-6-(methyloxy)quinazolin-4-amine | A | B | A | — | A | — |
| 63 | N-(3,4-dichlorophenyl)-6-(methyloxy)-7-[({3-[(2S)-pyrrolidin-2-yl]-1,2,4-oxadiazol-5-yl}methyl)oxy]quinazolin-4-amine | A | B | B | — | A | — |
| 64 | N-(3,4-dichlorophenyl)-6-(methyloxy)-7-[({2-[(2S)-pyrrolidin-2-yl]-1,3-thiazol-4-yl}methyl)oxy]quinazolin-4-amine | B | B | B | — | A | — |
| 65 | [4-({[4-[(3,4-dichlorophenyl)amino]-6-(methyloxy)quinazolin-7-yl]oxy}methyl)-1,3-thiazol-2-yl]methyl benzoate | C | C | C | — | A | — |
| 66 | [4-({[4-[(3,4-dichlorophenyl)amino]-6-(methyloxy)quinazolin-7-yl]oxy}methyl)-1,3-thiazol-2-yl]methanol | B | C | B | — | A | — |
| 67 | N-(3,4-dichlorophenyl)-6-(methyloxy)-7-{[(5-methyl-4,5,6,7-tetrahydro[1,3]thiazolo[5,4-c]pyridin-2-yl)methyl]oxy}quinazolin-4-amine | A | B | B | — | A | A |
| 68 | N-(3,4-dichlorophenyl)-6-(methyloxy)-7-[({2-[(4S)-1,3-thiazolidin-4-yl]-1,3-thiazol-4-yl}methyl)oxy]quinazolin-4-amine | B | B | B | — | A | — |
| 69 | N-(3,4-dichlorophenyl)-6-(methyloxy)-7-{[(2-piperidin-2-yl-1,3-thiazol-4-yl)methyl]oxy}quinazolin-4-amine | A | A | A | — | A | A |
| 70 | N-(3,4-dichlorophenyl)-6-(methyloxy)-7-({[2-(1-methylpiperidin-2-yl)-1,3-thiazol-4-yl]methyl}oxy)quinazolin-4-amine | B | B | A | — | A | — |
| 71 | N-(3,4-dichlorophenyl)-6-(methyloxy)-7-{[(2-piperidin-3-yl-1,3-thiazol-4-yl)methyl]oxy}quinazolin-4-amine | B | B | B | — | A | — |
| 72 | N-(3,4-dichlorophenyl)-6-(methyloxy)-7-({[2-(1-methylpiperidin-3-yl)-1,3-thiazol-4-yl]methyl}oxy)quinazolin-4-amine | B | B | B | — | A | B |
| 73 | N-(3,4-dichlorophenyl)-7-({[2-(1-ethylpiperidin-2-yl)-1,3-thiazol-4-yl]methyl}oxy)-6-(methyloxy)quinazolin-4-amine | B | B | A | — | A | — |
| 74 | N-(3,4-dichlorophenyl)-7-({[2-(1-ethylpiperidin-3-yl)-1,3-thiazol-4-yl]methyl}oxy)-6-(methyloxy)quinazolin-4-amine | B | B | — | A | — | — |
| 75 | N-(3,4-dichlorophenyl)-7-[({3-[(2S)-1-ethylpyrrolidin-2-yl]-1,2,4-oxadiazol-5-yl}methyl)oxy]-6-(methyloxy)quinazolin-4-amine | A | B | B | — | A | — |
| 76 | N-(3,4-dichlorophenyl)-7-[({2-[(2S)-1-ethylpyrrolidin-2-yl]-1,3-thiazol-4-yl}methyl)oxy]-6-(methyloxy)quinazolin-4-amine | B | B | B | — | A | — |
| 77 | N-(3,4-dichlorophenyl)-7-{[(5-ethyl-4,5,6,7-tetrahydro[1,3]thiazolo[5,4-c]pyridin-2-yl)methyl]oxy}-6-(methyloxy)quinazolin-4-amine | A | B | B | — | A | A |
| 78 | N-(3,4-dichlorophenyl)-6-(methyloxy)-7-{[(4-propyl-1,4-oxazepan-2-yl)methyl]oxy}quinazolin-4-amine | A | A | A | — | B | B |
| 79 | 7-({[4-(cyclopropylmethyl)-1,4-oxazepan-2-yl]methyl}oxy)-N-(3,4-dichlorophenyl)-6-(methyloxy)quinazolin-4-amine | A | A | A | — | A | — |
| 80 | N-(3,4-dichloropheny)-6-(methyloxy)-7-[({4-[2-(methyloxy)ethyl]-1,4-oxazepan-2-yl}methyl)oxy]quinazolin-4-amine | A | B | B | — | A | — |
| 81 | N-(3,4-dichlorophenyl)-7-({[4-(1-methylethyl)-1,4-oxazepan-2-yl]methyl}oxy)-6-(methyloxy)quinazolin-4-amine | B | B | B | — | A | — |
| 82 | N-(3,4-dichlorophenyl)-6-(methyloxy)-7-{[(2-piperazin-1-yl-1,3-thiazol-4-yl)methyl]oxy}quinazolin-4-amine | B | B | B | — | A | — |
| 83 | N-(3,4-dichlorophenyl)-6-(methyloxy)-7-{[(5-pyrrolidin-2-yl-1,2,4-oxadiazol-3-yl)methyl]oxy}quinazolin-4-amine | B | B | B | — | A | — |
| 84 | N-(3,4-dichlorophenyl)-7-({[5-(1-ethylpyrrolidin-2-yl)-1,2,4-oxadiazol-3-yl]methyl}oxy)-6-(methyloxy)quinazolin-4-amine | A | B | B | — | A | — |
| 85 | N-(3,4-dichlorophenyl)-6-(methyloxy)-7-[({3-[(2S)-1-methylpyrrolidin-2-yl]-1,2,4-oxadiazol-5-yl}methyl)oxy]quinazolin-4-amine | B | B | B | — | A | — |
| 86 | N-(3,4-dichlorophenyl)-6-(methyloxy)-7-[({2-[(2S)-1-methylpyrrolidin-2-yl]-1,3-thiazol-4-yl}methyl)oxy]quinazolin-4-amine | B | B | B | — | A | — |
| 87 | N-(3,4-dichlorophenyl)-7-({[2-(4-ethylpiperazin-1-yl)-1,3-thiazol-4-yl]methyl}oxy)-6-(methyloxy)quinazolin-4-amine | B | B | B | — | A | — |
| 88 | N-(3,4-dichlorophenyl)-7-{[(1,4-dimethylpiperazin-2-yl)methyl]oxy}-6-(methyloxy)quinazolin-4-amine | B | B | C | — | A | — |
| 89 | 7-{[(4-cyclopentylmorpholin-2-yl)methyl]oxy}-N-(3,4-dichlorophenyl)-6-(methyloxy)quinazolin-4-amine | B | A | A | — | A | — |
| 90 | N-(3,4-dichlorophenyl)-7-({[4-(1-methylethyl)morpholin-2-yl]methyl}oxy)-6-(methyloxy)quinazolin-4-amine | B | B | A | — | A | — |
| 91 | N-(3,4-dichlorophenyl)-6-(methyloxy)-7-({[4-(3-phenylpropyl)morpholin-2-yl]methyl}oxy)quinazolin-4-amine | B | B | B | — | A | — |
| 92 | N-(3,4-dichlorophenyl)-6-(methyloxy)-7-[({4-[2-(methyloxy)ethyl]morpholin-2-yl}methyl)oxy]quinazolin-4-amine | A | B | B | — | A | — |
| 93 | ethyl 2-[2-({[4-[(3,4-dichlorophenyl)amino]-6-(methyloxy)quinazolin-7-yl]oxy}methyl)morpholin-4-yl]propanoate | B | B | B | — | A | — |
| 94 | N-(3,4-dichlorophenyl)-7-{[(4-hex-5-en-1-ylmorpholin-2-yl)methyl]oxy}-6-(methyloxy)quinazolin-4-amine | A | A | A | — | A | — |
| 95 | 2-({2-[2-({[4-[(3,4-dichlorophenyl)amino]-6-(methyloxy)quinazolin-7-yl]oxy}methyl)morpholin-4-yl]ethyl}oxy)ethanol | B | B | B | — | A | — |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 96 | methyl 3-[2-({[4-[(3,4-dichlorophenyl)amino]-6-(methyloxy)quinazolin-7-yl]oxy}methyl)morpholin-4-yl]propanoate | A | A | A | — | A | — |
| 97 | 6-[2-({[4-[(3,4-dichlorophenyl)amino]-6-(methyloxy)quinazolin-7-yl]oxy}methyl)morpholin-4-yl]hexanenitrile | A | B | A | — | A | B |
| 98 | N-(3,4-dichlorophenyl)-6-(methyloxy)-7-({[4-(tetrahydro-2H-pyran-2-ylmethyl)morpholin-2-yl]methyl}oxy)quinazolin-4-amine | A | A | A | — | A | — |
| 99 | 4-[2-({[4-[(3,4-dichlorophenyl)amino]-6-(methyloxy)quinazolin-7-yl]oxy}methyl)morpholin-4-yl]butanenitrile | A | A | A | — | A | — |
| 100 | N-(3,4-dichlorophenyl)-7-[({4-[(4-fluorophenyl)methyl]morpholin-2-yl}methyl)oxy]-6-(methyloxy)quinazolin-4-amine | B | B | B | — | A | — |
| 101 | methyl 5-[2-({[4-[(3,4-dichlorophenyl)amino]-6-(methyloxy)quinazolin-7-yl]oxy}methyl)morpholin-4-yl]pentanoate | B | B | B | — | A | — |
| 102 | N-(3,4-dichlorophenyl)-6-(methyloxy)-7-{[(4-oct-7-en-1-ylmorpholin-2-yl)methyl]oxy}quinazolin-4-amine | B | B | B | — | A | — |
| 103 | N-(3,4-dichlorophenyl)-6-(methyloxy)-7-{[(4-propylmorpholin-2-yl)methyl]oxy}quinazolin-4-amine | A | B | B | — | A | — |
| 104 | 6-[2-({[4-[(3,4-dichlorophenyl)amino]-6-(methyloxy)quinazolin-7-yl]oxy}methyl)morpholin-4-yl]hexan-1-ol | A | B | A | — | A | — |
| 105 | 7-{[(4-acetylmorpholin-2-yl)methyl]oxy}-N-(3,4-dichlorophenyl)-6-(methyloxy)quinazolin-4-amine | A | B | B | — | A | — |
| 106 | 7-({[4-(cyclopropylmethyl)morpholin-2-yl]methyl}oxy)-N-(3,4-dichlorophenyl)-6-(methyloxy)quinazolin-4-amine | A | A | A | — | A | — |
| 107 | N-(3,4-dichlorophenyl)-6-(methyloxy)-7-{[(4-prop-2-yn-1-ylmorpholin-2-yl)methyl]oxy}quinazolin-4-amine | A | A | A | — | A | — |
| 108 | N-(3,4-dichlorophenyl)-6-(methyloxy)-7-{[(4-pyridin-4-ylmorpholin-2-yl)methyl]oxy}quinazolin-4-amine | A | A | A | — | A | — |
| 109 | N-(3,4-dichlorophenyl)-6-(methyloxy)-7-({[4-(pyridin-2-ylmethyl)morpholin-2-yl]methyl}oxy)quinazolin-4-amine | B | B | A | — | A | — |
| 110 | N-(3,4-dichloropheny)-6-(methyloxy)-7-{[(4-pent-2-yn-1-ylmorpholin-2-yl)methyl]oxy}quinazolin-4-amine | B | B | B | — | A | — |
| 111 | N-(3,4-dichlorophenyl)-6-(methyloxy)-7-({[2-(4-methylpiperazin-1-yl)-1,3-thiazol-4-yl]methyl}oxy)quinazolin-4-amine | B | B | B | — | A | B |
| 112 | N-(3,4-dichlorophenyl)-6-(methyloxy)-7-({[5-(1-methylpyrrolidin-2-yl)-1,2,4-oxadiazol-3-yl]methyl}oxy)quinazolin-4-amine | B | B | B | — | A | — |
| 113 | N-(3-chloro-4-fluorophenyl)-7-{[(4-methylmorpholin-2-yl)methyl]oxy}-6-(methyloxy)quinazolin-4-amine | B | B | B | — | A | — |
| 114 | 7-{[(4-acetyl-1-ethylpiperazin-2-yl)methyl]oxy}-N-(3,4-dichlorophenyl)-6-(methyloxy)quinazolin-4-amine | A | B | — | A | — | |
| 115 | N-[4-chloro-2,5-bis(methyloxy)phenyl]-7-{[(4-methylmorpholin-2-yl)methyl]oxy}-6-(methyloxy)quinazolin-4-amine | B | B | — | B | — | |
| 116 | N-(3-bromo-2-methylphenyl)-7-{[(4-methylmorpholin-2-yl)methyl]oxy}-6-(methyloxy)quinazolin-4-amine | B | B | B | — | A | — |
| 117 | 7-{[(4-methylmorpholin-2-yl)methyl]oxy}-6-(methyloxy)-N-(3,4,5-trichlorophenyl)quinazolin-4-amine | A | B | B | — | A | B |
| 118 | N-(3-chloro-2-methylphenyl)-7-{[(4-methylmorpholin-2-yl)methyl]oxy}-6-(methyloxy)quinazolin-4-amine | A | A | B | — | A | — |
| 119 | N-(3,4-dichlorophenyl)-7-{[(4-ethanimidoyl-1,4-oxazepan-2-yl)methyf]oxy}-6-(methyloxy)quinazolin-4-amine | A | A | A | — | A | A |
| 120 | N-(4-bromo-2-fluorophenyl)-7-{[(4-methylmorpholin-2-yl)methyl]oxy}-6-(methyloxy)quinazolin-4-amine | B | B | A | — | A | — |
| 121 | N-(5-chloro-2-fluorophenyl)-7-{[(4-methylmorpholin-2-yl)methyl]oxy}-6-(methyloxy)quinazolin-4-amine | B | B | B | — | A | — |
| 122 | N-(4-chloro-2-fluorophenyl)-7-{](4-methylmorpholin-2-yl)methyl]oxy}-6-(methyloxy)quinazolin-4-amine | B | B | A | — | A | — |
| 123 | N-(2,4-dichlorophenyl)-7-{[(4-methylmorpholin-2-yl)methyl]oxy}-6-(methyloxy)quinazolin-4-amine | B | B | B | — | A | — |
| 124 | N-(2,4-dibromophenyl)-7-{[(4-methylmorpholin-2-yl)methyl]oxy}-6-(methyloxy)quinazolin-4-amine | B | B | B | — | A | — |
| 125 | 7-{[(4-methylmorpholin-2-yl)methyl]oxy}-6-(methyloxy)-N-(2,3,4-trichlorophenyl)quinazolin-4-amine | A | A | A | — | A | B |
| 126 | N-(3,4-dichlorophenyl)-7-{[(1-ethyl-4-methylpiperazin-2-yl)methyl]oxy}-6-(methyloxy)quinazolin-4-amine | B | B | C | — | A | — |
| 127 | N'-cyano-2-({[4-[(3,4-dichlorophenyl)amino]-6-(methyloxy)quinazolin-7-yl]oxy}methyl)morpholine-4-carboximidamide | A | A | A | — | A | A |
| 128 | N-(3,4-dichlorophenyl)-6-(methyloxy)-7-({[2-(pyrrolidin-1-ylmethyl)-1,3-thiazol-4-yl]methyl}oxy)quinazolin-4-amine | B | B | B | — | A | — |
| 129 | N-(3,4-dichlorophenyl)-6-(methyloxy)-7-({[4-(tetrahydro-2H-pyran-4-yl)morpholin-2-yl]methyl}oxy)quinazolin-4-amine | A | B | B | — | A | — |
| 130 | N-(3,4-dichlorophenyl)-7-({[4-(2-ethylbutyl)morpholin-2-yl]methyl]oxy)-6-(methyloxy)quinazolin-4-amine | B | B | B | — | A | — |
| 131 | 7-({[4-(cyclohexylmethyl)morpholin-2-yl]methyl}oxy)-N-(3,4-dichlorophenyl)-6-(methyloxy)quinazolin-4-amine | B | B | B | — | A | — |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 132 | 2-[2-({14-I(3,4-dichlorophenyl)amino]-6-(methyloxy)quinazolin-7-yl]oxy}methyl)morpholin-4-yl]ethanol | B | B | B | — | A | — |
| 133 | 7-{[(4-but-2-yn-1-morpholin-2-yl)methyl]oxy}-N-(3,4-dichlorophenyl)-6-(methyloxy)quinazolin-4-amine | B | B | B | — | A | — |
| 134 | 7-{[(4-cyclobutylmorpholin-2-yl)methyl]oxy}-N-(3,4-dichlorophenyl)-6-(methyloxy)quinazolin-4-amine | B | B | A | — | A | — |
| 135 | N-(3,4-dichlorophenyl)-7-[({4-[2-(1,3-dioxolan-2-yl)ethyl]morpholin-2-yl}methyl)oxy]-6-(methyloxy)quinazolin-4-amine | A | B | B | — | A | — |
| 136 | 7-({[4-(2-cyclohexylethyl)morpholin-2-yl]methyl}oxy)-N-(3,4-dichlorophenyl)-6-(methyloxy)quinazolin-4-amine | B | B | B | — | A | — |
| 137 | N-(3,4-dichlorophenyl)-7-[({4-[2-(1,3-dioxan-2-yl)ethyl]morpholin-2-yl}methyl)oxy]-6-(methyloxy)quinazolin-4-amine | A | B | B | — | A | — |
| 138 | N-(3,4-dichlorophenyl)-6-(methyloxy)-7-{[(4-pent-4-en-1-ylmorpholin-2-yl)methyl]oxy}quinazolin-4-amine | A | B | A | — | A | — |
| 139 | N-(3,4-dichlorophenyl)-7-[({4-[(2R)-2-methylbutyl]morpholin-2-yl}methyl)oxy]-6-(methyloxy)quinazolin-4-amine | B | B | B | — | A | — |
| 140 | N-(3,4-dichlorophenyl)-7-({[4-(4-fluorobutyl)morpholin-2-yl]methyl}oxy)-6-(methyloxy)quinazolin-4-amine | A | B | A | — | A | — |
| 141 | 3-[2-({[4-[(3,4-dichlorophenyl)amino]-6-(methyloxy)quinazolin-7-yl]oxy}methyl)morpholin-4-yl]butan-2-one | B | B | B | — | A | — |
| 142 | 1-[2-({[4-[(3,4-dichlorophenyl)amino]-6-(methyloxy)quinazolin-7-yl]oxy}methyl)morpholin-4-yl]butan-2-one | B | B | B | — | A | — |
| 143 | N-(3,4-dichlorophenyl)-6-(methyloxy)-7-{[(4-pentylmorpholin-2-yl)methyl]oxy}quinazolin-4-amine | B | B | B | — | A | — |
| 144 | N-(3,4-dichlorophenyl)-7-{[(4-hexylmorpholin-2-yl)methyl]oxy}-6-(methyloxy)quinazolin-4-amine | B | B | B | — | A | — |
| 145 | N-(3,4-dichlorophenyl)-7-{[(4-heptylmorpholin-2-yl)methyl]oxy}-6-(methyloxy)quinazolin-4-amine | B | C | B | — | A | — |
| 146 | N-(3,4-dichlorophenyl)-6-(methyloxy)-7-{[(4-octylmorpholin-2-yl)methyl]oxy}quinazolin-4-amine | B | C | C | — | A | — |
| 147 | N-(3,4-dichlorophenyl)-6-(methyloxy)-7-({[4-(2-phenylethyl)morpholin-2-yl]methyl}oxy)quinazolin-4-amine | B | C | B | — | A | — |
| 148 | 7-{[(4-butylmorpholin-2-yl)methyl]oxy}-N-(3,4-dichlorophenyl)-6-(methyloxy)quinzolin-4-amine | A | B | A | — | A | B |
| 149 | N-(3,4-dichlorophenyl)-6-(methyloxy)-7-{[(4-prop-2-en-1-ylmorpholin-2-yl)methyl]oxy}quinazolin-4-amine | B | B | B | — | A | — |
| 150 | 2-[2-({[4-[(3,4-dichlorophenyl)amino]-6-(methyloxy)quinazolin-7-yl]oxy}methyl)morpholin-4-yl]-1-phenylethanone | B | B | B | — | A | — |
| 151 | N-(3,4-dichlorophenyl)-7-({[4-(2-fluoroethyl)morpholin-2-yl]methyl}oxy)-6-(methyloxy)quinazolin-4-amine | B | B | B | — | A | — |
| 152 | N-(3,4-dichlorophenyl)-7-({[4-(3-methylbut-2-en-1-yl)morpholin-2-yl]methyl}oxy)-6-(methyloxy)quinazolin-4-amine | B | B | B | — | A | — |
| 153 | 7-[({4-[(2E)-3-bromoprop-2-en-1-yl]morpholin-2-yl}methyl)oxy]-N-(3,4-dichlorophenyl)-6-(methyloxy)quinazolin-4-amine | B | B | B | — | A | — |
| 154 | 2-[2-({[4-[(3,4-dichlorophenyl)amino]-6-(methyloxy)quinazolin-7-yl]oxy}methyl)morpholin-4-yl]acetamide | A | B | B | — | A | A |
| 155 | N-(3,4-dichlorophenyl)-6-(methyloxy)-7-[({4-[3-(tetrahydro-2H-pyran-2-yloxy)propyl]-1,4-oxazepan-2-yl}methyl)oxy]quinazolin-4-amine | A | B | A | — | A | — |
| 156 | N-(3,4-dichlorophenyl)-7-({[4-(3-methylbutyl)-1,4-oxazepan-2-yl]methyl}oxy)-6-(methyloxy)quinazolin-4-amine | B | B | B | — | A | — |
| 157 | 7-({[4-(cyclohexylmethyl)-1,4-oxazepan-2-yl]methyl}oxy)-4-[(3,4-dichlorophenyl)methyl]-6-(methyloxy)quinazoline | B | B | A | — | A | — |
| 158 | 7-({[4-(2-cyclohexylethyl)-1,4-oxazepan-2-yl]methyl}oxy)-4-[(3,4-dichlorophenyl)methyl]-6-(methyloxy)quinazoline | B | B | B | — | A | — |
| 159 | N-(3,4-dichlorophenyl)-7-({[4-(2-ethylbutyl)-1,4-oxazepan-2-yl]methyl}oxy)-6-(methyloxy)quinazolin-4-amine | B | B | B | — | A | — |
| 160 | N-(3,4-dichlorophenyl)-6-(methyloxy)-7-({[4-(methylsulfonyl)-1,4-oxazepan-2-yl]methyl}oxy)quinazolin-4-amine | A | B | B | — | A | A |
| 161 | N-(3,4-dichlorophenyl)-6-(methyloxy)-7-({[4-(1-methylpiperidin-4-yl)morpholin-2-yl]methyl}oxy)quinazolin-4-amine | A | B | A | — | A | — |
| 162 | N-(3-chloro-2-fluorophenyl)-7-{[(4-methylmorpholin-2-methyl]oxy}-6-(methyloxy)quinazolin-4-amine | B | B | B | — | A | — |
| 163 | N'-cyano-2-({[4-[(3,4-dichlorophenyl)amino]-6-(methyloxy)quinazolin-7-yl]oxy}methyl)-1,4-oxazepane-4-carboximidamide | A | B | B | — | A | A |
| 164 | N-(3-bromo-4-methylphenyl)-7-{[(4-methylmorpholin-2-yl)methyl]oxy}-6-(methyloxy)quinazolin-4-amine | A | B | A | — | A | B |
| 165 | N-(3,4-dichlorophenyl)-7-{[(1,4-diethylpiperazin-2-yl)methyl]oxy}-6-(methyloxy)quinazoline-4-amine | B | B | C | — | A | — |
| 166 | 4-({(4-[(4-bromo-2-fluorophenyl)amino]-6-(methyloxy)quinazolin-7-yl]oxy}methyl)-N'-cyanopiperidine-1-carboximidamide | B | B | A | — | A | — |
| 167 | N-(3,4-dichlorophenyl)-6-(methyloxy)-7-({[4-(methylsulfonyl)morpholin-2-yl]methyl}oxy)quinazolin-4-amine | A | A | B | — | A | A |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 168 | N-(3,4-dichlorophenyl)-6-(methyloxy)-7-[({4-[(phenylmethyl)sulfonyl]morpholin-2-yl}methyl)oxy)quinazolin-4-amine | B | B | B | — | A | — |
| 169 | N-(3,4-dichlorophenyl)-7-[({4-[(4-fluorophenyl)sulfonyl]morpholin-2-yl}methyl)oxy]-6-(methyloxy)quinazolin-4-amine | B | C | B | — | A | — |
| 170 | N-(3,4-dichlorophenyl)-7-({[4-(ethylsulfonyl)morpholin-2-yl]methyl}oxy)-6-(methyloxy)quinazolin-4-amine | A | A | B | — | A | A |
| 171 | N-(3,4-dichlorophenyl)-6-(methyloxy)-7-({[4-(phenylsulfonyl)morpholin-2-yl]methyl}oxy)quinazolin-4-amine | B | C | B | — | A | — |
| 172 | 7-[({4-[(3-chloropropyl)sulfonyl]morpholin-2-yl}methyl)oxy]-N-(3,4-dichlorophenyl)-6-(methyloxy)quinazolin-4-amine | A | B | B | — | A | B |
| 173 | 7-({[4-(butylsulfonyl)morpholin-2-yl]methyl}oxy)-N-(3,4-dichlorophenyl)-6-(methyloxy)quinazolin-4-amine | B | B | B | — | A | — |
| 174 | N-(3,4-dichlorophenyl)-6-(methyloxy)-7-[({4-[(4-methylphenyl)sulfonyl]morpholin-2-yl}methyl)oxy]quinazolin-4-amine | C | C | B | — | A | — |
| 175 | N-(3,4-dichlorophenyl)-7-[({4-[(3,5-dimethylisoxazol-4-yl)carbonyl]morpholin-2-yl}methyl)oxy]-6-(methyloxy)quinazolin-4-amine | A | B | B | — | A | A |
| 176 | N-(3,4-dichlorophenyl)-6-(methyloxy)-7-{[(4-{[3 (methyloxy)phenyl]acetyl}morpholin-2-yl)methyl]oxy}quinazolin-4-amine | B | B | B | — | A | — |
| 177 | N-(3,4-dichlorophenyl)-6-(methyloxy)-7-({[4-(2-methylpentanoyl)morpholin-2-yl]methyl}oxy)quinazolin-4-amine | B | B | B | — | A | — |
| 178 | 7-[({4-[(4-butylphenyl)carbonyl]morpholin-2-yl}methyloxy-N-(3,4-dichlorophenyl)-6-(methyloxy)quinazolin-4-amine | C | C | C | — | A | — |
| 179 | 7-[({4-[(4-chlorophenyl)acetyl]morpholin-2-yl}methyl)oxy]-N-(3,4-dichlorophenyl)-6-(methyloxy)quinazolin-4-amine | B | C | B | — | A | — |
| 180 | N-(3,4-dichlorophenyl)-6-(methyloxy)-7-({[4-(2-propylpentanoyl)morpholin-2-yl]methyl}oxy)quinazolin-4-amine | B | B | B | — | A | — |
| 181 | N-(3,4-dichlorophenyl)-6-(methyloxy)-7-({[4-(4-methylpentanoyl)morpholin-2-yl]methyl}oxy)quinazolin-4-amine | B | B | B | — | A | — |
| 182 | N-(3,4-dichlorophenyl)-7-[({4-[(2,5-difluorophenyl)carbonyl]morpholin-2-yl}methyl)oxy]-6-(methyloxy)quinazolin-4-amine | B | B | B | — | A | — |
| 183 | 7-({[4-(cyclopentylcarbonyl)morpholin-2-yl]methyl}oxy)-N-(3,4-dichlorophenyl)-6-(methyloxy)quinazolin-4-amine | A | B | B | — | A | A |
| 184 | N-(3,4-dichlorophenyl)-6-(methyloxy)-7-({[4-(2-phenylbutanoyl)morpholin-2-yl]methyl}oxy)quinazolin-4-amine | B | C | B | — | A | — |
| 185 | N-(3,4-dichlorophenyl)-6-(methyloxy)-7-[({4-[(2,3,6-trifluorophenyl)carbonyl]morpholin-2-yl}methyl)oxy]quinazolin-4-amine | B | B | B | — | A | — |
| 186 | N-(3,4-dichlorophenyl)-7-({[4-(furan-3-ylcarbonyl)morpholin-2-yl]methyl}oxy)-6-(methyloxy)quinazolin-4-amine | A | B | B | — | A | — |
| 187 | N-(3,4-dichlorophenyl)-6-(methyloxy)-7-{[(4-propanoylmorpholin-2-yl)methyl]oxy}quinazolin-4-amine | A | B | B | — | A | A |
| 188 | N-(3,4-dichlorophenyl)-7-{[(4-hexanoylmorpholin-2-yl)methyl]oxy}-6-(methyloxy)quinazolin-4-amine | B | B | B | — | A | — |
| 189 | N-(3,4-dichlorophenyl)-7-({[4-(2-ethylhexanoyl)morpholin-2-yl]methyl}oxy)-6-(methyloxy)quinazolin-4-amine | B | B | B | — | A | — |
| 190 | N-(3,4-dichlorophenyl)-6-(methyloxy)-7-({[4-(3-phenylpropanoyl)morpholin-2-yl]methyl}oxy)quinazolin-4-amine | B | B | B | — | A | — |
| 191 | N-(3,4-dichlorophenyl)-7-({[4-(2,2-dimethylpropanoyl)morpholin 2-yl]methyl}oxy)-6-(methyloxy)quinazolin-4-amine | B | B | B | — | A | — |
| 192 | N-(3,4-dichlorophenyl)-6-(methyloxy)-7-({[4-(naphthalen-1-ylcarbonyl)morpholin-2-yl]methyl}oxy)quinazolin-4-amine | B | C | B | — | A | — |
| 193 | 7-[({4-[(2-chloropyridin-3-yl)carbonyl]morpholin-2-yl}methyl)oxy]-N-(3,4-dichlorophenyl)-6-(methyloxy)quinazolin-4-amine | A | B | A | — | A | A |
| 194 | 7-[({4-[(6-chloropyridin-3-yl)carbonyl]morpholin-2-yl}methyl)oxy]-N-(3,4-dichlorophenyl)-6-(methyloxy)quinazolin-4-amine | A | B | B | — | A | — |
| 195 | 7-({[4-(1,3-benzodioxol-5-ylcarbonyl)morpholin-2-yl]methyl}oxy)-N-(3,4-dichlorophenyl)-6-(methyloxy)quinazolin-4-amine | B | B | B | — | A | — |
| 196 | N-(3,4-dichlorophenyl)-6-[(1-methylethyl)oxy]-7-[(morpholin-2-yl)methyl)oxy]quinazolin-4-amine | A | A | A | — | A | A |
| 197 | N-(3,4-dichlorophenyl)-6-{[2-(methyloxy)ethyl]oxy}-7-[(morpholin-2-ylmethyl)oxy]quinazolin-4-amine | A | B | A | — | A | — |
| 198 | N-(3,4-dichlorophenyl)-6-(ethyloxy)-7-[(morpholin-2-ylmethyl)oxy]quinazolin-4-amine | A | A | A | — | A | A |
| 199 | N-(3,4-dichlorophenyl)-6-(ethyloxy)-7-{[(4-methylmorpholin-2-yl)methyl]oxy}quinazolin-4-amine | A | A | A | — | A | — |
| 200 | N-(4-bromo-2-methylphenyl)-7-{[(4-methylmorpholin-2-yl)methyl]oxy}-6-(methyloxy)quinazolin-4-amine | B | B | B | — | A | — |
| 201 | N-(4-chloro-3-methylphenyl)-7-{[(4-methylmorpholin-2-yl)methyl]oxy}-6-(methyloxy)quinazolin-4-amine | B | B | B | — | A | — |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 202 | N'-cyano-2-({[4-[(3,4-dichlorophenyl)amino]-6-(methyloxy)quinazolin-7-yl]oxy}methyl)-N-methylmorpholine-4-carboximidamide | A | B | B | — | A | A |
| 203 | N-(4-bromo-3-chlorophenyl)-7-{[(4-methylmorpholin-2-yl)methyl]oxy}-6-(methyloxy)quinazolin-4-amine | A | A | A | — | A | B |
| 204 | N-(3,4-dichlorophenyl)-6-[(1-methylethyl)oxy]-7-([[(4-methylmorpholin-2-yl)methyl]oxy}quinazolin-4-amine | A | A | A | — | A | A |
| 205 | N-(3,4-dichlorophenyl)-7-{[(4-methylmorpholin-2-yl)methyl]oxy}-6-([2-(methyloxy)ethyl]oxy)quinazolin-4-amine | A | B | B | — | A | — |
| 206 | N-(4-bromo-2-chlorophenyl)-7-{[(4-methylmorpholin-2-yl)methyl]oxy}-6-(methyloxy)quinazolin-4-amine | B | B | B | — | A | — |
| 207 | 7-{[(4-acetyl-1,4-oxazepan-2-yl)methyl]oxy}-N-(3,4-dichlorophenyl)-6-(methyloxy)quinazolin-4-amine | A | B | B | — | A | A |
| 208 | 4-[(3,4-dichlorophenyl)amino]-7-{[(4-methylmorpholin-2-yl)methyl]oxy}quinazolin-6-ol | B | B | B | — | A | — |
| 209 | N-(3-bromo-4-chlorophenyl)-7-{[(4-methylmorpholin-2-yl)methyl]oxy}-6-(methyloxy)quinazolin-4-amine | A | B | B | — | A | — |
| 210 | 3-[2-({[4-[(3,4-dichlorophenyl)amino]-6-(methyloxy)quinazolin-7-yl]oxy}methyl)morpholin-4-yl]-3-oxopropanoic acid | A | A | A | — | A | — |
| 211 | methyl 4-[2-({[4-[(3,4-dichlorophenyl)amino]-6-(methyloxy)quinazolin-7-yl]oxy}methyl)morpholin-4-yl]-4-oxobutanoate | B | B | B | — | A | — |
| 212 | N-(3,4-dichlorophenyl)-7-{[(4-methylmorpholin-3-yl)methyl]oxy}-6-(methyloxy)quinazolin-4-amine | B | B | C | — | A | — |
| 213 | N-(3-bromo-2-chlorophenyl)-7-{[(4-methylmorpholin-2-yl)methyl]oxy}-6-(methyloxy)quinazolin-4-amine | A | B | B | — | A | — |
| 214 | N'-cyano-2-({[4-[(3,4-dichlorophenyl)amino]-6-(methyloxy)quinazolin-7-yl]oxy}methyl)-N-[2-(methyloxy)ethyl]morpholine-4-carboximidamide | A | B | B | — | A | — |
| 215 | N'-cyano-2-({[4-[(3,4-dichlorophenyl)amino]-6-(methyloxy)quinazolin-7-yl]oxy}methyl)-N-ethylmorpholine-4-carboximidamide | A | B | B | — | A | A |
| 216 | [(1E)-[2-({(4-[(3,4-dichlorophenyl)amino]-6-(methyloxy)quinazolin-7-yl]oxy}methyl)morpholin-4-yl](piperidin-1-yl)methylidene]cyanamide | A | B | B | — | A | A |
| 217 | [(1E)-[2-({[4-[(3,4-dichlorophenyl)amino]-6-(methyloxy)quinazolin-7-yl]oxy}methyl)morpholin-4-yl](pyrrolidin-1-yl)methylidene]cyanamide | A | A | B | — | A | A |
| 218 | [(1E)-[2-({[4-[(3,4-dichlorophenyl)amino]-6-(methyloxy)quinazolin-7-yl]oxy}methyl)morpholin-4-yl](4-methylpiperazin-1-yl)methylidene]cyananide | A | B | A | — | A | — |
| 219 | N-(3,4-dichlorophenyl)-7-{[(6-ethyl-4,6-dimethylmorpholin-2-yl)methyl]oxy}-6-(methyloxy)quinazolin-4-amine | B | B | B | — | A | — |
| 220 | N-(4-bromo-3-methylphenyl)-7-{[(4-methylmorpholin-2-yl)methyl]oxy}-6-(methyloxy)quinazolin-4-amine | B | B | B | — | A | B |
| 221 | N-(3,4-dichlorophenyl)-7-{[(6,6-dimethylmorpholin-2-yl)methyl]oxy}-6-(methyloxy)quinazolin-4-amine | B | A | A | — | A | B |
| 222 | N-(3,4-dichlorophenyl)-6-(methyloxy)-7-{[(4,6,6-trimethylmorpholin-2-yl)methyl]oxy}quinazolin-4-amine | B | B | B | — | A | B |
| 223 | N-(3,4-dichlorophenyl)-7-{[2-(5,5-dimethylmorpholin-2-yl)ethyl]oxy}-6-(methyloxy)quinazolin-4-amine | B | B | B | — | A | B |
| 224 | N-(3,4-dichlorophenyl)-6-(methyloxy)-7-{[2-(4,5,5-trimethylmorpholin-2-yl)ethyl]oxy}quinazolin-4-amine | B | B | B | — | A | B |
| 225 | 1,1-dimethylethyl 2-(2-{[4-[(3,4-dichlorophenyl)amino]-6-(methyloxy)quinazolin-7-yl]oxy}ethyl)-5,5-dimethylmorpholine-4-carboxylate | C | C | C | — | A | C |
| 226 | N-(3,4-dichlorophenyl)-6-(methyloxy)-7-{[(4,5,5-trimethylmorpholin-2-yl)methyl]oxy}quinazolin-4-amine | A | B | A | — | A | A |
| 227 | N-(4-bromo-2,3-dichlorophenyl)-7-{[(4-methylmorpholin-2-yl)methyl]oxy}-6-(methyloxy)quinazolin-4-amine | A | B | B | — | A | B |
| 228 | N-(4,5-dichloro-2-fluorophenyl)-7-{[(4-methylmorpholin-2-yl)methyl]oxy}-6-(methyloxy)quinazolin-4-amine | A | B | B | — | A | B |
| 229 | N-(3,4-dichlorophenyl)-6-(methyloxy)-7-{[2-(4,6,6-trimethylmorpholin-2-yl)ethyl]oxy}quinazolin-4-amine | B | C | B | — | A | B |
| 230 | N-(4-bromo-2,3-difluorophenyl)-7-{[(4-methylmorpholin-2-yl)methyl]oxy}-6-(methyloxy)quinazolin-4-amine | B | B | A | — | A | B |
| 231 | N-(4-bromo-2,5-difluorophenyl)-7-{[(4-methylmorpholin-2-yl)methyl]oxy}-6-(methyloxy)quinazolin-4-amine | B | B | A | — | A | B |
| 232 | N-(4-bromo-3,5-difluorophenyl)-7-{[(4-methylmorpholin-2-yl)methyl]oxy}-6-(methyloxy)quinazolin-4-amine | B | B | A | — | A | B |
| 233 | N-(3,4-dichloro-2-methylphenyl)-7-{[(4-methylmorpholin-2-yl)methyl]oxy}-6-(methyloxy)quinazolin-4-amine | A | B | B | — | A | C |
| 234 | N-(4-bromo-3-chloro-2-methylphenyl)-7-{[(4-methylmorpholin-2-yl)methyl]oxy}-6-(methyloxy)quinazolin-4-amine | B | B | B | — | A | B |
| 2335 | N-(4-bromo-5-chloro-2-fluorophenyl)-7-{[(4-methylmorpholin-2-yl)methyl]oxy}-6-(methyloxy)quinazolin-4-amine | A | B | A | — | A | B |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 236 | N-(4-bromo-3-chloro-2-fluorophenyl)-7-{[(4-methylmorpholin-2-yl)methyl]oxy}-6-(methyloxy)quinazolin-4-amine | A | A | A | — | A | A |
| 237 | N-(3,4-dichloro-2-fluorophenyl)-7-{[(4-methylmorpholin-2-yl)methyl]oxy}-6-(methyloxy)quinazolin-4-amine | A | A | A | — | A | A |
| 238 | N-(3-chloro-2,4-difluorophenyl)-7-{[(4-methylmorpholin-2-yl)methyl]oxy}-6-(methyloxy)quinazolin-4-amine | A | A | A | — | A | A |
| 239 | N-(2,3-dichloro-4-methylphenyl)-7-{[(4-methylmorpholin-2-yl)methyl]oxy}-6-(methyloxy)quinazolin-4-amine | B | B | A | — | A | C |
| 240 | 6-({[4-[(3,4-dichlorophenyl)amino]-6-(methyloxy)quinazolin-7-yl]oxy}methyl)-3,3,4-trimethylmorpholin-2-one | A | B | B | — | A | B |
| 241 | N-(4-bromo-2,3-dichlorophenyl)-6-(methyloxy)-7-{[(4,5,5-trimethylmorpholin-2-yl)methyl]oxy}quinazolin-4-amine | A | A | B | — | A | B |
| 242 | N-(4-bromo-5-chloro-2-fluorophenyl)-6-(methyloxy)-7-{[(4,5,5-trimethylmorpholin-2-yl)methyl]oxy}qulnazolin-4-amine | A | A | A | — | A | B |
| 243 | N-(4-5-dichloro-2-fluorophenyl)-6-(methyloxy)-7-{[(4,5,5-trimethylmorpholin-2-yl)methyl]oxy}quinazolin-4-amine | A | A | A | — | A | A |
| 244 | N-(3,4-dichloro-2-fluorophenyl)-6-(methyloxy)-7-{[(4,5,5-trimethylmorpholin-2-yl)methyloxy}quinazolin-4-amine | A | A | A | — | A | A |
| 245 | N-(4-bromo-3-chloro-2-fluorophenyl)-6-(methyloxy)-7-{[(4,5,5-trimethylmorpholin-2-yl)methyl]oxy}quinazolin-4-amine | A | A | A | — | A | A |
| 246 | N-(3-chloro-2,4-difluorophenyl)-6-(methyloxy)-7-{[(4,5,5-trimethylmorpholin-2-yl)methyl]oxy}quinazolin-4-amine | A | A | B | — | A | B |
| 247 | (6S)-6-({[4-[(4-bromo-3-chloro-2-fluorophenyl)amino]-6-(methyloxy)quinazolin-7-yl]oxy}methyl)-4-methylpiperazin-2-one | B | B | B | — | A | B |
| 248 | (6S)-6-({[4-[(3,4-dichloro-2-fluorophenyl)amino]-6-(methyloxy)quinazolin-7-yl]oxy}methyl)-4-methylpiperazin-2-one | B | B | B | — | A | B |
| 249 | (6S)-6-({[4-[(4-bromo-3-chloro-2-fluorophenyl)amino]-6-(methyloxy)quinazolin-7-yl]oxy}methyl)-1,4-dimethylpiperazin-2-one | B | B | B | — | A | C |
| 250 | (6S)-6-({[4-[(3,4-dichloro-2-fluorophenyl)amino]-6-(methyloxy)quinazolin-7-yl]oxy}methyl)-1,4-dimethylpiperazin-2-one | B | B | B | — | A | C |
| 251 | N-(4-bromo-3-chlorophenyl)-7-{[(3a'[,4R,6'S,6a'R)-2,2-dimethyltetrahydrospiro[1,3-dioxolane-4,3'-furo[3,2-b]furan]-6'-yl]oxy}-6-(methyloxy)quinazolin-4-amine | B | C | C | — | A | C |
| 252 | 1,4:3,6-dianhydro-2-O-[4-[(4-bromo-3-chlorophenyl)amino]-6-(methyloxy)quinazolin-7-yl]-5-O-methyl-5-C-[(methyloxy)methyl]-D-glucitol | B | C | C | — | A | C |
| 253 | 1,4:3,6-dianhydro-2-O-[4-[(4-bromo-3-chlorophenyl)amino]-6-(methyloxy)quinazolin-7-yl]-5-O-(methylsulfonyl)-D-glucitol | C | C | C | — | A | C |
| 254 | 1,4:3,6-dianhydro-2-O-[4-[(4-bromo-3-chlorophenyl)amino]-6-(methyloxy)quinazolin-7-yl]-D-glucitol | B | C | C | — | A | B |
| 255 | 1,4:3,6-dianhydro-2-O-[4-[(4-bromo-3-chlorophenyl)amino]-6-(methyloxy)quinazolin-7-yl]-5-S-methyl-5-thio-L-iditol | B | C | C | — | A | C |
| 256 | 1,4:3,6-dianhydro-5-O-[4-[(4-bromo-3-chlorophenyl)amino]-6-(methyloxy)quinazolin-7-yl]-2-deoxy-2-morpholin-4-yl-L-iditol | B | C | C | — | A | C |
| 257 | 1,4:3,6-dianhydro-5-O-[4-[(4-bromo-3-chlorophenyl)amino]-6-14-[(4-bromo-3-chlorophenyl)amino]-6-(methyloxy)quinazolin-7-yl]-2-deoxy-2-(4-methylpiperazin-1-yl)-L-iditol | B | C | C | — | A | C |
| 258 | 1,4:3,6-dianhydro-5-O-[4-[(4-bromo-3-chlorophenyl)amino]-6-(methyloxy)quinazolin-7-yl]-2-deoxy-2-pyrrolidin-1-yl-L-iditol | B | C | C | — | A | C |
| 259 | 2-O-acetyl-1,4:3,6-dianhydro-5-O-[4-[(4-bromo-3-chlorophenyl)amino]-6-(methyloxy)quinazolin-7-yl]-L-iditol | B | C | C | — | A | C |
| 260 | 1,4:3,6-dianhydro-2-O-[4-[(4-bromo-3-chlorophenyl)amino]-6-(methyloxy)quinazolin-7-yl]-L-iditol | B | C | C | — | A | B |
| 261 | 1,4:3,6-dianhydro-5-O-[4-[(4-bromo-3-chlorophenyl)amino]-6-(methyloxy)quinazolin-7-yl]-2-deoxy-2-(methylsulfonyl)-L-iditol | B | C | C | — | A | B |
| 262 | 2-amino-1,4:3,6-dianhydro-5-O-[4-[(4-bromo-3-chlorophenyl)amino]-6-(methyloxy)quinazolin-7-yl]-2-deoxy-L-iditol | B | C | C | — | A | C |
| 263 | 1,4:3,6-dianhydro-5-O-[4-[(4-bromo-3-chlorophenyl)amino]-6-(methyloxy)quinazolin-7-yl]-2-deoxy-2-(dimethylamino)-L-iditol | B | C | C | — | A | C |
| 264 | 1,4:3,6-dianhydro-5-O-[4-[(4-bromo-3-chlorophenyl)amino]-6-(methyloxy)quinazolin-7-yl]-2-deoxy-2-(dimethylamino)-L-iditol | B | C | B | — | A | C |
| 265 | 1,4:3,6-dianhydro-5-O-[4-[(4-bromo-3-chlorophenyl)amino]-6-(methyloxy)quinazolin-7-yl]-2-deoxy-2-piperidin-1-yl-L-iditol | B | C | C | — | A | C |
| 266 | 2-(acetylamino)-1,4:3,6-dianhydro-5-O-[4-[(4-bromo-3-chlorophenyl)amino]-6-(methyloxy)quinazolin-7-yl]-2-deoxy-L-iditol | B | C | C | — | A | C |
| 267 | 1,4:3,6-dianhydro-2-O-[4-[(4-bromo-3-chlorophenyl)amino]-6-(methyloxy)quinazolin-7-yl]-2-deoxy-2-[methylsulfonyl)amino]-glucitol | C | C | C | — | A | B |
| 268 | 1,4:3,6-dianhydro-5-O-[4-[(4-bromo-3-chlorophenyl)amino]-6-(methyloxy)quinazolin-7-yl]-2-deoxy-2-[(methylsulfonyl)amino]-L-iditol | B | C | C | — | A | B |

TABLE 6-continued

| Entry | Name | EphB4 IC$_{50}$ | EphA2 IC$_{50}$ | KDR IC$_{50}$ | Flt-1 IC$_{50}$ | EGFR IC$_{50}$ | ErbB2 IC$_{50}$ |
|---|---|---|---|---|---|---|---|
| 269 | N-(4-bromo-3-chlorophenyl)-6-(methyloxy)-7-[(1-methylpyrrolidin-3-yl)oxy]quinazolin-4-amine | B | C | B | — | A | C |
| 270 | N-(4-bromo-3-chlorophenyl)-6-(methyloxy)-7-[(3R)-tetrahydrofuran-3-yloxy]quinazolin-4-amine | B | C | B | — | A | B |
| 271 | 1,4:3,6-dianhydro-5-O-[4-[(3-chloro-2-fluorophenyl)amino]-6-(methyloxy)quinazolin-7-yl]-2-deoxy-2-fluoro-L-iditol | B | C | C | — | A | B |
| 272 | N-(4-bromo-3-chlorophenyl)-6-(methyloxy)-7-{(3S,4R)-4-(methyloxy)tetrahydrofuran-3-yl]oxy}quinazolin-4-amine | B | C | C | — | A | B |
| 273 | 1,4:3,6-dianhydro-2-deoxy-2-fluoro-5-O-(6-(methylo,-)-4-{[4(4-methylpiperazin-1-yl)phenyl]amino}quinazolin-7-yl)-L-imiditol | C | C | C | — | A | C |
| 274 | 1,4:3,6-dianhydro-2-deoxy-2-fluoro-5-O-[4-{[3-fluoro-4-(4-methylpiperazin-1-yl)phenyl]amino}-6-(methyloxy)quinazolin-7-yl]-L-iditol | C | C | C | — | A | C |
| 275 | 1,4:3,6-dianhydro-2-deoxy-5-O-[4-{[23-dichloro-4-(4-methylpiperazin-1-yl)phenyl]amino}-6-(methyloxy)quinazolin-7-yl]-2-fluoro-L-iditol | C | C | C | — | A | C |
| 276 | 1,4:3,6-dianhydro-2-deoxy-5-O-[4-{[34-dichloro-2-(4-methylpiperazin-1-yl)phenyl]amino}-6-(methyloxy)quinazolin-7-yl]-2-fluoro-L-iditol | C | C | C | — | A | C |
| 277 | 1,4:3,6-dianhydro-2-O-[4-[(4-bromo-3-chlorophenyl)amino]-6-(methyloxy)quinazolin-7-yl]-5-C-(trifluoromethyl)-D-glucitol | B | C | C | — | A | B |

What is claimed is:

1. A compound of Formula I,

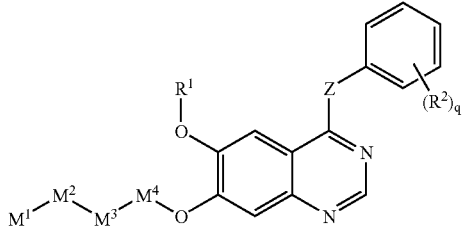

I or a single stereoisomer, racemate, enantiomer, or diastereomer, thereof and optionally as a pharmaceutically acceptable salt thereof, wherein, $R^1$ is methyl;

$R^2$ is selected from halogen, trihalomethyl, —CN, —NH$_2$, —NO$_2$, —OR$^3$, —N(R$^3$)R$^4$, —S(O)$_{0-2}$R$^4$, —SO$_2$N(R$^3$)R$^4$, —CO$_2$R$^3$, —C(=O)N(R$^3$)R$^4$, —N(R$^3$)SO$_2$R$^4$, —N(R$^3$)C(=O)R$^3$, —N(R$^3$)CO$_2$R$^4$, —C(=O)R$^3$, lower alkyl, lower alkenyl, and lower alkynyl;

$R^3$ is —H or R$^4$;

$R^4$ is selected from lower alkyl; lower alkyl substituted with one, two, or three halogen; aryl; aryl substituted with one, two, or three halogen; and unsubstituted lower arylalkyl; or $R^3$ and $R^4$, when taken together with a common nitrogen to which they are attached, form morpholinyl, pyrrolidinyl, piperidinyl, or piperazinyl optionally substituted by one, two, or three alkyl;

q is 0, 1, 2, 3, 4, or 5;

Z is —NR$^5$—;

$R^5$ is —H;

$M^1$-$M^2$-$M^3$-$M^4$- together are according to formula II:

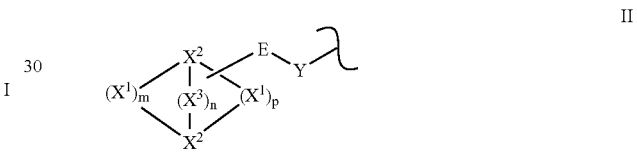

II wherein $X^1$, $X^2$, and optionally $X^3$, represent the atoms of a saturated bridged ring system, said saturated bridged ring system containing up to three annular heteroatoms represented by any of $X^1$, $X^2$, and $X^3$; wherein, each $X^1$ is independently selected from —C(R$^6$)R$^7$—, —O—, —S(O)$_{0-2}$—, and —NR$^8$—;

each $X^2$ is independently a bridgehead methine optionally substituted with R$^6$, or a bridgehead nitrogen;

each $X^3$ is independently selected from —C(R$^6$)R$^7$—, —O—, —S(O)$_{0-2}$—, and —NR$^8$—;

provided, for $X^1$, $X^2$, and $X^3$, there are no nitrogen-nitrogen annular bonds nor geminal di-nitrogen substitutions;

E is absent;

Y is —CH$_2$— provided that Y is not directly attached to any heteroatom represented by $X^1$, $X^2$ or $X^3$;

m and p are each independently 1, 2, 3, or 4;

n is 0, 1, or 2, when n is zero, then there is a direct single bond between the two bridgehead $X^2$'s;

$R^6$ and $R^7$ are each independently selected from —H, halogen, trihalomethyl, —CN, —NH$_2$, —NO$_2$, —OR$^3$, —N(R$^3$)R$^4$, —S(O)$_{0-2}$R$^4$, —SO$_2$N(R$^3$)R$^4$, —CO$_2$R$^3$, —C(O)N(R$^3$)R$^4$, —N(R$^3$)SO$_2$R$^4$, —N(R$^3$)C(O)R$^3$, —NCO$_2$R$^3$, —C(O)R$^3$, lower alkyl, aryl, and unsubstituted lower arylalkyl; or $R^6$ and $R^7$, when taken together are oxo; or $R^6$ and $R^7$, when taken together with a common carbon to which they are attached, form a three- to seven-membered spirocyclyl optionally containing at least one additional heteroatom selected from N, O, S, and P and wherein the spirocyclic ring is optionally substituted with one or two alkyl; and R$^8$ is selected from R$^3$, —SO$_2$N(R$^3$)R$^4$, —CO$_2$R$^3$, —C(O)N(R$^3$)R$^4$, —SO$_2$R$^4$, and —C(O)R$^3$;

with the proviso that when Y is a C$_{1-3}$ alkylene linker, E is absent, Z is —NH— or —N(CH$_3$)—, R$^1$ is a C$_{1-3}$ alkyl, R$^2$ is —H or halogen, n=0, and the atoms X$^1$ of one bridge of the saturated bridged ring system, when combined with both bridgehead atoms, X$^2$, of the saturated bridged ring system, represent:

either a pyrrolidine ring or a piperidine ring, and any atom, X$^1$ or X$^2$, of either of said pyrrolidine ring or said piperidine ring is attached to Y; then the other bridge of said saturated bridged ring system cannot be any one of —OC(O)CH$_2$—, —CH$_2$OC(O)—, —OC(O)CH$_2$CH$_2$—, —CH$_2$OC(O)CH$_2$—, —CH$_2$CH$_2$OC(O)—, —OC(O)CH$_2$NH—, —OC(O)CH$_2$N(C$_{1-4}$alkyl)-, and —OC(O)CH$_2$O—; and either a piperazine ring or a 4-(C$_{1-4}$ alkyl)-piperazine ring, and any atom, X$^1$ or X$^2$, of either of said piperazine ring or said 4-(C$_{1-4}$ alkyl)-piperazine ring is attached to Y; then the other bridge of said saturated bridged ring system, only when attached via the 2- and the 3-position of either of said piperazine ring or said 4-(C$_{1-4}$ alkyl)-piperazine ring, cannot be one of —CH$_2$OC(O)CH$_2$—, —CH$_2$CH$_2$OC(O)—, and either of the two aforementioned bridges substituted by one or two C$_{1-2}$ alkyl groups; and a piperazine ring, and any atom, X$^1$ or X$^2$, of said piperazine ring is attached to Y; then the other bridge of said saturated bridged ring system, only when attached via the 3- and the 4-position of said piperazine ring, cannot be —C(O)OCH$_2$CH$_2$—, —CH$_2$OC(O)CH$_2$—, —C(O)OCH$_2$CH$_2$— substituted with one or two C$_{1-2}$ alkyl groups, or —CH$_2$OC(O)CH$_2$— substituted with one or two C$_{1-2}$ alkyl groups (but only when the four above mentioned bridges are attached to the 3-position of said piperazine ring via their left-hand end as depicted above); and a 2-oxomorpholine ring, said 2-oxomorpholine ring attached to Y via its 4-position; then the other bridge of said saturated bridged ring system, only when attached via the 5- and the 6-position of said 2-oxomorpholine ring, cannot be one of —(CH$_2$)$_g$—, —CH$_2$WCH$_2$—, —CH$_2$WCH$_2$CH$_2$—, and —CH$_2$CH$_2$WCH$_2$—, wherein W is —O—, —S(O)$_{0-2}$—, —NH—, or —N(C$_{1-4}$ alkyl)- and wherein g is 2, 3, or 4.

2. The compound according to claim 1, wherein R$^2$ is selected from halogen, trihalomethyl, —CN, —NO$_2$, —OR$^3$, and lower alkyl; or a single stereoisomer, racemate, enantiomer, or diastereomer, thereof and optionally as a pharmaceutically acceptable salt thereof.

3. The compound according to claim 2, wherein the saturated bridged ring system has a geometry selected from the group consisting of [4.4.0], [4.3.0], [4.2.0], [4.1.0], [3.3.0], [3.2.0], [3.1.0], [3.3.3], [3.3.2], [3.3.1], [3.2.2], [3.2.1], [2.2.2], and [2.2.1]; or a single stereoisomer, racemate, enantiomer, or diastereomer, thereof and optionally as a pharmaceutically acceptable salt thereof.

4. The compound according to claim 3, wherein q is 1, 2, or 3; or a single stereoisomer, racemate, enantiomer, or diastereomer, thereof and optionally as a pharmaceutically acceptable salt thereof.

5. The compound according to claim 4, wherein the saturated bridged ring system has a geometry selected from the group consisting of [4.4.0], [4.3.0], [4.2.0], [4.1.0], [3.3.0], [3.2.0], and [3.1.0]; or a single stereoisomer, racemate, enantiomer, diastereomer, thereof and optionally as a pharmaceutically acceptable salt thereof.

6. The compound according to claim 5, wherein said saturated bridged ring system contains one or two annular nitrogens, said one or two annular nitrogens are selected from —NR$^8$—, when X$^1$, and a bridgehead nitrogen, when X$^2$; or a single stereoisomer, racemate, enantiomer, or diastereomer, thereof and optionally as a pharmaceutically acceptable salt thereof.

7. The compound according to claim 6 wherein said saturated bridged ring system is according to formula III;

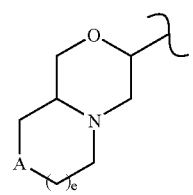

III wherein A is selected from —O—, —S(O)$_{0-2}$—, —NR$^8$—, and absent; and e is 0 or 1; or a single stereoisomer, racemate, enantiomer, or diastereomer, thereof and optionally as a pharmaceutically acceptable salt thereof.

8. The compound according to claim 7 wherein A is selected from —NR$^8$—, wherein R$^8$ is selected from —H, lower alkyl, —CO$_2$R$^3$, —C(O)N(R$^3$)R$^4$, —SO$_2$R$^4$, and —C(O)R$^3$; —O—; and absent; or a single stereoisomer, racemate, enantiomer, or diastereomer, thereof and optionally as a pharmaceutically acceptable salt thereof.

9. The compound according to claim 8, wherein

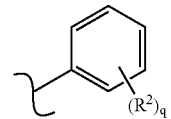

of I is selected from:

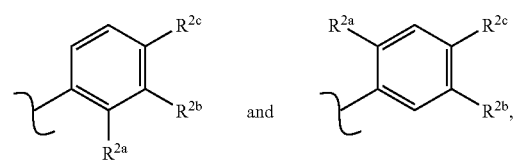

wherein R$^{2a}$, R$^{2b}$, and R$^{2c}$ are each independently selected from F, Cl, and Br; or a single stereoisomer, racemate, enantiomer, or diastereomer, thereof and optionally as a pharmaceutically acceptable salt thereof.

10. The compound according to claim 9, wherein R$^{2a}$ is F, R$^{2b}$ is Cl, and R$^{2c}$ is either Cl or Br; or a single stereoisomer, racemate, enantiomer, or diastereomer, thereof and optionally as a pharmaceutically acceptable salt thereof.

11. The compound according to claim 6, wherein said saturated bridged ring system is according to either formula V or formula VI;

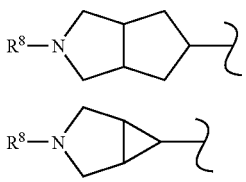

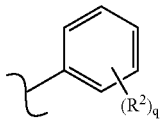

wherein R⁸ is selected from —H, lower alkyl, —CO₂R³, —C(O)N(R³)R⁴, —SO₂R⁴, and —C(O)R³; or a single stereoisomer, racemate, enantiomer, or diastereomer, thereof and optionally as a pharmaceutically acceptable salt thereof.

12. The compound according to claim 11, wherein

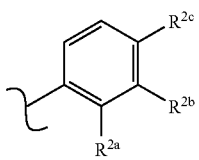

of I is selected from:

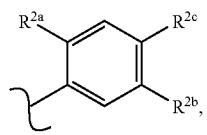

wherein $R^{2a}$, $R^{2b}$, and $R^{2c}$ are each independently selected from F, Cl, and Br; or a single stereoisomer, racemate, enantiomer, or diastereomer, thereof and optionally as a pharmaceutically acceptable salt thereof.

13. The compound according to claim 12, wherein $R^{2a}$ is F, $R^{2b}$ is Cl, and $R^{2c}$ is either Cl or Br; or a single stereoisomer, racemate, enantiomer, or diastereomer, thereof and optionally as a pharmaceutically acceptable salt thereof.

14. The compound according to claim 13, wherein R⁸ is methyl or ethyl; or a single stereoisomer, racemate, enantiomer, or diastereomer, thereof and optionally as a pharmaceutically acceptable salt thereof.

15. The compound according to claim 6, wherein said saturated bridged ring system is according to formula VII;

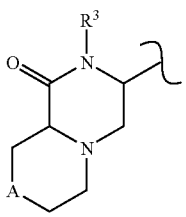

wherein A is selected from —O—, —S(O)₀₋₂—, —NR⁸—, —CR⁶R⁷—, and absent; or a single stereoisomer, racemate, enantiomer, or diastereomer, thereof and optionally as a pharmaceutically acceptable salt thereof.

16. The compound according to claim 15, wherein R³ is selected from —H and alkyl; or a single stereoisomer, racemate, enantiomer, or diastereomer, thereof and optionally as a pharmaceutically acceptable salt thereof.

17. The compound according to claim 16 wherein A is either —C(R⁶)R⁷— or absent; or a single stereoisomer, racemate, enantiomer, or diastereomer, thereof and optionally as a pharmaceutically acceptable salt thereof.

18. The compound according to claim 17, wherein A is either —CH₂— or absent; or a single stereoisomer, racemate, enantiomer, or diastereomer, thereof and optionally as a pharmaceutically acceptable salt thereof.

19. The compound according to claim 18, wherein q is 3; or a single stereoisomer, racemate, enantiomer, or diastereomer, thereof and optionally as a pharmaceutically acceptable salt thereof.

20. The compound according to claim 19, wherein

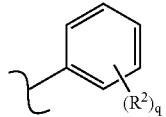

of I is selected from:

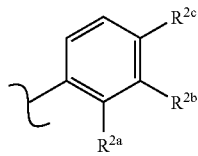

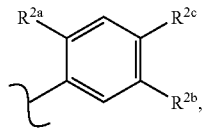

wherein $R^{2a}$, $R^{2b}$, and $R^{2c}$ are each independently selected from F, Cl, and Br; or a single stereoisomer, racemate, enantiomer, or diastereomer, thereof and optionally as a pharmaceutically acceptable salt thereof.

21. The compound according to claim 20, wherein $R^{2a}$ is F $R^{2b}$ is Cl, and $R^{2c}$ is either Cl or Br; or a single stereoisomer, racemate, enantiomer, or diastereomer, thereof and optionally as a pharmaceutically acceptable salt thereof.

22. The compound according to claim 4, wherein the saturated bridged ring system has a geometry selected from the group consisting of [3.3.1], [3.2.1], and [2.2.1]; or a single stereoisomer, racemate, enantiomer, or diastereomer, thereof and optionally as a pharmaceutically acceptable salt thereof.

23. The compound according to claim 22, wherein said saturated bridged ring system contains one or two annular nitrogens, said one or two annular nitrogens are selected from —NR⁸—, when X¹, and a bridgehead nitrogen, when X²; or a single stereoisomer, racemate, enantiomer, or diastereomer, thereof and optionally as a pharmaceutically acceptable salt thereof.

24. The compound according to claim 23, wherein said saturated bridged ring system is according to formula VIII or formula IX;

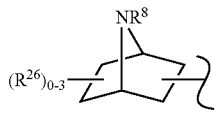

-continued

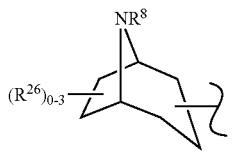

IX wherein $R^8$ is selected from —H, lower alkyl, —CO$_2$R$^3$, —C(O)N(R$^3$)R$^4$, —SO$_2$R$^4$, and —C(O)R$^3$; and $R^{26}$ is $C_{1-3}$ alkyl; or a single stereoisomer, racemate, enantiomer, or diastereomer, thereof and optionally as a pharmaceutically acceptable salt thereof.

25. A compound of Formula Ia,

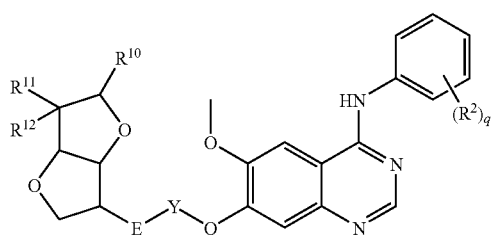

Ia or a single stereoisomer, racemate, enantiomer, or diastereomer, thereof and optionally as a pharmaceutically acceptable salt thereof, wherein, q is 1, 2, or 3;

$R^2$ is selected from halogen, trihalomethyl, —CN, —NO$_2$, —OR$^3$, lower alkyl, and piperazinyl substituted with methyl;

Y is —CH$_2$—;

E is absent;

$R^3$ is —H or $R^4$;

$R^4$ is selected from lower alkyl; lower alkyl substituted with one, two, or three halogen; aryl; aryl substituted with one, two, or three halogen; and unsubstituted lower arylalkyl; or $R^3$ and $R^4$, when taken together with a common nitrogen to which they are attached, form morpholinyl, pyrrolidinyl, piperidinyl, or piperazinyl optionally substituted by one, two, or three alkyl;

$R^{10}$ is selected from —H, alkyl, and —OR$^{13}$; and $R^{11}$ and $R^{12}$ are each independently selected from —H, —CF$_3$, —F, —N(R$^3$)R$^4$, —N(C=O)R$^3$, —N(R$^3$)SO$_2$R$^3$, —S(O)$_{0-2}$R$^{13}$, —OR$^{13}$, and —NH$_2$; or $R^{10}$ is selected from —H, and —OR$^{13}$; and $R^{11}$ and $R^{12}$, when taken together, are oxo or when taken together with the carbon to which they are attached, form a three- to seven-membered spirocyclyl; and $R^{13}$ is selected from —H; lower alkynyl; unsubstituted lower arylalkynyl; lower alkenyl; unsubstituted lower arylalkenyl; lower alkyl; lower alkyl substituted with one, two, or three halogen; unsubstituted lower arylalkyl; and aryl; or two $R^{13}$'s, when taken together, form 1) a corresponding spirocyclic ketal from $R^{11}$, $R^{12}$ and the carbon to which they are attached, when $R^{11}$ and $R^{12}$ are both —OR$^{13}$ which spirocyclic ketal is optionally substituted with one or two alkyl.

26. The Compound of claim 25 wherein q is 1, 2, or 3;

$R^2$ is selected from halogen, trihalomethyl, —CN, —NO$_2$, —OR$^3$, and lower alkyl;

Y is —CH$_2$—;

E is absent;

$R^3$ is —H or $R^4$;

$R^4$ is selected from lower alkyl; lower alkyl substituted with one, two, or three halogen; aryl; aryl substituted with one, two, or three halogen; and unsubstituted lower arylalkyl; or $R^3$ and $R^4$, when taken together with a common nitrogen to which they are attached, form morpholinyl, pyrrolidinyl, piperidinyl, or piperazinyl optionally substituted by one, two, or three alkyl;

$R^{10}$ is selected from —H, alkyl, and —OR$^{13}$; and $R^{11}$ and $R^{12}$ are each independently selected from —H, —CF$_3$, —F, —N(R$^3$)R$^4$, —N(C=O)R$^3$, —N(R$^3$)SO$_2$R$^3$, —S(O)$_{0-2}$R$^{13}$, and —OR$^{13}$; or $R^{10}$ is selected from —H, and —OR$^{13}$; and $R^{11}$ and $R^{12}$, when taken together, are oxo, exo-alkenyl, or when taken together with the carbon to which they are attached, form a three- to seven-membered spirocyclyl; and $R^{13}$ is selected from —H; lower alkynyl; unsubstituted lower arylalkynyl; lower alkenyl; unsubstituted lower arylalkenyl; lower alkyl; lower alkyl substituted with one, two, or three halogen; unsubstituted lower arylalkyl; and aryl; or two $R^{13}$'s, when taken together, form 1) a corresponding spirocyclic ketal from $R^{11}$, $R^{12}$ and the carbon to which they are attached, when $R^{11}$ and $R^{12}$ are both —OR$^3$; or a single stereoisomer, racemate, enantiomer, or diastereomer, thereof and optionally as a pharmaceutically acceptable salt thereof.

27. The compound according to claim 26, wherein one of $R^{11}$ and $R^{12}$ is —OR$^{13}$, wherein $R^{13}$ is selected from —H, lower alkyl, and lower alkyl substituted with one, two, or three halogen; and $R^{10}$ and the other of $R^{11}$ and $R^{12}$ are both —H; or a single stereoisomer, racemate, enantiomer, or diastereomer, thereof and optionally as a pharmaceutically acceptable salt thereof.

28. The compound according to claim 26, wherein one of $R^{11}$ and $R^{12}$ is —F; and $R^{10}$ and the other of $R^{11}$ and $R^{12}$ are both —H; or a single stereoisomer, racemate, enantiomer, or diastereomer, thereof and optionally as a pharmaceutically acceptable salt thereof.

29. The compound according to claim 26, wherein $R^{13}$ is a lower alkyl group containing at least one fluorine substitution thereon; or a single stereoisomer, racemate, enantiomer, or diastereomer, thereof and optionally as a pharmaceutically acceptable salt thereof.

30. The compound according to claim 26, wherein q is 2 or 3; or a single stereoisomer, racemate, enantiomer, or diastereomer, thereof and optionally as a pharmaceutically acceptable salt thereof.

31. The compound according to claim 30, wherein each $R^2$ is independently selected from —F, —Cl, —Br, —CF$_3$, —CH$_3$, and —OR$^{25}$; wherein $R^{25}$ is either methyl or aryl, each optionally substituted with one to three halogens; or a single stereoisomer, racemate, enantiomer, or diastereomer, thereof and optionally as a pharmaceutically acceptable salt thereof.

32. The compound of claim 1 selected from

N-(3,4-dichlorophenyl)-6-(methyloxy)-7-{[(8aR)-tetrahydro-1H-[1,3]thiazolo[4,3-c][1,4]oxazin-6-ylmethyl]oxy}quinazolin-4-amine;

N-(3,4-dichlorophenyl)-6-(methyloxy)-7-[(tetrahydro-1H-[1,3]thiazolo[4,3-c][1,4]oxazin-3-ylmethyl)oxy]quinazolin-4-amine; and N-(3,4-dichloro-2-fluorophenyl)-6-(methyloxy)-7-[(octahydro-2H-quinolizin-3-ylmethyl)oxy]quinazolin-4-amine; and a single stereoisomer, racemate, enantiomer, or diastereomer, thereof and optionally as a pharmaceutically acceptable salt thereof.

33. The Compound of claim 8 selected from

N-(4-bromo-2,3-dichlorophenyl)-7-{[(3R,9aS)-hexahydro-1H-[1,4]oxazino[3,4-c][1,4]oxazin-3-ylmethyl]oxy}-6-(methyloxy)quinazolin-4-amine;

N-(4,5-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine;

N-(4-bromo-5-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine;

N-(3-chloro-2,4-difluorophenyl)-7-{[(3R,9aS)-hexahydro-1H-[1,4]oxazino[3,4-c][1,4]oxazin-3-ylmethyl]oxy}-6-(methyloxy)quinazolin-4-amine;

N-(3,4-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine;

N-(4-bromo-3-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine;

N-(3-chloro-2,4-difluorophenyl)-7-{[(3S,9aS)-hexahydro-1H-[1,4]oxazino[3,4-c][1,4]oxazin-3-ylmethyl]oxy}-6-(methyloxy)quinazolin-4-amine;

N-(3,4-dichlorophenyl)-7-[(hexahydro-1H-[1,4]oxazino[3,4—C][1,4]oxazin-3-ylmethyl)oxy]-6-(methyloxy)quinazolin-4-amine;

N-(4,5-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine;

N-(4-bromo-2,3-dichlorophenyl)-7-{[(3S,9aS)-hexahydro-1H-[1,4]oxazino[3,4-c][1,4]oxazin-3-ylmethyl]oxy}-6-(methyloxy)quinazolin-4-amine;

N-(4-bromo-5-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine;

N-(3,4-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine; and N-(4-bromo-3-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine; and a single stereoisomer, racemate, enantiomer, or diastereomer, thereof and optionally as a pharmaceutically acceptable salt thereof.

34. The Compound of claim 8 selected from

N-(3,4-dichlorophenyl)-7-{[(3R,8aR)-hexahydro-1H-pyrrolo[2,1-c][1,4]oxazin-3-ylmethyl]oxy}-6-(methyloxy)quinazolin-4-amine;

N-(4-bromo-5-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine;

N-(3,4-dichlorophenyl)-7-{[(3S,8aR)-hexahydro-1H-pyrrolo[2,1-c][1,4]oxazin-3-ylmethyl]oxy}-6-(methyloxy)quinazolin-4-amine;

N-(3,4-dichlorophenyl)-7-{[(3S,8aS)-hexahydro-1H-pyrrolo[2,1-c][1,4]oxazin-3-ylmethyl]oxy}-6-(methyloxy)quinazolin-4-amine;

N-(3,4-dichlorophenyl)-7-{[(3R,8aS)-hexahydro-1H-pyrrolo[2,1-c][1,4]oxazin-3-ylmethyl]oxy}-6-(methyloxy)quinazolin-4-amine;

N-(3,4-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine;

N-(4-bromo-3-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine;

N-(3-chloro-2,4-difluorophenyl)-7-{[(3S,8aS)-hexahydro-1H-pyrrolo[2,1-c][1,4]oxazin-3-ylmethyl]oxy}-6-(methyloxy)quinazolin-4-amine;

N-(4-bromo-2,3-dichlorophenyl)-7-{[(3S,8aS)-hexahydro-1H-pyrrolo[2,1-c][1,4]oxazin-3-ylmethyl]oxy}-6-(methyloxy)quinazolin-4-amine; and N-(4,5-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine; and a single stereoisomer, racemate, enantiomer, or diastereomer, thereof and optionally as a pharmaceutically acceptable salt thereof.

35. The Compound of claim 11 selected from

N-(3,4-dichloro-2-fluorophenyl)-7-({[(3aR,6aS)-2-(1-methylethyl)octahydrocyclopenta[c]pyrrol-5-yl]methyl}oxy)-6-(methyloxy)quinazolin-4-amine;

N-(4-bromo-3-chloro-2-fluorophenyl)-7-({[(3aR,6aS)-2-(1-methylethyl)octahydrocyclopenta[c]pyrrol-5-yl]methyl}oxy)-6-(methyloxy)quinazolin-4-amine;

7-({[(3aR,6aS)-2-acetyloctahydrocyclopenta[c]pyrrol-5-yl]methyl}oxy)-N-(4-bromo-3-chloro-2-fluorophenyl)-6-(methyloxy)quinazolin-4-amine;

N-(4-bromo-3-chloro-2-fluorophenyl)-6-(methyloxy)-7-{[(3aR,6aS) -octahydrocyclopenta[c]pyrrol-5-ylmethyl]oxy}quinazolin-4-amine;

N-(4-bromo-3-chloro-2-fluorophenyl)-6-(methyloxy)-7-({[(3aR,6aS)-2-(methylsulfonyl)octahydrocyclopenta[c]pyrrol-5-yl]methyl}oxy)quinazolin-4-amine;

N-(3,4-dichloro-2-fluorophenyl)-7-({[(3aR,6aS)-2-ethyloctahydrocyclopenta[c]pyrrol-5-yl]methyl}oxy)-6-(methyloxy)quinazolin-4-amine;

N-(3,4-dichloro-2-fluorophenyl)-6-(methyloxy)-7-({[(3aR,6aS)-2-(2-methylpropyl)octahydrocyclopenta[c]pyrrol-5-yl]methyl}oxy)quinazolin-4-amine;

N-(3,4-dichloro-2-fluorophenyl)-7-({[(3aR,6aS)-2-methyloctahydrocyclopenta[c]pyrrol-5-yl]methyl}oxy)-6-(methyloxy)quinazolin-4-amine;

N-(4-bromo-3-chloro-2-fluorophenyl)-7-({[(3aR,6aS)-2-methyloctahydrocyclopenta[c]pyrrol-5-yl]methyl}oxy)-6-(methyloxy)quinazolin-4-amine;

N-(3-chloro-2,4-difluorophenyl)-7-({[(3aR,6aS)-2-methyloctahydrocyclopenta[c]pyrrol-5-yl]methyl}oxy)-6-(methyloxy)quinazolin-4-amine;

N-(4,5-dichloro-2-fluorophenyl)-7-({[(3aR,6aS)-2-methyloctahydrocyclopenta[c]pyrrol-5-yl]methyl}oxy)-6-(methyloxy)quinazolin-4-amine;

N-(4-bromo-5-chloro-2-fluorophenyl)-7-({[(3aR,6aS)-2-methyloctahydrocyclopenta[c]pyrrol-5-yl]methyl}oxy)-6-(methyloxy)quinazolin-4-amine;

N-(4-bromo-2,3-dichlorophenyl)-7-({[(3aR,6aS)-2-methyloctahydrocyclopenta[c]pyrrol-5-yl]methyl}oxy)-6-(methyloxy)quinazolin-4-amine;

N-(3,4-dichlorophenyl)-7-({[(3aR,6aS)-2-methyloctahydrocyclopenta[c]pyrrol-5-yl]methyl}oxy)-6-(methyloxy)quinazolin-4-amine;

N-(4-bromo-3-chloro-2-fluorophenyl)-7-({[(3aR,6aS)-2-ethyloctahydrocyclopenta[c]pyrrol-5-yl]methyl}oxy)-6-(methyloxy)quinazolin-4-amine; and
N-(4-bromo-3-chloro-2-fluorophenyl)-6-(methyloxy)-7-({[(3aR,6aS)-2-(2-methylpropyl)octahydrocyclopenta[c]pyrrol-5-yl]methyl}oxy)quinazolin-4-amine; and
a single stereoisomer, racemate, enantiomer, or diastereomer, thereof and optionally as a pharmaceutically acceptable salt thereof.

36. The Compound of claim 11 selected from
N-(3-chloro-2,4-difluorophenyl)-7-({[(3aR,5s,6aS-2-methyloctahydrocyclopenta[c]pyrrol-5-yl]methyl}oxy)-6-(methyloxy)quinazolin-4-amine;
N-(3-chloro-2,4-difluorophenyl)-7-({[(3aR,5r,6aS)-2-methyloctahydrocyclopenta-[c]pyrrol-5-y]methyl}oxy)-6-(methyloxy)quinazolin-4-amine;
N-(4-bromo-2,3-dichlorophenyl)-7-({[(3aR,5s,6aS)-2-methyloctahydrocyclopenta[c]pyrrol-5-yl]methyl}oxy)-6-(methyloxy)quinazolin-4-amine;
N-(4-bromo-2,3-dichlorophenyl)-7-({[(3aR,5r,6aS)-2-methyloctahydrocyclo-penta[c]pyrrol-5-yl]methyl}oxy)-6-(methyloxy)quinazolin-4-amine;
N-(3,4-dichlorophenyl)-7-({[(3aR,5s,6aS)-2-methyloctahydrocyclopenta[c]pyrrol-5-yl]methyl}oxy)-6-(methyloxy)quinazolin-4-amine; and
N-(3,4-dichlorophenyl)-7-({[(3aR,5r,6aS)-2-methyloctahydrocyclopenta[c]pyrrol-5-yl]methyl}oxy)-6-(methyloxy)quinazolin-4-amine; and
a single stereoisomer, racemate, enantiomer, or diastereomer, thereof and optionally as a pharmaceutically acceptable salt thereof.

37. The Compound of claim 13 selected from
N-(3,4-dichloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine;
N-(4-bromo-3-chloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine;
7-({[(3aR,5r,6aS)-2-acetyloctahydrocyclopenta[c]pyrrol-5-yl]methyl}oxy)-N-(4-bromo-3-chloro-2-fluorophenyl)-6-(methyloxy)quinazolin-4-amine;
N-(4-bromo-3-chloro-2-fluorophenyl)-6-(methyloxy)-7-{[(3aR,5r,6aS) -octahydrocyclopenta[c]pyrrol-5-ylmethyl]oxy}quinazolin-4-amine;
ethyl (3aR,6aS)-5-({[4-[(4-bromo-3-chloro-2-fluorophenyl)amino]-6-(methyloxy)quinazolin-7-yl]oxy}methyl)hexahydrocyclopenta[c]pyrrol-2(1H)-carboxylate;
ethyl (3aR,5r,6aS)-5-[({4-[(4-bromo-3-chloro-2-fluorophenyl)amino]-6-(methyloxy)quinazolin-7-yl}oxy)methyl]hexahydrocyclopenta[c]pyrrol-2(1H)-carboxylate;
N-(4-bromo-3-chloro-2-fluorophenyl)-6-(methyloxy)-7-({[(3aR,5r,6aS)-2-(methylsulfonyl)octahydrocyclopenta[c]pyrrol-5-yl]methyl}oxy)quinazolin-4-amine;
N-(3,4-dichloro-2-fluorophenyl)-7-({[(3aR,5r,6aS)-2-ethyloctahydrocyclopenta[c]pyrrol-5-yl]methyl}oxy)-6-(methyloxy)quinazolin-4-amine;
N-(3,4-dichloro-2-fluorophenyl)-6-(methyloxy)-7-({[(3aR,5r,6aS)-2-(2-methylpropyl)octahydrocyclopenta[c]pyrrol-5-yl]methyl}oxy)quinazolin-4-amine;
N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine;
N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine;
N-(4-bromo-3-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine;
N-(4-bromo-3-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine;
N-(4,5-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine;
N-(4,5-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine;
N-(4-bromo-5-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine;
N-(4-bromo-5-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine;
N-(4-bromo-3-chloro-2-fluorophenyl)-7-({[(3aR,5r,6aS)-2-ethyloctahydrocyclopenta[c]pyrrol-5-yl]methyl}oxy)-6-(methyloxy)quinazolin-4-amine;
N-(4-bromo-3-chloro-2-fluorophenyl)-6-(methyloxy)-7-({[(3aR,5r,6aS)-2-(2-methylpropyl)octahydrocyclopenta[c]pyrrol-5-yl]methyl}oxy)quinazolin-4-amine;
1,1-dimethylethyl (3aR,6aS)-5-({[4-[(4-bromo-3-chloro-2-fluorophenyl)amino]-6-(methyl-oxy)quinazolin-7-yl]oxy}methyl)hexahydrocyclopenta[c]pyrrol-2(1H)-carboxylate;
N-(3,4-dichloro-2-fluorophenyl)-6-(methyloxy)-7-{[[(3aR,5r,6aS) -octahydrocyclopenta[c]pyrrol-5-yl]methyl]oxy}quinazolin-4-amine; and
1,1-dimethylethyl (3aR,6aS)-5-({[4-[(3,4-dichloro-2-fluorophenyl)amino]-6-(methyloxy)quinazolin-7-yl]oxy}methyl) hexahydrocyclopenta-[c]pyrrol-2(1H)-carboxylate; and
a single stereoisomer, racemate, enantiomer, or diastereomer, thereof and optionally as a pharmaceutically acceptable salt thereof.

38. The Compound of claim 11 selected from
N-(3,4-dichloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine;
N-(4-bromo-3-chloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine;
7-({[(3aR,5r,6aS)-2-acetyloctahydrocyclopenta[c]pyrrol-5-yl]methyl}oxy)-N-(4-bromo-3-chloro-2-fluorophenyl)-6-(methyloxy)quinazolin-4-amine;
N-(4-bromo-3-chloro-2-fluorophenyl)-6-(methyloxy)-7-{[(3aR,5r,6aS) -octahydrocyclopenta[c]pyrrol-5-ylmethyl]oxy}quinazolin-4-amine;
ethyl (3aR,5r,6aS)-5-[({4-[(4-bromo-3-chloro-2-fluorophenyl)amino]-6-(methyloxy)quinazolin-7-yl}oxy)methyl]hexahydrocyclopenta[c]pyrrol-2(1H)-carboxylate;
N-(4-bromo-3-chloro-2-fluorophenyl)-6-(methyloxy)-7-({[(3aR,5r,6aS)-2-(methylsulfonyl)octahydrocyclopenta[c]pyrrol-5-yl]methyl}oxy)quinazolin-4-amine;
N-(3,4-dichloro-2-fluorophenyl)-7-({[(3aR,5r,6aS)-2-ethyloctahydrocyclopenta[c]pyrrol-5-yl]methyl}oxy)-6-(methyloxy)quinazolin-4-amine;
N-(3,4-dichloro-2-fluorophenyl)-6-(methyloxy)-7-({[(3aR,5r,6aS)-2-(2-methylpropyl)octahydrocyclopenta[c]pyrrol-5-yl]methyl}oxy)quinazolin-4-amine;
N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine;

N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine;

N-(4-bromo-3-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine;

N-(3-chloro-2,4-difluorophenyl)-7-({[(3aR,5r,6aS)-2-methyloctahydrocyclopenta-[c]pyrrol-5-yl]methyl}oxy)-6-(methyloxy)quinazolin-4-amine;

N-(4,5-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine;

N-(4-bromo-5-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine;

N-(4-bromo-2,3-dichlorophenyl)-7-({[(3aR,5r,6aS)-2-methyloctahydrocyclopenta[c]pyrrol-5-yl]methyl}oxy)-6-(methyloxy)quinazolin-4-amine;

N-(3,4-dichlorophenyl)-7-({[(3aR,5r,6aS)-2-methyloctahydrocyclopenta[c]pyrrol-5-yl]methyl}oxy)-6-(methyloxy)quinazolin-4-amine;

N-(4-bromo-3-chloro-2-fluorophenyl)-7-({[(3aR,5r,6aS)-2-ethyloctahydrocyclopenta[c]pyrrol-5-yl]methyl}oxy)-6-(methyloxy)quinazolin-4-amine;

N-(4-bromo-3-chloro-2-fluorophenyl)-6-(methyloxy)-7-({[(3aR,5r,6aS)-2-(2-methylpropyl)octahydrocyclopenta[c]pyrrol-5-yl]methyl}oxy)quinazolin-4-amine; and 1,1-dimethylethyl (3aR,6aS)-5-({[4-[(4-bromo-3-chloro-2-fluorophenyl)amino]-6-(methyl-oxy)quinazolin-7-yl]oxy}methyl)hexahydrocyclopenta[c]pyrrol-2(1H)-carboxylate;

N-(3,4-dichloro-2-fluorophenyl)-6-(methyloxy)-7-{[[(3aR,5r,6aS) -octahydrocyclopenta[c]pyrrol-5-yl]methyl]oxy}quinazolin-4-amine; and 1,1-dimethylethyl (3aR,6aS)-5-({[4-[(3,4-dichloro-2-fluorophenyl)amino]-6-(methyloxy)quinazolin-7-yl]oxy}methyl) hexahydrocyclopenta-[c]pyrrol-2(1H)-carboxylate; and a single stereoisomer, racemate, enantiomer, or diastereomer, thereof and optionally as a pharmaceutically acceptable salt thereof.

39. The Compound of claim 38 selected from N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine; N-(4-bromo-3-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine; and N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine; and optionally as a pharmaceutically acceptable salt thereof.

40. The pharmaceutical composition of claim 39.

41. The Compound of claim 38 selected from 1,1-dimethylethyl (3aR,6aS)-5-({[4-[(4-bromo-3-chloro-2-fluorophenyl)amino]-6-(methyl-oxy)quinazolin-7-yl]oxy}methyl) hexahydrocyclopenta[c]pyrrol-2(1H)—carboxylate; N-(4-bromo-3-chloro-2-fluorophenyl)-6-(methyloxy)-7-{[(3aR,5r,6aS)-octahydrocyclopenta[c]pyrrol-5-ylmethyl]oxy}quinazolin-4-amine; N-(3,4-dichloro-2-fluorophenyl)-6-(methyloxy)-7-{[[(3aR,5r,6aS)-octahydrocyclopenta[c]pyrrol-5-yl]methyl]oxy}quinazolin-4-amine; 1,1-dimethylethyl (3aR,6aS)-5-({[4-[(3,4-dichloro-2-fluorophenyl)amino]-6-(methyloxy)quinazolin-7-yl]oxy}methyl) hexahydrocyclopenta-[c]pyrrol-2(1H)-carboxylate; and a single, stereoisomer, racemate, enantiomer, or diastereomer, thereof and optionally as a pharmaceutically acceptable salt thereof.

42. The Compound of claim 39 named N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine optionally as a pharmaceutically acceptable salt thereof.

43. The pharmaceutical composition of claim 42.

44. The Compound of claim 21 selected from (3S,9aS)-3-({[4-[(3,4-dichloro-2-fluorophenyl)amino]-6-(methyloxy)quinazolin-7-yl]oxy}methyl)hexahydro-2H-pyrido[1,2-a]pyrazin-1(6H)-one;

(3S,9aR)-3-({[4-[(3,4-dichloro-2-fluorophenyl)amino]-6-(methyloxy)quinazolin-7-yl]oxy}methyl)hexahydro-2H-pyrido[1,2-a]pyrazin-1(6H)-one;

(3S,8aS)-3-({[4-[(3,4-dichloro-2-fluorophenyl)amino]-6-(methyloxy)quinazolin-7-yl]oxy}methyl)hexahydropyrrolo[1,2-a]pyrazin-1(2H)-one;

(3S,8aR)-3-({[4-[(3,4-dichloro-2-fluorophenyl)amino]-6-(methyloxy)quinazolin-7-yl]oxy}methyl)hexahydropyrrolo[1,2-a]pyrazin-1(2H)-one;

(3S,8aS)-3-({[4-[(4-bromo-3-chloro-2-fluorophenyl)amino]-6-(methyloxy)quinazolin-7-yl]oxy}methyl) hexahydropyrrolo[1,2-a]pyrazin-1(2H)-one; and (3S,8aS)-3-({[4-[(3,4-dichloro-2-fluorophenyl)amino]-6-(methyloxy)quinazolin-7-yl]oxy}methyl)-2-methyl-hexahydropyrrolo[1,2-a]pyrazin-1(2H)-one; and a single stereoisomer, racemate, enantiomer, or diastereomer, thereof and optionally as a pharmaceutically acceptable salt thereof.

45. The Compound of claim 24 selected from

N-(3,4-dichlorophenyl)-7-{[(8-methyl-8-azabicyclo[3.2.1]oct-3-yl)methyl]oxy}-6-(methyloxy)quinazolin-4-amine;

N-(3,4-dichlorophenyl)-7-({[(3-endo)-8-methyl-8-azabicyclo[3.2.1]oct-3-yl]methyl}oxy)-6-(methyloxy)quinazolin-4-amine; and 7-{[(3-endo)-8-azabicyclo[3.2.1]oct-3-ylmethyl]oxy}-N-(3,4-dichlorophenyl)-6-(methyloxy)quinazolin-4-amine; and a single stereoisomer, racemate, enantiomer, or diastereomer, thereof and optionally as a pharmaceutically acceptable salt thereof.

46. The Compound of claim 31 selected from 1,4:3,6-dianhydro-5-({[4-[(4-bromo-5-chloro-2-fluorophenyl)amino]-6-(methyloxy)quinazolin-7-yl]oxy}methyl)-5-deoxy-2-O-methyl-D-xylo-hexitol;

1,4:3,6-dianhydro-5-deoxy-5-({[4-[(3,4-dichlorophenyl)amino]-6-(methyloxy)quinazolin-7-yl]oxy}methyl)-2-O-methyl-D-glucitol;

1,4:3,6-dianhydro-5-deoxy-5-({[4-[(3,4-dichloro-2-fluorophenyl)amino]-6-(methyloxy)quinazolin-7-yl]oxy}methyl)-2-O-methyl-D-xylo-hexitol;

1,4:3,6-dianhydro-5-({[4-[(4-bromo-3-chloro-2-fluorophenyl)amino]-6-(methyloxy)quinazolin-7-yl]oxy}methyl)-5-deoxy-2-O-methyl-D-xylo-hexitol;

1,4:3,6-dianhydro-5-({[4-[(3-chloro-2,4-difluorophenyl)amino]-6-(methyloxy)quinazolin-7-yl]oxy}methyl)-5-deoxy-2-O-methyl-D-xylo-hexitol;

1,4:3,6-dianhydro-5-({[4-[(4-bromo-2,3-dichlorophenyl)amino]-6-(methyloxy)quinazolin-7-yl]oxy}methyl)-5-deoxy-2-O-methyl-D-glucitol;

1,4:3,6-dianhydro-2-deoxy-2-({[4-[(3,4-dichlorophenyl)amino]-6-(methyloxy)quinazolin-7-yl]oxy}methyl)-5-O-methyl-D-threo-hexitol; and 1,4:3,6-dianhydro-5-deoxy-5-({[4-[(4,5-dichloro-2-fluorophenyl)amino]-6-(methyloxy)quinazolin-7-yl]oxy}methyl)-2-O-methyl-D-glucitol; and a single stereoisomer, racemate, enantiomer, or diastereomer, thereof and optionally as a pharmaceutically acceptable salt thereof.

47. A pharmaceutical composition comprising a compound of formula I as defined in claim 1 or 38 or Ia as defined in claim 25 and a pharmaceutically acceptable carrier.

* * * * *

UNITED STATES PATENT AND TRADEMARK OFFICE
CERTIFICATE OF CORRECTION

PATENT NO. : 7,576,074 B2  Page 1 of 1
APPLICATION NO. : 10/522004
DATED : August 18, 2009
INVENTOR(S) : Rice et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (475) days Delete the phrase "by 475 days" and insert -- by 560 days --

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,576,074 B2 | |
| APPLICATION NO. | : 10/522004 | |
| DATED | : August 18, 2009 | |
| INVENTOR(S) | : Rice et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (560) days Delete the phrase "by 560 days" and insert -- by 1025 days --

Signed and Sealed this

Eighteenth Day of May, 2010

David J. Kappos
*Director of the United States Patent and Trademark Office*